(12) United States Patent
Van Ooijen

(10) Patent No.: US 11,450,409 B2
(45) Date of Patent: Sep. 20, 2022

(54) DETERMINATION OF NFKB PATHWAY ACTIVITY USING UNIQUE COMBINATION OF TARGET GENES

(71) Applicant: InnoSIGN B.V., Eindhoven (NL)

(72) Inventor: Hendrik Jan Van Ooijen, Eindhoven (NL)

(73) Assignee: InnoSIGN B.V., Eindhoven (NL)

( * ) Notice: Subject to any disclaimer, the term of this patent is extended or adjusted under 35 U.S.C. 154(b) by 878 days.

(21) Appl. No.: 15/235,478

(22) Filed: Aug. 12, 2016

(65) Prior Publication Data
US 2017/0046477 A1    Feb. 16, 2017

(30) Foreign Application Priority Data

Aug. 14, 2015 (EP) .................................... 15181029

(51) Int. Cl.
| | | |
|---|---|---|
| G01N 33/48 | (2006.01) | |
| G16B 25/20 | (2019.01) | |
| G01N 33/574 | (2006.01) | |
| A61K 31/336 | (2006.01) | |
| A61K 31/416 | (2006.01) | |
| A61K 38/05 | (2006.01) | |
| A61K 31/4985 | (2006.01) | |
| A61K 31/573 | (2006.01) | |
| G16B 25/00 | (2019.01) | |
| G16B 5/00 | (2019.01) | |
| C12Q 1/6886 | (2018.01) | |
| G16B 40/00 | (2019.01) | |
| G16B 5/20 | (2019.01) | |
| G06G 7/58 | (2006.01) | |

(52) U.S. Cl.
CPC ............ *G16B 25/20* (2019.02); *A61K 31/336* (2013.01); *A61K 31/416* (2013.01); *A61K 31/4985* (2013.01); *A61K 31/573* (2013.01); *A61K 38/05* (2013.01); *C12Q 1/6886* (2013.01); *G01N 33/57484* (2013.01); *G16B 5/00* (2019.02); *G16B 5/20* (2019.02); *G16B 25/00* (2019.02); *G16B 40/00* (2019.02); *C12Q 2600/158* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 5,436,134 | A  | 7/1995  | Haugland |
| 5,658,751 | A  | 8/1997  | Yue |
| 5,874,219 | A  | 2/1999  | Rava |
| 6,004,761 | A  | 12/1999 | Linsley |
| 6,146,897 | A  | 11/2000 | Cohenford |
| 6,171,798 | B1 | 1/2001  | Levine |
| 6,225,047 | B1 | 5/2001  | Hutchens |
| 6,308,170 | B1 | 10/2001 | Balaban |
| 6,391,550 | B1 | 5/2002  | Lockhart |
| 6,675,104 | B2 | 1/2004  | Paulse |
| 6,720,149 | B1 | 4/2004  | Rava |
| 6,844,165 | B2 | 1/2005  | Hutchens |
| 6,884,578 | B2 | 4/2005  | Warrington |
| 7,056,674 | B2 | 6/2006  | Baker |
| 7,081,340 | B2 | 7/2006  | Baker |
| 7,160,734 | B2 | 1/2007  | Hutchens |
| 7,208,470 | B2 | 4/2007  | Duan |
| 7,299,134 | B2 | 11/2007 | Rich |
| 7,526,637 | B2 | 4/2009  | Jung |
| 7,569,345 | B2 | 8/2009  | Cobleigh |
| 7,695,913 | B2 | 4/2010  | Cowens |
| 7,723,033 | B2 | 5/2010  | Baker |
| 7,754,431 | B2 | 7/2010  | Ring |
| 7,754,861 | B2 | 7/2010  | Boschei |
| 7,816,084 | B2 | 10/2010 | Ring |
| 7,838,224 | B2 | 11/2010 | Baker |
| 7,858,304 | B2 | 12/2010 | Baker |
| 7,888,019 | B2 | 2/2011  | Kiefer |
| 7,930,104 | B2 | 4/2011  | Baker |
| 7,939,261 | B2 | 5/2011  | Baker |
| 8,008,003 | B2 | 8/2011  | Baker |
| 8,021,894 | B2 | 9/2011  | Hutchens |

(Continued)

FOREIGN PATENT DOCUMENTS

| | | |
|---|---|---|
| EP | 2549399 A1 | 1/2013 |
| WO | 2012154567 A2 | 11/2012 |

(Continued)

OTHER PUBLICATIONS

Shen, Haige "Bayesian Analysis in Cancer Pathway Studies and Probabilistic Pathway Annotation", Duke University 2008.

(Continued)

*Primary Examiner* — Eric S Dejong
(74) *Attorney, Agent, or Firm* — Bond, Schoeneck & King, PLLC

(57) ABSTRACT

A bioinformatics process which provides an improved means to detect NFkB cellular signaling pathway in a subject, such as a human, based on the expression levels of at least six unique target genes of the NFkB cellular signaling pathway measured in a sample. The invention includes an apparatus comprising a digital processor configured to perform such a method, a non-transitory storage medium storing instructions that are executable by a digital processing device to perform such a method, and a computer program comprising program code means for causing a digital processing device to perform such a method. Kits are also provided for measuring expression levels of unique sets of NFkB cellular signaling pathway target genes.

21 Claims, 32 Drawing Sheets
Specification includes a Sequence Listing.

(56) References Cited

U.S. PATENT DOCUMENTS

| | | |
|---|---|---|
| 8,026,060 B2 | 9/2011 | Watson |
| 8,029,995 B2 | 10/2011 | Watson |
| 8,029,997 B2 | 10/2011 | Kennedy |
| 8,034,565 B2 | 10/2011 | Cobleigh |
| 8,067,178 B2 | 11/2011 | Baker |
| 8,071,286 B2 | 12/2011 | Baker |
| 8,148,076 B2 | 4/2012 | Baker |
| 8,153,378 B2 | 4/2012 | Cowens |
| 8,153,379 B2 | 4/2012 | Watson |
| 8,153,380 B2 | 4/2012 | Watson |
| 8,198,024 B2 | 6/2012 | Watson |
| 8,206,919 B2 | 6/2012 | Cobleigh |
| 8,273,537 B2 | 9/2012 | Watson |
| 8,367,345 B2 | 2/2013 | Cowens |
| 8,451,450 B2 | 5/2013 | Heng |
| 8,518,639 B2 | 8/2013 | Rihet |
| 8,632,980 B2 | 1/2014 | Baker |
| 8,703,736 B2 | 4/2014 | Whatcott |
| 8,725,426 B2 | 5/2014 | Shak |
| 8,741,605 B2 | 6/2014 | Cobleigh |
| 8,765,383 B2 | 7/2014 | Cowens |
| 8,808,994 B2 | 8/2014 | Kiefer |
| 8,868,352 B2 | 10/2014 | Baker |
| 8,906,625 B2 | 12/2014 | Kiefer |
| 8,911,940 B2 | 12/2014 | Weiss |
| 9,076,104 B2 | 7/2015 | Wang |
| 2004/0180341 A1 | 9/2004 | Sedivy |
| 2006/0234911 A1 | 10/2006 | Hoffmann |
| 2009/0105962 A1 | 4/2009 | Woolf |
| 2009/0186024 A1 | 7/2009 | Nevins |
| 2010/0131432 A1 | 5/2010 | Kennedy |
| 2010/0273711 A1 | 10/2010 | Potti |
| 2011/0053804 A1 | 3/2011 | Massague |
| 2011/0091377 A1 | 4/2011 | Alani |
| 2012/0009581 A1 | 1/2012 | Bankaitis-Davis |

FOREIGN PATENT DOCUMENTS

| | | |
|---|---|---|
| WO | 2013003384 A1 | 1/2013 |
| WO | 2013011479 A2 | 1/2013 |
| WO | 2013075059 A1 | 5/2013 |
| WO | 2014102668 A2 | 7/2014 |
| WO | 2014174003 A1 | 10/2014 |
| WO | 2015101635 A1 | 7/2015 |

OTHER PUBLICATIONS

Chen, Min et al. "A Powerful Bayesian Meta-Analysis Method to Integrate Multiple Gene Set Enrichment Studies", BIOINFORMATIC, vol. 29, No. 7, 2013, pp. 862-869.

Fanelli, Laise P. et al "Modeling TGF-Beta Signaling Pathway in Epithelial-Mesenchymal Transistion", AIP Advances, 2012, vol. 2, No. 1. Abstract Only.

Zhang, Ping et al "Joint Loading-Driven Bone Formation and Signaling Pathways Predicted from Genome-Wide Expression Profiles", SCIENCEDIRECT—Bone, vol. 44, 2009, pp. 989-998.

Derynck, Rik et al Smad-Dependent and Smad-lndependent Pathways in TGF-Beta Family Signalling:, Nature, vol. 425, 2003, pp. 577-584.

Wahdan-Alaswad, Reema S. et al "Inhibition of mTORCI Kinase Activates SmadS 1 and 5 but Not SmadS in Human Prostate Cancer Cells, Mediating Cytostatic Response to Rapamycin", Molecular Cancer Research, Signaling and Regulation, 2012, pp. 821-834.

Nacif, Michael et al. "Targeting Transforming Growth Factor BETA(TGF-BETA) in Cancer and Non-Neoplastic Diseases", Journal of Cancer Therapy, vol. 5, 2014, pp. 735-747.

Padua, David et al. "Roles of TGFp in Metastasis", Cell Research vol. 19, 2009, pp. 89-102.

Verhaegh, Wim et al "Selection of Personalized Patient Therapy through the Use of Knowledge-Based Computational Models That Identify Tumor-Driving Signal Transduction Pathways", Cancer Research, vol. 74, No. 11, 2014, pp. 2936-2945.

Sheen, Yhun Y. et al "Targeting the Transforming Growth Factor-b Signaling in Cancer Therapy", Biomolecules & Therapeutics, vol. 21, No. 5, 2013, pp. 323-331.

Sharkey, David J. et al "TGF-b Mediates Proinflammatory Seminal Fluid Signaling in Human Cervical Epithelial Dells", The Journal of Immunology, vol. 189, 2012, pp. 1024-1035.

Xing, Yujun et al "Subset of Genes Targeted by Transcription Factor NF-kB in TNF alpha-Stimulated Human HeLa Dells" Functional and Integrative Genomics, vol. 13, No. 1, Dec. 2012, pp. 143-154.

Feuerhake, Friedrich et al "NFkB Activity, Function, and Target-Gene Signatures in Primary Mediastinal Large B-Dell Lymphoma and Diffuse Large B-Cell Lymphoma Subtypes", Blood Journal, vol. 106, No. 4, 2005, ?pp. 1392-1399.

"GeneChip Human Genome Arrays" Jan. 2004.

Zellmer, Victoria R et al. "Evolving Concepts of Tumor Heterogeneity", Cell & Bioscience, vol. 4, 2014.

Compagno, Mara et al "Mutations of multiple genes cause deregulation of NF-kB in diffuse large B-cell lymphoma", Nature vol. 459, Jun. 2009, pp. 717-721.

Nelson, D.E. et al., "Oscillations in NF-kB Signaling Control the Dynamics of Gene Expression", Science, vol. 306, No. 5696, 2004, pp. 704 to 708.

Ayesha B. Alvero, "Recent insights into the role of NF-kappaB in ovarian carcinogenesis", Genome Medicine, vol. 2, No. 8, 2010, p. 56.

SEQUENCE LISTING

```
<160> NUMBER OF SEQ ID NOS: 94

<210> SEQ ID NO 1
<211> LENGTH: 6492
<212> TYPE: DNA
<213> ORGANISM: Homo sapiens

<400> SEQUENCE: 1
tttctgtgaa gcagaagtct gggaatcgat ctggaaatcc tcctaattt tactccctct        60 ccccgcgact cctgattcat tgggaagttt caaatcagct ataactggag agtgctgaag      120
```

```
attgatggga tcgttgcctt atgcatttgt tttggtttta caaaaaggaa acttgacaga    180
ggatcatgct gtacttaaaa aatacaacat cacagaggaa gtagactgat attaacaata    240
cttactaata ataacgtgcc tcatgaaata aagatccgaa aggaattgga ataaaatttt    300
cctgcatctc atgccaaggg ggaaacacca gaatcaagtg ttccgcgtga ttgaagacac    360
cccctcgtcc aagaatgcaa agcacatcca ataaaatagc tggattataa ctcctcttct    420
ttctctgggg gccgtgggt gggagctggg gcgagaggtg ccgttggccc ccgttgcttt    480
tcctctggga aggatggcgc acgctgggag aacagggtac gataaccggg agatagtgat    540
gaagtacatc cattataagc tgtcgcagag gggctacgag tgggatgcgg gagatgtggg    600
cgccgcgccc ccgggggccg ccccgcacc gggcatcttc tcctcccagc ccgggcacac    660
gccccatcca gccgcatccc gggacccggt cgccaggacc tcgccgctgc agaccccggc    720 tgccccggc gccgccgcgg ggcctgcgct cagcccggtg ccacctgtgg tccacctgac    780
cctccgccag gccggcgacg acttctcccg ccgctaccgc cgcgacttcg ccagatgtc    840 cagccagctg cacctgacgc ccttcaccgc gcggggacgc tttgccacgg tggtggagga    900
gctcttcagg gacggggtga actggggag gattgtggcc ttctttgagt cggtggggt    960 catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaggt tcactaaagc   1260 agtagaaata atatgcattg tcagtgatgt accatgaaac aaagctgcag gctgtttaag   1320
aaaaaataac acacatataa acatcacaca cacagacaga cacacacaca caacaatt   1380 aacagtcttc aggcaaaacg tcgaatcagc tatttactgc caaagggaaa tatcatttat   1440 ttttttacatt attaagaaaa aagatttat ttatttaaga cagtcccatc aaaactcctg   1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtgggggaa gtccatgcct ccctggcctg aagaagagac tctttgcata   1800
tgactcacat gatgcatacc tggtgggagg aaaagagttg ggaacttcag atggacctag   1860
tacccactga gatttccacg ccgaaggaca gcgatgggaa aaatgcccctt aaatcatagg   1920 aaagtatttt tttaagctac caattgtgcc gagaaaagca ttttagcaat ttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggcctcact ggcctcctcc aggatgatc aacagggcag   2280 tgtggtctcc gaatgtctgg aagctgatgg agctcagaat tccactgtca agaaagagca   2340 gtagagggt gtggctgggc ctgtcaccct ggggccctcc aggtaggccc gttttcacgt   2400
ggagcatggg agccacgacc cttcttaaga catgtatcac tgtagaggga aggaacagag   2460
```

```
gccctgggcc cttcctatca gaaggacatg gtgaaggctg ggaacgtgag gagaggcaat      2520
ggccacggcc cattttggct gtagcacatg gcacgttggc tgtgtggcct tggcccacct      2580
gtgagtttaa agcaaggctt taaatgactt tggagagggt cacaaatcct aaaagaagca      2640
ttgaagtgag gtgtcatgga ttaattgacc cctgtctatg gaattacatg taaaacatta      2700
tcttgtcact gtagtttggt tttatttgaa aacctgacaa aaaaaagtt ccaggtgtgg       2760 aatatggggg ttatctgtac atcctggggc attaaaaaaa aaatcaatgg tggggaacta     2820
taaagaagta acaaaagaag tgacatcttc agcaaataaa ctaggaaatt ttttttttctt    2880 ccagtttaga atcagccttg aaacattgat ggaataactc tgtggcatta ttgcattata     2940
taccatttat ctgtattaac tttggaatgt actctgttca atgtttaatg ctgtggttga     3000
tatttcgaaa gctgctttaa aaaaatacat gcatctcagc gttttttttgt ttttaattgt    3060 atttagttat ggcctataca ctatttgtga gcaaggtga tcgttttctg tttgagattt      3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt     3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggttga cctttagaga gttgctttac gtggcctgtt      3480
tcaacacaga cccacccaga gccctcctgc cctccttccg cgggggcttt ctcatggctg    3540
tccttcaggg tcttcctgaa atgcagtggt gcttacgctc caccaagaaa gcaggaaacc   3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcatttttaat ggagtcagtt    3780 tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc   4080
cttattgtta aaaacatgtt agaagcaatg aatgtatata aaagcctcaa ctagtcattt    4140
ttttctcctc ttctttttttt tcattatatc taattatttt gcagttgggc aacagagaac   4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata aatcgagagg agttataata    4740
atcaagatta aatgtaaata atcagggcaa tcccaacaca tgtctagctt tcacctccag    4800
gatctattga gtgaacagaa ttgcaaatag tctctatttg taattgaact tatcctaaaa    4860
```

| | |
|---|---|
| caaatagttt ataaatgtga acttaaactc taattaattc caactgtact tttaaggcag | 4920 |
| tggctgtttt tagactttct tatcacttat agttagtaat gtacacctac tctatcagag | 4980 |
| aaaaacagga aaggctcgaa atacaagcca ttctaaggaa attagggagt cagttgaaat | 5040 |
| tctattctga tcttattctg tggtgtcttt tgcagcccag acaaatgtgg ttacacactt | 5100 |
| tttaagaaat acaattctac attgtcaagc ttatgaaggt tccaatcaga tctttattgt | 5160 |
| tattcaattt ggatctttca gggattttt ttttaaatta ttatgggaca aaggacattt | 5220 |
| gttggagggg tgggagggag gaagaatttt taaatgtaaa acattcccaa gtttggatca | 5280 |
| gggagttgga agttttcaga ataaccagaa ctaagggtat gaaggacctg tattgggtc | 5340 |
| gatgtgatgc ctctgcgaag aaccttgtgt gacaaatgag aaacattttg aagtttgtgg | 5400 |
| tacgaccttt agattccaga gacatcagca tggctcaaag tgcagctccg tttggcagtg | 5460 |
| caatggtata aatttcaagc tggatatgtc taatgggtat ttaaacaata aatgtgcagt | 5520 |
| tttaactaac aggatattta atgacaacct tctggttggt agggacatct gtttctaaat | 5580 |
| gtttattatg tacaatacag aaaaaaattt tataaaatta agcaatgtga aactgaattg | 5640 |
| gagagtgata atacaagtcc tttagtctta cccagtgaat cattctgttc catgtctttg | 5700 |
| gacaaccatg accttggaca atcatgaaat atgcatctca ctggatgcaa agaaaatcag | 5760 |
| atggagcatg aatggtactg taccggttca tctggactgc cccagaaaaa taacttcaag | 5820 |
| caaacatcct atcaacaaca aggttgttct gcataccaag ctgagcacag aagatgggaa | 5880 |
| cactggtgga ggatggaaag gctcgctcaa tcaagaaaat tctgagacta ttaataaata | 5940 |
| agactgtagt gtagatactg agtaaatcca tgcacctaaa ccttttggaa aatctgccgt | 6000 |
| gggccctcca gatagctcat ttcattaagt ttttccctcc aaggtagaat ttgcaagagt | 6060 |
| gacagtggat tgcatttctt ttggggaagc tttcttttgg tggttttgtt tattatacct | 6120 |
| tcttaagttt tcaaccaagg tttgcttttg ttttgagtta ctggggttat ttttgtttta | 6180 |
| aataaaaata agtgtacaat aagtgttttt gtattgaaag cttttgttat caagattttc | 6240 |
| atacttttac cttccatggc tcttttaag attgatactt ttaagaggtg gctgatattc | 6300 |
| tgcaacactg tacacataaa aaatacggta aggatacttt acatggttaa ggtaaagtaa | 6360 |
| gtctccagtt ggccaccatt agctataatg gcactttgtt tgtgttgttg gaaaaagtca | 6420 |
| cattgccatt aaactttcct tgtctgtcta gttaatattg tgaagaaaaa taagtacag | 6480 |
| tgtgagatac tg | 6492 |

<210> SEQ ID NO 2
<211> LENGTH: 2575
<212> TYPE: DNA
<213> ORGANISM: Homo sapiens

<400> SEQUENCE: 2

| | |
|---|---|
| ggaggaggaa gcaagcgagg gggctggttc ctgagcttcg caattcctgt gtcgccttct | 60 |
| gggctcccag cctgccgggt cgcatgatcc ctccggccgg agctggtttt tttgccagcc | 120 |
| accgcgaggc cggctgagtt accggcatcc ccgcagccac ctcctctccc gacctgtgat | 180 |
| acaaaagatc ttccgggggc tgcacctgcc tgcctttgcc taaggcggat ttgaatctct | 240 |
| ttctctccct tcagaatctt atcttggctt tggatcttag aagagaatca ctaaccagag | 300 |
| acgagactca gtgagtgagc aggtgttttg gacaatggac tggttgagcc catccctatt | 360 |
| ataaaaatgt ctcagagcaa ccgggagctg gtggttgact ttctctccta caagctttcc | 420 |

-continued

```
cagaaaggat acagctggag tcagtttagt gatgtggaag agaacaggac tgaggcccca    480
gaagggactg aatcggagat ggagacccce agtgccatca atggcaaccc atcctggcac    540
ctggcagaca gccccgcggt gaatggagcc actggccaca gcagcagttt ggatgcccgg    600
gaggtgatcc ccatggcagc agtaaagcaa gcgctgaggg aggcaggcga cgagtttgaa    660
ctgcggtacc ggcgggcatt cagtgacctg acatcccagc tccacatcac cccagggaca    720
gcatatcaga gctttgaaca ggtagtgaat gaactcttcc gggatggggt aaactggggt    780
cgcattgtgg cctttttctc cttcggcggg gcactgtgcg tggaaagcgt agacaaggag    840
atgcaggtat tggtgagtcg gatcgcagct tggatggcca cttacctgaa tgaccaccta    900
gagccttgga tccaggagaa cggcggctgg gatacttttg tggaactcta tgggaacaat    960
gcagcagccg agagccgaaa gggccaggaa cgcttcaacc gctggttcct gacgggcatg   1020
actgtggccg gcgtggttct gctgggctca ctcttcagtc ggaaatgacc agacactgac   1080
catccactct accctcccac ccccttctct gctccaccac atcctccgtc cagccgccat   1140
tgccaccagg agaaccacta catgcagccc atgcccacct gccatcaca gggttgggcc    1200 cagatctggt cccttgcagc tagttttcta gaatttatca cacttctgtg agaccccac    1260 acctcagttc ccttggcctc agaattcaca aaatttccac aaaatctgtc caaggaggc    1320 tggcaggtat ggaagggttt gtggctgggg gcaggagggc cctacctgat tggtgcaacc   1380
cttacccctt agcctccctg aaaatgtttt tctgccaggg agcttgaaag ttttcagaac   1440
ctcttcccca gaaaggagac tagattgcct ttgttttgat gtttgtggcc tcagaattga   1500 tcatttcce ccactctcc ccacactaac ctgggttccc tttccttcca tccctacccc    1560
ctaagagcca tttaggggcc acttttgact agggattcag gctgcttggg ataaagatgc   1620
aaggaccagg actccctcct cacctctgga ctggctagag tcctcactcc cagtccaaat   1680
gtcctccaga agcctctggc tagaggccag ccccacccag gagggagggg gctatagcta   1740
caggaagcac cccatgccaa agctagggtg gcccttgcag ttcagcacca ccctagtccc   1800 ttccctccc tggctcccat gaccatactg agggaccaac tgggcccaag acagatgccc   1860
cagagctgtt tatggcctca gctgcctcac ttcctacaag agcagcctgt ggcatctttg   1920
ccttgggctg ctcctcatgg tgggttcagg ggactcagcc ctgaggtgaa agggagctat   1980
caggaacagc tatgggagcc ccagggtctt ccctacctca ggcaggaagg gcaggaagga   2040
gagcctgctg catggggtgg ggtagggctg actagaaggg ccagtcctgc ctggccaggc   2100
agatctgtgc cccatgcctg tccagcctgg gcagccaggc tgccaaggcc agagtggcct   2160
ggccaggagc tcttcaggcc tccctctctc ttctgctcca cccttggcct gtctcatccc   2220
caggggtccc agccaccccg ggctctctgc tgtacatatt tgagactagt ttttattcct   2280
tgtgaagatg atatactatt tttgttaagc gtgtctgtat ttatgtgtga ggagctgctg   2340
gcttgcagtg cgcgtgcacg tggagagctg gtgcccggag attggacggc ctgatgctcc   2400
ctcccctgcc ctggtccagg gaagctggcc gagggtcctg gctcctgagg ggcatctgcc   2460
cctcccccaa cccccacccc acacttgttc cagctctttg aaatagtctg tgtgaaggtg   2520
aaagtgcagt tcagtaataa actgtgttta ctcagtgaaa aaaaaaaaaa aaaaa        2575
```

<210> SEQ ID NO 3
<211> LENGTH: 6932
<212> TYPE: DNA
<213> ORGANISM: Homo sapiens

<400> SEQUENCE: 3

```
gcatttaaaa dacagcgtga gactcgcgcc ctccggcacg gaaaaggcca ggcgacaggt      60
gtcgcttgaa aagactgggc ttgtccttgc tggtgcatgc gtcgtcggcc tctgggcagc     120
aggtttacaa aggaggaaaa cgacttcttc tagattttt tttcagtttc ttctataaat     180
caaaacatct caaaatggag acctaaaatc cttaaaggga cttagtctaa tctcgggagg     240
tagttttgtg catgggtaaa caaattaagt attaactggt gttttactat ccaaagaatg     300
ctaattttat aaacatgatc gagttatata aggtatacca taatgagttt gattttgaat     360
ttgatttgtg gaaataaagg aaaagtgatt ctagctgggg catattgtta aagcattttt     420
ttcagagttg gccaggcagt ctcctactgg cacattctcc cattatgtag aatagaaata     480
gtacctgtgt ttgggaaaga ttttaaaatg agtgacagtt atttggaaca aagagctaat     540
aatcaatcca ctgcaaatta agaaacatg cagatgaaag ttttgacaca ttaaaatact     600
tctacagtga caagaaaaa tcaagaacaa agcttttga tatgtgcaac aaatttagag     660
gaagtaaaaa gataaatgtg atgattggtc aagaaattat ccagttattt acaaggccac     720
tgatatttta aacgtccaaa agtttgttta aatgggctgt taccgctgag aatgatgagg     780
atgagaatga tggttgaagg ttacatttta ggaaatgaag aaacttagaa aattaatata     840
aagacagtga tgaatacaaa gaagatttt ataacaatgt gtaaaatttt tggccaggga     900
aaggaatatt gaagttagat acaattactt acctttgagg gaaataattg ttggtaatga     960
gatgtgatgt ttctcctgcc acctggaaac aaagcattga agtctgcagt tgaaaagccc    1020
aacgtctgtg agatccagga aaccatgctt gcaaaccact ggtaaaaaaa aaaaaaaaa    1080 aaaaaaaag ccacagtgac ttgcttattg gtcattgcta gtattatcga ctcagaacct    1140
ctttactaat ggctagtaaa tcataattga gaaattctga attttgacaa ggtctctgct    1200
gttgaaatgg taaatttatt attttttttg tcatgataaa ttctggttca aggtatgcta    1260
tccatgaaat aatttctgac caaaactaaa ttgatgcaat ttgattatcc atcttagcct    1320
acagatggca tctggtaact tttgactgtt ttaaaaaata aatccactat cagagtagat    1380
ttgatgttgg cttcagaaac atttagaaaa acaaaagttc aaaaatgttt tcaggaggtg    1440
ataagttgaa taactctaca atgttagttc tttgaggggg acaaaaaatt taaaatcttt    1500
gaaaggtctt atttttacagc catatctaaa ttatcttaag aaaatttta acaaagggaa    1560 tgaaatatat atcatgattc tgttttcca aaagtaacct gaatatagca atgaagttca    1620
gttttgttat tggtagtttg ggcagagtct cttttgcag cacctgttgt ctaccataat    1680
tacagaggac atttccatgt tctagccaag tatactatta gaataaaaaa acttaacatt    1740
gagttgcttc aacagcatga aactgagtcc aaaagaccaa atgaacaaac acattaatct    1800
ctgattattt attttaaata gaatatttaa ttgtgtaaga tctaatagta tcattatact    1860
taagcaatca tattcctgat gatctatggg aaataactat tatttaatta atattgaaac    1920
caggttttaa gatgtgttag ccagtcctgt tactagtaaa tctctttatt tggagagaaa    1980
ttttagattg ttttgttctc cttattagaa ggattgtaga aagaaaaaaa tgactaattg    2040
gagaaaaatt ggggatatat catatttcac tgaattcaaa atgtcttcag ttgtaaatct    2100
taccattatt ttacgtacct ctaagaaata aaagtgcttc taattaaaat atgatgtcat    2160
taattatgaa atacttcttg ataacagaag ttttaaaata gccatcttag aatcagtgaa    2220
atatggtaat gtattatttt cctcctttga gttaggtctt gtgcttttt ttcctggcca    2280 ctaaatttca caatttccaa aaagcaaaat aaacatattc tgaatatttt tgctgtgaaa    2340
```

```
cacttgacag cagagctttc caccatgaaa agaagcttca tgagtcacac attacatctt   2400
tgggttgatt gaatgccact gaaacattct agtagcctgg agaagttgac ctacctgtgg   2460
agatgcctgc cattaaatgg catcctgatg gcttaataca catcactctt ctgtgaaggg   2520
ttttaatttt caacacagct tactctgtag catcatgttt acattgtatg tataaagatt   2580
atacaaaggt gcaattgtgt atttcttcct taaaatgtat cagtatagga tttagaatct   2640
ccatgttgaa actctaaatg catagaaata aaaataataa aaattttttc attttggctt   2700
ttcagcctag tattaaaact gataaaagca aagccatgca caaaactacc tccctagaga   2760
aaggctagtc ccttttcttc cccattcatt tcattatgaa catagtagaa acagcatat    2820
tcttatcaaa tttgatgaaa agcgccaaca cgtttgaact gaaatacgac ttgtcatgtg   2880
aactgtaccg aatgtctacg tattccactt ttcctgctgg ggttcctgtc tcagaaagga   2940
gtcttgctcg tgctggtttc tattacactg gtgtgaatga caaggtcaaa tgcttctgtt   3000
gtggcctgat gctggataac tggaaaagag gagacagtcc tactgaaaag cataaaaagt   3060
tgtatcctag ctgcagattc gttcagagtc taaattccgt taacaacttg gaagctacct   3120
ctcagcctac ttttccttct tcagtaacaa attccacaca ctcattactt ccgggtacag   3180
aaaacagtgg atatttccgt ggctcttatt caaactctcc atcaaatcct gtaaactcca   3240
gagcaaatca agattttct gccttgatga aagttccta ccactgtgca atgaataacg    3300
aaaatgccag attacttact tttcagacat ggccattgac ttttctgtcg ccaacagatc   3360
tggcaaaagc aggcttttac tacataggac ctggagacag agtggcttgc tttgcctgtg   3420
gtggaaaatt gagcaattgg gaaccgaagg ataatgctat gtcagaacac ctgagacatt   3480
ttcccaaatg cccatttata gaaaatcagc ttcaagacac ttcaagatac acagtttcta   3540
atctgagcat gcagacacat gcagcccgct ttaaaacatt cttttaactgg ccctctagtg   3600
ttctagttaa tcctgagcag cttgcaagtg cgggtttta ttatgtgggt aacagtgatg    3660
atgtcaaatg cttttgctgt gatggtggac tcaggtgttg ggaatctgga gatgatccat   3720
gggttcaaca tgccaagtgg tttccaaggt gtgagtactt gataagaatt aaaggacagg   3780
agttcatccg tcaagttcaa gccagttacc ctcatctact tgaacagctg ctatccacat   3840
cagacagccc aggagatgaa aatgcagagt catcaattat ccatttttgaa cctggagaag   3900
accattcaga agatgcaatc atgatgaata ctcctgtgat taatgctgcc gtggaaatgg   3960
gctttagtag aagcctggta aaacagacag ttcagagaaa aatcctagca actggagaga   4020
attatagact agtcaatgat cttgtgttag acttactcaa tgcagaagat gaaataaggg   4080
aagaggagag agaaagagca actgaggaaa aagaatcaaa tgatttatta ttaatccgga   4140
agaatagaat ggcacttttt caacatttga cttgtgtaat tccaatcctg atagtctac    4200
taactgccgg aattattaat gaacaagaac atgatgttat taaacagaag acacagacgt   4260
ctttacaagc aagagaactg attgatacga ttttagtaaa aggaaatatt gcagccactg   4320
tattcagaaa ctctctgcaa gaagctgaag ctgtgttata tgagcattta tttgtgcaac   4380
aggacataaa atatattccc acagaagatg tttcagatct accagtggaa gaacaattgc   4440
ggagactaca agaagaaga acatgtaaag tgtgtatgga caagaagtg tccatagtgt     4500
ttattccttg tggtcatcta gtagtatgca aagattgtgc tccttcttta agaaagtgtc   4560
ctatttgtag gagtacaatc aagggtacag ttcgtacatt tctttcatga agaagaacca   4620
aaacatcgtc taaactttag aattaattta ttaaatgtat tataacttta acttttatcc   4680
taatttggtt tccttaaaat ttttatttat ttacaactca aaaaacattg ttttgtgtaa   4740
```

```
catatttata tatgtatcta aaccatatga acatatattt tttagaaact aagagaatga   4800
taggcttttg ttcttatgaa cgaaaaagag gtagcactac aaacacaata ttcaatcaaa   4860
atttcagcat tattgaaatt gtaagtgaag taaaacttaa gatatttgag ttaaccttta   4920
agaattttaa atattttggc attgtactaa taccgggaac atgaagccag gtgtggtggt   4980
atgtgcctgt agtcccaggc tgaggcaaga gaattacttg agcccaggag tttgaatcca   5040
tcctgggcag catactgaga ccctgccttt aaaacaaac agaacaaaaa caaacacca    5100 gggacacatt tctctgtctt ttttgatcag tgtcctatac atcgaaggtg tgcatatatg   5160
ttgaatgaca ttttagggac atggtgtttt tataaagaat tctgtgagaa aaaatttaat   5220
aaagcaacaa aaattactct tattcttcat tgctttattt caatgacatt ggatagttta   5280
gtcactccca gactctttcc ataccttctt aaagcctctc aaatattgaa ctacagttta   5340
tactccttcc cataagatgc ttcttcattg acacttgtag aacacggggt caacacatca   5400
taaaatctat tatggaatgc ctgagacaag aatcaaacag tcccctttagt aagtttgttt   5460 attcacttct ctattgattc attcaagaag tctcatgcca gccccaccta ttggaagaag   5520
gtctgagttt tattcttatc tctttggtat taattctgaa acttagaaag tacactggtt   5580
agcaatgctt gggaccaaca ggttgttctg gtaaataaat ctgtttcata ttgtcagtgc   5640
aacaaaatgt cccctctgc attatgttat tggtactcaa cacgtccgag tcataactct    5700
gtcctttgct tcttatagag gtattaggtc ttcaagagca gaagtaagac tgtaataggg   5760
aatactcagg ggaaggcagg caaaggctag tcatctaaac cagttctaga tgtctgtata   5820
ggggcagatg gctctgtaag ggcagaaggg aaagacccct tcataagggt cacagctgac   5880
aatcctataa caaagacag gttaacaaga gaaaaactta acaaatttat ttaatcacag    5940
atttacatca ccgggggagcc ttcgtaatga agatccaaaa ttacagggga aactgtgcat   6000 tttttatgctt aggtttgata atgaatggac agccctgaag aatagtgatt ggaaaaaaag   6060
gatatgatct aatgggaata gacacaggtt ggggacccag caaggcctgt ctgttcagat   6120
tattcttggt ctctgtgcag cattccttcc tcctggatat agggcagggc ctgtatggga   6180
tggggatatt ataacctgct atcaagcaag gtaggtcaga gaatttattt atggccagct   6240
cttacatagt taggtgagga agattagag tactatcttt aagatgtaag tctggcattg    6300
tggaaagatg gttccagttt ctatgaccta ccttggggaa gaggaattca gtttctgtg    6360 gcttgccttc agggagaatg aggctgagac aggagggcag gataacatca gagaaaaact   6420
ttgcttctga ggccttcact ttgggttttc tgagccccaa catctgctag tgttgtaaag   6480
agaacaatta gggaccaagt gaggggagga aagaatccat ctctgcattc tgatgctggg   6540
agacttattt ccttgaaatg caattgattt tgcctctgct aagaggctct gctggctacc   6600
catgtactag ccagtgtcct gcatgggtgc taggctgaat tatttgtaat tgtgcttagg   6660
tgatttgtaa ctcaggtata gggtatttaa atagtaggca ccctttttgc accatgtgtt   6720
ttttttttta tctagttctt gtatactaca gataatattt gaactttgtc atctcactgt   6780 aaaactttg ttcatttctc attatggtaa taaatagcta ttataaccaa cccatttatt    6840
caaatatgtt atttccctaa gtgttatttt gacattttgt tttggaaaaa ataaatcacc   6900
atagataata aaaaaaaaaa aaaaaaaaa aa                                  6932
```

<210> SEQ ID NO 4
<211> LENGTH: 760
<212> TYPE: DNA

<213> ORGANISM: Homo sapiens

<400> SEQUENCE: 4

| | | | | | |
|---|---|---|---|---|---|
| gaggaaccga | gaggctgaga | ctaacccaga | aacatccaat | tctcaaactg | aagctcgcac | 60 |
| tctcgcctcc | agcatgaaag | tctctgccgc | ccttctgtgc | ctgctgctca | tagcagccac | 120 |
| cttcattccc | caagggctcg | ctcagccaga | tgcaatcaat | gccccagtca | cctgctgtta | 180 |
| taacttcacc | aataggaaga | tctcagtgca | gaggctcgcg | agctatagaa | gaatcaccag | 240 |
| cagcaagtgt | cccaaagaag | ctgtgatctt | caagaccatt | gtggccaagg | agatctgtgc | 300 |
| tgaccccaag | cagaagtggg | ttcaggattc | catggaccac | ctggacaagc | aaacccaaac | 360 |
| tccgaagact | tgaacactca | ctccacaacc | caagaatctg | cagctaactt | atttttcccct | 420 |
| agctttcccc | agacaccctg | ttttatttta | ttataatgaa | ttttgtttgt | tgatgtgaaa | 480 |
| cattatgcct | taagtaatgt | taattcttat | ttaagttatt | gatgttttaa | gtttatcttt | 540 |
| catggtacta | gtgttttta | gatacagaga | cttggggaaa | ttgcttttcc | tcttgaacca | 600 |
| cagttctacc | cctgggatgt | tttgagggtc | tttgcaagaa | tcattaatac | aaagaatttt | 660 |
| ttttaacatt | ccaatgcatt | gctaaaatat | tattgtggaa | atgaatattt | tgtaactatt | 720 |
| acaccaaata | aatatatttt | tgtacaaaaa | aaaaaaaaa | | | 760 |

<210> SEQ ID NO 5
<211> LENGTH: 813
<212> TYPE: DNA
<213> ORGANISM: Homo sapiens

<400> SEQUENCE: 5

| | | | | | |
|---|---|---|---|---|---|
| agctggtttc | agacttcaga | aggacacggg | cagcagacag | tggtcagtcc | tttcttggct | 60 |
| ctgctgacac | tcgagcccac | attccgtcac | ctgctcagaa | tcatgcaggt | ctccactgct | 120 |
| gcccttgctg | tcctcctctg | caccatggct | ctctgcaacc | agttctctgc | atcacttgct | 180 |
| gctgacacgc | cgaccgcctg | ctgcttcagc | tacacctccc | ggcagattcc | acagaatttc | 240 |
| atagctgact | actttgagac | gagcagccag | tgctccaagc | ccggtgtcat | cttcctaacc | 300 |
| aagcgaagcc | ggcaggtctg | tgctgacccc | agtgaggagt | gggtccagaa | atatgtcagc | 360 |
| gacctggagc | tgagtgcctg | aggggtccag | aagcttcgag | gcccagcgac | ctcggtgggc | 420 |
| ccagtgggga | ggagcaggag | cctgagcctt | gggaacatgc | gtgtgacctc | acagctacc | 480 |
| tcttctatgg | actggttgtt | gccaaacagc | cacactgtgg | gactcttctt | aacttaaatt | 540 |
| ttaatttatt | tatactattt | agttttttgta | atttatttc | gatttcacag | tgtgtttgtg | 600 |
| attgtttgct | ctgagagttc | ccctgtcccc | tcccccttcc | ctcacaccgc | gtctggtgac | 660 |
| aaccgagtgg | ctgtcatcag | cctgtgtagg | cagtcatggc | accaaagcca | ccagactgac | 720 |
| aaatgtgtat | cggatgcttt | tgttcagggc | tgtgatcggc | ctggggaaat | aataaagatg | 780 |
| ctcttttaaa | aggtaaaaaa | aaaaaaaaaa | aaa | | | 813 |

<210> SEQ ID NO 6
<211> LENGTH: 667
<212> TYPE: DNA
<213> ORGANISM: Homo sapiens

<400> SEQUENCE: 6

| | | | | | |
|---|---|---|---|---|---|
| agcacaggac | acagctgggt | tctgaagctt | ctgagttctg | cagcctcacc | tctgagaaaa | 60 |
| cctctttttcc | accaatacca | tgaagctctg | cgtgactgtc | ctgtctctcc | tcatgctagt | 120 |
| agctgccttc | tgctctccag | cgctctcagc | accaatgggc | tcagaccctc | ccaccgcctg | 180 |

```
ctgcttttct tacaccgcga ggaagcttcc tcgcaacttt gtggtagatt actatgagac    240
cagcagcctc tgctcccagc cagctgtggt attccaaacc aaaagaagca agcaagtctg    300
tgctgatccc agtgaatcct gggtccagga gtacgtgtat gacctggaac tgaactgagc    360
tgctcagaga caggaagtct tcagggaagg tcacctgagc ccggatgctt ctccatgaga    420
cacatctcct ccatactcag gactcctctc cgcagttcct gtcccttctc ttaatttaat    480
cttttttatg tgccgtgtta ttgtattagg tgtcatttcc attatttata ttagtttagc    540
caaaggataa gtgtccccta tgggatggt ccactgtcac tgtttctctg ctgttgcaaa    600
tacatggata acacatttga ttctgtgtgt tttcataata aactttaaa ataaaatgca    660 gacagtt                                                              667
```

<210> SEQ ID NO 7
<211> LENGTH: 1237
<212> TYPE: DNA
<213> ORGANISM: Homo sapiens

<400> SEQUENCE: 7

```
gctgcagagg attcctgcag aggatcaaga cagcacgtgg acctcgcaca gcctctccca     60
caggtaccat gaaggtctcc gcggcagccc tcgctgtcat cctcattgct actgccctct    120
gcgctcctgc atctgcctcc ccatattcct cggacaccac accctgctgc tttgcctaca    180
ttgcccgccc actgccccgt gcccacatca aggagtattt ctacaccagt ggcaagtgct    240
ccaacccagc agtcgtcttt gtcacccgaa agaaccgcca agtgtgtgcc aacccagaga    300
agaaatgggt tcgggagtac atcaactctt tggagatgag ctaggatgga gagtccttga    360
acctgaactt acacaaattt gcctgtttct gcttgctctt gtcctagctt gggaggcttc    420
ccctcactat cctaccccac ccgctccttg aagggcccag attctaccac acagcagcag    480
ttacaaaaac cttccccagg ctggacgtgg tggctcacgc ctgtaatccc agcactttgg    540
gaggccaagg tgggtggatc acttgaggtc aggagttcga ccagcctg gccaacatga     600 tgaaacccca tctctactaa aaatacaaaa aattagccgg gcgtggtagc gggcgcctgt    660
agtcccagct actcgggagg ctgaggcagg agaatggcgt gaacccggga ggcggagctt    720
gcagtgagcc gagatcgcgc cactgcactc cagcctgggc gacagagcga gactccgtct    780
caaaaaaaaa aaaaaaaaa aaaatacaaa aattagccgg gcgtggtggc ccacgcctgt    840
aatcccagct actcgggagg ctaaggcagg aaaattgttt gaacccagga ggtggaggct    900
gcagtgagct gagattgtgc cacttcactc cagcctgggt gacaaagtga gactccgtca    960
caacaacaac aacaaaaagc ttccccaact aaagcctaga agagcttctg aggcgctgct   1020
ttgtcaaaag gaagtctcta ggttctgagc tctggctttg ccttggcttt gccagggctc   1080
tgtgaccagg aaggaagtca gcatgcctct agaggcaagg aggggaggaa cactgcactc   1140
ttaagcttcc gccgtctcaa cccctcacag gagcttactg gcaaacatga aaaatcggct   1200
taccattaaa gttctcaatg caaccataaa aaaaaaa                            1237
```

<210> SEQ ID NO 8
<211> LENGTH: 851
<212> TYPE: DNA
<213> ORGANISM: Homo sapiens

<400> SEQUENCE: 8

```
agaatataac agcactccca agaactggg tactcaacac tgagcagatc tgttctttga     60
```

```
gctaaaaacc atgtgctgta ccaagagttt gctcctggct gctttgatgt cagtgctgct    120
actccacctc tgcggcgaat cagaagcagc aagcaacttt gactgctgtc ttggatacac    180
agaccgtatt cttcatccta aatttattgt gggcttcaca cggcagctgg ccaatgaagg    240
ctgtgacatc aatgctatca tctttcacac aaagaaaaag ttgtctgtgt gcgcaaatcc    300
aaaacagact tgggtgaaat atattgtgcg tctcctcagt aaaaaagtca agaacatgta    360
aaaactgtgg cttttctgga atggaattgg acatagccca agaacagaaa gaaccttgct    420
ggggttggag gtttcacttg cacatcatgg agggtttagt gcttatctaa tttgtgcctc    480
actggacttg tccaattaat gaagttgatt catattgcat catagtttgc tttgtttaag    540
catcacatta agttaaact gtattttatg ttatttatag ctgtaggttt tctgtgttta    600
gctatttaat actaattttc cataagctat tttggtttag tgcaaagtat aaaattatat    660 ttgggggga ataagattat atggactttc ttgcaagcaa caagctattt tttaaaaaaa    720
actatttaac attcttttgt ttatattgtt ttgtctccta aattgttgta attgcattat    780
aaaataagaa aaatattaat aagacaaata ttgaaaataa agaaacaaaa agttcttctg    840
ttaaaaaaaa a                                                        851
```

<210> SEQ ID NO 9
<211> LENGTH: 2933
<212> TYPE: DNA
<213> ORGANISM: Homo sapiens

<400> SEQUENCE: 9

```
gcagacacct gggctgagac atacaggaca gagcatggat cgcctacaga ctgcactcct     60
ggttgtcctc gtcctccttg ctgtggcgct tcaagcaact gaggcaggcc cctacggcgc    120
caacatggaa gacagcgtct gctgccgtga ttacgtccgt taccgtctgc ccctgcgcgt    180
ggtgaaacac ttctactgga cctcagactc ctgcccgagg cctggcgtgg tgttgctaac    240
cttcagggat aaggagatct gtgccgatcc cagagtgccc tgggtgaaga tgattctcaa    300
taagctgagc caatgaagag cctactctga tgaccgtggc cttggctcct ccaggaaggc    360
tcaggagccc tacctccctg ccattatagc tgctccccgc cagaagcctg tgccaactct    420
ctgcattccc tgatctccat ccctgtggct gtcacccttg gtcacctccg tgctgtcact    480
gccatctccc ccctgacccc tctaacccat cctctgcctc cctccctgca gtcagagggt    540
cctgttccca tcagcgattc ccctgcttaa accttccat gactccccac tgccctaagc    600
tgaggtcagt ctcccaagcc tggcatgtgg ccctctggat ctgggttcca tctctgtctc    660
cagcctgccc acttcccttc atgaatgttg ggttctagct ccctgttctc caaacccata    720
ctacacatcc cacttctggg tctttgcctg ggatgttgct gacacccaga agtcccacc    780 acctgcacat gtgtagcccc accagccctc caaggcattg ctcgcccaag cagctggtaa    840
ttccatttca tgtattagat gtccctggc cctctgtccc ctcttaataa ccctagtcac    900
agtctccgca gattcttggg atttgggggt tttctccccc acctctccac tagttggacc    960
aaggtttcta gctaagttac tctagtctcc aagcctctag catagagcac tgcagacagg   1020
ccctggctca gaatcagagc ccagaaagtg gctgcagaca aaatcaataa aactaatgtc   1080
cctcccctct ccctgccaaa aggcagttac atatcaatac agagactcaa ggtcactaga   1140
aatgggccag ctgggtcaat gtgaagcccc aaatttgccc agattcacct ttcttccccc   1200
actccctttt tttttttttt tttgagatgg agtttcgctc ttgtcaccca cgctggagtg   1260
caatggtgtg gtcttggctt attgaagcct ctgcctcctg ggttcaagtg attctcttgc   1320
```

```
ctcagcctcc tgagtagctg ggattacagg ttcctgctac cacgcccagc taattttttgt   1380 attttttagta gagacgaggc ttcaccatgt tggccaggct ggtctcgaac tcctgtcctc   1440
aggtaatccg cccacctcag cctcccaaag tgctgggatt acaggcgtga gccacagtgc   1500
ctggcctctt ccctctcccc accccccccc caacttttttt tttttttttat ggcagggtct   1560 cactctgtcg cccaggctgg agtgcagtgg cgtgatctcg gctcactaca acctcgacct   1620
cctgggttca gcgattctc ccaccccagc tcccaagta gctgggatta caggtgtgtg   1680
ccactacggc tggctaattt ttgtatttttt agtagagaca ggtttcacca tattggccag   1740
gctggtcttg aactcctgac ctcaagtgat ccaccttcct tgtgctccca aagtgctgag   1800
attacaggcg tgagctatca cacccagcct ccccttttt ttcctaatag gagactcctg   1860
tacctttctt cgtttacct atgtgtcgtg tctgcttaca tttccttctc ccctcaggct   1920
ttttttgggt ggtcctccaa cctccaatac ccaggcctgg cctcttcaga gtaccccca   1980 ttccactttc cctgcctcct tcctaaaata gctgacaatc aaattcatgc tatggtgtga   2040
aagactacct ttgacttggt attataagct ggagttatat atgtatttga aaacagagta   2100
aatacttaag aggccaaata gatgaatgga agaattttag gaactgtgag aggggggacaa   2160 ggtggagctt tcctggccct gggaggaagc tggctgtggt agcgtagcgc tctctctctc   2220
tgtctgtggc aggaggcaaa gagtagggtg taattgagtg aaggaatcct gggtagagac   2280
cattctcagg tggttgggcc aggctaaaga ctgggatttg ggtctatcta tgcctttctg   2340
gctgattttt gtagagacgg ggttttgcca tgttacccag gctggtctca aactcctggg   2400
ctcaagcgat cctcctggct cagcctccca agtgctggg attacaggcg tgagtcactg   2460
cgcctggctt cctcttcctc ttgagaaata ttcttttcat acagcaagta tgggacagca   2520
gtgtcccagg taaaggacat aaatgttaca agtgtctggt cctttctgag ggaggctggt   2580
gccgctctgc agggtatttg aacctgtgga attggaggag gccatttcac tccctgaacc   2640
cagcctgaca aatcacagtg agaatgttca ccttataggc ttgctgtggg gctcaggttg   2700
aaagtgtggg gagtgacact gcctaggcat ccagctcagt gtcatccagg gcctgtgtcc   2760
ctcccgaacc cagggtcaac ctgcctacca caggcactag aaggacgaat ctgcctactg   2820
cccatgaacg gggccctcaa gcgtcctggg atctccttct ccctcctgtc ctgtccttgc   2880
ccctcaggac tgctgaaaaa taaatccttt aaaatagtaa aaaaaaaaa aaa         2933
```

<210> SEQ ID NO 10  
<211> LENGTH: 800  
<212> TYPE: DNA  
<213> ORGANISM: Homo sapiens

<400> SEQUENCE: 10

```
acacagagag aaaggctaaa gttctctgga ggatgtggct gcagagcctg ctgctcttgg     60
gcactgtggc ctgcagcatc tctgcacccg cccgctcgcc cagccccagc acgcagccct    120
gggagcatgt gaatgccatc caggaggccc ggcgtctcct gaacctgagt agagacactg    180
ctgctgagat gaatgaaaca gtagaagtca tctcagaaat gtttgacctc caggagccga    240
cctgcctaca gacccgcctg gagctgtaca agcagggcct gcggggcagc ctcaccaagc    300
tcaagggccc cttgaccatg atggccagcc actacaagca gcactgccct ccaaccccgg    360
aaacttcctg tgcaacccag attatcacct ttgaaagttt caaagagaac ctgaaggact    420
ttctgcttgt catccccttt gactgctggg agccagtcca ggagtgagac cggccagatg    480
```

| | |
|---|---|
| aggctggcca agccggggag ctgctctctc atgaaacaag agctagaaac tcaggatggt | 540 |
| catcttggag ggaccaaggg gtgggccaca gccatggtgg gagtggcctg gacctgccct | 600 |
| gggccacact gaccctgata caggcatggc agaagaatgg gaatatttta tactgacaga | 660 |
| aatcagtaat atttatatat ttatattttt aaaatattta tttatttatt tatttaagtt | 720 |
| catattccat atttattcaa gatgttttac cgtaataatt attattaaaa atatgcttct | 780 |
| acttgaaaaa aaaaaaaaaa | 800 |

```
<210> SEQ ID NO 11
<211> LENGTH: 3338
<212> TYPE: DNA
<213> ORGANISM: Homo sapiens

<400> SEQUENCE: 11
```

| | |
|---|---|
| ataaaaagcc acagatctct ggcggcggca aggggacagc actgagctct gccgcctggc | 60 |
| tctagccgcc tgcctggccc cgccgggac tcttgcccac cctcagccat ggctccgata | 120 |
| tctctgtcgt ggctgctccg cttggccacc ttctgccatc tgactgtcct gctggctgga | 180 |
| cagcaccacg gtgtgacgaa atgcaacatc acgtgcagca agatgacatc aaagatacct | 240 |
| gtagctttgc tcatccacta tcaacagaac caggcatcat gcggcaaacg cgcaatcatc | 300 |
| ttggagacga gacagcacag gctgttctgt gccgacccga aggagcaatg ggtcaaggac | 360 |
| gcgatgcagc atctggaccg ccaggctgct gccctaactc gaaatggcgg caccttcgag | 420 |
| aagcagatcg gcgaggtgaa gcccaggacc accctgccg ccgggggaat ggacgagtct | 480 |
| gtggtcctgg agcccgaagc cacaggcgaa agcagtagcc tggagccgac tccttcttcc | 540 |
| caggaagcac agagggccct ggggacctcc ccagagctgc cgacgggcgt gactggttcc | 600 |
| tcagggacca ggctcccccc gacgccaaag gctcaggatg gagggcctgt gggcacggag | 660 |
| cttttccgag tgcctcccgt ctccactgcc gccacgtggc agagttctgc tccccaccaa | 720 |
| cctgggccca gcctctgggc tgaggcaaag acctctgagg cccgtccac ccaggacccc | 780 |
| tccacccagg cctccactgc gtcctcccca gccccagagg agaatgctcc gtctgaaggc | 840 |
| cagcgtgtgt ggggtcaggg acagagcccc aggccagaga actctctgga gcggaggag | 900 |
| atgggtcccg tgccagcgca cacggatgcc ttccaggact gggggcctgg cagcatggcc | 960 |
| cacgtctctg tggtccctgt ctcctcagaa gggaccccca gcaggagcc agtggcttca | 1020 |
| ggcagctgga cccctaaggc tgaggaaccc atccatgcca ccatggaccc ccagaggctg | 1080 |
| ggcgtccttc tcactcctgt ccctgacgcc caggctgcca cccggaggca ggcggtgggg | 1140 |
| ctgctggcct tccttggcct cctcttctgc ctggggtgg ccatgttcac ctaccagagc | 1200 |
| ctccagggct gccctcgaaa gatggcagga gagatggcgg agggccttcg ctacatcccc | 1260 |
| cggagctgtg gtagtaattc atatgtcctg gtgcccgtgt gaactcctct ggcctgtgtc | 1320 |
| tagttgtttg attcagacag ctgcctggga tccctcatcc tcatacccac ccccacccaa | 1380 |
| gggcctggcc tgagctggga tgattggagg ggggaggtgg gatcctccag gtgcacaagc | 1440 |
| tccaagctcc caggcattcc ccaggaggcc agccttgacc attctccacc tgccagggac | 1500 |
| agaggggtg gcctcccaac tcaccccagc cccaaaactc tcctctgctg ctggctggtt | 1560 |
| agaggttccc tttgacgcca tcccagcccc aatgaacaat tatttattaa atgcccagcc | 1620 |
| ccttctgacc catgctgccc tgtgagtact acagtcctcc catctcacac atgagcatca | 1680 |
| ggccaggccc tctgcccact ccctgcaacc tgattgtgtc tcttggtcct gctgcagttg | 1740 |
| ccagtcaccc cggccaccct cggtgctatc tcccccagcc ccatcctctg tacagagccc | 1800 |

```
acgcccccac tggtgacatg tcttttcttg catgaggcta gtgtggtgtt tcctggcact    1860
gcttccagtg aggctctgcc cttggttagg cattgtggga aggggagata agggtatctg    1920
gtgactttcc tctttggtct acactgtgct gagtctgaag gctgggttct gatcctagtt    1980
ccaccatcaa gccaccaaca tactcccatc tgtgaaagga agagggagg taaggaatac    2040 ctgtcccct gacaacactc attgacctga ggcccttctc tccagcccct ggatgcagcc    2100
tcacagtcct taccagcaga gcaccttaga cagtccctgc caatggacta acttgtcttt    2160
ggaccctgag gcccagaggg cctgcaaggg agtgagttga tagcacagac cctgccctgt    2220
gggcccccaa atggaaatgg gcagagcaga gaccatccct gaaggccccg cccaggctta    2280
gtcactgaga cagcccgggc tctgcctccc atcacccgct aagagggagg gagggctcca    2340
gacacatgtc caagaagccc aggaaaggct ccaggagcag ccacattcct gatgcttctt    2400
cagagactcc tgcaggcagc caggccacaa gacccttgtg gtcccacccc acacacgcca    2460
gattctttcc tgaggctggg ctcccttccc acctctctca ctccttgaaa acactgttct    2520
ctgccctcca agaccttctc cttcaccttt gtccccaccg cagacaggac cagggatttc    2580
catgatgttt tccatgagtc ccctgtttgt ttctgaaagg gacgctaccc gggaaggggg    2640
ctgggacatg ggaaagggga agttgtaggc ataaagtcag gggttccctt ttttggctgc    2700
tgaaggctcg agcatgcctg gatggggctg caccggctgg cctggcccct cagggtccct    2760
ggtggcagct cacctctccc ttggattgtc cccgacccct gccgtctacc tgaggggcct    2820
cttatgggct gggttctacc caggtgctag gaacactcct tcacagatgg gtgcttggag    2880
gaaggaaacc cagctctggt ccatagagag caagacgctg tgctgccctg cccacctggc    2940
ctctgcactc ccctgctggg tgtggcgcag catattcagg aagctcaggg cctggctcag    3000
gtggggtcac tctggcagct cagagagggt gggagtgggc caatgcact tgttctggc    3060 tcttccaggc tgggagagcc ttccagggggt gggacaccct gtgatggggc cctgcctcct    3120
ttgtgaggaa gccgctgggg ccagttggtc ccccttccat ggactttgtt agtttctcca    3180
agcaggacat ggacaaggat gatctaggaa gactttggaa agagtaggaa gactttggaa    3240
agacttttcc aaccctcatc accaacgtct gtgccatttt gtattttact aataaaattt    3300
aaaagtcttg tgaatcaaaa aaaaaaaaaa aaaaaaa                             3338
```

<210> SEQ ID NO 12
<211> LENGTH: 1184
<212> TYPE: DNA
<213> ORGANISM: Homo sapiens

<400> SEQUENCE: 12

```
cacagagccc gggccgcagg cacctcctcg ccagctcttc cgctcctctc acagccgcca      60
gacccgcctg ctgagcccca tggcccgcgc tgctctctcc gccgccccca gcaatccccg     120
gctcctgcga gtggcactgc tgctcctgct cctggtagcc gctggccggc gcgcagcagg     180
agcgtccgtg gccactgaac tgcgctgcca gtgcttgcag accctgcagg gaattcaccc     240
caagaacatc caaagtgtga acgtgaagtc ccccggaccc cactgcgccc aaaccgaagt     300
catagccaca ctcaagaatg gcggaaagc ttgcctcaat cctgcatccc ccatagttaa     360
gaaaatcatc gaaagatgc tgaacagtga caaatccaac tgaccagaag ggaggaggaa     420
gctcactggt ggctgttcct gaaggaggcc ctgcccttat aggaacagaa gaggaaagag     480
agacacagct gcagaggcca cctggattgt gcctaatgtg tttgagcatc gcttaggaga     540
```

-continued

```
agtcttctat ttatttattt attcattagt tttgaagatt ctatgttaat attttaggtg      600
taaaataatt aagggtatga ttaactctac ctgcacactg tcctattata ttcattcttt      660
ttgaaatgtc aaccccaagt tagttcaatc tggattcata tttaatttga aggtagaatg      720
ttttcaaatg ttctccagtc attatgttaa tatttctgag gagcctgcaa catgccagcc      780
actgtgatag aggctggcgg atccaagcaa atggccaatg agatcattgt gaaggcaggg      840
gaatgtatgt gcacatctgt tttgtaactg tttagatgaa tgtcagttgt tatttattga      900
aatgatttca cagtgtgtgg tcaacatttc tcatgttgaa actttaagaa ctaaaatgtt      960
ctaaatatcc cttggacatt ttatgtcttt cttgtaaggc atactgcctt gtttaatggt     1020
agttttacag tgtttctggc ttagaacaaa ggggcttaat tattgatgtt tcatagaga     1080 atataaaaat aaagcactta tagaaaaaac tcgtttgatt tttgggggga acaagggct     1140 acctttactg gaaaatctgg tgatttataa aaaaaaaaa aaaa                       1184

<210> SEQ ID NO 13
<211> LENGTH: 1234
<212> TYPE: DNA
<213> ORGANISM: Homo sapiens

<400> SEQUENCE: 13
gagctccggg aatttccctg gcccgggact ccgggctttc cagccccaac catgcataaa       60
aggggttcgc cgttctcgga gagccacaga gcccgggcca caggcagctc cttgccagct      120
ctcctcctcg cacagccgct cgaaccgcct gctgagcccc atggcccgcg ccacgctctc      180
cgccgccccc agcaatcccc ggctcctgcg ggtggcgctg ctgctcctgc tcctggtggc      240
cgccagccgg cgcgcagcag gagcgcccct ggccactgaa ctgcgctgcc agtgcttgca      300
gaccctgcag ggaattcacc tcaagaacat ccaaagtgtg aaggtgaagt cccccggacc      360
ccactgcgcc caaaccgaag tcatagccac actcaagaat gggcagaaag cttgtctcaa      420
ccccgcatcg cccatggtta agaaaatcat cgaaaagatg ctgaaaaatg gcaaatccaa      480
ctgaccagaa ggaaggagga agcttattgg tggctgttcc tgaaggaggc cctgccctta      540
caggaacaga gaggaaaga gagacacagc tgcagaggcc acctggattg cgcctaatgt      600
gtttgagcat cacttaggag aagtcttcta tttatttatt tattta tttttgtttgtt       660 ttagaagatt ctatgttaat attttatgtg taaaataagg ttatgattga atctacttgc      720
acactctccc attatattta ttgtttattt taggtcaaac ccaagttagt tcaatcctga      780
ttcatattta atttgaagat agaaggtttg cagatattct ctagtcattt gttaatattt      840
cttcgtgatg acatatcaca tgtcagccac tgtgatagag gctgaggaat ccaagaaaat      900
ggccagtgag atcaatgtga cggcagggaa atgtatgtgt gtctattttg taactgtaaa      960
gatgaatgtc agttgttatt tattgaaatg atttcacagt gtgtggtcaa catttctcat     1020
gttgaagctt taagaactaa aatgttctaa atatcccttg acatttat gtctttcttg      1080 taaggcatac tgccttgttt aatgttaatt atgcagtgtt tccctctgtg ttagagcaga     1140
gaggtttcga tatttattga tgttttcaca aagaacagga aaataaaata tttaaaaata     1200
taaaaaaaaa aaaaaaaaaa aaaaaaaaaa aaaa                                 1234

<210> SEQ ID NO 14
<211> LENGTH: 1166
<212> TYPE: DNA
<213> ORGANISM: Homo sapiens

<400> SEQUENCE: 14
```

```
gctccgggaa tttccctggc ccggccgctc cgggctttcc agtctcaacc atgcataaaa    60
agggttcgcc gatcttgggg agccacacag cccgggtcgc aggcacctcc ccgccagctc   120
tcccgcttct cgcacagctt cccgacgcgt ctgctgagcc ccatggccca cgccacgctc   180
tccgccgccc ccagcaatcc ccggctcctg cgggtggcgc tgctgctcct gctcctggtg   240
gccgccagcc ggcgcgcagc aggagcgtcc gtggtcactg aactgcgctg ccagtgcttg   300
cagacactgc agggaattca cctcaagaac atccaaagtg tgaatgtaag gtcccccgga   360
ccccactgcg cccaaaccga agtcatagcc acactcaaga atgggaagaa agcttgtctc   420
aaccccgcat cccccatggt tcagaaaatc atcgaaaaga tactgaacaa ggggagcacc   480
aactgacagg agagaagtaa gaagcttatc agcgtatcat tgacacttcc tgcagggtgg   540
tccctgccct taccagagct gaaaatgaaa aagagaacag cagctttcta gggacagctg   600
gaaaggactt aatgtgtttg actatttctt acgagggttc tacttattta tgtatttatt   660
tttgaaagct tgtattttaa tattttacat gctgttattt aaagatgtga gtgtgtttca   720
tcaaacatag ctcagtcctg attatttaat tggaatatga tgggttttaa atgtgtcatt   780
aaactaatat ttagtgggag accataatgt gtcagccacc ttgataaatg acagggtggg   840
gaactggagg gtgggggat tgaaatgcaa gcaattagtg gatcactgtt agggtaaggg    900
aatgtatgta cacatctatt ttttatactt ttttttaaa aaagaatgt cagttgttat    960
ttattcaaat tatctcacat tatgtgttca acatttttat gctgaagttt cccttagaca  1020
ttttatgtct tgcttgtagg gcataatgcc ttgtttaatg tccattctgc agcgtttctc  1080
tttcccttgg aaaagagaat ttatcattac tgttacattt gtacaaatga catgataata  1140
aaagttttat gaaaaaaaaa aaaaaa                                       1166
```

<210> SEQ ID NO 15
<211> LENGTH: 1227
<212> TYPE: DNA
<213> ORGANISM: Homo sapiens

<400> SEQUENCE: 15

```
ctttgcagat aaatatggca cactagcccc acgttttctg agacattcct caattgctta    60
gacatattct gagcctacag cagaggaacc tccagtctca gcaccatgaa tcaaactgcc   120
attctgattt gctgccttat ctttctgact ctaagtggca ttcaaggagt acctctctct   180
agaactgtac gctgtacctg catcagcatt agtaatcaac ctgttaatcc aaggtcttta   240
gaaaaacttg aaattattcc tgcaagccaa ttttgtccac gtgttgagat cattgctaca   300
atgaaaaaga agggtgagaa gagatgtctg aatccagaat cgaaggccat caagaattta   360
ctgaaagcag ttagcaagga aggtctaaa agatctcctt aaaaccagag gggagcaaaa   420
tcgatgcagt gcttccaagg atggaccaca cagaggctgc ctctcccatc acttccctac   480
atggagtata tgtcaagcca taattgttct tagtttgcag ttacactaaa aggtgaccaa   540
tgatggtcac caaatcagct gctactactc ctgtaggaag gttaatgttc atcatcctaa   600
gctattcagt aataactcta ccctggcact ataatgtaag ctctactgag gtgctatgtt   660
cttagtggat gttctgaccc tgcttcaaat atttccctca cctttcccat cttccaaggg   720
tactaaggaa tctttctgct ttggggttta tcagaattct cagaatctca ataactaaa    780
aggtatgcaa tcaaatctgc ttttaaaga atgctcttta cttcatggac ttccactgcc   840
atcctcccaa ggggcccaaa ttctttcagt ggctacctac atacaattcc aaacacatac   900
```

| | |
|---|---|
| aggaaggtag aaatatctga aaatgtatgt gtaagtattc ttatttaatg aaagactgta | 960 |
| caaagtagaa gtcttagatg tatatatttc ctatattgtt ttcagtgtac atggaataac | 1020 |
| atgtaattaa gtactatgta tcaatgagta acaggaaaat tttaaaaata cagatagata | 1080 |
| tatgctctgc atgttacata agataaatgt gctgaatggt tttcaaaata aaaatgaggt | 1140 |
| actctcctgg aaatattaag aaagactatc taaatgttga aagatcaaaa ggttaataaa | 1200 |
| gtaattataa ctaagaaaaa aaaaaaa | 1227 |

<210> SEQ ID NO 16
<211> LENGTH: 460
<212> TYPE: DNA
<213> ORGANISM: Homo sapiens

<400> SEQUENCE: 16

| | |
|---|---|
| gtggctgaat tctaacctct gtaatgagca ttgcacccaa taccagttct gaactctacc | 60 |
| tggtgaccag ggaccaggac ctttataagg tggaaggctt gatgtcctcc ccagactcag | 120 |
| ctcctggtga agctcccagc catcagccat gagggtcttg tatctcctct tctcgttcct | 180 |
| cttcatattc ctgatgcctc ttccaggtgt ttttggtggt ataggcgatc ctgttacctg | 240 |
| ccttaagagt ggagccatat gtcatccagt cttttgccct agaaggtata aacaaattgg | 300 |
| cacctgtggt ctccctggaa caaaatgctg caaaaagcca tgaggaggcc aagaagctgc | 360 |
| tgtggctgat gcggattcag aaagggctcc ctcatcagag acgtgcgaca tgtaaaccaa | 420 |
| attaaactat ggtgtccaaa gatacgcaaa aaaaaaaaaa | 460 |

<210> SEQ ID NO 17
<211> LENGTH: 1907
<212> TYPE: DNA
<213> ORGANISM: Homo sapiens

<400> SEQUENCE: 17

| | |
|---|---|
| agaatcagag agagagagat agagaaagag aaagacagag gtgtttccct tagctatgga | 60 |
| aactctataa gagagatcca gcttgcctcc tcttgagcag tcagcaacag ggtcccgtcc | 120 |
| ttgacacctc agcctctaca ggactgagaa gaagtaaaac cgtttgctgg ggctggcctg | 180 |
| actcaccagc tgccatgcag cagcccttca attacccata tccccagatc tactgggtgg | 240 |
| acagcagtgc cagctctccc tgggcccctc caggcacagt tcttccctgt ccaacctctg | 300 |
| tgcccagaag gcctggtcaa aggaggccac caccaccacc gccaccgcca ccactaccac | 360 |
| ctccgccgcc gccgccacca ctgcctccac taccgctgcc accctgaag aagagaggga | 420 |
| accacagcac aggcctgtgt ctccttgtga tgttttcat ggttctggtt gccttggtag | 480 |
| gattgggcct ggggatgttt cagctcttcc acctacagaa ggagctggca gaactccgag | 540 |
| agtctaccag ccagatgcac acagcatcat cttttggagaa gcaaataggc cacccagtc | 600 |
| cacccctga aaaaaggag ctgaggaaag tgcccatttt aacaggcaag tccaactcaa | 660 |
| ggtccatgcc tctggaatgg gaagacacct atggaattgt cctgctttct ggagtgaagt | 720 |
| ataagaaggg tggccttgtg atcaatgaaa ctgggctgta cttgtatat tccaaagtat | 780 |
| acttccgggg tcaatcttgc aacaacctgc ccctgagcca aaggtctac atgaggaact | 840 |
| ctaagtatcc ccaggatctg gtgatgatgg aggggaagat gatgagctac tgcactactg | 900 |
| ggcagatgtg ggcccgcagc agctacctgg gggcagtgtt caatcttacc agtgctgatc | 960 |
| atttatatgt caacgtatct gagctctctc tggtcaattt tgaggaatct cagacgtttt | 1020 |
| tcggcttata taagctctaa gagaagcact ttgggattct ttccattatg attctttgtt | 1080 |

| | | | | |
|---|---|---|---|---|
| acaggcaccg | agaatgttgt | attcagtgag | ggtcttctta | catgcatttg | aggtcaagta | 1140 |
| agaagacatg | aaccaagtgg | accttgagac | cacagggttc | aaaatgtctg | tagctcctca | 1200 |
| actcacctaa | tgtttatgag | ccagacaaat | ggaggaatat | gacggaagaa | catagaactc | 1260 |
| tgggctgcca | tgtgaagagg | gagaagcatg | aaaaagcagc | taccaggtgt | tctacactca | 1320 |
| tcttagtgcc | tgagagtatt | taggcagatt | gaaaaggaca | ccttttaact | cacctctcaa | 1380 |
| ggtgggcctt | gctacctcaa | gggggactgt | ctttcagata | catggttgtg | acctgaggat | 1440 |
| ttaagggatg | gaaaggaag | actagaggct | tgcataataa | gctaagagg | ctgaaagagg | 1500 |
| ccaatgcccc | actggcagca | tcttcacttc | taaatgcata | tcctgagcca | tcggtgaaac | 1560 |
| taacagataa | gcaagagaga | tgttttgggg | actcatttca | ttcctaacac | agcatgtgta | 1620 |
| tttccagtgc | aattgtaggg | gtgtgtgtgt | gtgtgtgtgt | gtgtgtgtgt | gtatgactaa | 1680 |
| agagagaatg | tagatattgt | gaagtacata | ttaggaaaat | atgggttgca | tttggtcaag | 1740 |
| attttgaatg | cttcctgaca | atcaactcta | atagtgctta | aaaatcattg | attgtcagct | 1800 |
| actaatgatg | ttttcctata | ataataaa | tatttatgta | gatgtgcatt | tttgtgaaat | 1860 |
| gaaaacatgt | aataaaaagt | atatgttagg | atacaaaaaa | aaaaaaa | | 1907 |

<210> SEQ ID NO 18
<211> LENGTH: 3823
<212> TYPE: DNA
<213> ORGANISM: Homo sapiens

<400> SEQUENCE: 18

| | | | | | | |
|---|---|---|---|---|---|---|
| ataaaacctg | gagcgcagga | tcgcgcccag | gagcggcgag | ctagcggacg | caaagactgg | 60 |
| gcatgctccg | cggcggcgca | ggttttggtc | acaagtagga | agaagccagt | gcaccagacc | 120 |
| ggcaaagaga | agcgggagcc | gccgcggcag | cgcggccgtg | gggtccgccg | ccgccgcatc | 180 |
| ggagcgggag | gaggagcagc | ggggagggcg | aggccgccgg | gccgagagcc | gtcccgcctg | 240 |
| ctctcggtct | tctgccttcg | cctccgcgcg | gtgcgtcgga | cccagggtct | gtcacctggg | 300 |
| cgccaggggc | cgccgccggg | gagccggagc | gggcaggacc | ctccctccgc | cgactgcggc | 360 |
| ccgagagcgc | ccccgcgggg | tggagcggca | gccgccttct | gcgggcggct | gagtgtccgt | 420 |
| ctcgcgcccg | gagcgggcga | ccgccgtcag | cccggaggag | gaggaggagg | aggaggggc | 480 |
| ggccatgggg | ctgctgtccc | agggctcgcc | gctgagctgg | gaggaaacca | agcgccatgc | 540 |
| cgaccacgtg | cggcggcacg | ggatcctcca | gttcctgcac | atctaccacc | cgtcaaggga | 600 |
| ccggcacaag | gacgttctca | agtggggcga | tgaggtggaa | tacatgttgg | tatcttttga | 660 |
| tcatgaaaat | aaaaagtcc | ggttggtcct | gtctggggag | aaagttcttg | aaactctgca | 720 |
| agagaagggg | gaaaggacaa | acccaaacca | tcctacccctt | tggagaccag | agtatgggag | 780 |
| ttacatgatt | gaagggacac | caggacagcc | ctacggagga | acaatgtccg | agttcaatac | 840 |
| agttgaggcc | aacatgcgaa | aacgccggaa | ggaggctact | tctatattag | aagaaaatca | 900 |
| ggctctttgc | acaataactt | catttcccag | attaggctgt | cctgggttca | cactgcccga | 960 |
| ggtcaaaccc | aacccagtgg | aaggaggagc | ttccaagtcc | ctcttctttc | cagatgaagc | 1020 |
| aataaacaag | caccctcgct | tcagtacctt | aacaagaaat | atccgacata | ggagaggaga | 1080 |
| aaaggttgtc | atcaatgtac | caatatttaa | ggacaagaat | acaccatctc | catttataga | 1140 |
| aacatttact | gaggatgatg | aagcttcaag | ggcttctaag | ccggatcata | tttcatggaa | 1200 |
| tgccatggga | tttggaatgg | gcaattgctg | tctccaggtg | acattccaag | cctgcagtat | 1260 |

```
atctgaggcc agatacctttt atgatcagtt ggctactatc tgtccaattg ttatggcttt    1320
gagtgctgca tctccctttt accgaggcta tgtgtcagac attgattgtc gctggggagt    1380
gatttctgca tctgtagatg atagaactcg ggaggagcga ggactggagc cattgaagaa    1440
caataactat aggatcagta aatcccgata tgactcaata dacagctatt tatctaagtg    1500
tggtgagaaa tataatgaca tcgacttgac gatagataaa gagatctacg aacagctgtt    1560
gcaggaaggc attgatcatc tcctggccca gcatgttgct catctctttta ttagagaccc    1620 actgacactg tttgaagaga aaatacacct ggatgatgct aatgagtctg accattttga    1680
gaatattcag tccacaaatt ggcagacaat gagatttaag ccccctcctc caaactcaga    1740
cattggatgg agagtagaat tcgacccat ggaggtgcaa ttaacagact tgagaactc    1800 tgcctatgtg gtgttttgtgg tactgctcac cagagtgatc ctttcctaca aattggattt    1860
tctcattcca ctgtcaaagg ttgatgagaa catgaaggta gcacagaaaa gagatgctgt    1920
cttgcaggga atgttttatt tcaggaaaga tatttgcaaa ggtggcaatg cagtggtgga    1980
tggttgtggc aaggcccaga acagcacgga gctcgctgca gaggagtaca ccctcatgag    2040
catagacacc atcatcaatg ggaaggaagg tgtgtttcct ggactgatcc caattctgaa    2100
ctcttacctt gaaaacatgg aagtggatgt ggacaccaga tgtagtattc tgaactacct    2160
aaagctaatt aagaagagag catctggaga actaatgaca gttgccagat ggatgaggga    2220
gtttatcgca aaccatcctg actacaagca agacagtgtc ataactgatg aaatgaatta    2280
tagccttatt ttgaagtgta accaaattgc aaatgaatta tgtgaatgcc cagagttact    2340
tggatcagca tttaggaaag taaaatatag tggaagtaaa actgactcat ccaactagac    2400
attctacaga aagaaaaatg cattattgac gaactggcta cagtaccatg cctctcagcc    2460
agcccgtgtg tataatatga agaccaaatg atagaactgt actgttttct gggccagtga    2520
gccagaaatt gattaaggct ttctttggta ggtaaatcta gagtttatac agtgtacatg    2580
tacatagtaa agtattttg attaacaatg tatttaata acatatctaa agtcatcatg    2640
aactggcttg tacatttta aattcttact ctggagcaac ctactgtcta agcagtttttg    2700 taaatgtact ggtaattgta caatacttgc attccagagt taaaatgtttt actgtaaatt    2760 tttgttcttt taaagactac ctgggacctg atttattgaa atttttctct ttaaaaacat    2820
tttctctcgt taattttcct ttgtcatttc ctttgttgtc tacattaaaat cacttgaatc    2880 cattgaaagt gcttcaaggg taatcttggg tttctagcac cttatctatg atgtttctttt    2940 tgcaattgga ataatcactt ggtcacctttg ccccaagctt tccctctga ataaataccc    3000 attgaactct gatggctgtt atcaaaggaa cttttctttg tttaaatttg ctgatgcagg    3060
aattaagttt aaacacaact ctatagaaag aaaggagatt attccccaga attcacatgt    3120
agtgattatt aaggacaatt ttttttttta actaaaaaag ttggcggcag gggtgggggg    3180 tgcaatcat ttttcttcct atacatacaa aggatattgt caaaaatggc gttcttctct    3240
tgtggcctgt tattctgatt gctgctgtat acagttttgt cactctttag tttttagtta    3300
agcatactga tagactttcc tctaaaagcc attcactcca gattttacct ggggaatatt    3360
ctacatactg cttactttct ctataaaact catcaataaa tcatgaaagg cactgagttt    3420
tgtaaatcag gaccctaaat gtttaattgt aaataagtttt cagataatta ttatagcttt    3480
gcgttgaagt ttgttgttttt ttttctcaac tagttaagtc aactgcttct gaaataactc    3540
tgtattgtag attatgcaga tctttacagg cataaatatt taaactgtaa tatgctaact    3600
tgaagagatt gcaataaagc tgcttcagct aaccctgttt atgtttaaat actagggttt    3660
```

-continued

| | |
|---|---|
| gttctatatt ttatacatgc attttggatg attaaagaat gcctggtttt cgtttgcaat | 3720 |
| ttgcttgtgt aaatcaggtt gtaaaaaggc agataaattg aaatgtttgt ggtatgagga | 3780 |
| aataaaagaa tggaattagc tttcattcag aaaaaaaaaa aaa | 3823 |

<210> SEQ ID NO 19
<211> LENGTH: 3249
<212> TYPE: DNA
<213> ORGANISM: Homo sapiens

<400> SEQUENCE: 19

| | |
|---|---|
| caagcttagc ctggccggga acgggaggc gtggaggccg ggagcagccc ccggggtcat | 60 |
| cgccctgcca ccgccgcccg attgctttag cttggaaatt ccggagctga agcggccagc | 120 |
| gagggaggat gaccctctcg gcccgggcac cctgtcagtc cggaaataac tgcagcattt | 180 |
| gttccggagg ggaaggcgcg aggtttccgg aaagcagca ccgcccttg gccccaggt | 240 |
| ggctagcgct ataaaggatc acgcgcccca gtcgacgctg agctcctctg ctactcagag | 300 |
| ttgcaacctc agcctcgcta tggctcccag cagccccgg cccgcgctgc ccgcactcct | 360 |
| ggtcctgctc ggggctctgt tcccaggacc tggcaatgcc cagacatctg tgtcccctc | 420 |
| aaaagtcatc ctgccccggg gaggctccgt gctggtgaca tgcagcacct cctgtgacca | 480 |
| gcccaagttg ttgggcatag agaccccgtt gcctaaaaag gagttgctcc tgcctgggaa | 540 |
| caaccggaag gtgtatgaac tgagcaatgt gcaagaagat agccaaccaa tgtgctattc | 600 |
| aaactgccct gatgggcagt caacagctaa aaccttcctc accgtgtact ggactccaga | 660 |
| acgggtggaa ctggcacccc tcccctcttg gcagccagtg ggcaagaacc ttaccctacg | 720 |
| ctgccaggtg gagggtgggg caccccgggc caacctcacc gtggtgctgc tccgtggga | 780 |
| gaaggagctg aaacgggagc cagctgtggg ggagcccgct gaggtcacga ccacggtgct | 840 |
| ggtgaggaga gatcaccatg gagccaattt ctcgtgccgc actgaactgg acctgcggcc | 900 |
| ccaagggctg gagctgtttg agaacaccct ggcccctac cagctccaga cctttgtcct | 960 |
| gccagcgact cccccacaac ttgtcagccc ccgggtccta gaggtggaca cgcagggac | 1020 |
| cgtggtctgt tccctggacg ggctgttccc agtctcggag gcccaggtcc acctggcact | 1080 |
| gggggaccag aggttgaacc ccacagtcac ctatggcaac gactccttct cggccaaggc | 1140 |
| ctcagtcagt gtgaccgcag aggacgaggg caccccagcgg ctgacgtgtg cagtaatact | 1200 |
| ggggaaccag agccaggaga cactgcagac agtgaccatc tacagctttc ggcgcccaa | 1260 |
| cgtgattctg acgaagccag aggtctcaga agggaccgag gtgacagtga agtgtgaggc | 1320 |
| ccaccctaga gccaaggtga cgctgaatgg ggttccagcc cagccactgg cccgagggc | 1380 |
| ccagctcctg ctgaaggcca cccagagga caacgggcgc agcttctcct gctctgcaac | 1440 |
| cctggaggtg gccggccagc ttatacacaa gaaccagacc cgggagcttc gtgtcctgta | 1500 |
| tggccccga ctgacgaga gggattgtcc gggaaactgg acgtggccag aaaattccca | 1560 |
| gcagactcca atgtgccagg cttggggaa cccattgccc gagctcaagt gtctaaagga | 1620 |
| tggcactttc ccactgccca tcggggaatc agtgactgtc actcgagatc ttgagggcac | 1680 |
| ctacctctgt cggccagga gcactcaagg ggaggtcacc cgcaaggtga ccgtgaatgt | 1740 |
| gctctccccc cggtatgaga ttgtcatcat cactgtggta gcagccgcag tcataatggg | 1800 |
| cactgcaggc ctcagcacgt acctctataa ccgccagcgg aagatcaaga aatcagact | 1860 |
| acaacaggcc caaaagggga ccccatgaa accgaacaca caagccacgc ctccctgaac | 1920 |

```
ctatcccggg acagggcctc ttcctcggcc ttcccatatt ggtggcagtg gtgccacact    1980
gaacagagtg gaagacatat gccatgcagc tacacctacc ggccctggga cgccggagga    2040
cagggcattg tcctcagtca gatacaacag catttgggc catggtacct gcacacctaa     2100
aacactaggc cacgcatctg atctgtagtc acatgactaa gccaagagga aggagcaaga    2160
ctcaagacat gattgatgga tgttaaagtc tagcctgatg agaggggaag tggtggggga    2220
gacatagccc caccatgagg acatacaact gggaaatact gaaacttgct gcctattggg    2280
tatgctgagg ccccacagac ttacagaaga agtggccctc catagacatg tgtagcatca    2340
aaacacaaag gcccacactt cctgacggat gccagcttgg gcactgctgt ctactgaccc    2400
caacccttga tgatatgtat ttattcattt gttattttac cagctattta ttgagtgtct    2460
tttatgtagg ctaaatgaac ataggtctct ggcctcacgg agctcccagt cctaatcaca    2520
ttcaaggtca ccaggtacag ttgtacaggt tgtacactgc aggagagtgc ctggcaaaaa    2580
gatcaaatgg ggctgggact tctcattggc caacctgcct ttccccagaa ggagtgattt    2640
ttctatcggc acaaaagcac tatatggact ggtaatggtt acaggttcag agattaccca    2700
gtgaggcctt attcctccct tccccccaaa actgacacct tgttagcca cctcccacc     2760 cacatacatt tctgccagtg ttcacaatga cactcagcgg tcatgtctgg acatgagtgc    2820
ccagggaata tgcccaagct atgccttgtc ctcttgtcct gtttgcattt cactgggagc    2880
ttgcactatg cagctccagt ttcctgcagt gatcagggtc ctgcaagcag tggggaaggg    2940
ggccaaggta ttggaggact ccctcccagc tttggaagcc tcatccgcgt gtgtgtgt      3000 gtgtatgtgt agacaagctc tcgctctgtc acccaggctg gagtgcagtg gtgcaatcat    3060
ggttcactgc agtcttgacc ttttgggctc aagtgatcct cccacctcag cctcctgagt    3120
agctgggacc ataggctcac aaccaccac ctggcaaatt tgattttttt tttttttcca     3180
gagacggggt ctcgcaacat tgcccagact tcctttgtgt tagttaataa agctttctca    3240
actgccaaa                                                            3249
```

<210> SEQ ID NO 20
<211> LENGTH: 1254
<212> TYPE: DNA
<213> ORGANISM: Homo sapiens

<400> SEQUENCE: 20

```
ctcacttggc cttacactcc gctcggctca ccatgtgtca ctctcgcagc tgccacccga     60
ccatgaccat cctgcaggcc ccgaccccgg cccctccac catcccggga ccccggcggg     120
gctccggtcc tgagatcttc accttcgacc ctctcccgga gcccgcagcg gcccctgccg    180
ggcgccccag cgcctctcgc gggcaccgaa agccgcagccg cagggttctc taccctcgag   240
tggtccggcg ccagctgcca gtcgaggaac cgaacccagc caaaaggctt ctctttctgc    300
tgctcaccat cgtcttctgc cagatcctga tggctgaaga gggtgtgccg gcgcccctgc    360
ctccagagga cgcccctaac gccgcatccc tggcgcccac ccctgtgtcc gccgtcctcg    420 agcccttta  tctgacttcg gagccctcgg actacgctct ggacctcagc actttcctcc    480
agcaacaccc ggccgccttc taactgtgac tccccgcact ccccaaaaag aatccgaaaa    540
accacaaaga aacaccaggc gtacctggtg cgcgagagcg tatcccaac tgggacttcc     600 gaggcaactt gaactcagaa cactacagcg gagacgccac ccggtgcttg aggcgggacc    660
gaggcgcaca gagaccgagg cgcatagaga ccgaggcaca gccagctggg gctaggccc     720 ggtgggaagg agagcgtcgt taatttattt cttattgctc ctaattaata tttatatgta    780
```

```
tttatgtacg tcctcctagg tgatggagat gtgtacgtaa tatttatttt aacttatgca      840
agggtgtgag atgttccccc tgctgtaaat gcaggtctct tggtatttat tgagctttgt      900
gggactggtg aagcaggac acctggaact gcggcaaagt aggagaagaa atggggagga       960
ctcgggtggg ggaggacgtc ccggctggga tgaagtctgg tggtgggtcg taagtttagg     1020
aggtgactgc atcctccagc atctcaactc cgtctgtcta ctgtgtgaga cttcggcgga     1080
ccattaggaa tgagatccgt gagatccttc catcttcttg aagtcgcctt tagggtggct     1140
gcgaggtaga gggttggggg ttggtgggct gtcacggagc gactgtcgag atcgcctagt     1200
atgttctgtg aacacaaata aaattgattt actgtctgca aaaaaaaaaa aaaa           1254
```

<210> SEQ ID NO 21
<211> LENGTH: 840
<212> TYPE: DNA
<213> ORGANISM: Homo sapiens

<400> SEQUENCE: 21

```
acattctaac tgcaaccttt cgaagccttt gctctggcac aacaggtagt aggcgacact       60
gttcgtgttg tcaacatgac caacaagtgt ctcctccaaa ttgctctcct gttgtgcttc      120
tccactacag ctcttttccat gagctacaac ttgcttggat tcctacaaag aagcagcaat     180
tttcagtgtc agaagctcct gtggcaattg aatgggaggc ttgaatactg cctcaaggac      240
aggatgaact ttgacatccc tgaggagatt aagcagctgc agcagttcca aaggaggac       300 gccgcattga ccatctatga gatgctccag aacatctttg ctattttcag acaagattca     360
tctagcactg gctggaatga gactattgtt gagaacctcc tggctaatgt ctatcatcag      420
ataaaccatc tgaagacagt cctggaagaa aaactggaga aagaagattt caccagggga     480
aaactcatga gcagtctgca cctgaaaaga tattatggga ggattctgca ttacctgaag      540
gccaaggagt acagtcactg tgcctggacc atagtcagag tggaaatcct aaggaacttt      600
tacttcatta acagacttac aggttacctc cgaaactgaa gatctcctag cctgtgcctc     660
tgggactgga caattgcttc aagcattctt caaccagcag atgctgttta agtgactgat      720
ggctaatgta ctgcatatga aaggacacta gaagattttg aaattttat taaattatga      780 gttatttta tttatttaaa ttttattttg aaaataaat tattttggt gcaaaagtca        840
```

<210> SEQ ID NO 22
<211> LENGTH: 2347
<212> TYPE: DNA
<213> ORGANISM: Homo sapiens

<400> SEQUENCE: 22

```
ctgtttcagg gccattggac tctccgtcct gcccagagca agatgtgtca ccagcagttg       60
gtcatctctt ggttttcct ggtttttctg gcatctcccc tcgtggccat atgggaactg       120
aagaaagatg tttatgtcgt agaattggat tggtatccgg atgcccctgg agaaatggtg      180
gtcctcacct gtgacacccc tgaagaagat ggtatcacct ggaccttgga ccagagcagt      240
gaggtcttag gctctggcaa aaccctgacc atccaagtca aagagtttgg agatgctggc     300
cagtacacct gtcacaaagg aggcgaggtt ctaagccatt cgctcctgct gcttcacaaa     360
aaggaagatg gaatttggtc cactgatatt ttaaaggacc agaaagaacc caaaaataag      420 accttttctaa gatgcgaggc caagaattat tctggacgtt tcacctgctg gtggctgacg      480
acaatcagta ctgatttgac attcagtgtc aaaagcagca gaggctcttc tgacccccaa      540
```

```
ggggtgacgt gcggagctgc tacactctct gcagagagag tcagagggga caacaaggag    600
tatgagtact cagtggagtg ccaggaggac agtgcctgcc cagctgctga ggagagtctg    660
cccattgagg tcatggtgga tgccgttcac aagctcaagt atgaaaacta caccagcagc    720
ttcttcatca gggacatcat caaacctgac ccacccaaga acttgcagct gaagccatta    780
aagaattctc ggcaggtgga ggtcagctgg gagtaccctg acacctggag tactccacat    840
tcctacttct ccctgacatt ctgcgttcag gtccagggca agagcaagag agaaaagaaa    900
gatagagtct tcacggacaa gacctcagcc acggtcatct gccgcaaaaa tgccagcatt    960
agcgtgcggg cccaggaccg ctactatagc tcatcttgga gcgaatgggc atctgtgccc   1020
tgcagttagg ttctgatcca ggatgaaaat ttggaggaaa agtggaagat attaagcaaa   1080
atgtttaaag acacaacgga atagacccaa aaagataatt tctatctgat ttgctttaaa   1140
acgttttttt aggatcacaa tgatatcttt gctgtatttg tatagttaga tgctaaatgc   1200
tcattgaaac aatcagctaa tttatgtata gattttccag ctctcaagtt gccatgggcc   1260
ttcatgctat ttaaatattt aagtaattta tgtatttatt agtatattac tgttatttaa   1320
cgtttgtctg ccaggatgta tggaatgttt catactctta tgacctgatc catcaggatc   1380
agtccctatt atgcaaaatg tgaatttaat tttatttgta ctgacaactt ttcaagcaag   1440
gctgcaagta catcagtttt atgacaatca ggaagaatgc agtgttctga taccagtgcc   1500
atcatacact tgtgatggat gggaacgcaa gagatactta catggaaacc tgacaatgca   1560
aacctgttga aagatccag gagaacaaga tgctagttcc catgtctgtg aagacttcct   1620
ggagatggtg ttgataaagc aatttagggc cacttacact tctaagcaag tttaatcttt   1680
ggatgcctga attttaaaag ggctagaaaa aaatgattga ccagcctggg aaacataaca   1740
agaccccgtc tctacaaaaa aaatttaaaa ttagccaggc gtggtggctc atgcttgtgg   1800
tcccagctgt tcaggaggat gaggcaggag gatctcttga gcccaggagg tcaaggctat   1860
ggtgagccgt gattgtgcca ctgcatacca gcctaggtga cagaatgaga ccctgtctca   1920 aaaaaaaaa tgattgaaat taaaattcag ctttagcttc catggcagtc ctcaccccca   1980
cctctctaaa agacacagga ggatgacaca gaaacaccgt aagtgtctgg aaggcaaaaa   2040
gatcttaaga ttcaagagag aggacaagta gttatggcta aggacatgaa attgtcagaa   2100
tggcaggtgg cttcttaaca gccctgtgag aagcagacag atgcaaagaa aatctggaat   2160
ccctttctca ttagcatgaa tgaacctgat acacaattat gaccagaaaa tatggctcca   2220
tgaaggtgct acttttaagt aatgtatgtg cgctctgtaa agtgattaca tttgtttcct   2280
gtttgtttat ttatttattt attttttgcat tctgaggctg aactaataaa aactcttctt   2340
tgtaatc                                                             2347
```

<210> SEQ ID NO 23
<211> LENGTH: 1498
<212> TYPE: DNA
<213> ORGANISM: Homo sapiens

<400> SEQUENCE: 23

```
accaaacctc ttcgaggcac aaggcacaac aggctgctct gggattctct tcagccaatc     60
ttcattgctc aagtgtctga agcagccatg gcagaagtac ctgagctcgc cagtgaaatg    120
atggcttatt acagtggcaa tgaggatgac ttgttctttg aagctgatgg ccctaaacag    180
atgaagtgct ccttccagga cctgaccctc tgccctctgg atgcggcat ccagctacga    240 atctccgacc accactacag caagggcttc aggcaggccg cgtcagttgt tgtggccatg    300
```

```
gacaagctga ggaagatgct ggttccctgc ccacagacct tccaggagaa tgacctgagc     360
accttctttc ccttcatctt tgaagaagaa cctatcttct tcgacacatg ggataacgag     420
gcttatgtgc acgatgcacc tgtacgatca ctgaactgca cgctccggga ctcacagcaa     480
aaaagcttgg tgatgtctgg tccatatgaa ctgaaagctc tccacctcca gggacaggat     540
atggagcaac aagtggtgtt ctccatgtcc tttgtacaag agaagaaag taatgacaaa     600 atacctgtgg ccttgggcct caaggaaaag aatctgtacc tgtcctgcgt gttgaaagat     660
gataagccca ctctacagct ggagagtgta gatcccaaaa attacccaaa gaagaagatg     720
gaaaagcgat ttgtcttcaa caagataaa atcaataaca agctggaatt tgagtctgcc     780
cagttcccca actggtacat cagcacctct caagcagaaa acatgcccgt cttcctggga     840
gggaccaaag gcggccagga tataactgac ttcaccatgc aatttgtgtc ttcctaaaga     900
gagctgtacc cagagagtcc tgtgctgaat gtggactcaa tccctagggc tggcagaaag     960
ggaacagaaa ggttttgag tacggctata gcctggactt tcctgttgtc tacaccaatg    1020
cccaactgcc tgccttaggg tagtgctaag aggatctcct gtccatcagc caggacagtc    1080
agctctctcc tttcagggcc aatccccagc ccttttgttg agccaggcct ctctcacctc    1140
tcctactcac ttaaagcccg cctgacagaa accacggcca catttggttc taagaaaccc    1200
tctgtcattc gctcccacat tctgatgagc aaccgcttcc ctatttattt atttatttgt    1260
ttgtttgttt tattcattgg tctaatttat tcaaggggg caagaagtag cagtgtctgt    1320
aaaagagcct agttttaat agctatgaa tcaattcaat ttggactggt gtgctctctt    1380
taaatcaagt cctttaatta agactgaaaa tatataagct cagattattt aaatgggaat    1440
atttataaat gagcaaatat catactgttc aatggttctg aaataaactt cactgaag      1498
```

<210> SEQ ID NO 24
<211> LENGTH: 822
<212> TYPE: DNA
<213> ORGANISM: Homo sapiens

<400> SEQUENCE: 24

```
agttccctat cactctcttt aatcactact cacagtaacc tcaactcctg ccacaatgta      60
caggatgcaa ctcctgtctt gcattgcact aagtcttgca cttgtcacaa acagtgcacc     120
tacttcaagt tctacaaaga aaacacagct acaactggag catttactgc tggatttaca     180
gatgattttg aatggaatta ataattacaa gaatcccaaa ctcaccagga tgctcacatt     240
taagttttac atgcccaaga aggccacaga actgaaacat cttcagtgtc tagaagaaga     300
actcaaacct ctggaggaag tgctaaattt agctcaaagc aaaaactttc acttaagacc     360
cagggactta atcagcaata tcaacgtaat agttctggaa ctaaagggat ctgaaacaac     420
attcatgtgt gaatatgctg atgagacagc aaccattgta gaatttctga acagatggat     480 tacctttgt caaagcatca tctcaacact gacttgataa ttaagtgctt cccacttaaa     540
acatatcagg ccttctatt atttaaatat ttaaatttta tatttattgt tgaatgtatg     600
gtttgctacc tattgtaact attattctta atcttaaaac tataaatatg gatcttttat     660
gattcttttt gtaagcccta ggggctctaa atggtttca cttatttatc ccaaaatatt     720
tattattatg ttgaatgtta aatatagtat ctatgtagat tggttagtaa aactatttaa     780
taaatttgat aaatataaaa aaaaaaaaaa aaaaaaaaaa aa                        822
```

<210> SEQ ID NO 25

```
<211> LENGTH: 1049
<212> TYPE: DNA
<213> ORGANISM: Homo sapiens

<400> SEQUENCE: 25
aaaacaacag gaagcagctt acaaactcgg tgaacaactg agggaaccaa accagagacg      60
cgctgaacag agagaatcag gctcaaagca agtggaagtg ggcagagatt ccaccaggac     120
tggtgcaagg cgcagagcca gccagatttg agaagaaggc aaaaagatgc tggggagcag     180
agctgtaatg ctgctgttgc tgctgccctg acagctcag gcagagctg tgcctggggg       240
cagcagccct gcctggactc agtgccagca gctttcacag aagctctgca cactggcctg     300
gagtgcacat ccactagtgg gacacatgga tctaagagaa gagggagatg aagagactac     360
aaatgatgtt ccccatatcc agtgtggaga tggctgtgac ccccaaggac tcagggacaa     420
cagtcagttc tgcttgcaaa ggatccacca gggtctgatt ttttatgaga agctgctagg     480
atcggatatt ttcacagggg agccttctct gctccctgat agccctgtgg gccagcttca     540
tgcctcccta ctgggcctca gccaactcct gcagcctgag ggtcaccact gggagactca     600
gcagattcca agcctcagtc ccagccagcc atggcagcgt ctccttctcc gcttcaaaat     660
ccttcgcagc ctccaggcct tgtggctgt agccgcccgg gtctttgccc atggagcagc      720
aaccctgagt ccctaaaggc agcagctcaa ggatggcact cagatctcca tggcccagca     780
aggccaagat aaatctacca ccccaggcac ctgtgagcca acaggttaat tagtccatta     840
attttagtgg gacctgcata tgttgaaaat taccaatact gactgacatg tgatgctgac     900
ctatgataag gttgagtatt tattagatgg aagggaaat ttggggatta tttatcctcc      960
tggggacagt ttggggagga ttatttattg tatttatatt gaattatgta cttttttcaa    1020
taaagtctta tttttgtggc taaaaaaaa                                      1049

<210> SEQ ID NO 26
<211> LENGTH: 1201
<212> TYPE: DNA
<213> ORGANISM: Homo sapiens

<400> SEQUENCE: 26
aatattagag tctcaacccc caataaatat aggactggag atgtctgagg ctcattctgc      60
cctcgagccc accgggaacg aaagagaagc tctatctccc ctccaggagc ccagctatga     120
actccttctc cacaagcgcc ttcggtccag ttgccttctc cctggggctg ctcctggtgt     180
tgcctgctgc cttccctgcc ccagtacccc caggagaaga ttccaaagat gtagccgccc     240
cacacagaca gccactcacc tcttcagaac gaattgacaa acaaattcgg tacatcctcg     300
acggcatctc agccctgaga aaggagacat gtaacaagag taacatgtgt gaaagcagca     360
aagaggcact ggcagaaaac aacctgaacc ttccaaagat ggctgaaaaa gatggatgct     420
tccaatctgg attcaatgag gagacttgcc tggtgaaaat catcactggt cttttggagt     480
tgaggtata cctagagtac ctccagaaca gatttgagag tagtgaggaa caagccagag      540
ctgtgcagat gagtacaaaa gtcctgatcc agttcctgca gaaaaaggca aagaatctag     600
atgcaataac caccctgac ccaaccacaa atgccagcct gctgacgaag ctgcaggcac      660
agaaccagtg gctgcaggac atgacaactc atctcattct gcgcagcttt aaggagttcc     720
tgcagtccag cctgagggct cttcggcaaa tgtagcatgg gcacctcaga ttgttgttgt     780
taatgggcat tccttcttct ggtcagaaac ctgtccactg gcacagaac ttatgttgtt      840
ctctatggag aactaaaagt atgagcgtta ggacactatt ttaattattt ttaatttatt     900
```

```
aatatttaaa tatgtgaagc tgagttaatt tatgtaagtc atatttatat ttttaagaag      960
taccacttga acattttat gtattagttt tgaaataata atggaaagtg gctatgcagt     1020
ttgaatatcc tttgtttcag agccagatca tttcttggaa agtgtaggct tacctcaaat    1080
aaatggctaa cttatacata tttttaaaga aatatttata ttgtatttat ataatgtata    1140
aatggttttt ataccaataa atggcattt aaaaaattca gcaaaaaaa aaaaaaaaa       1200 a                                                                    1201
```

<210> SEQ ID NO 27
<211> LENGTH: 1718
<212> TYPE: DNA
<213> ORGANISM: Homo sapiens

<400> SEQUENCE: 27

```
gagggtgcat aagttctcta gtagggtgat gatataaaaa gccaccggag cactccataa     60
ggcacaaact ttcagagaca gcagagcaca caagcttcta ggacaagagc caggaagaaa    120
ccaccggaag gaaccatctc actgtgtgta acatgactt ccaagctggc cgtggctctc     180
ttggcagcct cctgatttc tgcagctctg tgtgaaggtg cagttttgcc aaggagtgct    240
aaagaactta gatgtcagtg cataaagaca tactccaaac ctttccaccc caaatttatc   300
aaagaactga gagtgattga gagtggacca cactgcgcca acacagaaat tattgtaaag   360
ctttctgatg gaagagagct ctgtctggac cccaaggaaa actgggtgca gagggttgtg   420
gagaagtttt tgaagagggc tgagaattca taaaaaaatt cattctctgt ggtatccaag   480
aatcagtgaa gatgccagtg aaacttcaag caaatctact tcaacacttc atgtattgtg   540
tgggtctgtt gtagggttgc cagatgcaat acaagattcc tggttaaatt tgaatttcag   600
taaacaatga atagttttc attgtaccat gaaatatcca gaacatactt atatgtaaag    660
tattatttat ttgaatctac aaaaaacaac aaataatttt taaatataag gattttccta   720
gatattgcac gggagaatat acaaatagca aaattgaggc caagggccaa gagaatatcc   780
gaactttaat ttcaggaatt gaatgggttt gctagaatgt gatatttgaa gcatcacata   840
aaaatgatgg gacaataaat tttgccataa agtcaaattt agctggaaat cctggatttt   900
tttctgttaa atctggcaac cctagtctgc tagccaggat ccacaagtcc ttgttccact   960
gtgccttggt ttctccttta tttctaagtg aaaaagtat tagccaccat cttacctcac    1020
agtgatgttg tgaggacatg tggaagcact ttaagttttt tcatcataac ataaattatt   1080
ttcaagtgta acttattaac ctatttatta tttatgtatt tatttaagca tcaaatattt   1140
gtgcaagaat ttggaaaaat agaagatgaa tcattgattg aatagttata agatgttat    1200 agtaaattta ttttattta gatattaaat gatgttttat tagataaatt tcaatcaggg    1260
tttttagatt aaacaaacaa acaattgggt acccagttaa attttcattt cagataaaca   1320
acaaataatt ttttagtata agtacattat tgtttatctg aaatttttaat tgaactaaca   1380 atcctagttt gatactccca gtcttgtcat tgccagctgt gttggtagtg ctgtgttgaa   1440
ttacggaata atgagttaga actattaaaa cagccaaaac tccacagtca atattagtaa   1500
tttcttgctg gttgaaactt gtttattatg tacaaataga ttcttataat attatttaaa   1560
tgactgcatt tttaaataca aggcttata tttttaactt taagatgttt ttatgtgctc    1620
tccaaatttt tttactgtt tctgattgta tggaaatata aagtaaaata tgaaacattt    1680
aaaatataat ttgttgtcaa agtaaaaaaa aaaaaaaa                            1718
```

<210> SEQ ID NO 28
<211> LENGTH: 3567
<212> TYPE: DNA
<213> ORGANISM: Homo sapiens

<400> SEQUENCE: 28

| | | | | | | |
|---|---|---|---|---|---|---|
| agagctcgcc | actccttagt | cgaggcaaga | cgtgcgcccg | agcccgccg | aaccgaggcc | 60 |
| acccggagcc | gtgcccagtc | cacgccggcc | gtgcccggcg | gccttaagaa | cccggcaacc | 120 |
| tctgccttct | tccctcttcc | actcggagtc | gcgctccgcg | cgccctcact | gcagcccctg | 180 |
| cgtcgccggg | accctcgcgc | gcgaccgccg | aatcgctcct | gcagcagagc | caacatgccc | 240 |
| atcactcgga | tgcgcatgag | accctggcta | gagatgcaga | ttaattccaa | ccaaatcccg | 300 |
| gggctcatct | ggattaataa | agaggagatg | atcttccaga | tcccatggaa | gcatgctgcc | 360 |
| aagcatggct | gggacatcaa | caaggatgcc | tgtttgttcc | ggagctgggc | cattcacaca | 420 |
| ggccgataca | aagcagggga | aaaggagcca | gatcccaaga | cgtggaaggc | caactttcgc | 480 |
| tgtgccatga | actccctgcc | agatatcgag | gaggtgaaag | accagagcag | gaacaagggc | 540 |
| agctcagctg | tgcgagtgta | ccggatgctt | ccacctctca | ccaagaacca | gagaaaagaa | 600 |
| agaaagtcga | agtccagccg | agatgctaag | agcaaggcca | agaggaagtc | atgtgggat | 660 |
| tccagccctg | ataccttctc | tgatggactc | agcagctcca | ctctgcctga | tgaccacagc | 720 |
| agctacacag | ttccaggcta | catgcaggac | ttggaggtgg | agcaggccct | gactccagca | 780 |
| ctgtcgccat | gtgctgtcag | cagcactctc | ccgactggc | acatcccagt | ggaagttgtg | 840 |
| ccggacagca | ccagtgatct | gtacaacttc | caggtgtcac | ccatgccctc | cacctctgaa | 900 |
| gctacaacag | atgaggatga | ggaagggaaa | ttacctgagg | acatcatgaa | gctcttggag | 960 |
| cagtcggagt | ggcagccaac | aaacgtggat | gggaaggggt | acctactcaa | tgaacctgga | 1020 |
| gtccagccca | cctctgtcta | tggagacttt | agctgtaagg | aggagccaga | aattgacagc | 1080 |
| ccaggggggg | atattgggct | gagtctacag | cgtgtcttca | cagatctgaa | gaacatggat | 1140 |
| gccacctggc | tggacagcct | gctgacccca | gtccggttgc | cctccatcca | ggccattccc | 1200 |
| tgtgcaccgt | agcagggccc | ctgggcccct | cttattcctc | taggcaagca | ggacctggca | 1260 |
| tcatggtgga | tatggtgcag | agaagctgga | cttctgtggg | cccctcaaca | gccaagtgtg | 1320 |
| accccactgc | caagtgggga | tggggcctcc | ctccttgggt | cattgacctc | tcagggcctg | 1380 |
| gcaggccagt | gtctgggttt | tcttgtggt | gtaaagctgg | ccctgcctcc | tgggaagatg | 1440 |
| aggttctgag | accagtgtat | caggtcaggg | acttggacag | gagtcagtgt | ctggcttttt | 1500 |
| cctctgagcc | cagctgcctg | gagagggtct | cgctgtcact | ggctggctcc | tagggaaca | 1560 |
| gaccagtgac | cccagaaaag | cataacacca | atcccaggc | tggctctgca | ctaagagaaa | 1620 |
| attgcactaa | atgaatctcg | ttcccaaaga | actaccccct | tttcagctga | gccctgggga | 1680 |
| ctgttccaaa | gccagtgaaa | tgtgaaggaa | agtggggtcc | ttcggggcga | tgctccctca | 1740 |
| gcctcagagg | agctctaccc | tgctccctgc | tttggctgag | gggcttggga | aaaaaacttg | 1800 |
| gcactttttc | gtgtggatct | tgccacattt | ctgatcagag | gtgtacacta | acatttcccc | 1860 |
| cgagctcttg | gcctttgcat | ttatttatac | agtgccttgc | tcggcgccca | ccaccccctc | 1920 |
| aagcccagc | agccctcaac | aggcccaggg | agggaagtgt | gagcgccttg | gtatgactta | 1980 |
| aaattggaaa | tgtcatctaa | ccattaagtc | atgtgtgaac | acataaggac | gtgtgtaaat | 2040 |
| atgtacattt | gtcttttat | aaaaagtaaa | ttgtttataa | ggggtgtggc | cttttttagag | 2100 |
| agaaatttaa | cttgtagatg | attttacttt | ttatggaaac | actgatggac | ttattattgg | 2160 |

```
catcccgcct gaacttgact ttggggtgaa cagggacatg catctattat aaaatccttt      2220
cggccaggcg cggtggctca cacctgtaat cccagcactt tgggaggccg agatgggtgg      2280
atcacctgag gtcaggagtt cgagaccagc ctggtgaaac tccatttcta ctaaaaatgc      2340
aaaaattagc tgggcgtggt ggcgggtgct tgtaatccca gctactcagg aggctgaggc      2400
aagagaatcg cttgaacctg ggaggtggag gttgcagtga gccgagaaca tgccattgca      2460
ctccagcccg ggcaccaaaa aaaaaaaaa aaaaaaaac ctttcatttg gccgggcatg       2520
gtggcttatg cctgtaatcc tggcactttg ggaggccaag gtgggcagat cacctgaggt      2580
caggagtttg agaccagcct ggccaacatg gtgaaacctc atctctacta aaaatacaaa      2640
aattaggccg ggcacggtgg ctcacgcctg taatcccagc actttgggag gcagaggcgg      2700
gcggatcacg aggtcaggag atcaagacca tcctggctaa cacggtgaaa ccccgtctct      2760
actaaaaata taaaaaatta gccgggccta gtggcgggtg cctgtagtcc cagctactcg      2820
ggaggctgag gcaggagaat ggcatgaacc ccggaggcag agcttgcagt gagccgagat      2880
tgcaccactg cactacagcc tgggcgacag agcgagactc cgtctcaaaa aaaaaaaaa      2940 aaattagccg ggcctggtgg cgggcgcctg taatcccagc tactgtggag gctgaagcac      3000
aagaatcact tgaacccggg agatggaggt tgcagtgagc tgagactgtg ccactgcact      3060
ccagcctggg tgacaagagt gagactttgt ctcaaaaaaa aaaaaatcct tttgtttatg      3120
ttcacataga caatggcaga aggaggggac attcctgtca taggaacatg cttatataaa      3180
catagtcacc tgtccttgac tatcaccagg gctgtcagtt gattctgggc tcctggggcc      3240
caaggagtgt taagttttga ggcatgtgcc ataggtgatg tgtcctgcta acacacagat      3300
gctgctccaa aaagtcagtt gatatgcaca agtcacagac agaacagtca gcagcccaag      3360
aaaggtcctc acggctgctg tgctgggtag cacttgccat ccagtttcta gagtgatgaa      3420
atgctctgtc tgtaccgttc aatacagtag gcactggcac tagccacatg tgccagctaa      3480
gcacttgaaa tgtggccagt gcaataagga attgaacttt taattgcatt taataaactg      3540
tatgtaaata gtcaaaaaaa aaaaaaa                                          3567
```

<210> SEQ ID NO 29
<211> LENGTH: 2387
<212> TYPE: DNA
<213> ORGANISM: Homo sapiens

<400> SEQUENCE: 29

```
agacacctct gccctcacca tgagcctctg gcagcccctg gtcctggtgc tcctggtgct       60
gggctgctgc tttgctgccc ccagacagcg ccagtccacc cttgtgctct tccctggaga      120
cctgagaacc aatctcaccg acaggcagct ggcagaggaa tacctgtacc gctatggtta      180
cactcgggtg cagagatgc gtggagagtc gaaatctctg gggcctgcgc tgctgcttct      240
ccagaagcaa ctgtccctgc ccgagaccgg tgagctggat agcgccacgc tgaaggccat      300
gcgaacccca cggtgcgggg tcccagacct gggcagattc caaacctttg agggcgacct      360
caagtggcac caccacaaca tcacctattg gatccaaaac tactcggaag acttgccgcg      420
ggcggtgatt gacgacgcct ttgcccgcgc cttcgcactg tggagcgcgg tgacgccgct      480
caccttcact cgcgtgtaca gccgggacgc agacatcgtc atccagtttg tgtcgcgga       540 gcacggagac gggtatccct tcgacgggaa ggacgggctc ctggcacacg ccttttcctcc      600 tggccccggc attcagggag acgcccattt cgacgatgac gagttgtggt ccctgggcaa      660
```

```
gggcgtcgtg gttccaactc ggtttggaaa cgcagatggc gcggcctgcc acttcccctt    720
catcttcgag ggccgctcct actctgcctg caccaccgac ggtcgctccg acggcttgcc    780
ctggtgcagt accacggcca actacgacac cgacgaccgg tttggcttct gccccagcga    840
gagactctac acccaggacg gcaatgctga tgggaaaccc tgccagtttc cattcatctt    900
ccaaggccaa tcctactccg cctgcaccac ggacggtcgc tccgacggct accgctggtg    960
cgccaccacc gccaactacg accgggacaa gctcttcggc ttctgcccga cccgagctga   1020
ctcgacggtg atgggggca actcggcggg ggagctgtgc gtcttcccct tcactttcct   1080
gggtaaggag tactcgacct gtaccagcga ggggccgcgga gatgggcgcc tctggtgcgc   1140
taccacctcg aactttgaca gcgacaagaa gtggggcttc tgcccggacc aaggatacag   1200
tttgttcctc gtggcggcgc atgagttcgg ccacgcgctg gcttagatc attcctcagt    1260 gccggaggcg ctcatgtacc ctatgtaccg cttcactgag gggcccccct tgcataagga   1320
cgacgtgaat ggcatccggc acctctatgg tcctcgcct gaacctgagc cacggcctcc   1380
aaccaccacc acaccgcagc ccacggctcc ccgacggtc tgccccaccg accccccac    1440 tgtccacccc tcagagcgcc ccacagctgg ccccacaggt ccccctcag ctggccccac    1500 aggtccccc actgctggcc cttctacggc cactactgtg cctttgagtc cggtggacga   1560
tgcctgcaac gtgaacatct tcgacgccat cgcggagatt gggaaccagc tgtatttgtt   1620
caaggatggg aagtactggc gattctctga gggcaggggg agccggccgc agggcccctt   1680
ccttatcgcc gacaagtggc ccgcgctgcc ccgcaagctg gactcggtct ttgaggagcg   1740
gctctccaag aagcttttct tcttctctgg gcgccaggtg tgggtgtaca caggcgcgtc   1800
ggtgctgggc ccgaggcgtc tggacaagct gggcctggga gccgacgtgg cccaggtgac   1860
cggggccctc cggagtggca gggggaagat gctgctgttc agcgggcggc gcctctggag   1920
gttcgacgtg aaggcgcaga tggtggatcc ccggagcgcc agcgaggtgg accggatgtt   1980 cccccggggtg cctttggaca cgcacgacgt cttccagtac cgagagaaag cctatttctg   2040
ccaggaccgc ttctactggc gcgtgagttc ccggagtgag ttgaaccagg tggaccaagt   2100
gggctacgtg acctatgaca tcctgcagtg ccctgaggac tagggctccc gtcctgcttt   2160
ggcagtgcca tgtaaatccc cactgggacc aaccctgggg aaggagccag tttgccggat   2220
acaaactggt attctgttct ggaggaaagg gaggagtgga ggtgggctgg ccctctctt   2280 ctcacctttg ttttttgttg gagtgtttct aataaacttg gattctctaa ccttttaaaaa   2340 aaaaaaaaa aaaaaaaaa aaaaaaaaa aaaaaaaaa aaaaaaa                      2387
```

<210> SEQ ID NO 30
<211> LENGTH: 2379
<212> TYPE: DNA
<213> ORGANISM: Homo sapiens

<400> SEQUENCE: 30

```
gaccccccgag ctgtgctgct cgcggccgcc accgccgggc cccggccgtc cctggctccc     60
ctcctgcctc gagaagggca gggcttctca gaggcttggc gggaaaaaga acggagggag    120
ggatcgcgct gagtataaaa gccggttttc ggggctttat ctaactcgct gtagtaattc    180
cagcgagagg cagggagc gagcgggcgg ccggctaggt ggaagagcc gggcgagcag      240 agctgcgctg cgggcgtcct gggaaggag atcggagcg aataggggc ttcgcctctg      300 gcccagccct cccgctgatc ccccagccag cggtccgcaa cccttgccgc atccacgaaa    360
ctttgcccat agcagcgggc gggcactttg cactggaact tacaacaccc gagcaaggac    420
```

```
gcgactctcc cgacgcgggg aggctattct gcccatttgg ggacacttcc ccgccgctgc      480
caggacccgc ttctctgaaa ggctctcctt gcagctgctt agacgctgga ttttttttcgg     540 gtagtggaaa accagcagcc tcccgcgacg atgcccctca cgttagctt caccaacagg       600 aactatgacc tcgactacga ctcggtgcag ccgtatttct actgcgacga ggaggagaac      660
ttctaccagc agcagcagca gagcgagctg cagcccccgg cgcccagcga ggatatctgg      720
aagaaattcg agctgctgcc caccccgccc ctgtccccta gcgccgctc cgggctctgc       780 tcgccctcct acgttgcggt cacacccttc tcccttcggg gagacaacga cggcggtggc      840
gggagcttct ccacgccga ccagctggag atggtgaccg agctgctggg aggagacatg       900
gtgaaccaga gtttcatctg cgacccggac gacgagacct tcatcaaaaa catcatcatc     960
caggactgta tgtggagcgg cttctcggcc gccgccaagc tcgtctcaga gaagctggcc     1020
tcctaccagg ctgcgcgcaa agacagcggc agcccgaacc ccgcccgcgg ccacagcgtc     1080
tgctccacct ccagcttgta cctgcaggat ctgagcgccg ccgcctcaga gtgcatcgac     1140
ccctcggtgg tcttccccta ccctctcaac gacagcagct cgcccaagtc ctgcgcctcg     1200
caagactcca gcgccttctc tccgtcctcg gattctctgc tctcctcgac ggagtcctcc     1260
ccgcagggca gccccgagcc cctggtgctc catgaggaga caccgccac caccagcagc      1320 gactctgagg aggaacaaga agatgaggaa gaaatcgatg ttgtttctgt ggaaaagagg     1380
caggctcctg gcaaaaggtc agagtctgga tcaccttctg ctggaggcca cagcaaacct     1440
cctcacagcc cactggtcct caagaggtgc acgtctcca cacatcagca caactacgca      1500
gcgcctccct ccactcggaa ggactatcct gctgccaaga gggtcaagtt ggacagtgtc     1560
agagtcctga cacagatcag caacaaccga aaatgcacca gccccaggtc ctcggacacc     1620
gaggagaatg tcaagaggcg aacacacaac gtcttggagc gccagaggag gaacgagcta     1680
aaacggagct ttttgccct gcgtgaccag atccccgagt tggaaaacaa tgaaaaggcc      1740
cccaaggtag ttatccttaa aaaagccaca gcatacatcc tgtccgtcca agcagaggag     1800
caaaagctca tttctgaaga ggacttgttg cggaaacgac gagaacagtt gaaacacaaa     1860
cttgaacagc tacggaactc ttgtgcgtaa ggaaaagtaa ggaaaacgat tccttctaac     1920
agaaatgtcc tgagcaatca cctatgaact tgtttcaaat gcatgatcaa atgcaacctc     1980
acaaccttgg ctgagtcttg agactgaaag atttagccat aatgtaaact gcctcaaatt     2040
ggactttggg cataaaagaa cttttttatg cttaccatct tttttttttc tttaacagat     2100
ttgtatttaa gaattgtttt taaaaaattt taagatttac acaatgtttc tctgtaaata     2160
ttgccattaa atgtaaataa ctttaataaa acgtttatag cagttacaca gaatttcaat     2220
cctagtatat agtacctagt attataggta ctataaaccc taattttttt tatttaagta     2280
cattttgctt tttaaagttg attttttttct attgttttta gaaaaaataa aataactggc     2340
aaatatatca ttgagccaaa tcttaaaaaa aaaaaaaaa                            2379
```

<210> SEQ ID NO 31
<211> LENGTH: 3125
<212> TYPE: DNA
<213> ORGANISM: Homo sapiens

<400> SEQUENCE: 31

```
ccgcaaccag agccgccgcc acggtgagtg gctggattca gacccctggg tggccgggac       60
aagagaaaag agggaggagg gcctttagcg gacagcgcct ggggctggag agcagcagct      120
```

```
gcacacagcc ggaaagggcg cgcaggcgac gacactcgga tccacgtcga caccgttgta    180
caaagatacg cggacccgcg ggcgtctaaa attctgggaa gcagaacctg gccggagcca    240
ctagacagag ccgggcctag cccagagaca tggagagttg ctacaaccca ggtctggatg    300
gtattattga atatgatgat ttcaaattga actcctccat tgtggaaccc aaggagccag    360
ccccagaaac agctgatggc ccctacctgg tgatcgtgga acagcctaag cagagaggct    420
tccgatttcg atatggctgt gaaggcccct cccatggagg actgcccggt gcctccagtg    480
agaagggccg aaagacctat cccactgtca agatctgtaa ctacgaggga ccagccaaga    540
tcgaggtgga cctggtaaca cacagtgacc cacctcgtgc tcatgcccac agtctggtgg    600
gcaagcaatg ctcggagctg ggatctgcg  ccgtttctgt ggggcccaag gacatgactg    660
cccaatttaa caacctgggt gtcctgcatg tgactaagaa gaacatgatg gggactatga    720
tacaaaaact tcagaggcag cggctccgct ctaggcccca gggccttacg gaggccgagc    780
agcgggagct ggagcaagag gccaaagaac tgaagaaggt gatggatctg agtatagtgc    840
ggctgcgctt ctctgccttc cttagagcca gtgatggctc cttctccctg ccctgaagc    900 cagtcatctc ccagcccatc catgacagca atctccgggg gcatcaaac  ctgaagattt    960 ctcgaatgga caagacagca ggctctgtgc ggggtgagga tgaagtttat ctgctttgtg    1020
acaaggtgca gaaagatgac attgaggttc ggttctatga ggatgatgag aatggatggc    1080
aggcctttgg ggacttctct cccacagatg tgcataaaca gtatgccatt gtgttccgga    1140 cacccccta  tcacaagatg aagattgagc ggcctgtaac agtgtttctg caactgaaac    1200
gcaagcgagg aggggacgtg tctgattcca aacagttcac ctattaccct ctggtggaag    1260
acaaggaaga ggtgcagcgg aagcggagga aggccttgcc caccttctcc cagcccttcg    1320
ggggtggctc ccacatgggt ggaggctctg ggggtgcagc cggggctac  ggaggagctg    1380 gaggaggtgg cagcctcggt ttcttcccct cctccctggc ctacagcccc taccagtccg    1440
gcgcgggccc catgggctgc tacccgggag gcggggcgg  ggcgcagatg gccgccacgg    1500
tgcccagcag ggactccggg gaggaagccg cggagccgag cgcccccctcc aggaccccc    1560 agtgcgagcc gcaggccccg gagatgctgc agcgagctcg agagtacaac gcgcgcctgt    1620
tcggcctggc gcagcgcagc gcccgagccc tactcgacta cggcgtcacc gcggacgcgc    1680
gcgcgctgct ggcgggacag cgccacctgc tgacggcgca ggacgagaac ggagacacac    1740
cactgcacct agccatcatc cacgggcaga ccagtgtcat tgagcagata gtctatgtca    1800
tccaccacgc ccaggacctc ggcgttgtca acctcaccaa ccacctgcac cagacgcccc    1860
tgcacctggc ggtgatcacg gggcagacga gtgtggtgag ctttctgctg cgggtaggtg    1920
cagacccagc tctgctggat cggcatgag  actcagccat gcatctggcg ctgcgggcag    1980
gcgctggtgc tcctgagctg ctgcgtgcac tgcttcagag tggagctcct gctgtgcccc    2040
agctgttgca tatgcctgac tttgaggac  tgtatccagt acacctggcg gtccgagccc    2100
gaagccctga gtgcctggat ctgctggtgg acagtgggc  tgaagtggag ccacagagc    2160 ggcaggggg  acgaacagcc ttgcatctag ccacagagat ggaggagctg gggttggtca    2220
cccatctggt caccaagctc cgggccaacg tgaacgctcg cacctttgcg ggaaacacac    2280
ccctgcacct ggcagctgga ctggggtacc cgaccctcac ccgcctcctt ctgaaggctg    2340
gtgctgacat ccatgctgaa aacgaggagc cctgtgccc  actgccttca ccccctacct    2400
ctgatagcga ctcggactct gaagggcctg agaaggacac ccgaagcagc ttccggggcc    2460
acacgcctct tgacctcact tgcagcacca aggtgaagac cttgctgcta aatgctgctc    2520
```

| | |
|---|---:|
| agaacaccat ggagccaccc ctgaccccgc ccagcccagc agggccggga ctgtcacttg | 2580 |
| gtgatacagc tctgcagaac ctggagcagc tgctagacgg ccagaagcc cagggcagct | 2640 |
| gggcagagct ggcagagcgt ctggggctgc gcagcctggt agacacgtac cgacagacaa | 2700 |
| cctcacccag tggcagcctc ctgcgcagct acgagctggc tggcggggac ctggcaggtc | 2760 |
| tactggaggc cctgtctgac atgggcctag aggagggagt gaggctgctg aggggtccag | 2820 |
| aaacccgaga caagctgccc agcacagcag aggtgaagga agacagtgcg tacgggagcc | 2880 |
| agtcagtgga gcaggaggca gagaagctgg gcccacccc tgagccacca ggagggctct | 2940 |
| gccacgggca cccccagcct caggtgcact gacctgctgc ctgccccag ccccttccc | 3000 |
| ggaccccctg tacagcgtcc ccacctattt caaatcttat ttaacacccc acccaccc | 3060 |
| ctcagttggg acaaataaag gattctcatg ggaaggggag gacccctcct tcccaactta | 3120 |
| tggca | 3125 |

<210> SEQ ID NO 32
<211> LENGTH: 1579
<212> TYPE: DNA
<213> ORGANISM: Homo sapiens

<400> SEQUENCE: 32

| | |
|---|---:|
| agcccacagc agtccgtgcc gccgtcccgc ccgccagcgc cccagcgagg aagcagcgcg | 60 |
| cagcccgcgg cccagcgcac ccgcagcagc gcccgcagct cgtccgcgcc atgttccagg | 120 |
| cggccgagcg cccccaggag tgggccatgg agggccccg cgacgggctg aagaaggagc | 180 |
| ggctactgga cgaccgccac gacagcggcc tggactccat gaaagacgag gagtacgagc | 240 |
| agatggtcaa ggagctgcag gagatccgcc tcgagccgca ggaggtgccg cgcggctcgg | 300 |
| agccctggaa gcagcagctc accgaggacg gggactcgtt cctgcacttg gccatcatcc | 360 |
| atgaagaaaa ggcactgacc atggaagtga tccgccaggt gaagggagac ctggccttcc | 420 |
| tcaacttcca gaacaacctg cagcagactc cactccactt ggctgtgatc accaaccagc | 480 |
| cagaaattgc tgaggcactt ctgggagctg gctgtgatcc tgagctccga gactttcgag | 540 |
| gaaataccc cctacacctt gcctgtgagc agggctgcct ggccagcgtg ggagtcctga | 600 |
| ctcagtcctg caccaccccg cacctccact ccatcctgaa ggctaccaac tacaatggcc | 660 |
| acacgtgtct acacttagcc tctatccatg gctacctggg catcgtggag cttttggtgt | 720 |
| ccttgggtgc tgatgtcaat gctcaggagc cctgtaatgg ccggactgcc cttcacctcg | 780 |
| cagtggacct gcaaaatcct gacctggtgt cactcctgtt gaagtgtggg ctgatgtca | 840 |
| acagagttac ctaccagggc tattctccct accagctcac ctgggccgc caagcaccc | 900 |
| ggatacagca gcgctgggc cagctgacac tagaaaacct tcagatgctg ccagagagtg | 960 |
| aggatgagga gagctatgac acagagtcag agttcacgga gttcacagag gacgagctgc | 1020 |
| cctatgatga ctgtgtgttt ggaggccagc gtctgacgtt atgagcgcaa aggggctgaa | 1080 |
| agaacatgga cttgtatatt tgtacaaaaa aaaagttta ttttctaaa aaagaaaaa | 1140 |
| agaagaaaaa atttaaaggg tgtacttata tccacactgc acactgcctg gcccaaaacg | 1200 |
| tcttattgtg gtaggatcag ccctcatttt gttgcttttg tgaactttt gtaggggacg | 1260 |
| agaaagatca ttgaaattct gagaaaactt cttttaaacc tcacctttgt ggggttttg | 1320 |
| gagaaggtta tcaaaaattt catggaagga ccacatttta tatttattgt gcttcgagtg | 1380 |
| actgacccca gtggtatcct gtgacatgta acagccagga gtgttaagcg ttcagtgatg | 1440 |

```
tggggtgaaa agttactacc tgtcaaggtt tgtgttaccc tcctgtaaat ggtgtacata    1500
atgtattgtt ggtaattatt ttggtacttt tatgatgtat atttattaaa cagatttta     1560 caaatgaaaa aaaaaaaaa                                                 1579

<210> SEQ ID NO 33
<211> LENGTH: 2581
<212> TYPE: DNA
<213> ORGANISM: Homo sapiens

<400> SEQUENCE: 33
aatgaatgaa tgaatgaatg agtgaatgaa tcaacgaagg agtgagtcaa ggcccgggaa      60
ccacagactc caagcctacg cagagcccgg gaaggggat tccggagggg cggggcctct      120
ttccggaagc gcccgccggg ggcggggagg gggcggggcc atccgcgtga ggcgaccctg     180
ttggtccgga ggggcggggc gaggaggagg acccgcttgg gcggttcggc tgcccacagt    240
aaccgctggg tggacctggc cagcgctccg aaccttgtcc tcgctgcgcg ccggcccctc     300 ggagcccac agcccgggaa ggaggccgcc gcgggccggg cgcccgctct gccaagcgga      360
cccgcaaccc ggaaaggcgg cgcggcggag cctggagccg gatcctgctc agaccgggcc    420
ccggccggcc agagccgcgg gcatgtcgga ggcgcggaag gggccggacg aggcggagga    480
gagccagtac gactctggca ttgagtctct gcgctctctg cgctccctac ccgagtccac    540
ctcggctcca gcctccgggc cctcggacgg cagcccccag ccctgcaccc atcctccggg    600
acccgtcaag gaaccacagg agaaggaaga cgcggatggg gagcgggctg attccaccta    660
tggctcctcc tcgctcacct acaccctgtc cttgctgggg ggccccgagg ctgaggaccc    720
ggccccacgc ctgccactcc cccacgtggg ggcgctgagc cctcagcagc tggaagcact    780
cacttacatc tccgaggacg gagacacgct ggtccacctg gcagtgattc atgaggcccc    840
agcggtgctg ctctgttgcc tggctttgct gccccaggag gtcctggaca ttcaaaataa    900
cctttaccag acagcactcc atctggctgt acatctggac caaccgggcg cagttcgggc    960
actggtgctg aaggggccca gccgggcact acaggaccgg catggtgaca cagcccttca   1020
tgtggcctgc cagcgccagc acttggcctg tgcccgctgc ctgctggaag gcggccaga    1080 gccaggcaga ggaacatctc actctctgga cctccagctg caaaactggc aaggtctggc    1140
ttgtctccac attgccaccc ttcagaagaa ccaaccactc atggaattgc tgcttcggaa    1200
tggagctgac attgatgtgc aggagggcac cagtggtaag acagcgctgc acctggctgt    1260
ggaaacccaa gagcggggcc tggtacagtt cctgctccag gctggtgccc aggtagatgc    1320
ccgcatgctg aacgggtgca cacccctgca cctggcagct ggccggggtc tcatgggcat    1380
ctcatccact ctgtgcaagg cgggtgctga ctccctgctg cggaatgtgg aggatgagac    1440
gccccaggac ctgactgagg aatcccttgt ccttttgccc tttgatgacc tgaagatctc    1500
agggaaactg ctgctgtgta ccgactgaag ccaggcaggg tctgggatcc tcagggctcc    1560
acctctccat ctggaagccg gagccataac tgctgcagtt gggcccagg ctatgtgctc     1620 ttctggtgcc ctagggactg ctgtggccag agcctggggc cagccagtac agtcctgagc    1680
cgaggaggag ggactgcaag tggaagagag ccagtctgga aggaagagct ttccaggtgg    1740
acagggcttc ttggaagacc cccaaagccc caggtatcct gggtgaagcc tgtttgcctc    1800
tcttgaaaat ggcaggtgct cttgttttac ccatgttggg tcagcctgaa actgccaacc    1860
agtaggaagc atggactctc ctgagtgaga agagactgaa ataggagcaa gcagaaccct    1920
gagaggtgtc ccatcttatt gctgttgagg accctgaaac accgttgttt aaagacttca    1980
```

| | |
|---|---|
| cacagaaggc tctgaactga gccactgggg aagggaagtt tcagtaacat gacactaaaa | 2040 |
| tggcagagac gttaaaaaaa gttttccct tctagagctg ttttgcgcgc atgcatgtct | 2100 |
| gtgtgcattg gggcttttta gacaggcctg ccctgtgact tgtggtaga ggcagagaga | 2160 |
| aggaaattgt ccctgagca cggtagggcc ttgctgggtg gggtcagagg ccagtagttc | 2220 |
| caggcctttc tctgtgtcca gcacagaccc ttgtccttgc tgtggaaatg atgagggatg | 2280 |
| gagggacaag aggaagaatg agaggacaca cgccctggag ccctcaccac tgccctgggg | 2340 |
| gttgccatct ggaggagcct gggataagg gtaacccagg gaggctgggc acgagggagc | 2400 |
| tgactccacg tttttcccccc cgttcctcac cttcgagggc cctgctaggt caccctatg | 2460 |
| ctggcatgaa gagcatgggg caataaacca gcacagtctc tgaccacttg gagcgtctca | 2520 |
| tccagtgaga gagacagccg ttaaaagcat aaacatccaa ataaagatgc ctttccaagt | 2580 |
| t | 2581 |

```
<210> SEQ ID NO 34
<211> LENGTH: 4206
<212> TYPE: DNA
<213> ORGANISM: Homo sapiens

<400> SEQUENCE: 34
```

| | |
|---|---|
| ataactttgt agcgagtcga aaactgaggc tccggccgca gagaactcag cctcattcct | 60 |
| gctttaaaat ctctcggcca cctttgatga ggggactggg cagttctaga cagtcccgaa | 120 |
| gttctcaagg cacaggtctc ttcctggttt gactgtcctt accccgggga ggcagtgcag | 180 |
| ccagctgcaa gccccacagt gaagaacatc tgagctcaaa tccagataag tgacataagt | 240 |
| gacctgcttt gtaaagccat agagatggcc tgtccttgga aatttctgtt caagaccaaa | 300 |
| ttccaccagt atgcaatgaa tggggaaaaa gacatcaaca acaatgtgga gaaagccccc | 360 |
| tgtgccacct ccagtccagt gacacaggat gaccttcagt atcacaacct cagcaagcag | 420 |
| cagaatgagt ccccgcagcc cctcgtggag acgggaaaga gtctccaga atctctggtc | 480 |
| aagctggatg caaccccatt gtcctcccca cggcatgtga ggatcaaaaa ctggggcagc | 540 |
| gggatgactt tccaagacac acttcaccat aaggccaaag ggatttaac ttgcaggtcc | 600 |
| aaatcttgcc tggggtccat tatgactccc aaaagtttga ccagaggacc cagggacaag | 660 |
| cctaccccctc cagatgagct tctacctcaa gctatcgaat ttgtcaacca atattacggc | 720 |
| tccttcaaag aggcaaaaat agaggaacat ctggccaggg tggaagcggt aacaaaggag | 780 |
| atagaaacaa caggaaccta ccaactgacg ggagatgagc tcatcttcgc caccaagcag | 840 |
| gcctggcgca atgccccacg ctgcattggg aggatccagt ggtccaacct gcaggtcttc | 900 |
| gatgcccgca gctgttccac tgcccggaa atgtttgaac acatctgcag acacgtgcgt | 960 |
| tactccacca caatggcaa catcaggtcg gccatcaccg tgttccccca gcggagtgat | 1020 |
| ggcaagcacg acttccgggt gtggaatgct cagctcatcc gctatgctgg ctaccagatg | 1080 |
| ccagatggca gcatcagagg ggaccctgcc aacgtggaat tcactcagct gtgcatcgac | 1140 |
| ctgggctgga agcccaagta cggccgcttc gatgtggtcc ccctggtcct gcaggccaat | 1200 |
| ggccgtgacc ctgagctctt cgaaatccca cctgaccttg tgcttgaggt ggccatggaa | 1260 |
| catcccaaat acgagtggtt tcgggaactg gagctaaagt ggtacgccct gcctgcagtg | 1320 |
| gccaacatgc tgcttgaggt gggcggcctg gagttcccag ggtgcccctt caatggctgg | 1380 |
| tacatgggca cagagatcgg agtccgggac ttctgtgacg tccagcgcta caacatcctg | 1440 |

```
gaggaagtgg gcaggagaat gggcctggaa acgcacaagc tggcctcgct ctggaaagac     1500
caggctgtcg ttgagatcaa cattgctgtg ctccatagtt tccagaagca gaatgtgacc     1560
atcatggacc accactcggc tgcagaatcc ttcatgaagt acatgcagaa tgaataccgg     1620
tcccgtgggg gctgcccggc agactggatt tggctggtcc ctcccatgtc tgggagcatc     1680 accccgtgt ttcaccagga gatgctgaac tacgtcctgt ccccttttcta ctactatcag     1740 gtagaggcct ggaaaaccca tgtctggcag gacgagaagc ggagacccaa gagaagagag     1800
attccattga aagtcttggt caaagctgtg ctctttgcct gtatgctgat gcgcaagaca     1860
atggcgtccc gagtcagagt caccatcctc tttgcgacag agacaggaaa atcagaggcg     1920
ctggcctggg acctggggc cttattcagc tgtgccttca accccaaggt tgtctgcatg     1980
gataagtaca ggctgagctg cctggaggag aacggctgc tgttggtggt gaccagtacg     2040
tttggcaatg gagactgccc tggcaatgga gagaaactga gaaatcgct cttcatgctg     2100 aaagagctca acaacaaatt caggtacgct gtgtttggcc tcggctccag catgtaccct     2160
cggttctgcg cctttgctca tgacattgat cagaagctgt cccacctggg ggcctctcag     2220
ctcaccccga tgggagaagg ggatgagctc agtgggcagg aggacgcctt ccgcagctgg     2280
gccgtgcaaa ccttcaaggc agcctgtgag acgtttgatg tccgaggcaa acagcacatt     2340
cagatcccca gctctacac ctccaatgtg acctgggacc cgcaccacta caggctcgtg     2400
caggactcac agcctttgga cctcagcaaa gccctcagca gcatgcatgc caagaacgtg     2460
ttcaccatga ggctcaaatc tcggcagaat ctacaaagtc cgacatccag ccgtgccacc     2520
atcctggtgg aactctcctg tgaggatggc caaggcctga actacctgcc gggggagcac     2580
cttggggttt gcccaggcaa ccagccggcc ctggtccaag gtatcctgga gcgagtggtg     2640
gatgccccca cccccacca gacagtgcgc ctggaggccc tggatgagag tggcagctac     2700
tgggtcagtg acaagaggct gccccctgc tcactcagcc aggccctcac ctacttcctg     2760
gacatcacca cacccccaac ccagctgctg ctccaaaagc tggcccaggt ggccacagaa     2820
gagcctgaga cagagggct ggaggccctg tgccagccct cagagtacag caagtggaag     2880
ttcaccaaca gccccacatt cctggaggtg ctagaggagt ccccgtccct gcgggtgtct     2940
gctggcttcc tgcttttccca gctccccatt ctgaagccca ggttctactc catcagctcc     3000
tcccgggatc acacgccccac agagatccac ctgactgtgg ccgtggtcac ctaccacacc     3060
cgagatggcc agggtccct gcaccacggc gtctgcagca catggctcaa cagcctgaag     3120
ccccaagacc cagtgccctg ctttgtgcgg aatgccagcg gcttccacct ccccgaggat     3180
ccctcccatc cttgcatcct catcgggcct ggcacaggca tcgcgccctt ccgcagtttc     3240
tggcagcaac ggctccatga ctcccagcac aagggagtgc ggggaggccg catgaccttg     3300
gtgtttgggt gccgccgccc agatgaggac cacatctacc aggaggagat gctggagatg     3360
gcccagaagg gggtgctgca tgcggtgcac acagcctatt cccgcctgcc tggcaagccc     3420
aaggtctatg ttcaggacat cctgcggcag cagctggcca cgaggtgct ccgtgtgctc     3480 cacaaggagc caggccacct ctatgttgc ggggatgtgc gcatggcccg ggacgtggcc     3540
cacaccctga gcagctggt ggctgccaag ctgaaattga atgaggagca ggtcgaggac     3600
tatttctttc agctcaagag ccagaagcgc tatcacgaag atatctttgg tgctgtattt     3660
ccttacgagg cgaagaagga cagggtggcg gtgcagccca gcagcctgga gatgtcagcg     3720
ctctgagggc ctacaggagg ggttaaagct gccggcacag aacttaagga tggagccagc     3780
tctgcattat ctgaggtcac agggcctggg gagatggagg aaagtgatat ccccccagcct     3840
```

| | | | |
|---|---|---|---|
| caagtcttat | ttcctcaacg | ttgctcccca | tcaagcccttt tacttgacct cctaacaagt | 3900 |
| agcaccctgg | attgatcgga | gcctcctctc | tcaaactggg gcctccctgg tcccttggag | 3960 |
| acaaaatctt | aaatgccagg | cctggcaagt | gggtgaaaga tggaacttgc tgctgagtgc | 4020 |
| accacttcaa | gtgaccacca | ggaggtgcta | tcgcaccact gtgtatttaa ctgccttgtg | 4080 |
| tacagttatt | tatgcctctg | tatttaaaaa | actaacaccc agtctgttcc ccatggccac | 4140 |
| ttgggtcttc | cctgtatgat | tccttgatgg | agatatttac atgaattgca ttttacttta | 4200 |
| atcaca | | | | 4206 |

<210> SEQ ID NO 35
<211> LENGTH: 4507
<212> TYPE: DNA
<213> ORGANISM: Homo sapiens

<400> SEQUENCE: 35

| | | | |
|---|---|---|---|
| gaccaattgt | catacgactt | gcagtgagcg | tcaggagcac gtccaggaac tcctcagcag | 60 |
| cgcctccttc | agctccacag | ccagacgccc | tcagacagca aagcctaccc ccgcgccgcg | 120 |
| ccctgcccgc | cgctgcgatg | ctcgcccgcg | ccctgctgct gtgcgcggtc ctggcgctca | 180 |
| gccatacagc | aaatccttgc | tgttcccacc | catgtcaaaa ccgaggtgta tgtatgagtg | 240 |
| tgggatttga | ccagtataag | tgcgattgta | cccggacagg attctatgga gaaaactgct | 300 |
| caacaccgga | atttttgaca | gaataaaaat | tatttctgaa acccactcca aacacagtgc | 360 |
| actacatact | tacccacttc | aagggatttt | ggaacgttgt gaataacatt cccttccttc | 420 |
| gaaatgcaat | tatgagttat | gtgttgacat | ccagatcaca tttgattgac agtccaccaa | 480 |
| cttacaatgc | tgactatggc | tacaaaagct | gggaagcctt ctctaacctc tcctattata | 540 |
| ctagagccct | tcctcctgtg | cctgatgatt | gcccgactcc cttgggtgtc aaaggtaaaa | 600 |
| agcagcttcc | tgattcaaat | gagattgtgg | aaaaattgct tctaagaaga aagttcatcc | 660 |
| ctgatcccca | gggctcaaac | atgatgtttg | cattctttgc ccagcacttc acgcatcagt | 720 |
| ttttcaagac | agatcataag | cgagggccag | cttttcaccaa cgggctgggc catggggtgg | 780 |
| acttaaatca | tatttacggt | gaaactctgg | ctagacagcg taaactgcgc cttttcaagg | 840 |
| atggaaaaat | gaaatatcag | ataattgatg | gagagatgta tcctcccaca gtcaaagata | 900 |
| ctcaggcaga | gatgatctac | cctcctcaag | tccctgagca tctacggttt gctgtggggc | 960 |
| aggaggtctt | tggtctggtg | cctggtctga | tgatgtatgc cacaatctgg ctgcgggaac | 1020 |
| acaacagagt | atgcgatgtg | cttaaacagg | agcatcctga tggggtgat gagcagttgt | 1080 |
| tccagacaag | caggctaata | ctgataggag | agactattaa gattgtgatt gaagattatg | 1140 |
| tgcaacactt | gagtggctat | cacttcaaac | tgaaatttga cccagaacta cttttcaaca | 1200 |
| aacaattcca | gtaccaaaat | cgtattgctg | ctgaatttaa caccctctat cactggcatc | 1260 |
| cccttctgcc | tgacaccttt | caaattcatg | accagaaata caactatcaa cagtttatct | 1320 |
| acaacaactc | tatattgctg | gaacatggaa | ttacccagtt tgttgaatca ttcaccaggc | 1380 |
| aaattgctgg | cagggttgct | ggtggtagga | atgttccacc cgcagtacag aaagtatcac | 1440 |
| aggcttccat | tgaccagagc | aggcagatga | ataccagtc ttttaatgag taccgcaaac | 1500 |
| gctttatgct | gaagccctat | gaatcatttg | aagaacttac aggagaaaag gaaatgtctg | 1560 |
| cagagttgga | agcactctat | ggtgacatcg | atgctgtgga gctgtatcct gcccttctgg | 1620 |
| tagaaaagcc | tcggccagat | gccatctttg | gtgaaaccat ggtagaagtt ggagcaccat | 1680 |

```
tctccttgaa aggacttatg ggtaatgtta tatgttctcc tgcctactgg aagccaagca   1740
cttttggtgg agaagtgggt tttcaaatca tcaacactgc ctcaattcag tctctcatct   1800
gcaataacgt gaagggctgt cccttactt cattcagtgt tccagatcca gagctcatta   1860
aaacagtcac catcaatgca agttcttccc gctccggact agatgatatc aatcccacag   1920
tactactaaa agaacgttcg actgaactgt agaagtctaa tgatcatatt tatttattta   1980
tatgaaccat gtctattaat ttaattattt aataatattt atattaaact ccttatgtta   2040
cttaacatct tctgtaacag aagtcagtac tcctgttgcg gagaaaggag tcatacttgt   2100
gaagactttt atgtcactac tctaaagatt ttgctgttgc tgttaagttt ggaaaacagt   2160
ttttattctg ttttataaac cagagagaaa tgagttttga cgtctttta cttgaatttc   2220 aacttatatt ataagaacga aagtaaagat gtttgaatac ttaaacactg tcacaagatg   2280
gcaaaatgct gaaagttttt acactgtcga tgtttccaat gcatcttcca tgatgcatta   2340
gaagtaacta atgtttgaaa ttttaaagta cttttggtta tttttctgtc atcaaacaaa   2400
aacaggtatc agtgcattat taaatgaata tttaaattag acattaccag taatttcatg   2460 tctactttt aaaatcagca atgaaacaat aatttgaaat ttctaaattc atagggtaga   2520
atcacctgta aaagcttgtt tgatttctta aagttattaa acttgtacat ataccaaaaa   2580
gaagctgtct tggatttaaa tctgtaaaat cagtagaaat tttactacaa ttgcttgtta   2640
aaatatttta taagtgatgt tcctttttca ccaagagtat aaacctttt agtgtgactg   2700 ttaaaacttc cttttaaatc aaaatgccaa atttattaag gtggtggagc cactgcagtg   2760
ttatcttaaa ataagaatat tttgttgaga tattccagaa tttgtttata tggctggtaa   2820
catgtaaaat ctatatcagc aaaagggtct accttaaaa taagcaataa caaagaagaa   2880
aaccaaatta ttgttcaaat ttaggtttaa acttttgaag caaacttttt tttatccttg   2940
tgcactgcag gcctggtact cagattttgc tatgaggtta atgaagtacc aagctgtgct   3000
tgaataatga tatgttttct cagattttct gttgtacagt ttaatttagc agtccatatc   3060
acattgcaaa agtagcaatg acctcataaa atacctcttc aaaatgctta aattcatttc   3120
acacattaat tttatctcag tcttgaagcc aattcagtag gtgcattgga atcaagcctg   3180
gctacctgca tgctgttcct tttcttttct tcttttagcc attttgctaa gagacacagt   3240
cttctcatca cttcgtttct cctattttgt tttactagtt ttaagatcag agttcacttt   3300
ctttggactc tgcctatatt ttcttacctg aacttttgca agttttcagg taaacctcag   3360
ctcaggactg ctatttagct cctcttaaga agattaaaag agaaaaaaa aggcccttt   3420 aaaaatagta tacacttatt ttaagtgaaa agcagagaat tttatttata gctaatttta   3480
gctatctgta accaagatgg atgcaaagag gctagtgcct cagagagaac tgtacggggt   3540
ttgtgactgg aaaaagttac gttcccattc taattaatgc cctttcttat ttaaaaacaa   3600
aaccaaatga tatctaagta gttctcagca ataataataa tgacgataat acttcttttc   3660
cacatctcat tgtcactgac atttaatggt actgtatatt acttaattta ttgaagatta   3720
ttatttatgt cttattagga cactatggtt ataaactgtg tttaagccta caatcattga   3780
tttttttttg ttatgtcaca atcagtatat tttcttggg gttacctctc tgaatattat   3840
gtaaacaatc caagaaatg attgtattaa gatttgtgaa taaattttta gaaatctgat   3900 tgcatattg agatatttaa ggttgaatgt ttgtccttag ataggccta tgtgctagcc   3960 cacaaagaat attgtctcat tagcctgaat gtgcctaaag actgaccttt taaaatgttt   4020
tgagggatct gtggatgctt cgttaatttg ttcagccaca atttattgag aaaatattct   4080
```

```
gtgtcaagca ctgtgggttt taatattttt aaatcaaacg ctgattacag ataatagtat    4140
ttatataaat aattgaaaaa aattttcttt tgggaagagg gagaaaatga aataaatatc    4200
attaaagata actcaggaga atcttcttta caattttacg tttagaatgt ttaaggttaa    4260
gaaagaaata gtcaatatgc ttgtataaaa cactgttcac tgtttttttt aaaaaaaaaa    4320
cttgatttgt tattaacatt gatctgctga caaaacctgg gaatttgggt tgtgtatgcg    4380
aatgtttcag tgcctcagac aaatgtgtat ttaacttatg taaaagataa gtctggaaat    4440
aaatgtctgt ttatttttgt actatttaaa aattgacaga tcttttctga agaaaaaaaa    4500
aaaaaaa                                                               4507

<210> SEQ ID NO 36
<211> LENGTH: 3875
<212> TYPE: DNA
<213> ORGANISM: Homo sapiens

<400> SEQUENCE: 36
agctgttctt ggctgacttc acatcaaaac tcctatactg acctgagaca gaggcagcag      60
tgatacccac ctgagagatc ctgtgtttga caactgcttt cccaaaacgg aaagtatttc     120
aagcctaaac ctttgggtga aaagaactct tgaagtcatg attgcttcac agtttctctc     180
agctctcact ttggtgcttc tcattaaaga gagtggagcc tggtcttaca cacctccac     240 ggaagctatg acttatgatg aggccagtgc ttattgtcag caaaggtaca cacacctggt     300
tgcaattcaa acaaagaag agattgagta cctaaactcc atattgagct attcaccaag     360
ttattactgg attggaatca gaaaagtcaa caatgtgtgg gtctgggtag gaacccagaa     420
acctctgaca gaagaagcca agaactgggc tccaggtgaa cccaacaata ggcaaaaaga     480
tgaggactgc gtggagatct acatcaagag agaaaaagat gtgggcatgt ggaatgatga     540
gaggtgcagc aagaagaagc ttgccctatg ctacacagct gcctgtacca atacatcctg     600
cagtggccac ggtgaatgtg tagagaccat caataattac acttgcaagt gtgaccctgg     660
cttcagtgga ctcaagtgtg agcaaattgt gaactgtaca gccctggaat cccctgagca     720
tggaagcctg gtttgcagtc acccactggg aaacttcagc tacaattctt cctgctctat     780
cagctgtgat aggggttacc tgccaagcag catggagacc atgcagtgta tgtcctctgg     840
agaatggagt gctcctattc cagcctgcaa tgtggttgag tgtgatgctg tgacaaatcc     900
agccaatggg ttcgtggaat gtttccaaaa ccctggaagc ttcccatgga acacaacctg     960
tacatttgac tgtgaagaag gatttgaact aatgggagcc cagagccttc agtgtaccct    1020
atctgggaat tgggacaacg agaagccaac gtgtaaagct gtgacatgca gggccgtccg    1080
ccagcctcag aatggctctg tgaggtgcag ccattcccct gctggagagt tcaccttcaa    1140
atcatcctgc aacttcacct gtgaggaagg cttcatgttg caggaccag cccaggttga    1200 atgcaccact caagggcagt ggacacagca atcccagtt tgtgaagctt ccagtgcac    1260 agccttgtcc aaccccgagc gaggctacat gaattgtctt cctagtgctt ctggcagttt    1320
ccgttatggg tccagctgtg agttctcctg tgagcagggt tttgtgttga gggatccaa    1380 aaggctccaa tgtggcccca gggagtg ggacaacaga aagcccacat gtgaagctgt    1440
gagatgcgat gctgtccacc agcccccgaa gggtttggtg aggtgtgctc attccctat    1500 tggagaattc acctacaagt cctcttgtgc cttcagctgt gaggaggat ttgaattaca    1560 tggatcaact caacttgagt gcacatctca gggacaatgg acagaagagg ttccttcctg    1620
```

```
ccaagtggta aaatgttcaa gcctggcagt tccgggaaag atcaacatga gctgcagtgg      1680
ggagcccgtg tttggcactg tgtgcaagtt cgcctgtcct gaaggatgga cgctcaatgg      1740
ctctgcagct cggacatgtg gagccacagg acactggtct ggcctgctac ctacctgtga      1800
agctcccact gagtccaaca ttcccttggt agctggactt tctgctgctg gactctccct      1860
cctgacatta gcaccatttc tcctctggct tcggaaatgc ttacggaaag caaagaaatt      1920
tgttcctgcc agcagctgcc aaagccttga atcagatgga agctaccaaa agccttctta      1980
catcctttaa gttcaaaaga atcagaaaca ggtgcatctg gggaactaga gggatacact      2040
gaagttaaca gagacagata actctcctcg ggtctctggc ccttcttgcc tactatgcca      2100
gatgccttta tggctgaaac cgcaacaccc atcaccactt caatagatca aagtccagca      2160
ggcaaggacg gccttcaact gaaaagactc agtgttccct ttcctactct caggatcaag      2220
aaagtgttgg ctaatgaagg gaaaggatat tttcttccaa gcaaaggtga agagaccaag      2280
actctgaaat ctcagaattc cttttctaac tctcccttgc tcgctgtaaa atcttggcac      2340
agaaacacaa tattttgtgg ctttctttct tttgcccttc acagtgtttc gacagctgat      2400
tacacagttg ctgtcataag aatgaataat aattatccag agtttagagg aaaaaaatga      2460
ctaaaaatat tataacttaa aaaaatgaca gatgttgaat gcccacaggc aaatgcatgg      2520
agggttgtta atggtgcaaa tcctactgaa tgctctgtgc gagggttact atgcacaatt      2580
taatcacttt catccctatg ggattcagtg cttcttaaag agttcttaag gattgtgata      2640 ttttacttg cattgaatat attataatct tccatacttc ttcattcaat acaagtgtgg      2700
tagggactta aaaaacttgt aaatgctgtc aactatgata tggtaaaagt tacttattct      2760
agattacccc ctcattgttt attaacaaat tatgttacat ctgttttaaa tttatttcaa      2820
aaagggaaac tattgtcccc tagcaaggca tgatgttaac cagaataaag ttctgagtgt      2880
ttttactaca gttgtttttt gaaaacatgg tagaattgga gagtaaaaac tgaatggaag      2940
gtttgtatat tgtcagatat ttttttcagaa atatgtggtt tccacgatga aaaacttcca      3000
tgaggccaaa cgttttgaac taataaaagc ataaatgcaa acacacaaag gtataatttt      3060
atgaatgtct ttgttggaaa agaatacaga aagatggatg tgctttgcat tcctacaaag      3120
atgtttgtca gatatgatat gtaaacataa ttcttgtata ttatggaaga ttttaaattc      3180
acaatagaaa ctcaccatgt aaaagagtca tctggtagat ttttaacgaa tgaagatgtc      3240
taatagttat tccctatttg ttttcttctg tatgttaggg tgctctggaa gagaggaatg      3300
cctgtgtgag caagcattta tgtttattta taagcagatt taacaattcc aaaggaatct      3360
ccagttttca gttgatcact ggcaatgaaa aattctcagt cagtaattgc caaagctgct      3420
ctagccttga gggagtgtgag aatcaaaact ctcctacact tccattaact tagcatgtgt      3480
tgaaaaaaaa gtttcagaga agttctggct gaacactggc aacaacaaag ccaacagtca      3540
aaacagagat gtgataagga tcagaacagc agaggttctt ttaaagggc agaaaaactc      3600 tgggaaataa gagagaacaa ctactgtgat caggctatgt atggaataca gtgttatttt      3660
ctttgaaatt gtttaagtgt tgtaaatatt tatgtaaact gcattagaaa ttagctgtgt      3720
gaaataccag tgtggtttgt gtttgagttt tattgagaat tttaaattat aacttaaaat      3780
attttataat tttttaaagta tatatttatt taagcttatg tcagacctat ttgacataac      3840
actataaagg ttgacaataa atgtgcttat gttta                                3875

<210> SEQ ID NO 37
<211> LENGTH: 1593
```

```
<212> TYPE: DNA
<213> ORGANISM: Homo sapiens

<400> SEQUENCE: 37
gcggtgccct tgcggcgcag ctggggtcgc ggccctgctc cccgcgcttt cttaaggccc    60
gcgggcggcg caggagcggc actcgtggct gtggtggctt cggcagcggc ttcagcagat   120
cggcggcatc agcggtagca ccagcactag cagcatgttg agccgggcag tgtgcggcac   180
cagcaggcag ctggctccgg ttttggggta tctgggctcc aggcagaagc acagcctccc   240
cgacctgccc tacgactacg cgccctgga acctcacatc aacgcgcaga tcatgcagct   300
gcaccacagc aagcaccacg cggcctacgt gaacaacctg aacgtcaccg aggagaagta   360
ccaggaggcg ttggccaagg gagatgttac agcccagata gctcttcagc ctgcactgaa   420
gttcaatggt ggtggtcata tcaatcatag cattttctgg acaaacctca gccctaacgg   480
tggtggagaa cccaaagggg agttgctgga agccatcaaa cgtgactttg gttcctttga   540
caagtttaag gagaagctga cggctgcatc tgttggtgtc caaggctcag gttgggttg   600 gcttggtttc aataaggaac ggggacactt acaaattgct gcttgtccaa atcaggatcc   660
actgcaagga acaacaggcc ttattccact gctggggatt gatgtgtggg agcacgctta   720
ctaccttcag tataaaaatg tcaggcctga ttatctaaaa gctatttgga atgtaatcaa   780
ctgggagaat gtaactgaaa gatacatggc ttgcaaaaag taaaccacga tcgttatgct   840
gagtatgtta agctctttat gactgttttt gtagtggtat agagtactgc agaatacagt   900
aagctgctct attgtagcat ttcttgatgt tgcttagtca cttatttcat aaacaactta   960
atgttctgaa taatttctta ctaaacattt tgttattggg caagtgattg aaaatagtaa  1020
atgctttgtg tgattgaatc tgattggaca ttttcttcag agagctaaat tacaattgtc  1080
atttataaaa ccatcaaaaa tattccatcc atatactttg gggacttgta gggatgcctt  1140
tctagtccta ttctattgca gttatagaaa atctagtctt ttgccccagt tacttaaaaa  1200
taaaatatta acactttccc aagggaaaca ctcggctttc tatagaaaat tgcacttttt  1260
gtcgagtaat cctctgcagt gatacttctg gtagatgtca cccagtggtt tttgttaggt  1320
caaatgttcc tgtatagttt ttgcaaatag agctgtatac tgtttaaatg tagcaggtga  1380
actgaactgg ggtttgctca cctgcacagt aaaggcaaac ttcaacagca aaactgcaaa  1440
aaggtggttt ttgcagtagg agaaaggagg atgtttattt gcagggcgcc aagcaaggag  1500
aattgggcag ctcatgcttg agacccaatc tccatgatga cctacaagct agagtattta  1560
aaggcagtgg taaatttcag gaaagcagaa gtt                               1593

<210> SEQ ID NO 38
<211> LENGTH: 4314
<212> TYPE: DNA
<213> ORGANISM: Homo sapiens

<400> SEQUENCE: 38
agacaggata ttcactgctg tggcaaggcc tgtagagagt ttcgaagtta ggaggactca    60
agacggtccc tccctggact tttctgaagg ggctcaaaag atgacacgcg ccagagctgg   120
aaggcgtcgc caattggtcc acttttccct cctcccttt tgcggatgag aaaactgagg   180
cccaggtttg ggattccag agcccgggat ttcccggcaa cgcccgacaa ccacattccc   240
ccggctattc tgacccgccc cggttccggg acgctccctg ggagccgccg ccgagggcct   300
gctgggactc ccgggggacc ccgccgtcgg ggcagccccc acgcccggcg ccgcccgccg   360
```

```
ggaacggccg ccgctgttgc gcacttgcag gggagccggc gactgagggc gaggcaggga    420
gggagcaagc ggggctggga gggctgctgg cgcgggctcg cgcgctgtgt atggtctatc    480
gcaggcagct gacctttgag gaggaaatcg ctgctctccg ctccttcctg tagtaacagc    540
cgccgctgcc gccgccgcca ggaaccccgg ccgggagcga gagccgcggg gcgcagagcc    600
ggcccggctg ccggacggtg cggccccacc aggtgaacgg ccatggcggg ctggatccag    660
gcccagcagc tgcagggaga cgcgctgcgc cagatgcagg tgctgtacgg ccagcacttc    720
cccatcgagg tccggcacta cttggcccag tggattgaga gccagccatg ggatgccatt    780
gacttggaca atccccagga cagagcccaa gccacccagc tcctggaggg cctggtgcag    840
gagctgcaga agaaggcgga gcaccaggtg ggggaagatg ggttttttact gaagatcaag    900 ctggggcact acgccacgca gctccagaaa acatatgacc gctgccccct ggagctggtc    960
cgctgcatcc ggcacattct gtacaatgaa cagaggctgg tccgagaagc caacaattgc   1020
agctctccgg ctgggatcct ggttgacgcc atgtcccaga agcaccttca gatcaaccag   1080
acatttgagg agctgcgact ggtcacgcag gacacagaga atgagctgaa gaaactgcag   1140
cagactcagg agtacttcat catccagtac caggagagcc tgaggatcca agctcagttt   1200
gcccagctgg cccagctgag cccccaggag cgtctgagcc gggagacggc cctccagcag   1260
aagcaggtgt ctctggaggc ctggttgcag cgtgaggcac agacactgca gcagtaccgc   1320
gtggagctgg ccgagaagca ccagaagacc ctgcagctgc tgcggaagca gcagaccatc   1380
atcctggatg acgagctgat ccagtggaag cggcggcagc agctggccgg gaacggcggg   1440 cccccccgagg gcagcctgga cgtgctacag tcctggtgtg agaagttggc cgagatcatc   1500
tggcagaacc ggcagcagat ccgcagggct gagcacctct gccagcagct gcccatcccc   1560
ggcccagtgg aggagatgct ggccgaggtc aacgccacca tcacggacat tatctcagcc   1620
ctggtgacca gcacattcat cattgagaag cagcctcctc aggtcctgaa gacccagacc   1680
aagtttgcag ccaccgtacg cctgctggtg ggcgggaagc tgaacgtgca catgaatccc   1740
ccccaggtga aggccaccat catcagtgag cagcaggcca agtctctgct taaaaatgag   1800
aacacccgca acgagtgcag tggtgagatc ctgaacaact gctgcgtgat ggagtaccac   1860
caagccacgg gcaccctcag tgcccacttc aggaacatgt cactgaagag gatcaagcgt   1920
gctgaccggc ggggtgcaga gtccgtgaca gaggagaagt tcacagtcct gtttgagtct   1980
cagttcagtg ttggcagcaa tgagcttgtg ttccaggtga agactctgtc cctacctgtg   2040
gttgtcatcg tccacggcag ccaggaccac aatgccacgg ctactgtgct gtgggacaat   2100
gcctttgctg agccgggcag ggtgccattt gccgtgcctg acaaagtgct gtggccgcag   2160
ctgtgtgagg cgctcaacat gaaattcaag gccgaagtgc agagcaaccg gggcctgacc   2220
aaggagaacc tcgtgttcct ggcgcagaaa ctgttcaaca acagcagcag ccacctggag   2280
gactacagtg gcctgtccgt gtcctggtcc cagttcaaca gggagaactt gccgggctgg   2340
aactacacct tctggcagtg gtttgacggg gtgatggagg tgttgaagaa gcaccacaag   2400
ccccactgga atgatggggc catcctaggt tttgtgaata agcaacaggc ccacgacctg   2460
ctcatcaaca agcccgacgg gaccttcttg ttgcgcttta gtgactcaga aatcgggggc   2520
atcaccatcg cctggaagtt tgactccccg gaacgcaacc tgtggaacct gaaaccattc   2580
accacgcggg atttctccat caggtccctg gctgaccggc tgggggacct gagctatctc   2640
atctatgtgt ttcctgaccg cccccaaggat gaggtcttct ccaagtacta cactcctgtg   2700
ctggctaaag ctgttgatgg atatgtgaaa ccacagatca agcaagtggt ccctgagttt   2760
```

```
gtgaatgcat ctgcagatgc tgggggcagc agcgccacgt acatggacca ggcccctcc      2820 ccagctgtgt gcccccaggc tccctataac atgtacccac agaaccctga ccatgtactc     2880
gatcaggatg gagaattcga cctggatgag accatggatg tggccaggca cgtggaggaa     2940
ctcttacgcc gaccaatgga cagtcttgac tcccgcctct cgcccctgc cggtcttttc     3000 acctctgcca gaggctccct ctcatgaatg tttgaatccc acgcttctct ttggaaacaa     3060
tatgcaatgt gaagcggtcg tgttgtgagt ttagtaaggc tgtgtacact gacacctttg     3120
caggcatgca tgtgcttgtg tgtgtgtgtg tgtgtgtgtc cttgtgcatg agctacgcct     3180
gcctcccctg tgcagtcctg ggatgtggct gcagcagcgg tggcctcttt tcagatcatg     3240
gcatccaaga gtgcgccgag tctgtctctg tcatggtaga gaccgagcct ctgtcactgc     3300
aggcactcaa tgcagccaga cctattcctc ctgggcccct catctgctca gcagctattt     3360
gaatgagatg attcagaagg ggaggggaga caggtaacgt ctgtaagctg aagtttcact     3420
ccggagtgag aagctttgcc ctcctaagag agagagacag agagacagag agagagaaag     3480
agagagtgtg tgggtctatg taaatgcatc tgtcctcatg tgttgatgta accgattcat     3540
ctctcagaag ggaggctggg gttcattttc gagtagtatt ttatacttta gtgaacgtgg     3600
actccagact ctctgtgaac cctatgagag cgcgtctggg cccggccatg tccttagcac     3660 agggggggccg ccggtttgag tgagggtttc tgagctgctc tgaattagtc cttgcttggc     3720
tgcttggcct tgggcttcat tcaagtctat gatgctgttg cccacgtttc ccgggatata     3780
tattctctcc cctccgttgg gccccagcct tctttgcttg cctctctgtt tgtaaccttg     3840
tcgacaaaga ggtagaaaag attgggtcta ggatatggtg ggtggacagg ggccccggga     3900
cttggagggt tggtcctctt gcctcctgga aaaacaaaa acaaaaaact gcagtgaaag     3960
acaagctgca aatcagccat gtgctgcgtg cctgtggaat ctggagtgag gggtaaaagc     4020
tgatctggtt tgactccgct ggaggtgggg cctggagcag gccttgcgct gttgcgtaac     4080
tggctgtgtt ctggtgaggc cttgctccca accccacacg ctcctccctc tgaggctgta     4140
ggactcgcag tcaggggcag ctgaccatgg aagattgaga gcccaaggtt taaacttctc     4200
tgaagggagg tggggatgag aagagggggtt tttttgtact ttgtacaaag accacacatt     4260
tgtgtaaaca gtgttttgga ataaatatt tttttcataa aaaaaaaaa aaaa             4314
```

<210> SEQ ID NO 39
<211> LENGTH: 1686
<212> TYPE: DNA
<213> ORGANISM: Homo sapiens

<400> SEQUENCE: 39

```
cagacgctcc ctcagcaagg acagcagagg accagctaag agggagagaa gcaactacag       60
accccccctg aaaacaaccc tcagacgcca catccctga caagctgcca ggcaggttct       120
cttcctctca catactgacc cacggctcca ccctctctcc cctggaaagg acaccatgag      180
cactgaaagc atgatccggg acgtggagct ggccgaggag gcgctcccca agaagacagg      240
ggggccccag ggctccaggc ggtgcttgtt cctcagcctc ttctccttcc tgatcgtggc      300
aggcgccacc acgtcttct gcctgctgca ctttggagtt atcggcccc agaggaaga       360 gttcccagg gacctctctc taatcagccc tctgcccag gcagtcagat catcttctcg       420
aaccccgagt gacaagcctg tagcccatgt tgtagcaaac cctcaagctg aggggcagct      480
ccagtggctg aaccgccggg ccaatgccct cctggccaat ggcgtggagc tgagagataa     540
```

```
ccagctggtg gtgccatcag agggcctgta cctcatctac tcccaggtcc tcttcaaggg      600
ccaaggctgc ccctccaccc atgtgctcct cacccacacc atcagccgca tcgccgtctc      660
ctaccagacc aaggtcaacc tcctctctgc catcaagagc cctgccaga gggagacccc       720 agaggggct gaggccaagc cctggtatga gcccatctat ctgggagggg tcttccagct       780 ggagaaggt gaccgactca gcgctgagat caatcggccc gactatctcg actttgccga       840
gtctgggcag gtctactttg ggatcattgc cctgtgagga ggacgaacat ccaaccttcc      900
caaacgcctc ccctgcccca atccctttat taccccctcc ttcagacacc ctcaacctct      960
tctggctcaa aaagagaatt gggggcttag ggtcggaacc caagcttaga actttaagca     1020
acaagaccac cacttcgaaa cctgggattc aggaatgtgt ggcctgcaca gtgaagtgct     1080
ggcaaccact aagaattcaa actggggcct ccagaactca ctggggccta cagctttgat     1140
ccctgacatc tggaatctgg agaccaggga gcctttggtt ctggccagaa tgctgcagga     1200
cttgagaaga cctcacctag aaattgacac aagtggacct taggccttcc tctctccaga     1260
tgtttccaga cttccttgag acacggagcc cagccctccc catggagcca gctccctcta     1320
tttatgtttg cacttgtgat tatttattat ttatttatta tttatttatt tacagatgaa     1380
tgtatttatt tgggagaccg gggtatcctg ggggacccaa tgtaggagct gccttggctc     1440
agacatgttt tccgtgaaaa cggagctgaa caataggctg ttcccatgta gcccctggc     1500 ctctgtgcct tcttttgatt atgttttttta aaatatttat ctgattaagt tgtctaaaca    1560
atgctgattt ggtgaccaac tgtcactcat tgctgagcct ctgctcccca ggggagttgt     1620
gtctgtaatc gccctactat tcagtggcga gaaataaagt ttgcttagaa agaaaaaaaa     1680
aaaaaa                                                                1686

<210> SEQ ID NO 40
<211> LENGTH: 4180
<212> TYPE: DNA
<213> ORGANISM: Homo sapiens

<400> SEQUENCE: 40
ccagggtgat gctgaagatg atgaccttct tccaaggcct ctagagccat cagcctgtgc       60
caggcaccct cgacttgcct agaggccccc aaaagttgca gtccacatca gaggcagagt      120
cagaggcctc catgtcggag gcctcctctg aggacctggt gccaccctg gagggtgggg        180 cagccccata tagggaggag gaagaggcgg cgaagaagaa gaaggagaag aagaagaagt      240
ccaaaggcct ggccaatgtg ttctgcgtct tcaccaaagg gaagaagaag aagggtcagc      300
ccagctcagc ggagcccgag gacgcagccg ggtccaggca ggggctggat ggcccgcccc      360
ccacagtgga ggagctgaag gcggcgctgg agcgcgggca gctggaggcg gcgcggccgc      420
tgctggcgct ggagcgggag ctggcggcgg cggcggcgga gggcggtgtg agcgaggagg      480
agctggtgcg gcgccagagc aaggtggagg cgctgtacga gctgctgcgc gaccaggtgc      540
tgggcgtgct gcgcggccg ctggaggcgc gcccgagcg gctgcgccag cgctggccg         600 tggtggcgga gcaggagcgc gaggaccgcc aggcggcggc ggcggggccg ggacctcgg       660 ggctggcggc cacgcgcccg cggcgctggc tgcagctgtg gcggcgcggc gtggcggagg      720
cggccgagga gcgcatgggc cagcggccgg ccgcgggcgc cgaggtcccc gagagcgtct      780
ttctgcactt gggccgcacc atgaaggagg acctggagcc cgtggtggag cggctgaagc      840
cgctgttccc cgccgagttc ggcgtcgtgg cggcctacgc cgagagctac caccagcact      900
tcgcggccca cctggccgcc gtggcgcagt tcgagctgtg cgagcgcgac acctacatgc      960
```

```
tgctgctctg ggtgcagaac ctctacccca atgacatcat caacagcccc aagctggtgg    1020
gtgagctgca gggtatgggg ctcgggagcc tcctgccccc caggcagatc cgactgctgg    1080
aggccacatt cctgtccagt gaggcggcca atgtgaggga gttgatggac cgagctctgg    1140
agctagaggc acggcgctgg gctgaggatg tgcctcccca gaggctggac ggccactgcc    1200
acagcgagct ggccatcgac atcatccaga tcacctccca ggcccaggcc aaggccgaga    1260
gcatcacgct ggacttgggc tcacagataa agcgggtgct gctggtggag ctgcctgcgt    1320
tcctgaggag ctaccagcgc gcctttaatg aatttctgga gagaggcaag cagctgacga    1380
attacagggc caatgttatt gccaacatca acaactgcct gtccttccgg atgtccatgg    1440
agcagaattg gcaggtaccc caggacaccc tgagcctcct gctgggcccc ctgggtgagc    1500
tcaagagcca cggctttgac accctgctcc agaacctgca tgaggacctg aagccactgt    1560
tcaagaggtt cacgcacacc cgctgggcgg cccctgtgga gaccctggaa acatcatcg    1620 ccactgtaga cacgaggctg cctgagttct cagagctgca gggctgtttc cgggaggagc    1680
tcatggaggc cttgcacctg cacctggtga aggagtacat catccaactc agcaaggggc    1740
gcctggtcct caagacggcc gagcagcagc agcagctggc tgggtacatc ctggccaatg    1800
ctgacaccat ccagcacttc tgcacccagc acggctcccc ggcgacctgg ctgcagcctg    1860
ctctccctac gctggccgag atcattcgcc tgcaggaccc cagtgccatc aagattgagg    1920
tggccactta tgccacctgc taccctgact tcagcaaagg ccacctgagc gctatcctgg    1980
ccatcaaggg gaacctatcc aacagtgagg tcaagcgcat ccggagcatc ttggacgtca    2040 gcatggggc gcaggagccc tcccggcccc tattttccct tataaaggtt ggttagcttt    2100
tcctgtggcc tgacctgcct gtgagtgcca agcaagcctt gggcacaccc cgctgggagc    2160
tgttaagagc agcgctggtt ctcggttcct cccgggtctc ctgtgctctg atgctacttc    2220
tgcctagccc tggcggaggt gcaggccctg tcagctggaa ctggacagac cttggtttgt    2280
ttacatgtcc gatgggggca ggagctccca tcctgggcag ccaaccaggc aacaccaagg    2340
actctttgta aacgatagct gatcgtgtgc acgcaaggaa agaaccagga gggagagtgc    2400
agccaggctc agggatcccc ggacacctct gtccagagcc cctccacagt cggcctcatg    2460
actgtcctcc tcgtgggtgg ggccgagggc cctcttcagc tctctggaga caggggccga    2520
gcctcaccca tctgccctct gcagcccagg ccgccgtga gcgggattca gcaatggtgg    2580
aatggaagac agaactggaa gagaaagaag gaaagatga gctctcgtct ggcaggggct    2640
tttagggtcc tgtggcgagc tgtgagcacc gccagcatta gacgtcacat ccaggtggcc    2700
ccacggcccc tacaggctgg ccctgcaatg ggccctgag ccctccctct tcatccccca    2760
aggcctcaac tagagggtgg tccccgagg gcttggtgtc tactaccgaa gggcccaaga    2820
cctcctgggt cctctcaggc tccccttcc ccaaggcagg acaggccct ggggtgcca    2880 ccgtgggccc tgccacccag aagtctggct gaggtctggg caggggcagg gcaagcttga    2940
cctctcactg ttgacccttt ggcctctgta tttgtttcct attgccgtga caggtttcca    3000
caaacttcgt ggatcaaaac gaggtcttcc agttctgcgg gtcagaaggc tgacccgggg    3060
ctcaaatctg ggtgtcggca gtcctgcact ccttctggag gctctagggg agaattcatt    3120
tctggccttt tcattttag aggctgaccg taattcttga cttcaggctc ctccatcttc    3180
agagccagct gtgggtagtt gaatcttttt cccgtcacct cattgaggcc tcccctctcc    3240
tgcctccctc caccacttttt tttttttttt ttttgagaca gggtcttgct gtgttgccca    3300
```

```
ggctggagtg cagtggcctg gtcatggcat caaggctcac tgcagcctgg acctcctggt    3360
tcaagtgatc ctcttgtctc agtcccctga gacaatcccc cacgcccagc tacatatttt    3420
ttgtggatac agggtctcat tctgttgcct aggcttgtct ggaactcctg ggctcaaggg    3480
atcttgtagc cttagcctcc taaagtgctg ggattatagg catgagtcac tgtacccggc    3540
ctgctctacc gcttttaagg acgcttatga tcacattgcg cctacccaga aacccaggt    3600 cgtcttttcta ttttcaggtc agctgattag ccaccttagt tccatctgca actttagttc    3660
ccactggctg tgtaacctaa catagtcaca ggctctgggg actgtcacgt ggacatcttt    3720
gggaggccgt tattctgccc accgcaccct ccgttcatcc cctgccctgc cgggcacctc    3780
gctctacccc aggaaaatgt gagctcgttt tcctgctcgg catgtgctcc ccctaaggct    3840
ctgctcctcc ctgggcctga agttccttc tcagcctgag agggggccct tcggactcag    3900
gcatgactca gcccggctga tgcctctgca gtgctgagtc aggatttggg gccggctctc    3960
ttgggtccgt cccctttttcc caggtactgc cttacaaagc tgtggccagg aagtggccgg    4020
tataaaggat gcccaaggtc tttgtacgtg tgtaggagtt agcgtgtttg atattgttaa    4080
tataataata attatttttt agagtactgc ttttgtatgt atgttgaaca ggatccaggt    4140
ttttatagct tgatataaaa cagaattcaa aagtgaaaaa                          4180

<210> SEQ ID NO 41
<211> LENGTH: 2933
<212> TYPE: DNA
<213> ORGANISM: Homo sapiens

<400> SEQUENCE: 41
agtctccggg gactttccca ggggtggggc ggcccggcca ggcccccggc acttcctcgt      60
cctcggcccg ggtgccctgc ccccgtccag gagccctagg agtgctacgg ggggccggag     120
ccttgcccgg gccgctgccc cgtccctgga ttcggggctg gacgcagcaa gcggggcgct     180
gtgtccccaa gctcccgtc ctcggccagg cgggcaccac ggcaggggct gagctaccct     240
catggaaggg agaggaccgt accggatcta cgaccctggg ggcagcgtgc cctcaggaga     300
ggcatccgca gcttttgagc gcctagtgaa ggagaattcc cggctgaagg aaaaaatgca     360
agggataaag atgttagggg agcttttgga agagtcccag atggaagcga ccaggctccg     420
gcagaaggca gaggagctag tgaaggacaa cgagctgctc ccaccacctt ctccctcctt     480
gggctccttc gaccccctgg ctgagctcac aggaaaggac tcaaatgtca cagcatctcc     540
cacagcccct gcatgcccca gtgacaagcc agcaccagtc cagaagcctc catccagtgg     600
cacctcctct gaatttgaag tggtcactcc tgaggagcag aattcaccag agagcagcag     660
ccatgccaat gcgatggcgc tgggcccccct gcccgtgag gacggcaacc tgatgctgca     720
cctgcagcgc ctggagacca cgctgagtgt tgtgccgag gagccggacc acggccagct     780
cttcacccac ctgggccgca tggccctgga gttcaaccga ctggcatcca aggtgcacaa     840
gaatgagcag cgcacctcca ttctgcagac cctgtgtgag cagcttcgga aggagaacga     900
ggctctgaag gccaagttgg ataagggcct ggaacagcgg gatcaggctg ccgagaggct     960
gcgggaggaa aatttggagc tcaagaagtt gttgatgagc aatggcaaca aagagggtgc    1020
gtctgggcgg ccaggctcac cgaagatgga agggacaggc aagaaggcag tggctggaca    1080
gcagcaggct agtgtgacgg caggtaaggt cccagaggtg gtggccttgg gcgcagccga    1140
gaagaaggtg aagatgctgg agcagcagcg cagtgagctc ctggaagtga caagcagtg    1200 ggaccagcat ttccggtcca tgaagcagca gtatgagcag aagatcactg agctgcgtca    1260
```

```
gaagctggct gatttgcaga agcaggtgac tgacctggag gccgagcggg agcagaagca    1320
gcgtgacttt gaccgcaagc tcctcctggc caagtccaag attgaaatgg aggagaccga    1380
caaggagcag ctgacagcag aggccaagga gctgcgccaa aaggtcaagt acctgcagga    1440
tcagctgagc ccactcaccc gacagcgtga gtaccaggaa aaggagatcc agcggctcaa    1500
caaggccctg gaggaagcac tgagcatcca acccc gcca tcatctccac caacagcatt    1560
```
```
caaggccctg gaggaagcac tgagcatcca accccgcca  tcatctccac caacagcatt    1560
tgggagccca aaggagcag gggccctcct aaggaaacag gagctggtca cgcagaatga    1620
gttgctgaaa cagcaggtga agatcttcga ggaggacttc cagagggagc gcagtgatcg    1680
tgagcgcatg aatgaggaga aggaagagct gaagaagcaa gtggagaagc tgcaggccca    1740
ggtcaccctg tcaaatgccc agctaaaagc attcaaagat gaggagaagg caagagaagc    1800
cctcagacag cagaagagga aagcaaaggc ctcaggagag cgttaccatg tggagcccca    1860
cccagaacat ctctgcgggg cctacccct a cgcctacccg cccatgccag ccatggtgcc    1920
acaccatggc ttcgaggact ggtcccagat ccgctacccc cctccccca  tggccatgga    1980 gcacccgccc ccactcccca actcgcgcct cttccatctg ccggaataca cctggcgtct    2040
accctgtgga ggggttcgaa atccaaatca gagctcccaa gtgatggacc ctcccacagc    2100
caggcctaca gaaccagagt ctccaaaaaa tgaccgtgag gggcctcagt gagaccagat    2160
tgtgtcattt ggctccacct tcatcttgca gagccagctg atctcagatt gccaagaaac    2220
tagaagccac ttgcacggtg tggccagagc ctcagctgga tgagaggctg agatgggtgg    2280
ccagcttgta caccagtccc tgaactgagc tgtttacagg actggggagg ctccacccag    2340
aaggctttca tttgtactct gctgggagtg actgggaaaa actccttccc tgctgctgag    2400
tggagagagg cctcatccgg ctttgaccca ccatccgttg cagaagcctc caggagcagc    2460
aatcctaaga gtgggaggca gccaagaccc ccttccttca aaacctcccg gaagtggttt    2520
caggccctct agttgccatg accaatttgt gtgtgtgttt aattttttgct tcaagctctg    2580 tagcaggacc tgccccacgc acacccctac ccctctgtga ggagctgtgg gaagtgtggg    2640
tttgtctcca gaacagaaga gaatgatgga tattctggct ctggggccct ctccaccacc    2700
actcacagta gccttgctga agccatcaca gatgggagaa ggccatgcca gccacgtccg    2760
ccgaggggcg ccagcctgaa gctgccaggc cctgaggttc agaccctgga ccccatagct    2820
ggaggcctgt ggtgccagaa gcccagatta gggtggctgt ccatccctgg atagctatt t    2880 gcacgaatca tggacataaa tccaagttga agaagatcaa caaaaaaaaa aaa           2933
```

<210> SEQ ID NO 42
<211> LENGTH: 4450
<212> TYPE: DNA
<213> ORGANISM: Homo sapiens

<400> SEQUENCE: 42

```
gtaaagtggt ggcacctgac cggagcatgt agccacctat gacttcctga gtggggtggt      60
gtggggaggg ccctgaggag tctgtggtcc taggccttgg atttcatcag ggctttcctg     120
ctccttctgg ttgcctcagt cccaggcaag atagggtccc agaatcttac agcccagagg     180
ccacctgttg caacttcttt tttacagatg gagtcatcag aacccactgt gaggaagtga     240
cttctccttg aggtcaccca gacactccaa acagagcaga gcaaaagcgc ctagaacttg     300
aaattttgga cctgtctcca acaccctggg gatttccacc aggaagcctt cagtcaccat     360
ccaggggatt tttatcgcca caaagggtaa ttcctgctcc atccctgctg tgactcagct     420
```

-continued

| | |
|---|---|
| gtgacgttga accacacaag ccagagagaa aagataaag tcatcagagc tcctactcac | 480 |
| cagagagtga ggcccaggcc aggactccac aaggctggtc ccctgccctg gagcaactta | 540 |
| aacaggccct ctggccagcc tggaaccctg agatggcctc cagctcaggc agcagtcctc | 600 |
| gcccggcccc tgatgagaat gagtttccct ttgggtgccc tcccaccgtc tgccaggacc | 660 |
| caaaggagcc cagggctctc tgctgtgcag gctgtctctc tgagaacccg aggaatggcg | 720 |
| aggatcagat ctgccccaaa tgcagagggg aagacctcca gtctataagc ccaggaagcc | 780 |
| gtcttcgaac tcaggagaag gctcaccccg aggtggctga ggctggaatt gggtgcccct | 840 |
| ttgcaggtgt cggctgctcc ttcaagggaa gcccacagtc tgtgcaagag catgaggtca | 900 |
| cctcccagac ctcccaccta aacctgctgt tggggttcat gaaacagtgg aaggcccggc | 960 |
| tgggctgtgg cctggagtct gggcccatgg ccctggagca gaacctgtca gacctgcagc | 1020 |
| tgcaggcagc cgtggaagtg gcgggggacc tggaggtcga ttgctaccgg gcaccctgct | 1080 |
| ccgagagcca ggaggagctg gccctgcagc acttcatgaa ggagaagctt ctggctgagc | 1140 |
| tggagggaa gctgcgtgtg tttgagaaca ttgttgctgt cctcaacaag gaggtggagg | 1200 |
| cctcccacct ggccctggcc acctctatcc accagagcca gctggaccgt gagcgcatcc | 1260 |
| tgagcttgga gcagagggtg gtggagcttc agcagaccct ggcccagaaa gaccaggccc | 1320 |
| tgggcaagct ggagcagagc ttgcgcctca tggaggaggc ctccttcgat ggcactttcc | 1380 |
| tgtgaagat caccaatgtc caggcggt gccatgagtc ggcctgtggc aggaccgtca | 1440 |
| gcctcttctc cccagccttc tacactgcca agtatggcta caagttgtgc ctgcggctgt | 1500 |
| acctgaatgg agatggcact ggaaagagaa cccatctgtc gctcttcatc gtgatcatga | 1560 |
| gagggagta tgatgcgctg ctgccgtggc ccttccggaa caaggtcacc ttcatgctgc | 1620 |
| tggaccagaa caaccgtgag cacgccattg acgccttccg gcctgaccta agctcagcgt | 1680 |
| ccttccagag gccccagagt gaaaccaacg tggccagtgg atgcccactc ttcttcccc | 1740 |
| tcagcaaact gcagtcaccc aagcacgcct acgtgaagga cgacacaatg ttcctcaagt | 1800 |
| gcattgtgga gaccagcact tagggtgggc ggggctcctg agggagctcc aactcagaag | 1860 |
| ggagctagcc agaggactgt gatgccctgc ccttggcacc caagacctca gggcacaaag | 1920 |
| atgggtgaag gctggcatga tccaagcaag actgagggt cgacttcggg ctggccatct | 1980 |
| ggttaggatg gcaggacgtg ggctgggccc acaaaggcaa agggtccaga aggagacagg | 2040 |
| cagagctgct cccctctgca cggaccatgc gacactggga ggccagtgag ccactccggc | 2100 |
| cccgaatgtt gaggtggact ctcaccaaat gagaagaaaa tggaaccagg cttggaaccg | 2160 |
| taggacccaa gcagagaagc tctcgggcta ggaagatctc tgcagggccg ccagggagac | 2220 |
| ctggacacag gcctgctctc tttttctcca gggtcagaaa caggaccggg tggaagggat | 2280 |
| ggggtgccag tttgaatgca gtctgtccag gctcgtcatt ggaggtgaac aagcaaaccc | 2340 |
| agacggctcc actaggactt caaattgggg gttggatttg aagactttta agtttccttc | 2400 |
| cagcccagaa agtctctcat tctaggcctc ctggcccagg tgagtcctag agctacaggg | 2460 |
| gttctggaaa cattcaggag cttcctgtcc tcccagctcc tcactcacct tcagtaaccc | 2520 |
| ccactggact gacctggtcc acagggcacc tgccaccctg ggcctggcag ctcagcttcc | 2580 |
| ccaacacgca ggagcacacc cagcccccac atcctgtgcc tccatcagct aaacaccacg | 2640 |
| tcacttcatg caggtgaaac ccagtcactg tgagctccca ggtgcagcca gaggcacctc | 2700 |
| aagaagaaga ggggcataaa ctttcctctt cctgcctaga ggcccacct ttggtgcttt | 2760 |
| ccagaatccc gtaacacctg attaactgag gcatccactt cttcagcag actgatcagg | 2820 |

```
acctccaagc cactgagcaa tgtataaccc caaagaaata attttagaa tctctttcga    2880 agttttccta aagtgtatgg tttgggagtt gtttgtactg agccaggttt gaaaaggcca    2940
ttgctgagtt tgaggtggtg ccaccagttt tgcaggtggc atcagaggct ggcatgctgg    3000
caggaacatc ccctcttagc cccagtcttc tcttttctat aatgagaccc accccagctt    3060
gcctccctcc ctggcttctc tgaccctcaa aggagatgcc acgcaggaca gactggagag    3120
agaagcctgg gcaatactgc ccgcctgtca tggcctggtg gtgggcccaca cctatcttct    3180 caccttggag gccacaccca actttccaaa gaccctgaga caagtcagga ccctactact    3240
ctcccctgct gctttcctga cagcttactc ttcctccacc tgctgagcct gtgccagact    3300
ccattgctca aatcgttagg gttgcttcta taaaaatggg tcagtagccc ttcctgttct    3360
ctccagccca gcatacagga ggatcaaagg aggtgacgga gcatcgtggc acggcagtct    3420
caatgggtca gaaacccagg ccagctgggc tctaagcctg gcatcctgtc atgcttagtc    3480
cttcagctga agatcagagg aagcctctcc cttgccctct ccagctctag ggttttcag    3540 gaggcccaac tgcaataatg gagcactagt gcttttatgt gcaatggtgt cgtccatgca    3600
cgacagcagc aaacattctg gggctgcttt ttattgttcc cacggctgac agcgtggcag    3660
cggagactgt ggaggcagtg gagactgact tcttcctgct gacagctgga tgtcacacat    3720
gaaggtctgg cctagcgagt gatgggtcta ggccctgaaa ctgatgtcct agcaataacc    3780
tcttgatccc tactcaccga gtgttgagcc caagggggga tttgtagaac aagcccccat    3840
gagaaacagc tgttactcta cacttttgat tgcctatttc tgatggcaag agatacatac    3900
tctcttcaaa gagcatgaga tgcagccatt cttcagcaa agcttcattg acacctgcac    3960
ctgttaactg tgttcgacat tgaagggaga aaggcaagat gtgcactctg gactcaagaa    4020
actcttagtt cagtggagga aatgagcaga taagtagatc attatgattg agagtaggag    4080
aagcttagag aaagcacaga atcccagatc cagctggtga aggagggaag gcttcaggcc    4140
tttaagctca gcctgagaat attgtgaaat gcagaggatg gggaaaaggg aagagtaccg    4200
acttgaaaac ggagagctgt cttggctgag ggcagggtct gtgtggcagg atgggggagg    4260
gagtcagaag ggtcagatga actggagtgt agacagcatc agatgcagca gtgcccaccg    4320
cccccccccc cacccccgc cctgcccaca gagcacctgc tggtaacct gggcctattg    4380 aaaagcaggat gagatgataa tttaagacac tgaatgattt cttttccaac aaagctctat    4440
gttaagtgca                                                           4450

<210> SEQ ID NO 43
<211> LENGTH: 3220
<212> TYPE: DNA
<213> ORGANISM: Homo sapiens

<400> SEQUENCE: 43
aaactttttt ccctggctct gccctgggtt tccccttgaa gggatttccc tccgcctctg      60
caacaagacc ctttataaag cacagacttt ctatttcact ccgcggtatc tgcatcgggc     120
ctcactggct tcaggagctg aatacccctcc caggcacaca caggtgggac acaaataagg    180
gttttggaac cactatttc tcatcacgac agcaacttaa aatgcctggg aagatggtcg      240
tgatccttgg agcctcaaat atactttgga taatgtttgc agcttctcaa gcttttaaaa     300
tcgagaccac cccagaatct agatatcttg ctcagattgg tgactccgtc tcattgactt     360
gcagcaccac aggctgtgag tccccatttt tctcttggag aacccagata gatagtccac     420
```

```
tgaatgggaa ggtgacgaat gaggggacca catctacgct gacaatgaat cctgttagtt    480
ttgggaacga acactcttac ctgtgcacag caacttgtga atctaggaaa ttggaaaaag    540
gaatccaggt ggagatctac tcttttccta aggatccaga gattcatttg agtggccctc    600
tggaggctgg gaagccgatc acagtcaagt gttcagttgc tgatgtatac ccatttgaca    660
ggctggagat agacttactg aaaggagatc atctcatgaa gagtcaggaa tttctggagg    720
atgcagacag gaagtccctg gaaaccaaga gtttggaagt aacctttact cctgtcattg    780
aggatattgg aaaagttctt gtttgccgag ctaaattaca cattgatgaa atggattctg    840
tgcccacagt aaggcaggct gtaaaagaat tgcaagtcta catatcaccc aagaatacag    900
ttatttctgt gaatccatcc acaaagctgc aagaaggtgg ctctgtgacc atgacctgtt    960
ccagcgaggt tctaccagct ccagagattt tctggagtaa gaaattagat aatgggaatc   1020
tacagcacct ttctggaaat gcaactctca ccttaattgc tatgaggatg aagattctg   1080 gaatttatgt gtgtgaagga gttaatttga ttgggaaaaa cagaaaagag gtggaattaa   1140
ttgttcaaga gaaaccattt actgttgaga tctcccctgg accccggatt gctgctcaga   1200
ttggagactc agtcatgttg acatgtagtg tcatgggctg tgaatcccca tctttctcct   1260
ggagaaccca gatagacagc cctctgagcg ggaaggtgag gagtgagggg accaattcca   1320
cgctgaccct gagccctgtg agttttgaga acgaacactc ttatctgtgc acagtgactt   1380
gtggacataa gaaactggaa aagggaatcc aggtggagct ctactcattc cctagagatc   1440
cagaaatcga gatgagtggt ggcctcgtga atgggagctc tgtcactgta agctgcaagg   1500
ttcctagcgt gtaccccctt gaccggctgg agattgaatt acttaagggg gagactattc   1560
tggagaatat agagttttg gaggatacgg atatgaaatc tctagagaac aaaagtttgg   1620
aaatgacctt catccctacc attgaagata ctggaaaagc tcttgtttgt caggctaagt   1680
tacatattga tgacatggaa ttcgaaccca acaaaggca gagtacgcaa acactttatg   1740
tcaatgttgc ccccagagat acaaccgtct tggtcagccc ttcctccatc ctggaggaag   1800
gcagttctgt gaatatgaca tgcttgagcc agggctttcc tgctccgaaa atcctgtgga   1860
gcaggcagct ccctaacggg gagctacagc ctctttctga gaatgcaact ctcaccttaa   1920
tttctacaaa aatggaagat tctggggttt atttatgtga aggaattaac caggctggaa   1980
gaagcagaaa ggaagtggaa ttaattatcc aagttactcc aaaagacata aaacttacag   2040
cttttccttc tgagagtgtc aaagaaggag acactgtcat catctcttgt acatgtggaa   2100
atgttccaga acatggata atcctgaaga aaaaagcgga gacaggagac acagtactaa   2160
aatctataga tggcgcctat accatccgaa aggcccagtt gaaggatgcg ggagtatatg   2220
aatgtgaatc taaaaacaaa gttggctcac aattaagaag tttaacactt gatgttcaag   2280
gaagagaaaa caacaaagac tattttctc ctgagcttct cgtgctctat tttgcatcct   2340
ccttaataat acctgccatt ggaatgataa tttacttttgc aagaaaagcc aacatgaagg   2400
ggtcatatag tcttgtagaa gcacagaagt caaaagtgta gctaatgctt gatatgttca   2460
actggagaca ctatttatct gtgcaaatcc ttgatactgc tcatcattcc ttgagaaaaa   2520
caatgagctg agaggcagac ttccctgaat gtattgaact tggaaagaaa tgcccatcta   2580
tgtcccttgc tgtgagcaag aagtcaaagt aaaacttgct gcctgaagaa cagtaactgc   2640
catcaagatg agagaactgg aggagttcct tgatctgtat atacaataac ataatttgta   2700
catatgtaaa ataaaattat gccatagcaa gattgcttaa aatagcaaca ctctatattt   2760
agattgttaa aataactagt gttgcttgga ctattataat ttaatgcatg ttaggaaaat   2820
```

-continued

| | |
|---|---|
| ttcacattaa tatttgctga cagctgacct ttgtcatctt tcttctattt tattcccttt | 2880 |
| cacaaaattt tattcctata tagtttattg acaataattt caggttttgt aaagatgccg | 2940 |
| ggttttatat ttttatagac aaataataag caaagggagc actgggttga ctttcaggta | 3000 |
| ctaaataccct caacctatgg tataatggtt gactgggttt ctctgtatag tactggcatg | 3060 |
| gtacggagat gtttcacgaa gtttgttcat cagactcctg tgcaactttc ccaatgtggc | 3120 |
| ctaaaaatgc aacttctttt tatttctctt tgtaaatgtt taggttttt tgtatagtaa | 3180 |
| agtgataatt tctggaatta gaaaaaaaaa aaaaaaaaa | 3220 |

<210> SEQ ID NO 44
<211> LENGTH: 20
<212> TYPE: DNA
<213> ORGANISM: Homo sapiens

<400> SEQUENCE: 44
ggcagccttc ctgatttctg                                              20

<210> SEQ ID NO 45
<211> LENGTH: 21
<212> TYPE: DNA
<213> ORGANISM: Homo sapiens

<400> SEQUENCE: 45
ggtggaaagg tttggagtat g                                            21

<210> SEQ ID NO 46
<211> LENGTH: 24
<212> TYPE: DNA
<213> ORGANISM: Homo sapiens

<400> SEQUENCE: 46
cagctctgtg tgaaggtgca gttt                                         24

<210> SEQ ID NO 47
<211> LENGTH: 22
<212> TYPE: DNA
<213> ORGANISM: Homo sapiens

<400> SEQUENCE: 47
ggagttcatc cgtcaagttc aa                                           22

<210> SEQ ID NO 48
<211> LENGTH: 19
<212> TYPE: DNA
<213> ORGANISM: Homo sapiens

<400> SEQUENCE: 48
tttcatctcc tgggctgtc                                               19

<210> SEQ ID NO 49
<211> LENGTH: 25
<212> TYPE: DNA
<213> ORGANISM: Homo sapiens

<400> SEQUENCE: 49
accctcatct acttgaacag ctgct                                        25

<210> SEQ ID NO 50
<211> LENGTH: 20
<212> TYPE: DNA

<213> ORGANISM: Homo sapiens

<400> SEQUENCE: 50
tgcagtaata ctggggaacc                                    20

<210> SEQ ID NO 51
<211> LENGTH: 21
<212> TYPE: DNA
<213> ORGANISM: Homo sapiens

<400> SEQUENCE: 51
gcttcgtcag aatcacgttg g                                  21

<210> SEQ ID NO 52
<211> LENGTH: 23
<212> TYPE: DNA
<213> ORGANISM: Homo sapiens

<400> SEQUENCE: 52
tgaccatcta cagctttccg gcg                                23

<210> SEQ ID NO 53
<211> LENGTH: 19
<212> TYPE: DNA
<213> ORGANISM: Homo sapiens

<400> SEQUENCE: 53
cctccactcc atcctgaag                                     19

<210> SEQ ID NO 54
<211> LENGTH: 20
<212> TYPE: DNA
<213> ORGANISM: Homo sapiens

<400> SEQUENCE: 54
gccatggata gaggctaagt                                    20

<210> SEQ ID NO 55
<211> LENGTH: 23
<212> TYPE: DNA
<213> ORGANISM: Homo sapiens

<400> SEQUENCE: 55
accaactaca atggccacac gtg                                23

<210> SEQ ID NO 56
<211> LENGTH: 23
<212> TYPE: DNA
<213> ORGANISM: Homo sapiens

<400> SEQUENCE: 56
tttcaagaca gatcataagc gag                                23

<210> SEQ ID NO 57
<211> LENGTH: 22
<212> TYPE: DNA
<213> ORGANISM: Homo sapiens

<400> SEQUENCE: 57
agccagagtt tcaccgtaaa ta                                 22

<210> SEQ ID NO 58
<211> LENGTH: 23

```
<212> TYPE: DNA
<213> ORGANISM: Homo sapiens

<400> SEQUENCE: 58
tgggccatgg ggtggactta aat                                    23

<210> SEQ ID NO 59
<211> LENGTH: 18
<212> TYPE: DNA
<213> ORGANISM: Homo sapiens

<400> SEQUENCE: 59
ccaaccgcga gaagatga                                          18

<210> SEQ ID NO 60
<211> LENGTH: 20
<212> TYPE: DNA
<213> ORGANISM: Homo sapiens

<400> SEQUENCE: 60
ccagaggcgt acagggatag                                        20

<210> SEQ ID NO 61
<211> LENGTH: 23
<212> TYPE: DNA
<213> ORGANISM: Homo sapiens

<400> SEQUENCE: 61
ccatgtacgt tgctatccag gct                                    23

<210> SEQ ID NO 62
<211> LENGTH: 19
<212> TYPE: DNA
<213> ORGANISM: Homo sapiens

<400> SEQUENCE: 62
agtcctgagt ccggatgaa                                         19

<210> SEQ ID NO 63
<211> LENGTH: 18
<212> TYPE: DNA
<213> ORGANISM: Homo sapiens

<400> SEQUENCE: 63
cctccctcag tcgtctct                                          18

<210> SEQ ID NO 64
<211> LENGTH: 24
<212> TYPE: DNA
<213> ORGANISM: Homo sapiens

<400> SEQUENCE: 64
tgacggaggg tggcatcaaa tacc                                   24

<210> SEQ ID NO 65
<211> LENGTH: 22
<212> TYPE: DNA
<213> ORGANISM: Homo sapiens

<400> SEQUENCE: 65
gccagcttgt cttcaatgaa at                                     22

<210> SEQ ID NO 66
```

```
<211> LENGTH: 21
<212> TYPE: DNA
<213> ORGANISM: Homo sapiens

<400> SEQUENCE: 66
caaagccagc ttctgttcaa g                                              21

<210> SEQ ID NO 67
<211> LENGTH: 24
<212> TYPE: DNA
<213> ORGANISM: Homo sapiens

<400> SEQUENCE: 67
atccaccatg agttggtagg cagc                                           24

<210> SEQ ID NO 68
<211> LENGTH: 23
<212> TYPE: DNA
<213> ORGANISM: Homo sapiens

<400> SEQUENCE: 68
gccaagaaga aagtgaacat cat                                            23

<210> SEQ ID NO 69
<211> LENGTH: 20
<212> TYPE: DNA
<213> ORGANISM: Homo sapiens

<400> SEQUENCE: 69
atagggattc cgggagtcat                                                20

<210> SEQ ID NO 70
<211> LENGTH: 24
<212> TYPE: DNA
<213> ORGANISM: Homo sapiens

<400> SEQUENCE: 70
tcagaacaac agcctgccac ctta                                           24

<210> SEQ ID NO 71
<211> LENGTH: 22
<212> TYPE: DNA
<213> ORGANISM: Homo sapiens

<400> SEQUENCE: 71
tgactccttc aacaccttct tc                                             22

<210> SEQ ID NO 72
<211> LENGTH: 18
<212> TYPE: DNA
<213> ORGANISM: Homo sapiens

<400> SEQUENCE: 72
tgccagtgcg aacttcat                                                  18

<210> SEQ ID NO 73
<211> LENGTH: 24
<212> TYPE: DNA
<213> ORGANISM: Homo sapiens

<400> SEQUENCE: 73
ccgggctgtg tttgtagact tgga                                           24
```

```
<210> SEQ ID NO 74
<211> LENGTH: 17
<212> TYPE: DNA
<213> ORGANISM: Homo sapiens

<400> SEQUENCE: 74
agccacatca tccctgt                                                    17

<210> SEQ ID NO 75
<211> LENGTH: 22
<212> TYPE: DNA
<213> ORGANISM: Homo sapiens

<400> SEQUENCE: 75
cgtagatgtt atgtctgctc at                                              22

<210> SEQ ID NO 76
<211> LENGTH: 22
<212> TYPE: DNA
<213> ORGANISM: Homo sapiens

<400> SEQUENCE: 76
tttagcagca tctgcaaccc gc                                              22

<210> SEQ ID NO 77
<211> LENGTH: 24
<212> TYPE: DNA
<213> ORGANISM: Homo sapiens

<400> SEQUENCE: 77
gaggatttgg aaagggtgtt tatt                                            24

<210> SEQ ID NO 78
<211> LENGTH: 21
<212> TYPE: DNA
<213> ORGANISM: Homo sapiens

<400> SEQUENCE: 78
acagagggct acaatgtgat g                                               21

<210> SEQ ID NO 79
<211> LENGTH: 26
<212> TYPE: DNA
<213> ORGANISM: Homo sapiens

<400> SEQUENCE: 79
acgtcttgct cgagatgtga tgaagg                                          26

<210> SEQ ID NO 80
<211> LENGTH: 18
<212> TYPE: DNA
<213> ORGANISM: Homo sapiens

<400> SEQUENCE: 80
taaaccctgc gtggcaat                                                   18

<210> SEQ ID NO 81
<211> LENGTH: 27
<212> TYPE: DNA
<213> ORGANISM: Homo sapiens

<400> SEQUENCE: 81
acatttcgga taatcatcca atagttg                                         27
```

```
<210> SEQ ID NO 82
<211> LENGTH: 24
<212> TYPE: DNA
<213> ORGANISM: Homo sapiens

<400> SEQUENCE: 82
aagtagttgg acttccaggt cgcc                                    24

<210> SEQ ID NO 83
<211> LENGTH: 17
<212> TYPE: DNA
<213> ORGANISM: Homo sapiens

<400> SEQUENCE: 83
ccgtggcctt agctgtg                                            17

<210> SEQ ID NO 84
<211> LENGTH: 21
<212> TYPE: DNA
<213> ORGANISM: Homo sapiens

<400> SEQUENCE: 84
ctgctggatg acgtgagtaa a                                       21

<210> SEQ ID NO 85
<211> LENGTH: 24
<212> TYPE: DNA
<213> ORGANISM: Homo sapiens

<400> SEQUENCE: 85
tctctctttc tggcctggag gcta                                    24

<210> SEQ ID NO 86
<211> LENGTH: 25
<212> TYPE: DNA
<213> ORGANISM: Homo sapiens

<400> SEQUENCE: 86
aaatgttaac aaatgtggca attat                                   25

<210> SEQ ID NO 87
<211> LENGTH: 20
<212> TYPE: DNA
<213> ORGANISM: Homo sapiens

<400> SEQUENCE: 87
aacaatgcct ccactccaaa                                         20

<210> SEQ ID NO 88
<211> LENGTH: 20
<212> TYPE: DNA
<213> ORGANISM: Homo sapiens

<400> SEQUENCE: 88
tccacacaac accaggactt                                         20

<210> SEQ ID NO 89
<211> LENGTH: 22
<212> TYPE: DNA
<213> ORGANISM: Homo sapiens

<400> SEQUENCE: 89
tgaaaactac ccctaaaagc ca                                      22
```

```
<210> SEQ ID NO 90
<211> LENGTH: 21
<212> TYPE: DNA
<213> ORGANISM: Homo sapiens

<400> SEQUENCE: 90
tatccaagac ccaggcatac t                                        21

<210> SEQ ID NO 91
<211> LENGTH: 21
<212> TYPE: DNA
<213> ORGANISM: Homo sapiens

<400> SEQUENCE: 91
tagattcggg caagtccacc a                                        21

<210> SEQ ID NO 92
<211> LENGTH: 20
<212> TYPE: DNA
<213> ORGANISM: Homo sapiens

<400> SEQUENCE: 92
aagatgaggc agaggtccaa                                          20

<210> SEQ ID NO 93
<211> LENGTH: 20
<212> TYPE: DNA
<213> ORGANISM: Homo sapiens

<400> SEQUENCE: 93
tccagaatgt cacaggtcca                                          20

<210> SEQ ID NO 94
<211> LENGTH: 20
<212> TYPE: DNA
<213> ORGANISM: Homo sapiens

<400> SEQUENCE: 94
tgctggtaca agttgtggga                                          20
```

DETERMINATION OF NFKB PATHWAY ACTIVITY USING UNIQUE COMBINATION OF TARGET GENES

RELATED APPLICATIONS

This application claims the benefit of European Patent Application No. EP15181029.8, filed Aug. 14, 2015, the entirety of the specification and claims thereof is hereby incorporated by reference for all purposes.

INCORPORATION-BY-REFERENCE OF MATERIAL SUBMITTED ON AS A TEXT FILE VIA THE OFFICE ELECTRONIC FILING SYSTEM (EFS-WEB)

A Sequence Listing associated with this application is provided in text format in lieu of a paper copy, and is hereby incorporated by reference into the specification. The name of the text file containing the Sequence Listing is 2015PF00604_2016-08-11_sequencelisting_ST25.txt. The text file is 143 KB, was created on Aug. 11, 2016, and is being submitted electronically via EFS-Web.

FIELD OF THE INVENTION

The present invention is in the field of systems biology, bioinformatics, genomic mathematical processing and proteomic mathematical processing. In particular, the invention includes a systems-based mathematical process for determining the activity of a NFkB cellular signaling pathway in a subject based on expression levels of a unique set of selected target genes in a subject. The invention further provides an apparatus that includes a digital processor configured to perform such a method, a non-transitory storage medium storing instructions that are executable by a digital processing device to perform such a method, and a computer program comprising a program code means for causing a digital processing device to perform such a method. The present invention also includes kits for the determination of expression levels of the unique combinations of target genes.

BACKGROUND OF THE INVENTION

As knowledge of tumors including cancers evolve, it becomes more clear that they are extraordinarily heterogeneous and multifactorial. Tumors and cancers have a wide range of genotypes and phenotypes, they are influenced by their individualized cell receptors (or lack thereof), microenvironment, extracellular matrix, tumor vascularization, neighboring immune cells, and accumulations of mutations, with differing capacities for proliferation, migration, stem cell properties and invasion. This scope of heterogeneity exists even among same classes of tumors. See generally: *Nature* Insight: Tumor Heterogeneity (entire issue of articles), 19 Sep. 2013 (Vol. 501, Issue 7467); Zellmer and Zhang, "Evolving concepts of tumor heterogeneity", *Cell and Bioscience* 2014, 4:69.

Traditionally, physicians have treated tumors, including cancers, as the same within class type (including within receptor type) without taking into account the enormous fundamental individualized nature of the diseased tissue. Patients have been treated with available chemotherapeutic agents based on class and receptor type, and if they do not respond, they are treated with an alternative therapeutic, if it exists. This is an empirical approach to medicine.

There has been a growing trend toward taking into account the heterogeneity of tumors at a more fundamental level as a means to create individualized therapies, however, this trend is still in its formative stages. What is desperately needed are approaches to obtain more metadata about the tumor to inform therapeutic treatment in a manner that allows the prescription of approaches more closely tailored to the individual tumor, and perhaps more importantly, avoiding therapies destined to fail and waste valuable time, which can be life-determinative.

A number of companies and institutions are active in the area of classical, and some more advanced, genetic testing, diagnostics, and predictions for the development of human diseases, including, for example: Affymetrix, Inc.; Bio-Rad, Inc; Roche Diagnostics; Genomic Health, Inc.; Regents of the University of California; Illumina; Fluidigm Corporation; Sequenom, Inc.; High Throughput Genomics; NanoString Technologies; Thermo Fisher; Danaher; Becton, Dickinson and Company; bioMerieux; Johnson & Johnson, Myriad Genetics, and Hologic.

Several companies have developed technology or products directed to gene expression profiling and disease classification. For example, Genomic Health, Inc. is the assignee of numerous patents pertaining to gene expression profiling, for example: U.S. Pat. Nos. 7,081,340; 8,808,994; 8,034,565; 8,206,919; 7,858,304; 8,741,605; 8,765,383; 7,838,224; 8,071,286; 8,148,076; 8,008,003; 8,725,426; 7,888,019; 8,906,625; 8,703,736; 7,695,913; 7,569,345; 8,067,178; 7,056,674; 8,153,379; 8,153,380; 8,153,378; 8,026,060; 8,029,995; 8,198,024; 8,273,537; 8,632,980; 7,723,033; 8,367,345; 8,911,940; 7,939,261; 7,526,637; 8,868,352; 7,930,104; 7,816,084; 7,754,431 and 7,208,470, and their foreign counterparts.

U.S. Pat. No. 9,076,104 to the Regents of the University of California titled "Systems and Methods for Identifying Drug Targets using Biological Networks" claims a method with computer executable instructions by a processor for predicting gene expression profile changes on inhibition of proteins or genes of drug targets on treating a disease, that includes constructing a genetic network using a dynamic Bayesian network based at least in part on knowledge of drug inhibiting effects on a disease, associating a set of parameters with the constructed dynamic Bayesian network, determining the values of a joint probability distribution via an automatic procedure, deriving a mean dynamic Bayesian network with averaged parameters and calculating a quantitative prediction based at least in part on the mean dynamic Bayesian network, wherein the method searches for an optimal combination of drug targets whose perturbed gene expression profiles are most similar to healthy cells.

Affymetrix has developed a number of products related to gene expression profiling. Non-limiting examples of U.S. patents to Affymetrix include: U.S. Pat. Nos. 6,884,578; 8,029,997; 6,308,170; 6,720,149; 5,874,219; 6,171,798; and 6,391,550.

Likewise, Bio-Rad has a number of products directed to gene expression profiling. Illustrative examples of U.S. patents to Bio-Rad include: U.S. Pat. Nos. 8,021,894; 8,451,450; 8,518,639; 6,004,761; 6,146,897; 7,299,134; 7,160,734; 6,675,104; 6,844,165; 6,225,047; 7,754,861 and 6,004,761.

Koninklijke Philips N. V. (NL) has filed a number of patent applications in the general area of assessment of cellular signaling pathway activity using various mathematical models, including U.S. Ser. No. 14/233,546 (WO 2013/011479), titled "Assessment of Cellular Signaling Pathway Using Probabilistic Modeling of Target Gene Expression";

U.S. Ser. No. 14/652,805 (WO 2014/102668) titled "Assessment of Cellular Signaling Pathway Activity Using Linear Combinations of Target Gene Expressions"; WO 2014/174003 titled "Medical Prognosis and Prediction of Treatment Response Using Multiple Cellular Signaling Pathway Activities"; and WO 2015/101635 titled "Assessment of the PI3K Cellular Signaling Pathway Activity Using Mathematical Modeling of Target Gene Expression".

Despite this progress, more work is needed to definitively characterize tumor cellular behavior. In particular, there is a critical need to determine which pathways have become pathogenic to the cell. However, it is difficult to identify and separate abnormal cellular signaling from normal cellular pathway activity.

Nuclear factor-kappa B (NFkB or NFκB) is an inducible transcription factor that regulates the expression of many genes involved in the immune response. The NFkB cellular signaling pathway is a key cellular signaling pathway involved in immune, inflammatory, and acute phase response, but is also implicated in the control of cell survival, proliferation, and apoptosis. In healthy, non-activated cells, the NFkB cellular signaling pathway associated transcription factors that are composed of dimers originating from five genes (NFKB1 or p50/p105, NFKB2 or p52/p100, RELA or p65, REL, and RELB) are predominantly cytoplasmic due to their interaction with the inhibitors of NFkB (IkBs) and therefore remain transcriptionally inactive, thus keeping the NFkB cellular signaling pathway inactive. Upon activation of the upstream signaling cascade, the IkBs become phosphorylated and undergo ubiquitin-dependent degradation by the proteasome, and NFkB dimers are translocated to the nucleus where they act as transcription factors. Besides this canonical NFkB cellular signaling pathway there is also an alternative pathway that is able to initiate NFkB regulated transcription (see FIG. 1; CP=canonical pathway; AP=alternative pathway; PS=proteasome; NC=nucleus). The term "NFkB cellular signaling pathway" herein preferably refers to any signaling process that leads to transcriptional activity of the above mentioned NFkB transcription factors.

Although activity of the NFkB cellular signaling pathway is known to be associated with different types of cancer and to support the pro-survival phenotypes of cancer cells, there is no clinical assay available to assess the activity of the NFkB cellular signaling pathway. Thus, it is desirable to be able to improve the possibilities of characterizing patients that have a cancer, e.g., a diffuse large B-cell lymphoma (DLBCL), a multiple myeloma, a cancer of another haematological origin, or a solid tumor, such as a breast, melanoma, or prostate tumor, which is at least partially driven by a deregulated NFkB cellular signaling pathway, and that are therefore likely to respond to inhibitors of the NFkB cellular signaling pathway.

It is therefore an object of the invention to provide a more accurate process to determine the tumorigenic propensity of the NFkB cellular signaling pathway in a cell, as well as associated methods of therapeutic treatment, kits, systems, etc.

SUMMARY OF THE INVENTION

The present invention includes methods and apparatuses for determining the activity level of a NFkB cellular signaling pathway in a subject, typically a human with diseased tissue such as a tumor or cancer, wherein the activity level of the NFkB cellular signaling pathway is determined by calculating a level of NFkB transcription factor element in a sample of the involved tissue isolated from the subject, wherein the level of the NFkB transcription factor element in the sample are determined by measuring the expression levels of a unique set of target genes controlled by the NFkB transcription factor element using a calibrated pathway model that compares the expression levels of the target genes in the sample with expression levels of the target genes in the calibrated pathway model.

In particular, the unique set of target genes whose expression level is analyzed in the model includes at least six target genes, at least seven target genes, at least eight target genes, at least nine target genes, at least ten or more target genes selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1. In one embodiment, the unique set of target genes whose expression level is analyzed in the model is selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the unique set of target genes comprises at least three target genes, at least four target genes, at least five target genes, at least six or more target genes selected from CCL2, CCL5, CCL20, CXCL1, CXCL2, CXCL3, ICAM1, IL6, IL8, MMP9, NFKB2, NFKBIA, and TNFAIP2. In one embodiment, the unique set of target genes comprises at least three target genes, at least four target genes, at least five target genes, at least six or more target genes selected from CCL5, CXCL2, ICAM1, IL6, IL8, NFKBIA, and TNFAIP2.

Using this invention, health care providers will be able to more accurately assess the functional state of the NFkB cellular signaling pathway at specific points in disease progression. Without being bound by any particular theory, it is believed that the identified target genes of the present invention in combination with the analytical methods described herein reduces the noise associated with the use of large subsets of target genes as previously described in the literature. Furthermore, as described and exemplified below, the use of specific combinations of select target genes allows for the precise determination of cellular signaling activity, and allows for an increased accuracy in the determination of disease state and prognosis. Accordingly, such cellular signaling pathway status can be used to, for example but not limited to, identify the presence or absence of disease and/or particular disease state or advancement, identify the presence or absence of a disorder or disease state, identify a particular subtype within a disease or disorder based one the activity level of the NFkB cellular signaling pathway, derive a course of treatment based on the presence or absence of NFkB signaling activity for example by administering a NFkB inhibitor, and/or monitor disease progression in order to, for example, adjust therapeutic protocols based on a predicted drug efficacy in light of the determined activity of the NFkB cellular signaling pathway in the sample.

The term "NFkB transcriptional factor element" or "NFkB TF element" or "TF element" refers to a protein complex containing at least one or, preferably, a dimer of the NFkB members (NFKB1 or p50/p105, NFKB2 or p52/p100, RELA or p65, REL, and RELB), which is capable of binding to specific DNA sequences, thereby controlling transcription of target genes.

The present invention is based on the realization of the inventors that a suitable way of identifying effects occurring in the NFkB cellular signaling pathway can be based on a measurement of the signaling output of the NFkB cellular signaling pathway, which is—amongst others—the transcription of the unique target genes described herein by a NFkB transcription factor (TF) element controlled by the NFkB cellular signaling pathway. This realization by the inventors assumes that the TF level is at a quasi-steady state in the sample which can be detected by means of—amongst others—the expression values of the target genes. The NFkB cellular signaling pathway targeted herein is known to be associated with different types of cancer and to support the pro-survival phenotypes of cancer cells as the NFkB cellular signaling pathway is known to regulate genes that control cell proliferation and cell survival processes. Many different types of human tumors are found to have a deregulated activity of the NFkB cellular signaling pathway. Furthermore, studies have shown that the inhibition of constitutive NFkB cellular signaling pathway activity blocks the oncogenic potential of cancerous cells.

The present invention makes it possible to determine the activity of the NFkB cellular signaling pathway by (i) determining a level of an NFkB TF element in the sample, wherein the determining is based at least in part on evaluating a mathematical model relating expression levels of at least six target genes of the NFkB cellular signaling pathway, the transcription of which is controlled by the NFkB TF element, to the level of the NFkB TF element, and by (ii) inferring the activity of the NFkB cellular signaling pathway based on the determined level of the NFkB TF element in the sample. This preferably allows improving the possibilities of characterizing patients that have a cancer, e.g., a diffuse large B-cell lymphoma (DLBCL), a multiple myeloma, a cancer of another haematological origin, or a solid tumor, such as a breast, melanoma, or prostate tumor, which is at least partially driven by a deregulated NFkB cellular signaling pathway, and that are therefore likely to respond to inhibitors of the NFkB cellular signaling pathway. An important advantage of the present invention is that it makes it possible to determine the activity of the NFkB cellular signaling pathway using a single sample, rather than requiring a plurality of samples extracted at different points in time. In particular embodiments, treatment determination can be based on specific NFkB activity. In a particular embodiment the NFkB cellular signaling status can be set at a cutoff value of odds of the NFkB cellular signaling pathway being activate of, for example, 10:1, 5:1, 4:1, 2:1, 1:1, 1:2, 1:4, 1:5, or 1:10.

In one aspect of the invention, provided herein is a computer implemented method for determining the activity level of a NFkB cellular signaling pathway in a subject performed by a computerized device having a processor comprising:
  a. calculating an activity level of NFkB transcription factor element in a sample isolated from the subject, wherein the activity level of NFkB transcription factor element in the sample is calculated by:
    i. receiving data on the expression levels of at least six target genes derived from the sample, wherein the NFkB transcription factor element controls transcription of the at least six target genes, and wherein the at least six target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1;
    ii. calculating the activity level of the NFkB transcription factor element in the sample using a calibrated pathway model, wherein the calibrated pathway model compares the expression levels of the at least six target genes in the sample with expression levels of the at least six target genes in the model which define an activity level of NFkB transcription factor element; and,
  b. calculating the activity level of the NFkB cellular signaling pathway in the sample based on the calculated activity levels of NFkB transcription factor element in the sample.

In one embodiment, the method further comprises assigning a NFkB cellular signaling pathway activity status to the calculated activity level of the NFkB cellular signaling pathway in the sample wherein the activity status is indicative of either an active NFkB cellular signaling pathway or a passive NFkB cellular signaling pathway.

In one embodiment, the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2. In one embodiment, the at least three target genes are selected from CCL5, CXCL2, ICAM1, IL6, IL8, NFKBIA, and TNFAIP2.

In one embodiment, the status of the NFkB cellular signaling pathway is established by establishing a specific threshold for activity as described further below. In one embodiment, the threshold is set as a probability that the cellular signaling pathway is active, for example, a 10:1, 5:1, 4:1, 3:1, 2:1, 1:1, 1:2, 1:4, 1:5, or 1:10. In one embodiment, the activity status is based, for example, on a minimum calculated activity. In one embodiment, the method further comprises assigning to the calculated NFkB cellular signaling in the sample a probability that the NFkB cellular signaling pathway is active.

As contemplated herein, the level of the NFkB transcription factor element is determined using a calibrated pathway model executed by one or more computer processors, as further described below. The calibrated pathway model compares the expression levels of the at least six target genes in the sample with expression levels of the at least six target genes in the calibrated pathway model which define a level of a NFkB transcription factor element. In one embodiment, the calibrated pathway model is a probabilistic model incorporating conditional probabilistic relationships that compare the expression levels of the at least six target genes in the sample with expression levels of the at least six target genes in the model which define a level of a NFkB transcription factor element to determine the level of the NFkB transcription factor element in the sample. In one embodiment, the probabilistic model is a Bayesian network model. In an alternative embodiment, the calibrated pathway model can be a linear or pseudo-linear model. In an embodiment, the linear or pseudo-linear model is a linear or pseudo-linear combination model.

As contemplated herein, the expression levels of the unique set of target genes can be determined using standard methods known in the art. For example, the expression levels of the target genes can be determined by measuring the level of mRNA of the target genes, through quantitative reverse transcriptase-polymerase chain reaction techniques, using probes associated with a mRNA sequence of the target genes, using a DNA or RNA microarray, and/or by measuring the protein level of the protein encoded by the target genes. Once the expression level of the target genes is determined, the expression levels of the target genes within the sample can be utilized in the model in a raw state or, alternatively, following normalization of the expression level data. For example, expression level data can be normalized by transforming it into continuous data, z-score data, discrete data, or fuzzy data.

As contemplated herein, the calculation of NFkB signaling in the sample is performed on a computerized device having a processor capable of executing a readable program code for calculating the NFkB signaling in the sample according to the methods described above. Accordingly, the computerized device can include means for receiving expression level data, wherein the data is expression levels of at least six target genes derived from the sample, a means for calculating the level of a NFkB transcription factor element in the sample using a calibrated pathway model, wherein the calibrated pathway model compares the expression levels of the at least six target genes in the sample with expression levels of the at least six target genes in the model which define a level a NFkB transcription factor element; a means for calculating the NFkB cellular signaling in the sample based on the calculated levels of a NFkB transcription factor element in the sample; and a means for assigning a NFkB cellular signaling pathway activity probability or status to the calculated NFkB cellular signaling in the sample, and, optionally, a means for displaying the NFkB signaling pathway activity probability or status.

In accordance with another disclosed aspect, further provided herein is a non-transitory storage medium capable of storing instructions that are executable by a digital processing device to perform the method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

Further contemplated herein are methods of treating a subject having a disease or disorder associated with an activated NFkB cellular signaling pathway, or a disorder whose advancement or progression is exacerbated or caused by, whether partially or wholly, an activated NFkB cellular signaling pathway, wherein the determination of the NFkB cellular signaling pathway activity is based on the methods described above, and administering to the subject a NFkB inhibitor if the information regarding the activity level of NFkB cellular signaling pathway is indicative of an active NFkB cellular signaling pathway. In one embodiment, the disorder is one of an auto-immune and other immune disorders, cancer, bronchial asthma, heart disease, diabetes, hereditary hemorrhagic telangiectasia, Marfan syndrome, Vascular Ehlers-Danlos syndrome, Loeys-Dietz syndrome, Parkinson's disease, Chronic kidney disease, Multiple Sclerosis, fibrotic diseases such as liver, lng, or kidney fibrosis, Dupuytren's disease, or Alzheimer's disease. In a particular embodiment, the subject is suffering from a cancer, for example, a breast cancer, lung cancer, a colon cancer, pancreatic cancer, brain cancer, or breast cancer. In a more particular embodiment, the cancer is a breast cancer.

Also contemplated herein is a kit for measuring the expression levels of at least six or more NFkB cellular signaling pathway target genes, for example, seven, eight, nine, ten, eleven, twelve, or more target genes as described herein. In one embodiment, the kit includes one or more components, for example probes, for example labeled probes, and/or PCR primers, for measuring the expression levels of at least six target genes, at least seven target genes, at least eight target genes, or at least nine or more target genes selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1. In one embodiment, the kit includes one or more components for measuring the expression levels of at least six target genes, at least seven target genes, at least eight target genes, or at least nine or more target genes selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the one or more components comprise one or more components for measuring the expression levels of at least three target genes, at least four target genes, at least five target genes, or at least six or more target genes selected from CCL2, CCL5, CCL20, CXCL1, CXCL2, CXCL3, ICAM1, IL6, IL8, MMP9, NFKB2, NFKBIA, and TNFAIP2. In one embodiment, the one or more components comprise one or more components for measuring the expression levels of at least three target genes, at least four target genes, at least five target genes, or at least six or more target genes selected from CCL5, CXCL2, ICAM1, IL6, IL8, NFKBIA, and TNFAIP2.

As contemplated herein, the one or more components or means for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to a portion of an mRNA or cDNA sequence of the targeted genes as described herein. In one embodiment, the kit includes a set of primers and probes directed to a portion of an mRNA or cDNA sequence of the targeted genes as described further below, wherein, for example, the set includes specific primers or probes selected from the sequences of Table 1. In one embodiment, the labeled probes are contained in a standardized 96-well plate. In one embodiment, the kit further includes primers or probes directed to a set of reference genes, for example, as represented in Table 2. Such reference genes can be, for example, constitutively expressed genes useful in normalizing or standardizing expression levels of the target gene expression levels described herein.

In one embodiment, the kit further includes a non-transitory storage medium containing instructions that are executable by a digital processing device to perform a method according to the present invention as described herein. In one embodiment, the kit includes an identification code that provides access to a server or computer network for analyzing the activity level of the NFkB cellular signaling pathway based on the expression levels of the target genes and the methods described herein.

et al., "NF-kB in development and progression of human cancer", Virchows Archives, Vol. 446. No. 5, 2005, pages 475 to 482).

Figure 1:
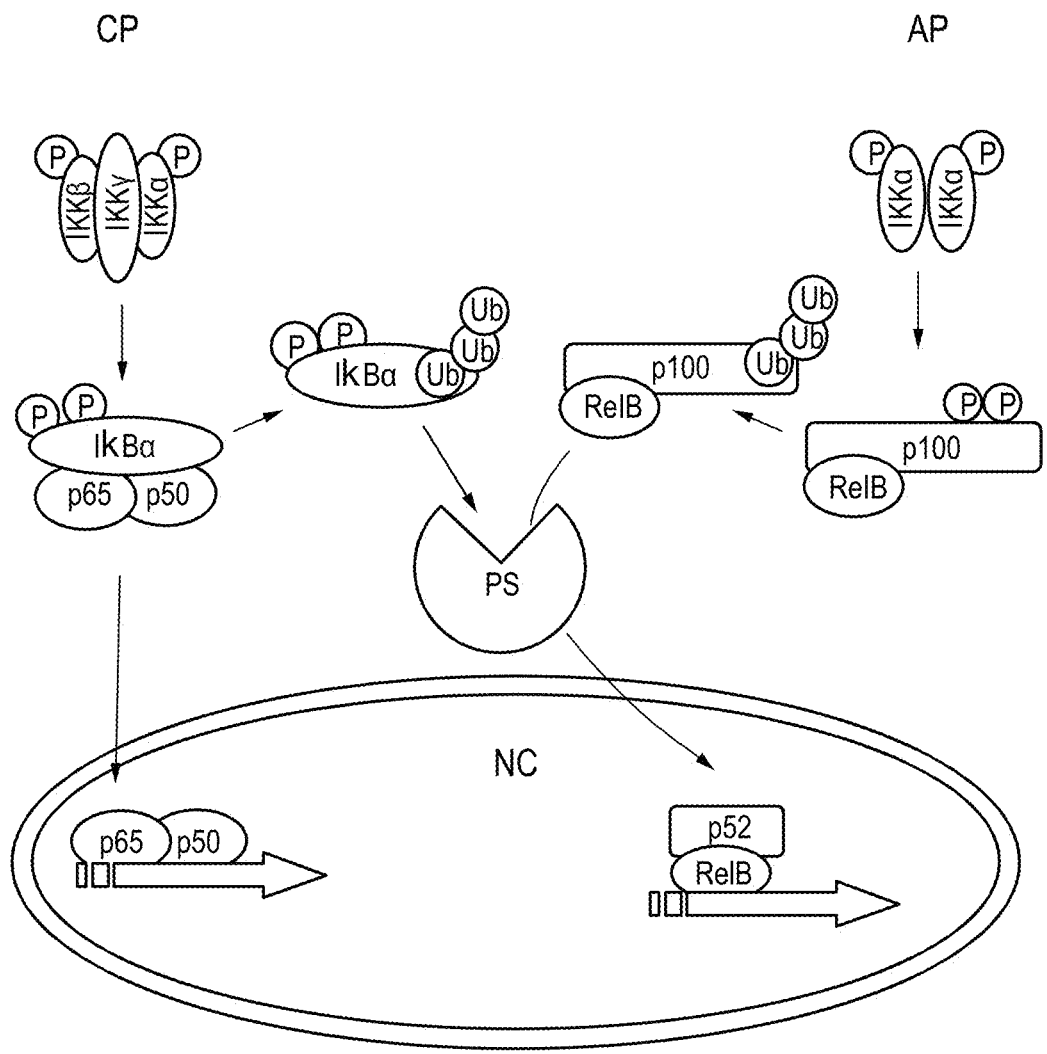
FIG. 1 shows schematically and exemplarily canonical and alternative pathways of NFkB activation (see Dolcet X.
Figure 2:
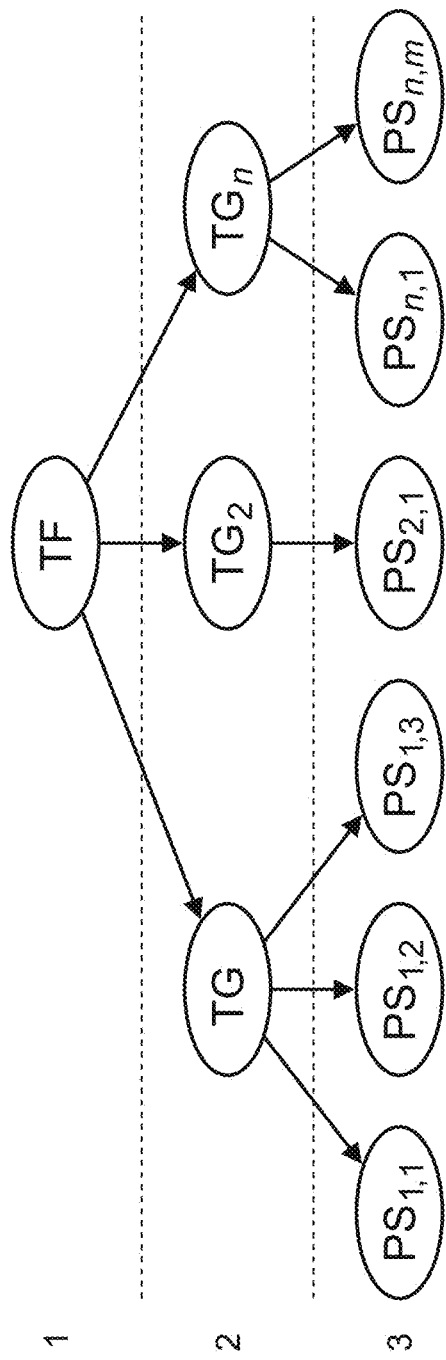

FIG. 2 shows schematically and exemplarily a mathematical model, herein, a Bayesian network model, useful in modelling the transcriptional program of the NFkB cellular signaling pathway.

Figure 3:
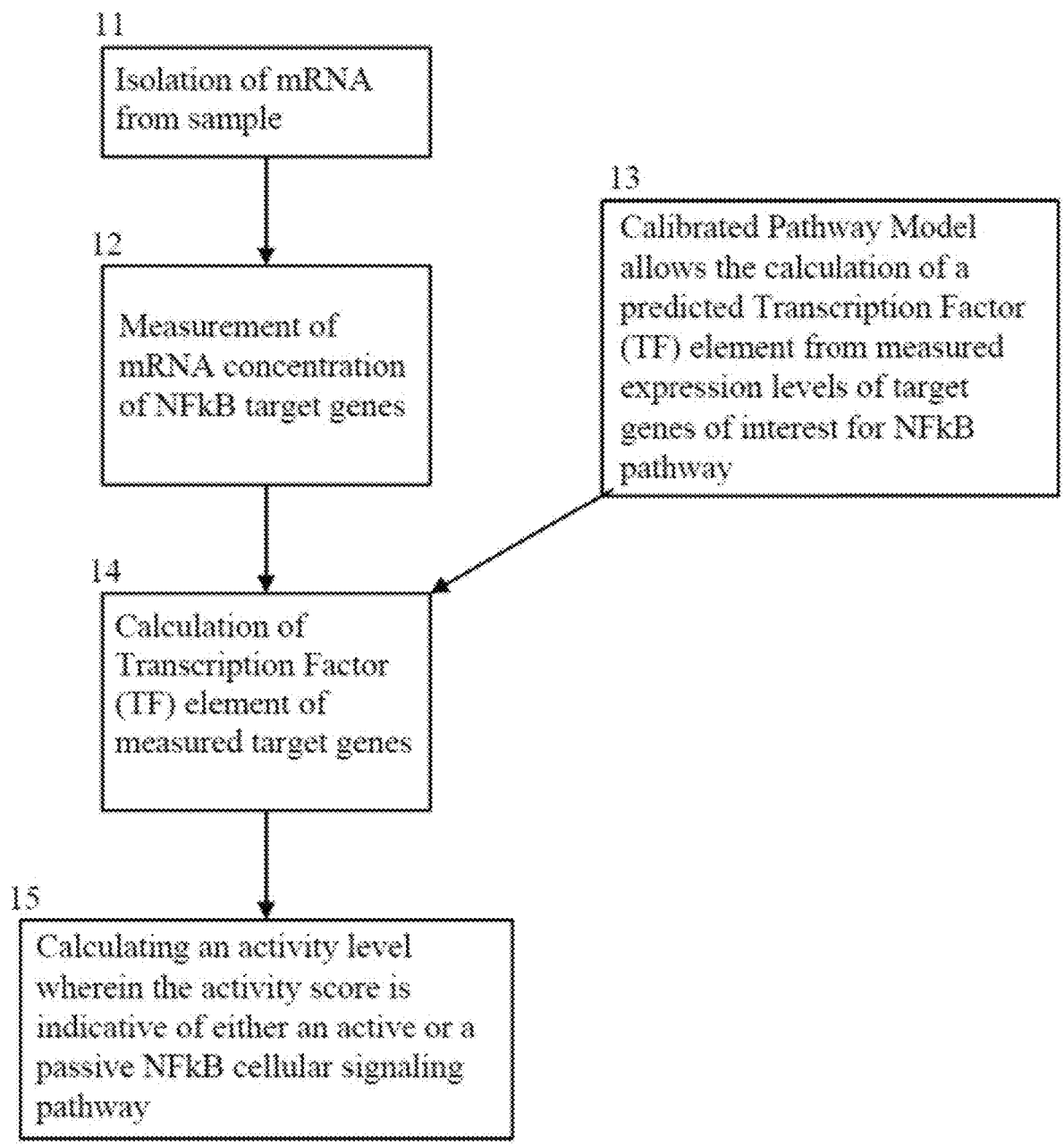

FIG. 3 shows an exemplary flow chart for calculating the activity level of the NFkB cellular signaling pathway based on expression levels of target genes derived from a sample.

Figure 4:
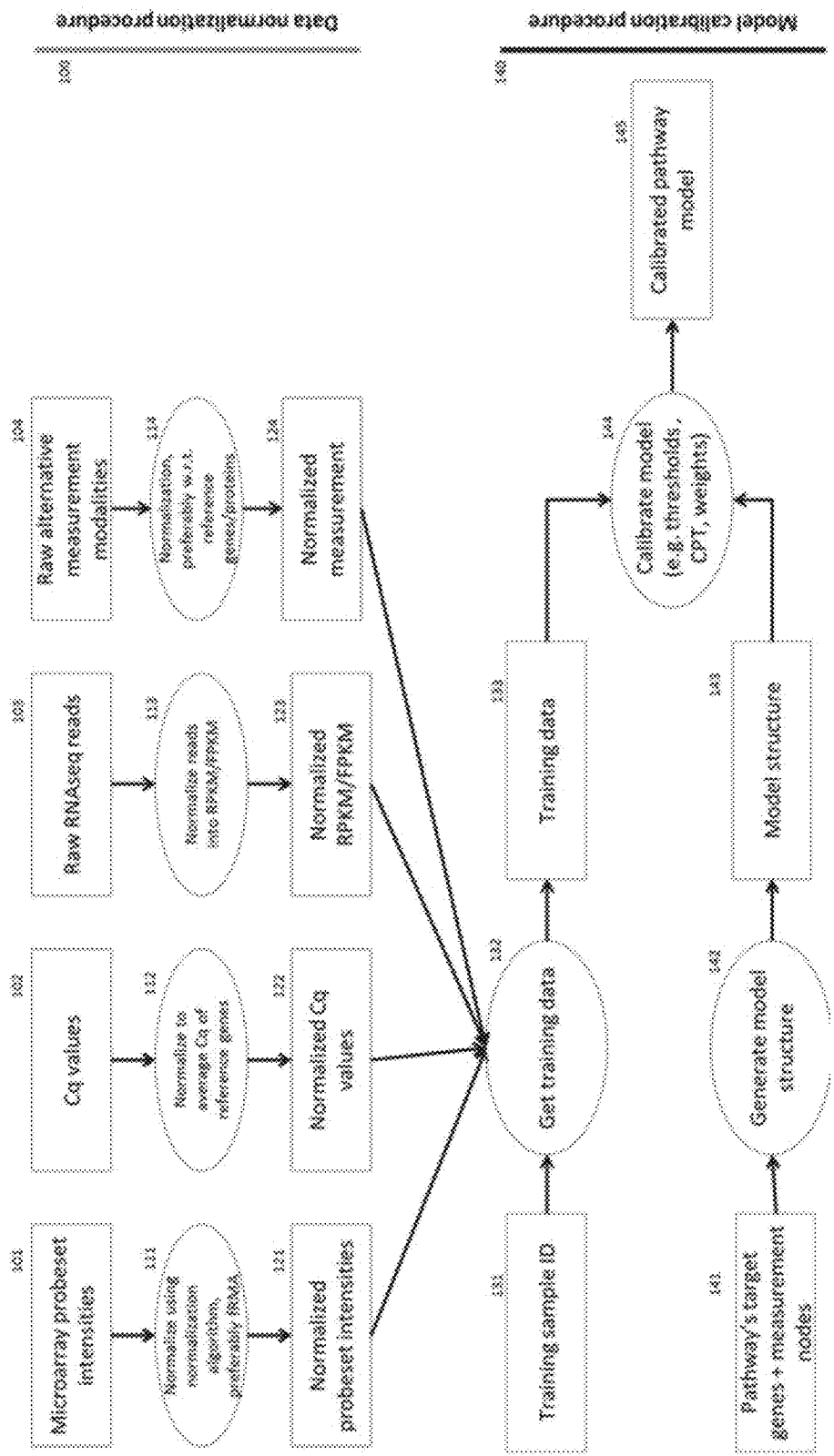

FIG. 4 shows an exemplary flow chart for obtaining a calibrated pathway model as described herein.

Figure 5:
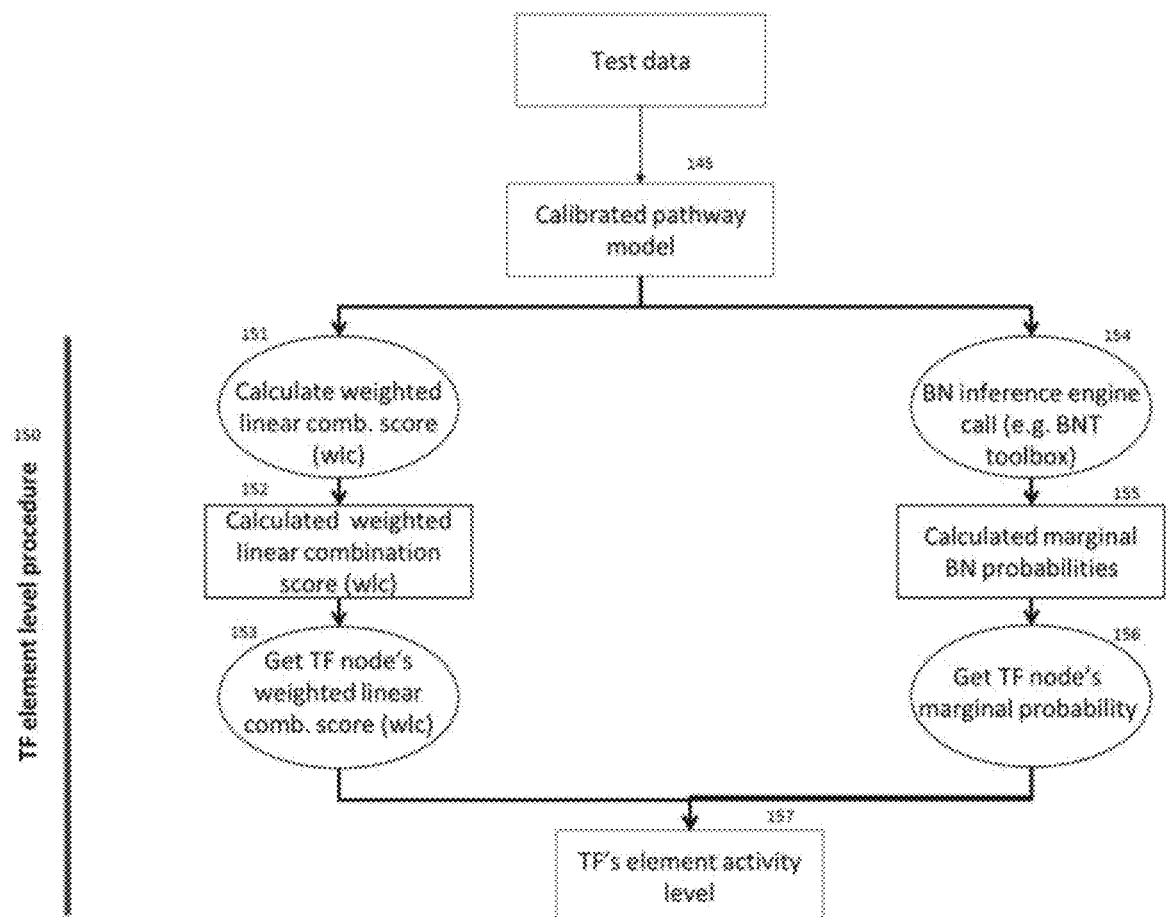

FIG. 5 shows an exemplary flow chart for calculating the Transcription Factor (TF) Element as described herein.

Figure 6:
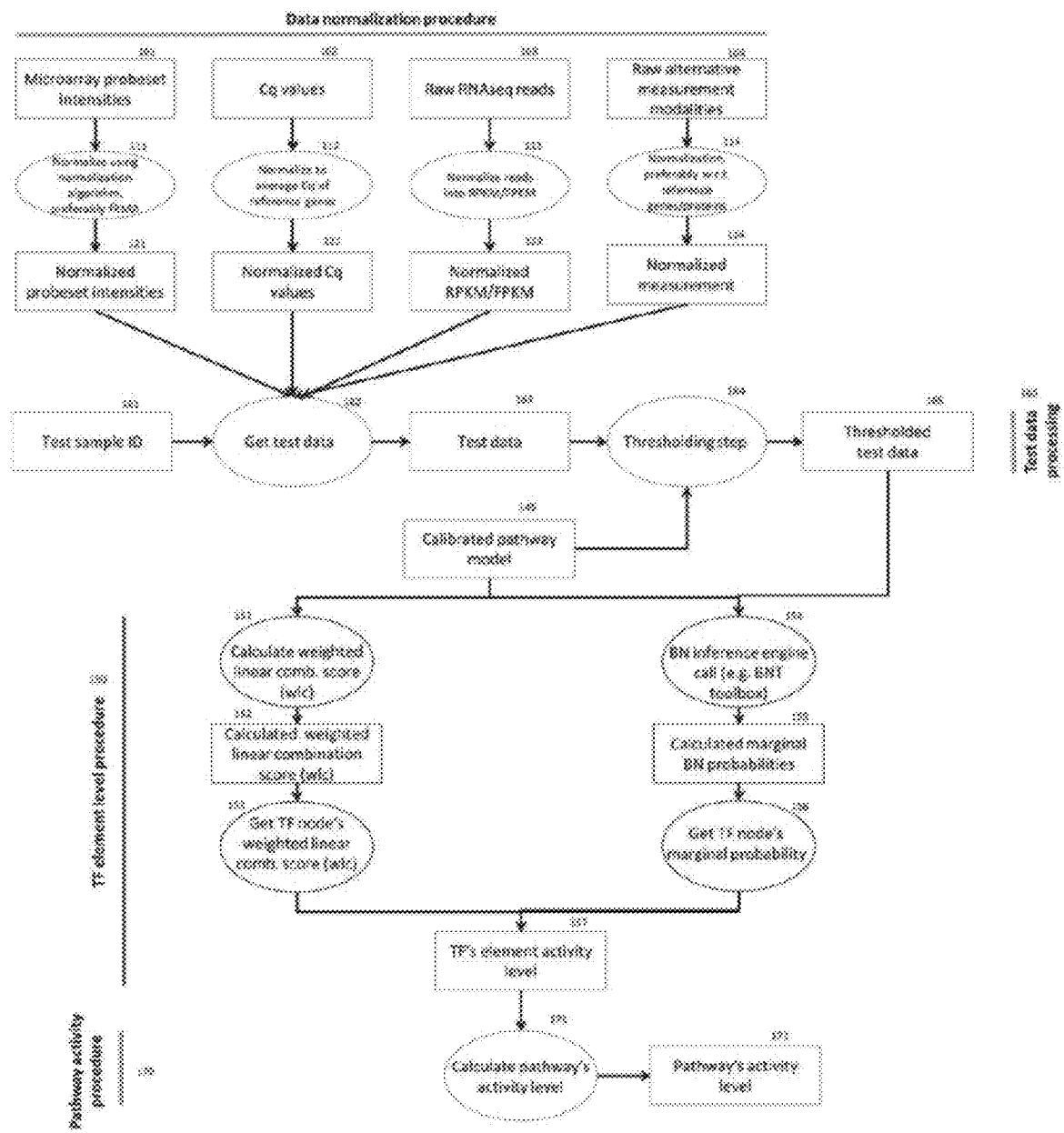

FIG. 6 shows an exemplary flow chart for calculating the NFkB cellular signaling pathway activity level using discretized observables.

Figure 7:
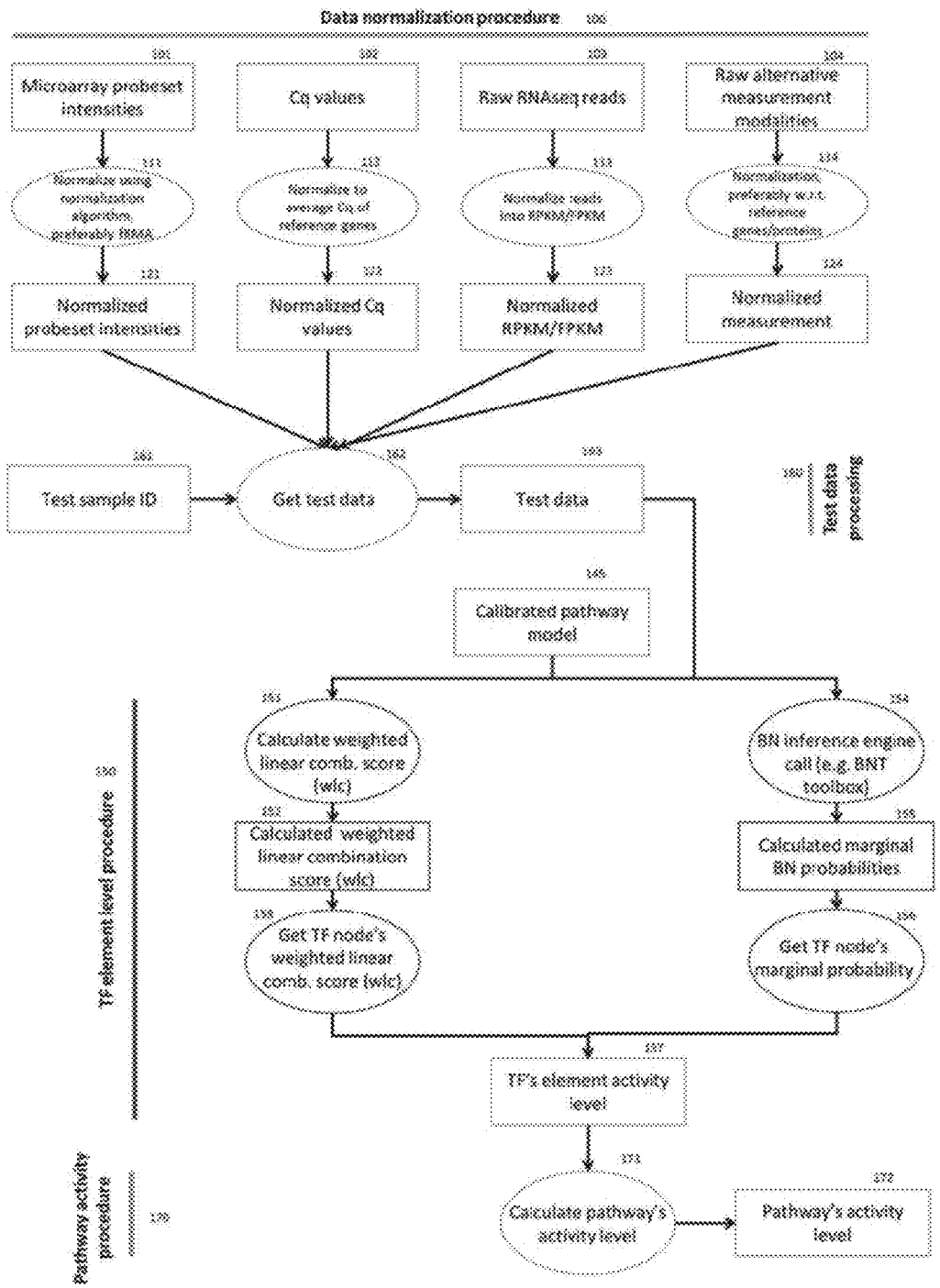

FIG. 7 shows an exemplary flow chart for calculating the NFkB cellular signaling pathway activity level using continuous observables.

Figure 8:
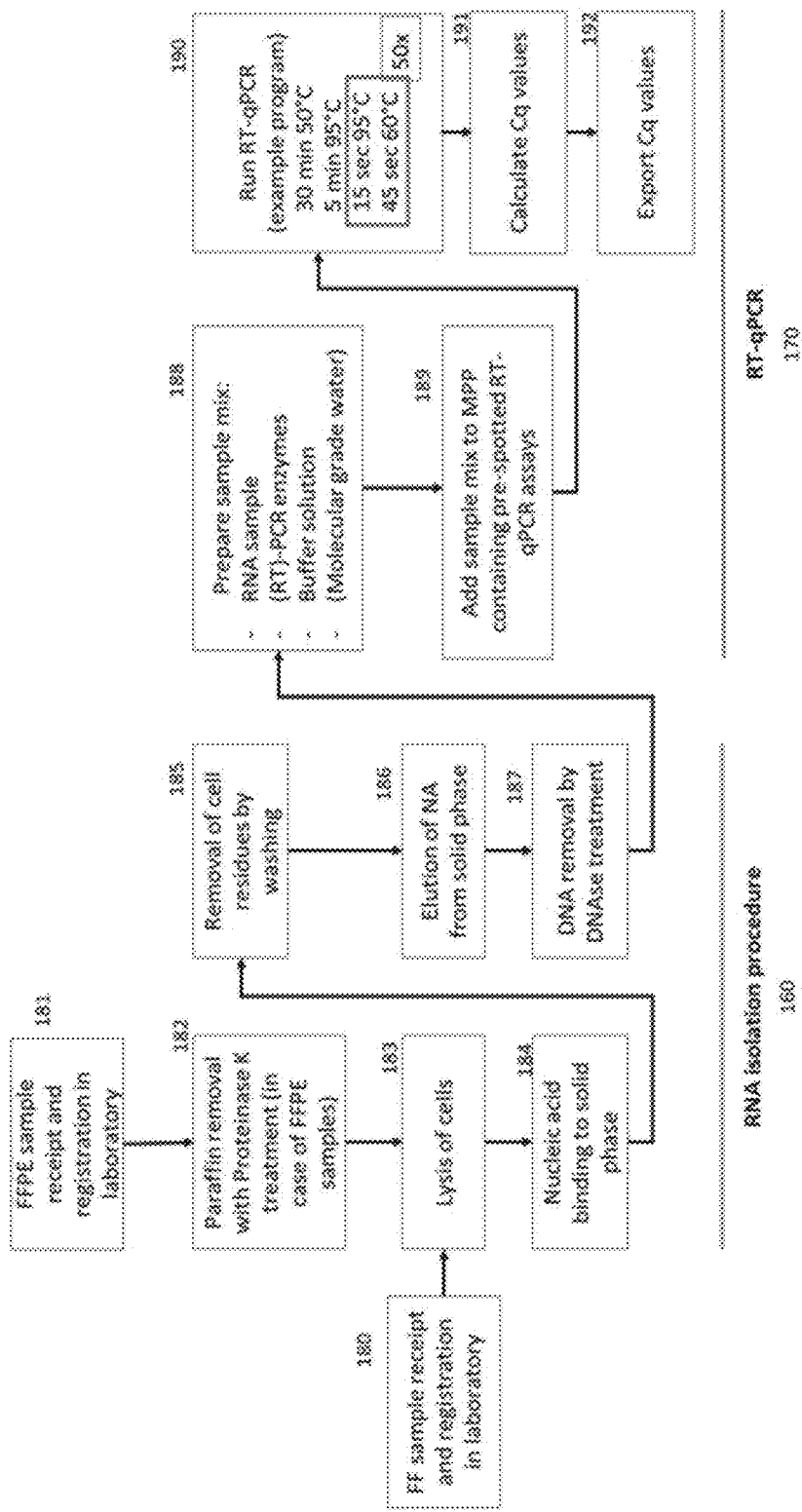
Figure 9:
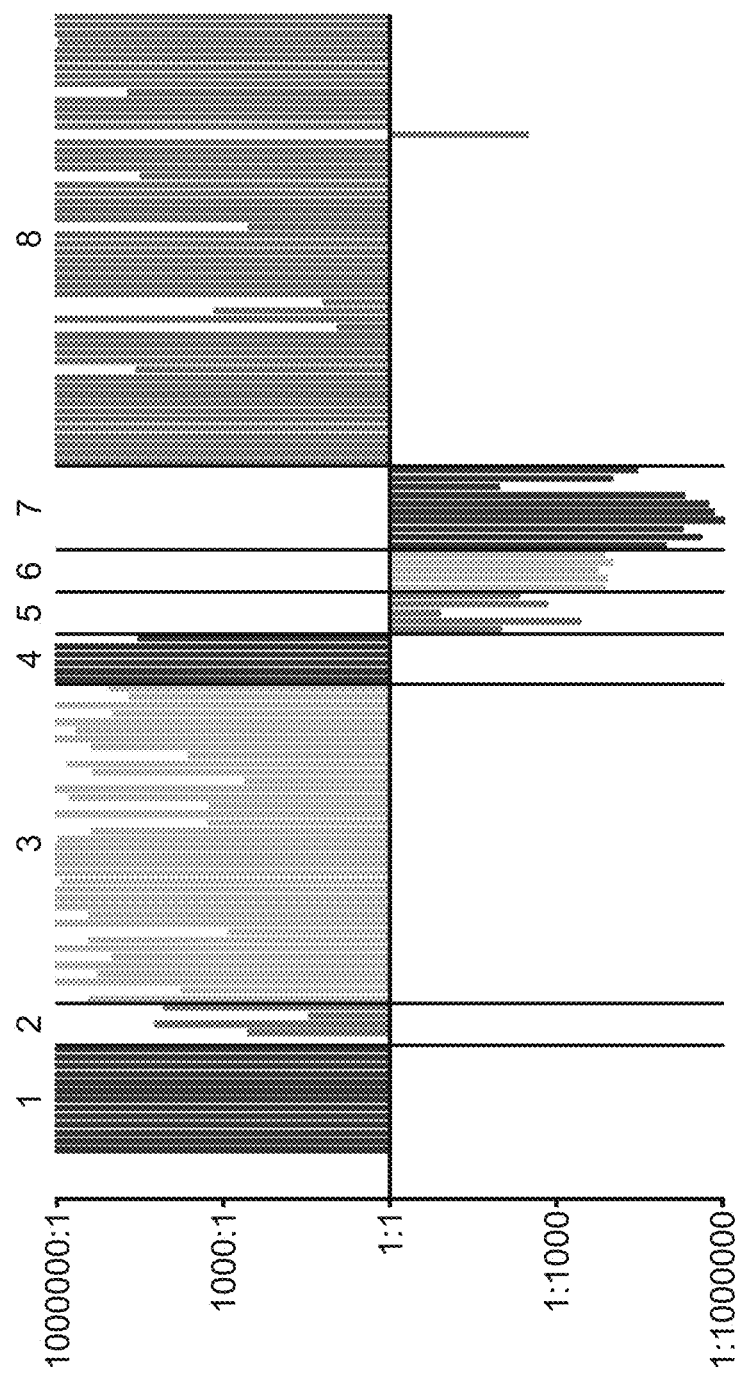
Figure 10:
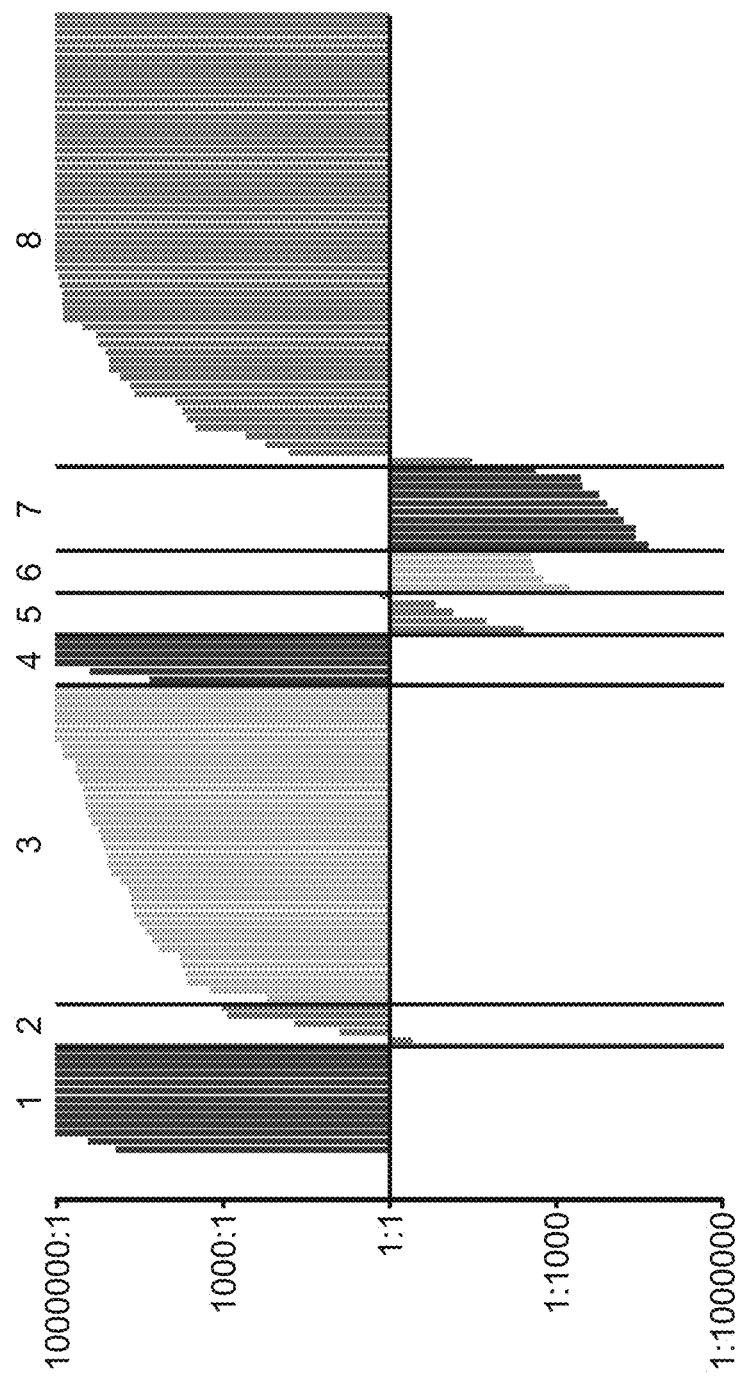
Figure 11:
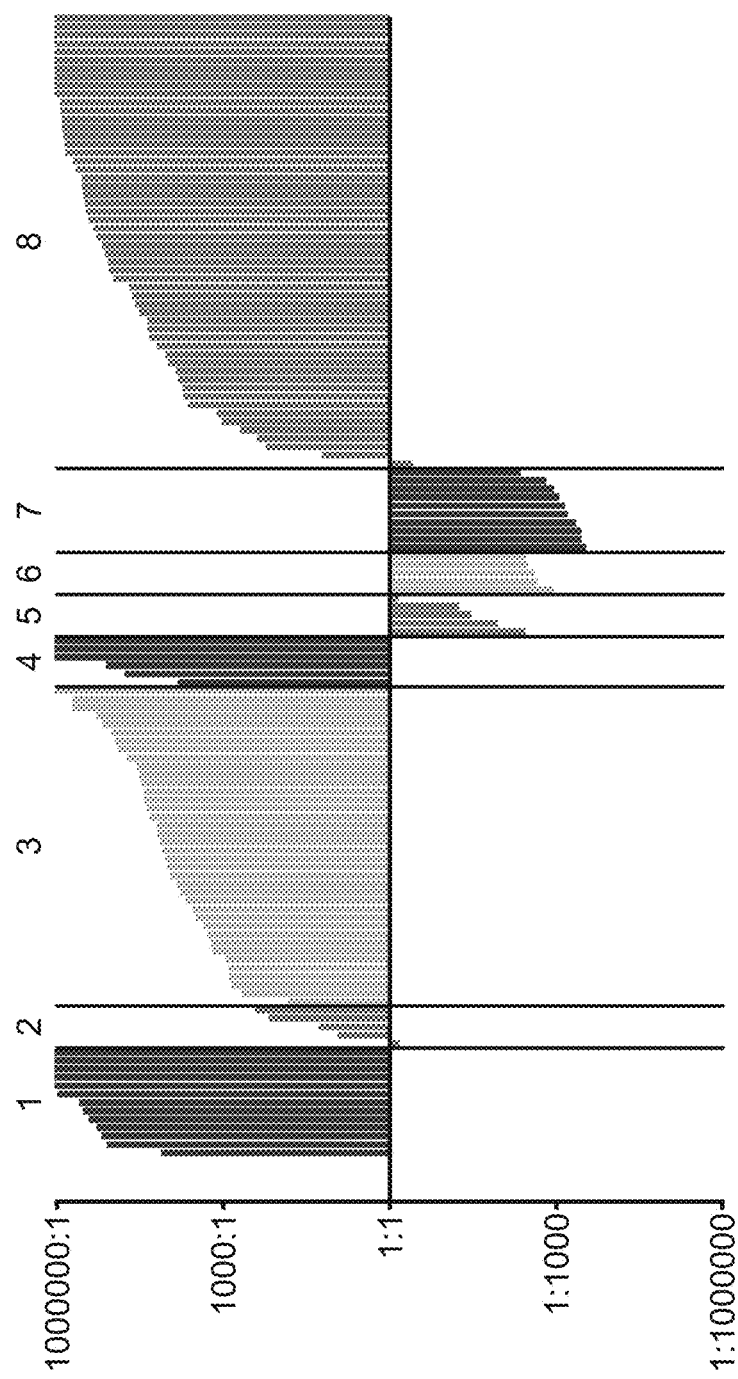
Figure 12:
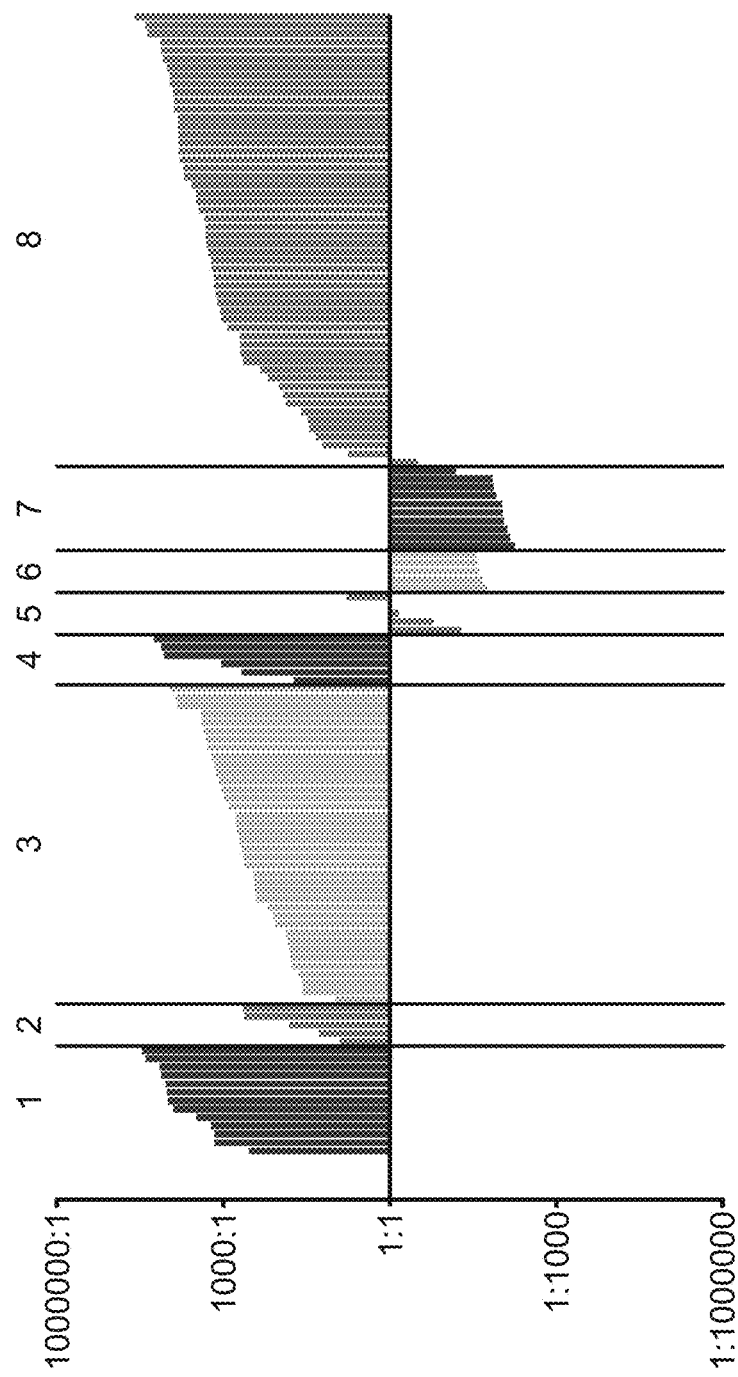

FIG. 8 shows an exemplary flow chart for determining Cq values from RT-qPCR analysis of the target genes of the NFkB cellular signaling pathway.

FIGS. 9 to 12 show training results of the exemplary Bayesian network model based on the evidence curated list of target genes (FIG. 9), the 19 target genes shortlist (FIG. 10), the 13 target genes shortlist (FIG. 11), and the 7 target genes shortlist of the NFkB cellular signaling pathway (FIG. 12) (see Tables 3 to 6), respectively. (Legend: 1—ABC DLBCL; 2—Lymphoblastoid cell line; 3—Follicular lymphoma; 4—GCB DLBCL; 5—Memory B-cells; 6—Naïve B-cells; 7—Normal; 8—DLBCL unknown subtype)

Figure 13:
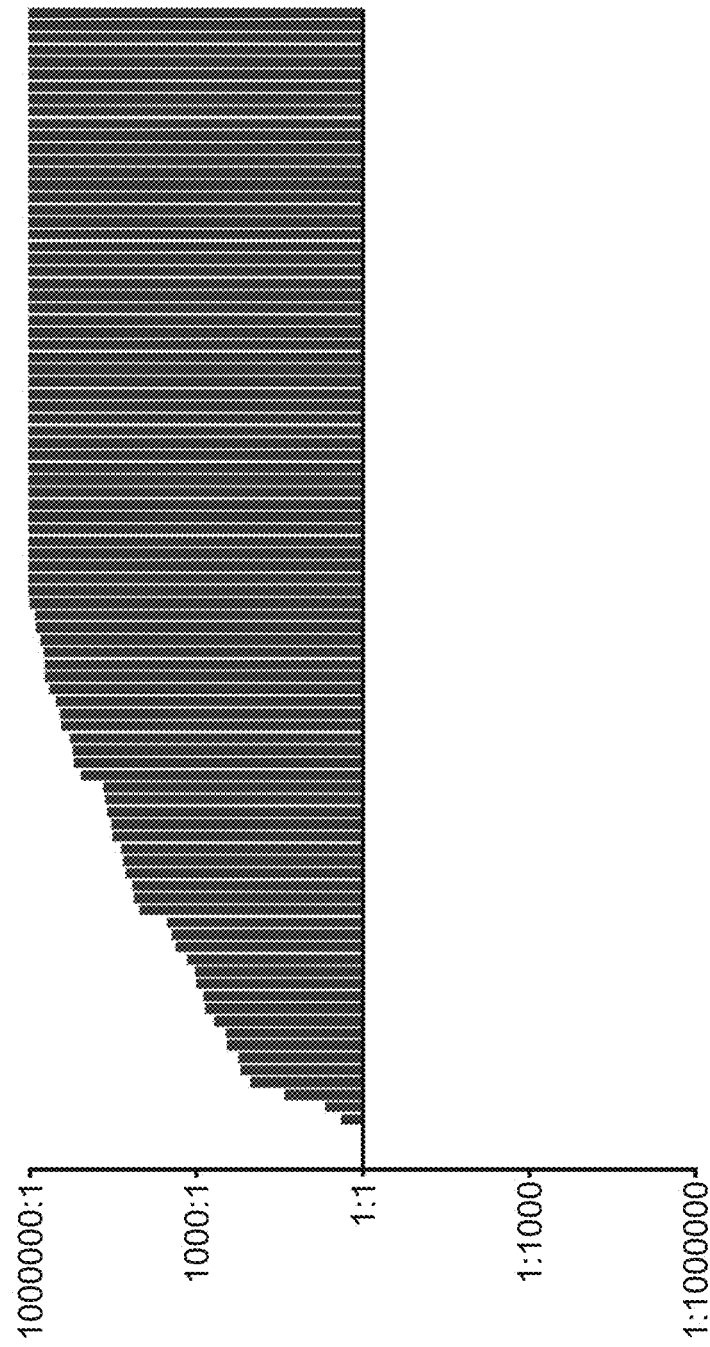
Figure 14:
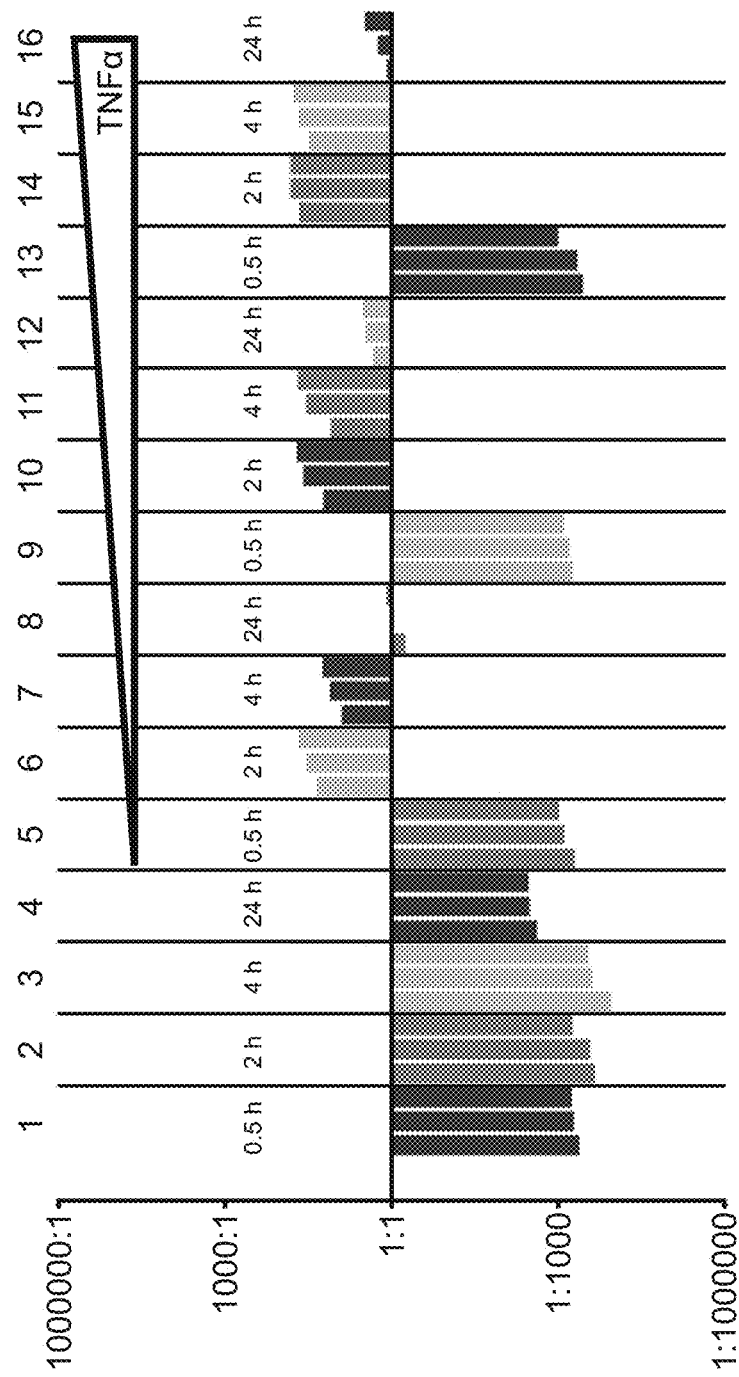
Figure 15:
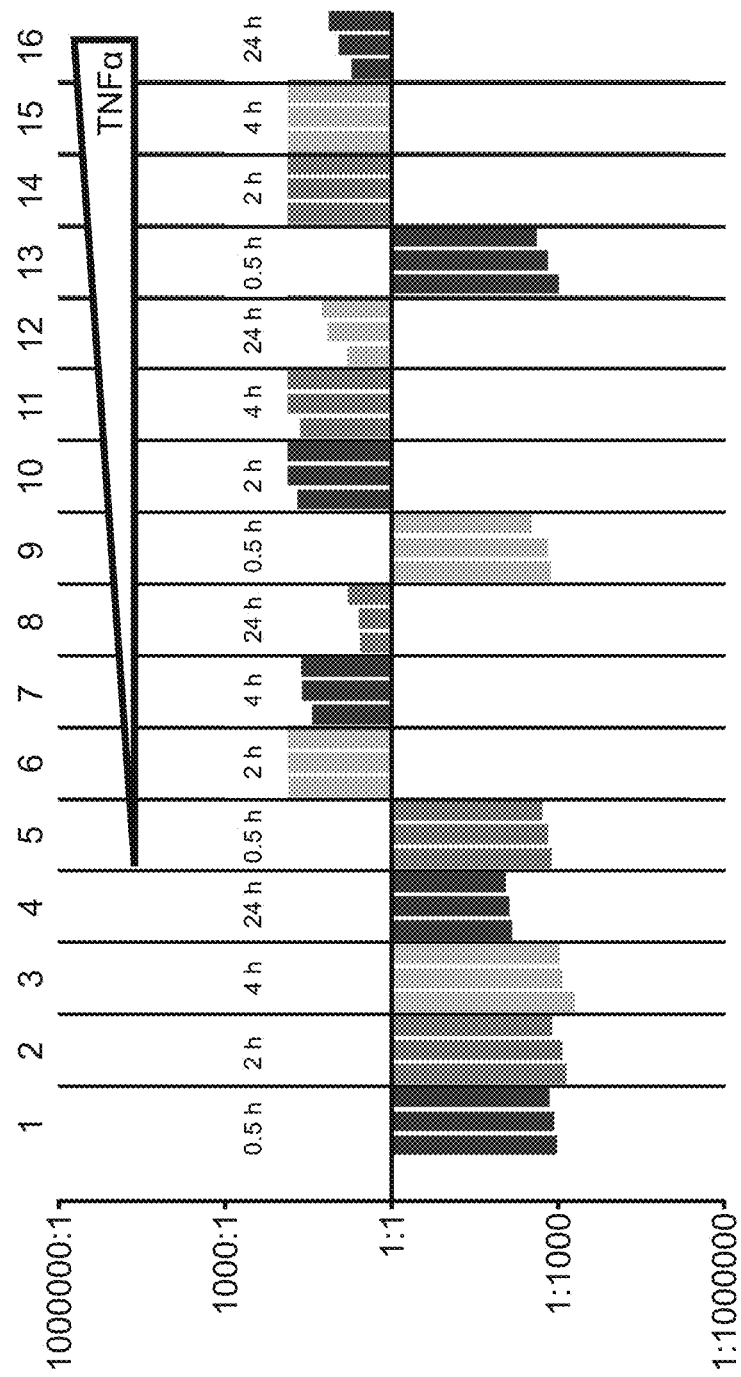
Figure 16:
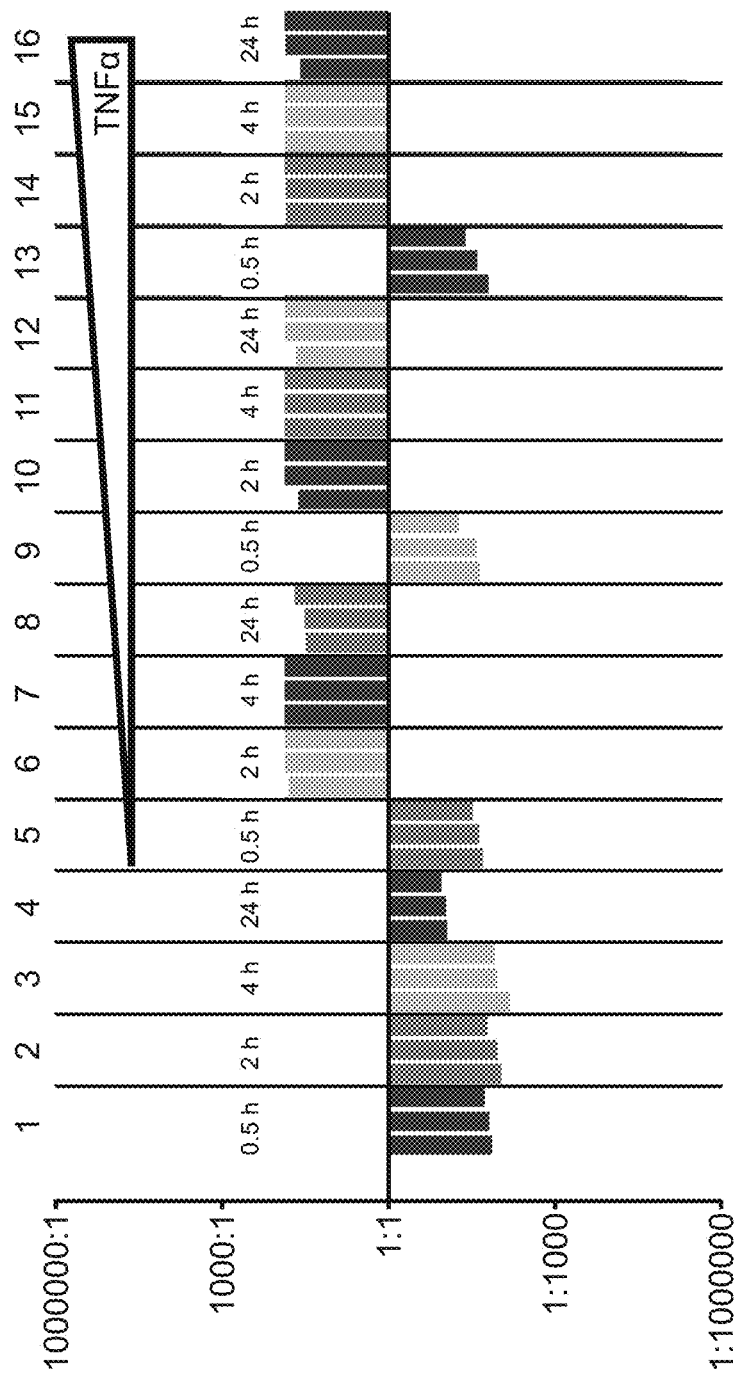
Figure 17:
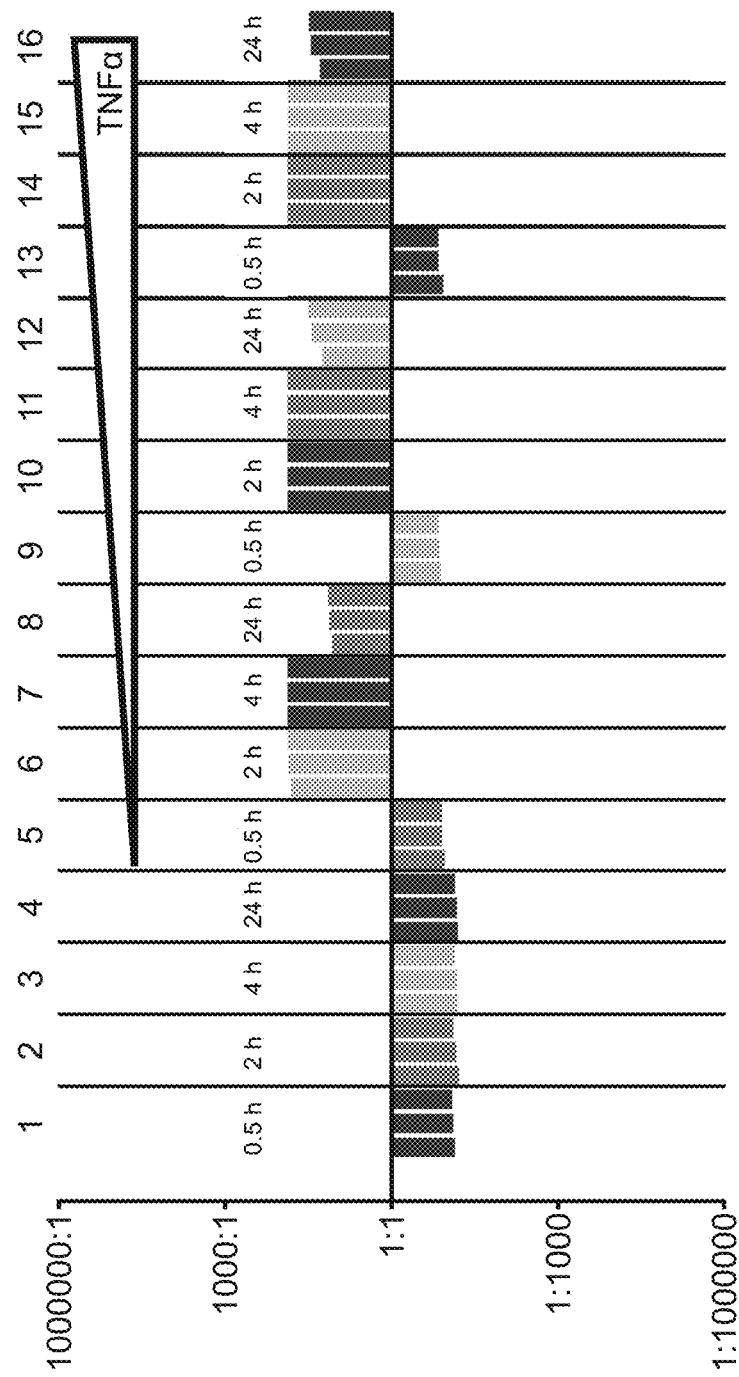

FIG. 13 shows NFkB cellular signaling pathway activity predictions of the trained exemplary Bayesian network model using the evidence curated list of target genes (see Table 3) for diffuse large B-cell lymphoma (DLBCL) samples from GSE34171.

FIGS. 14 to 17 show NFkB cellular signaling pathway activity predictions of the trained exemplary Bayesian network model using the evidence curated list of target genes (FIG. 14), the 19 target genes shortlist (FIG. 15), the 13 target genes shortlist (FIG. 16), and the 7 target genes shortlist (FIG. 17) (see Tables 3 to 6), respectively, for normal human bronchial epithelial (NHBE) cell line samples from E-MTAB-1312, which were stimulated with different TNFα concentrations for different stimulation times. (Legend: 1—No TNFα (0.5 h); 2—No TNFα (2 h); 3—No TNFα (4 h); 4—No TNFα (24 h); 5—Low TNFα (0.5 h); 6—Low TNFα (2 h); 7—Low TNFα (4 h); 8—Low TNFα (24 h); 9—Medium TNFα (0.5 h); 10—Medium TNFα (2 h); 11—Medium TNFα (4 h); 12—Medium TNFα (24 h); 13—High TNFα (0.5 h); 14—High TNFα (2 h); 15—High TNFα (4 h); 16—High TNFα (24 h))

Figure 18:
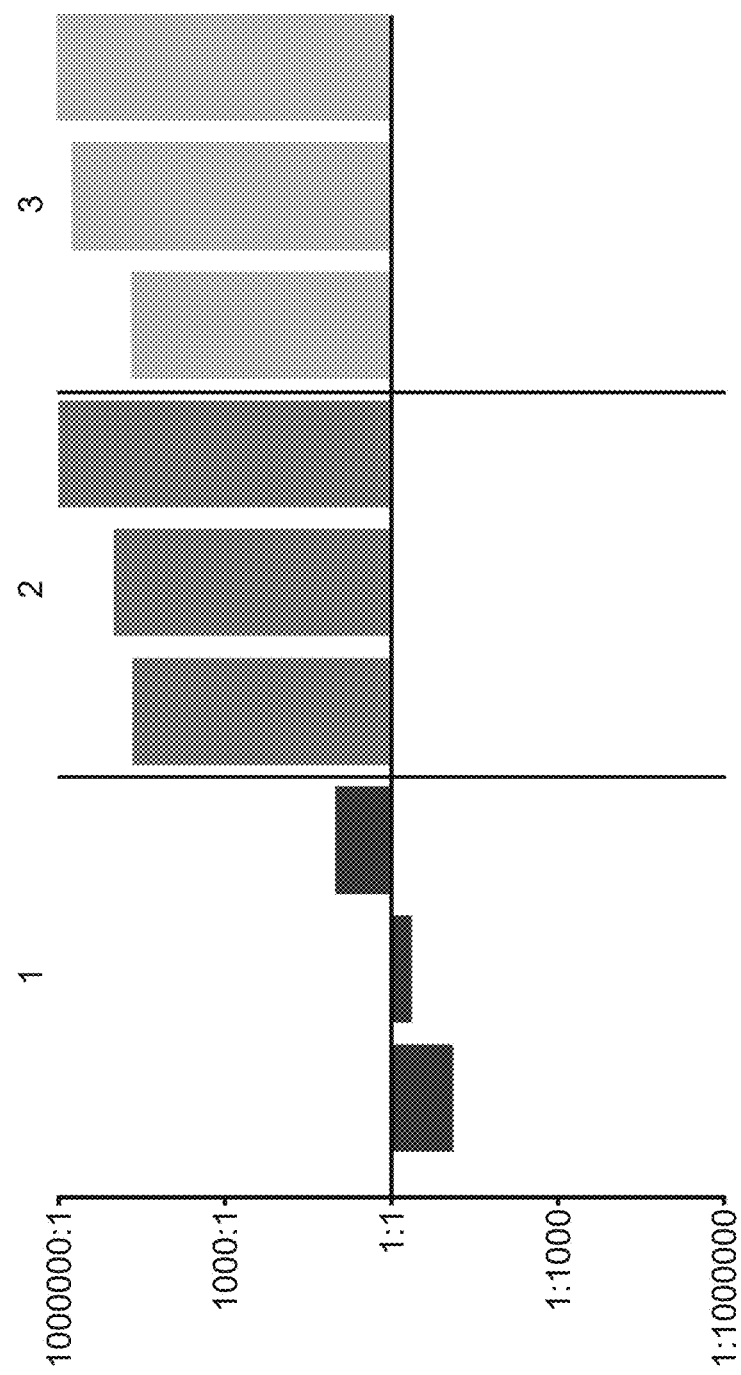
Figure 19:
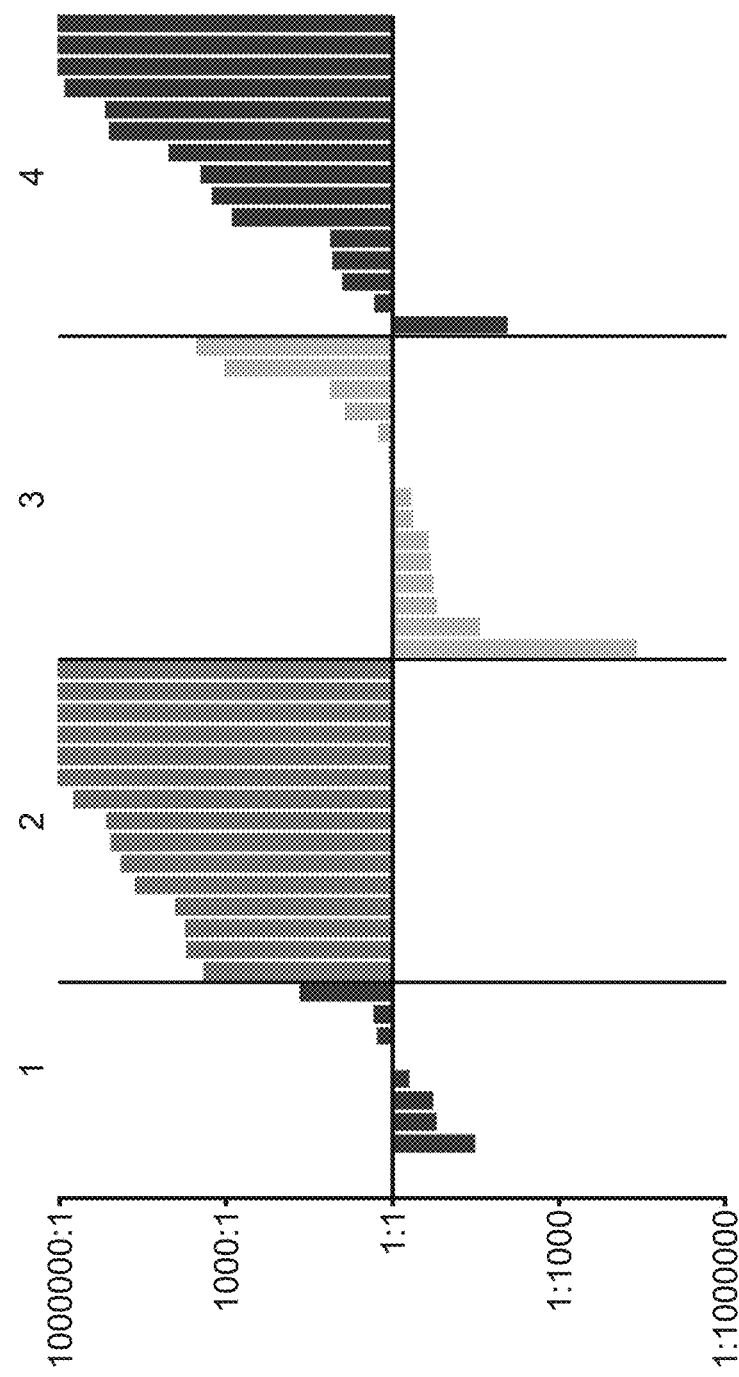
Figure 20:
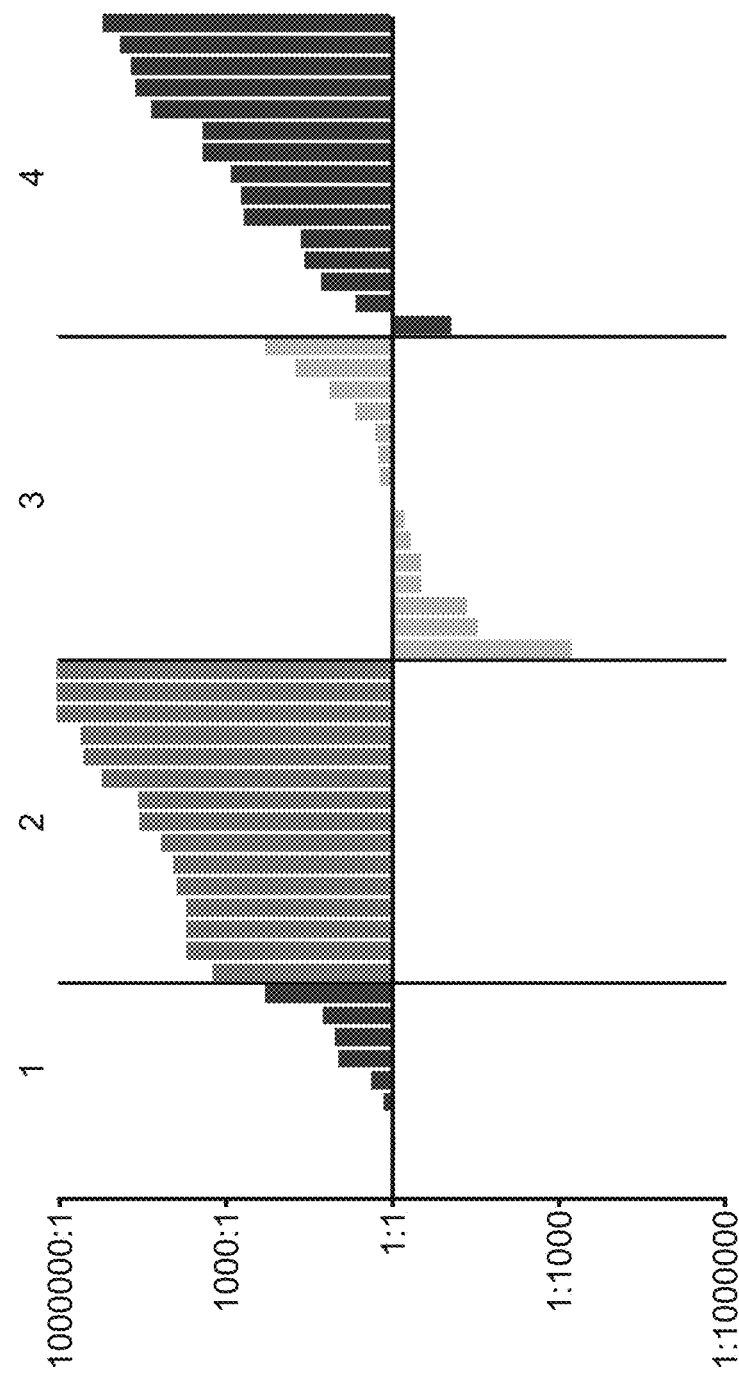
Figure 21:
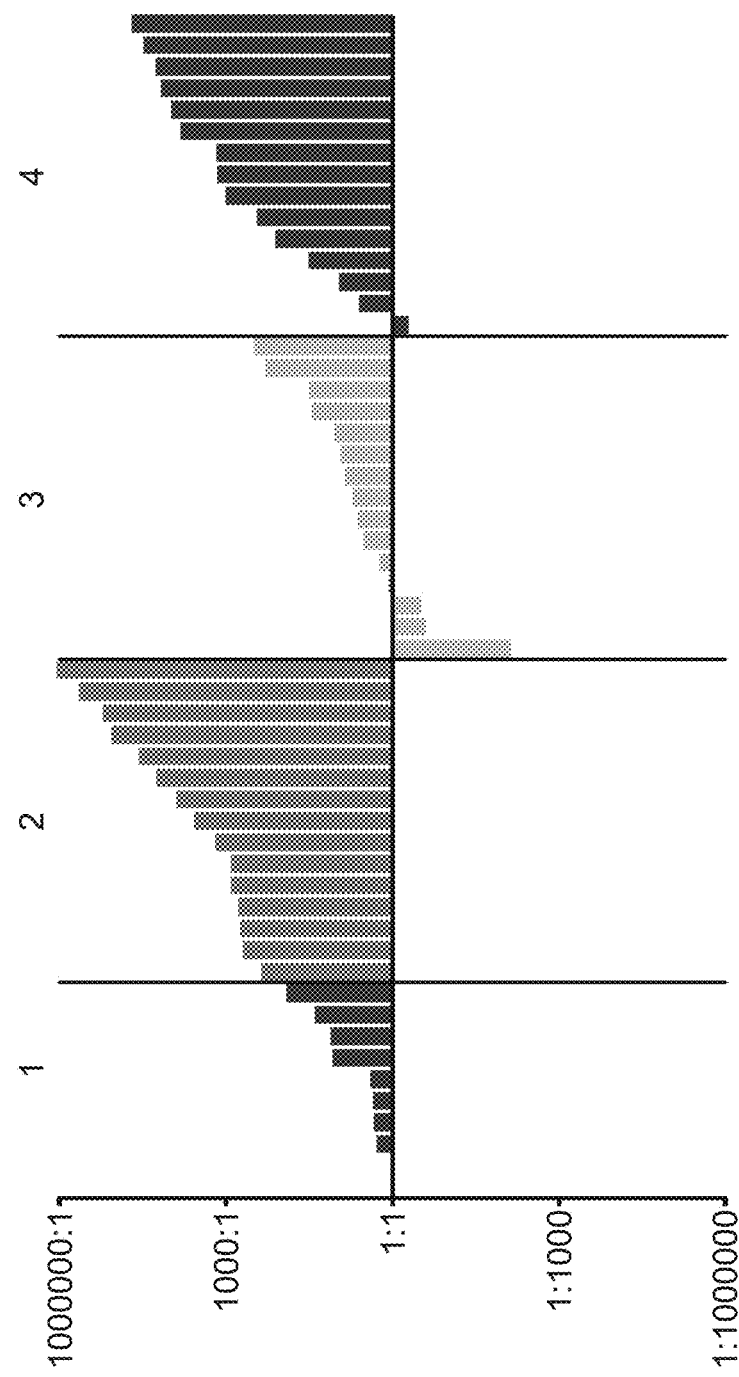
Figure 22:
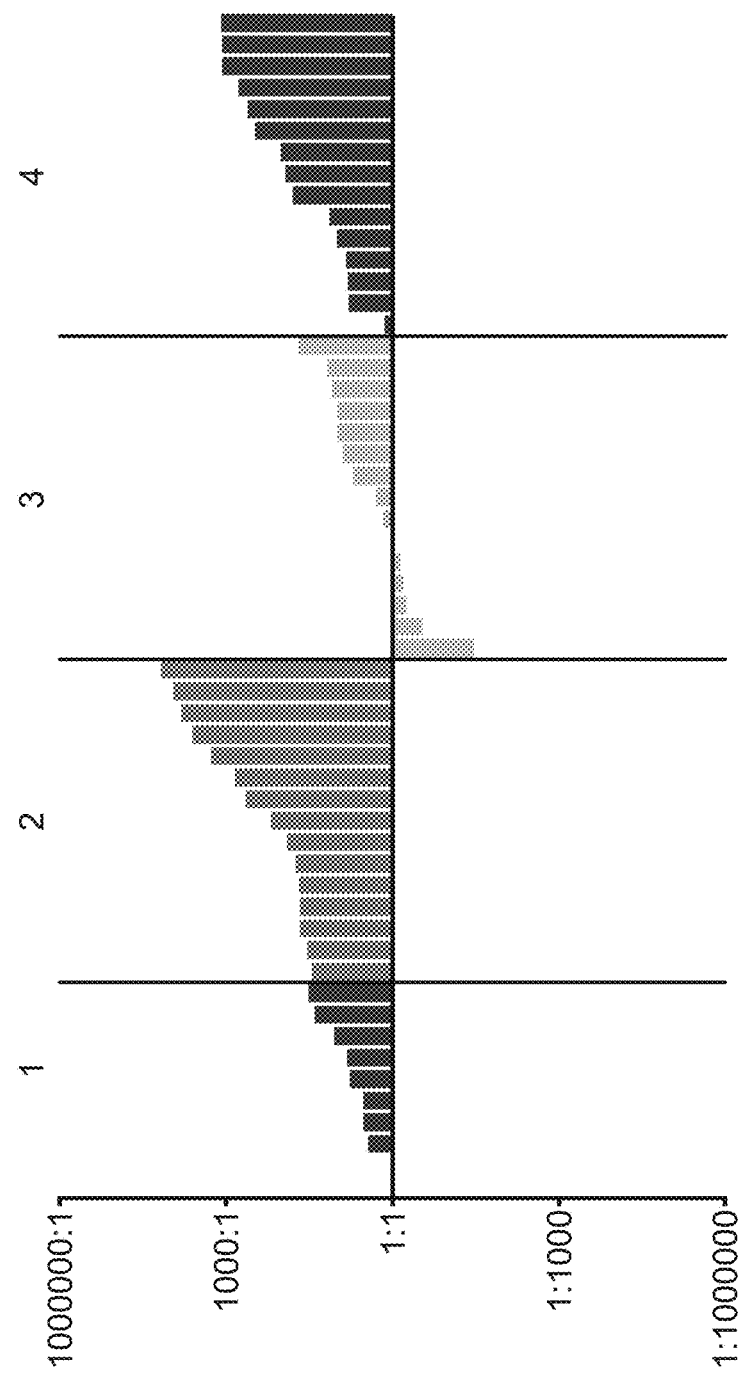

FIG. 18 shows NFkB cellular signaling pathway activity predictions of the trained exemplary Bayesian network model using the evidence curated list of target genes (see Table 3) for THP-1 monocytic cells. (Legend: 1—No LPS; 2—LPS stimulation; 3—LPS stimulation+coenzyme Q10)

FIGS. 19 to 22 show NFkB cellular signaling pathway activity predictions of the trained exemplary Bayesian network model using the evidence curated list of target genes (FIG. 19), the 19 target genes shortlist (FIG. 20), the 13 target genes shortlist (FIG. 21), and the 7 target genes shortlist (FIG. 22) (see Tables 3 to 6), respectively, for colon samples from GSE4183. (Legend: 1—Normal colon; 2—IBD; 3—Adenoma; 4—CRC)

Figure 23:
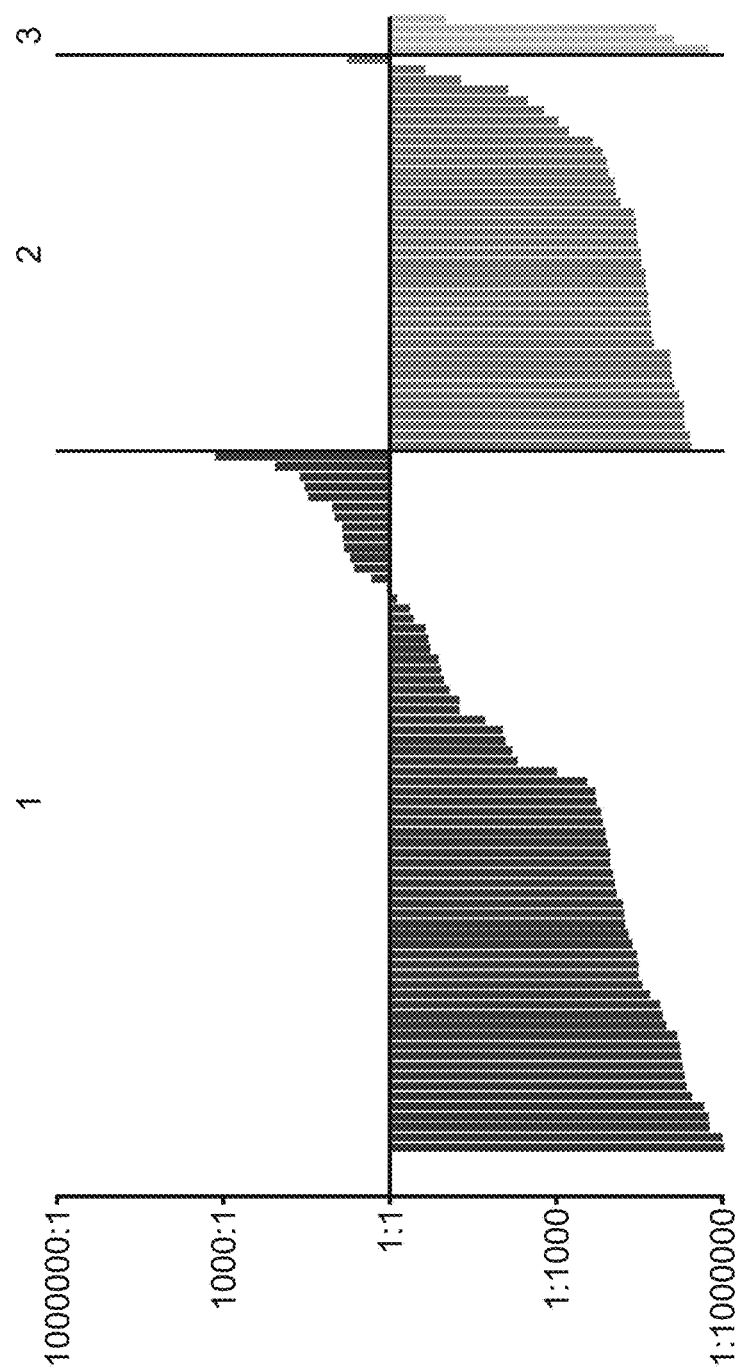

FIG. 23 shows NFkB cellular signaling pathway activity predictions of the trained exemplary Bayesian network model using the evidence curated list of target genes (see Table 3) for breast cancer cell lines from GSE10890. (Legend: 1 and 2—Unknown cellular signaling pathway driven cell lines; 3: Wnt cellular signaling pathway driven cell lines)

Figure 24:
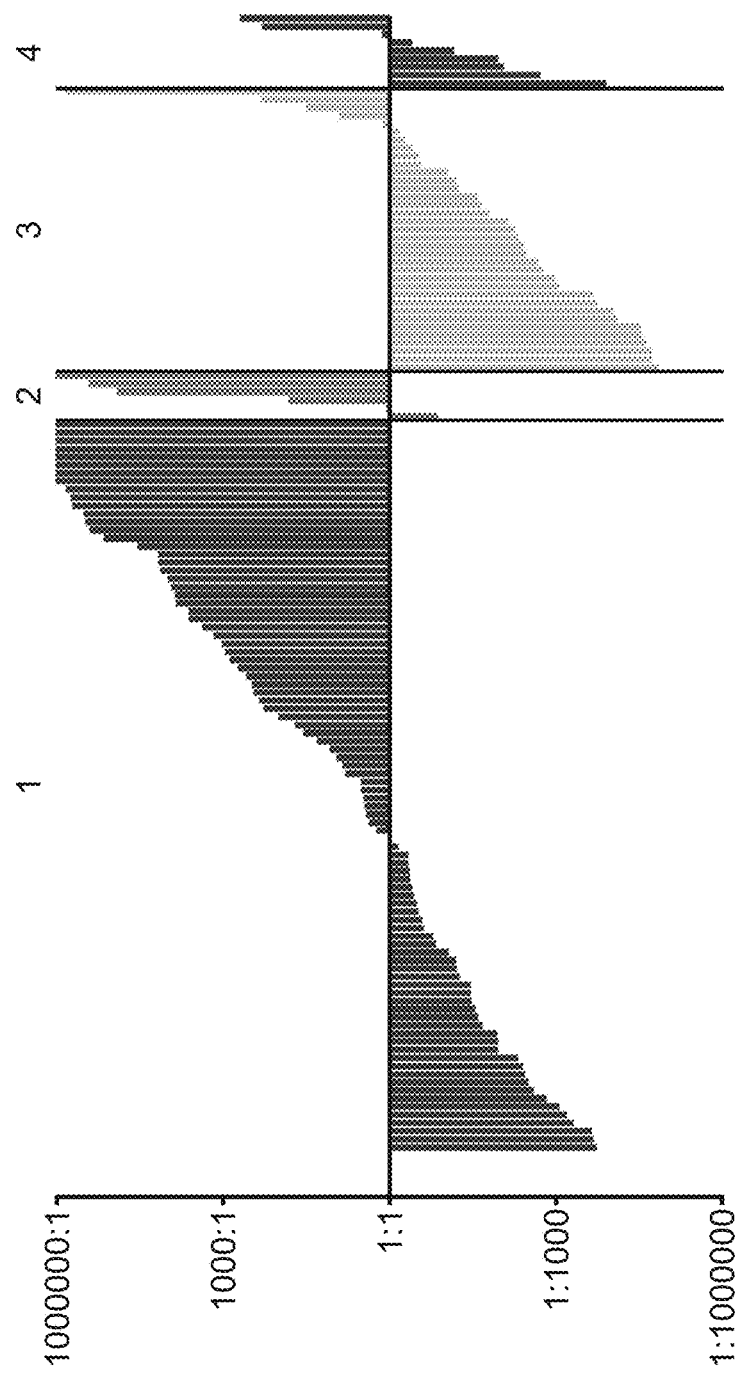

FIG. 24 shows NFkB cellular signaling pathway activity predictions of the trained exemplary Bayesian network model using the evidence curated list of target genes (see Table 3) for ovarian samples from GSE20565. (Legend: 1—Primary ovarian carcinoma; 2—Plausible primary ovarian carcinoma; 3—Breast metastasis in ovary; 4—Plausible breast metastasis in ovary)

Figure 25:
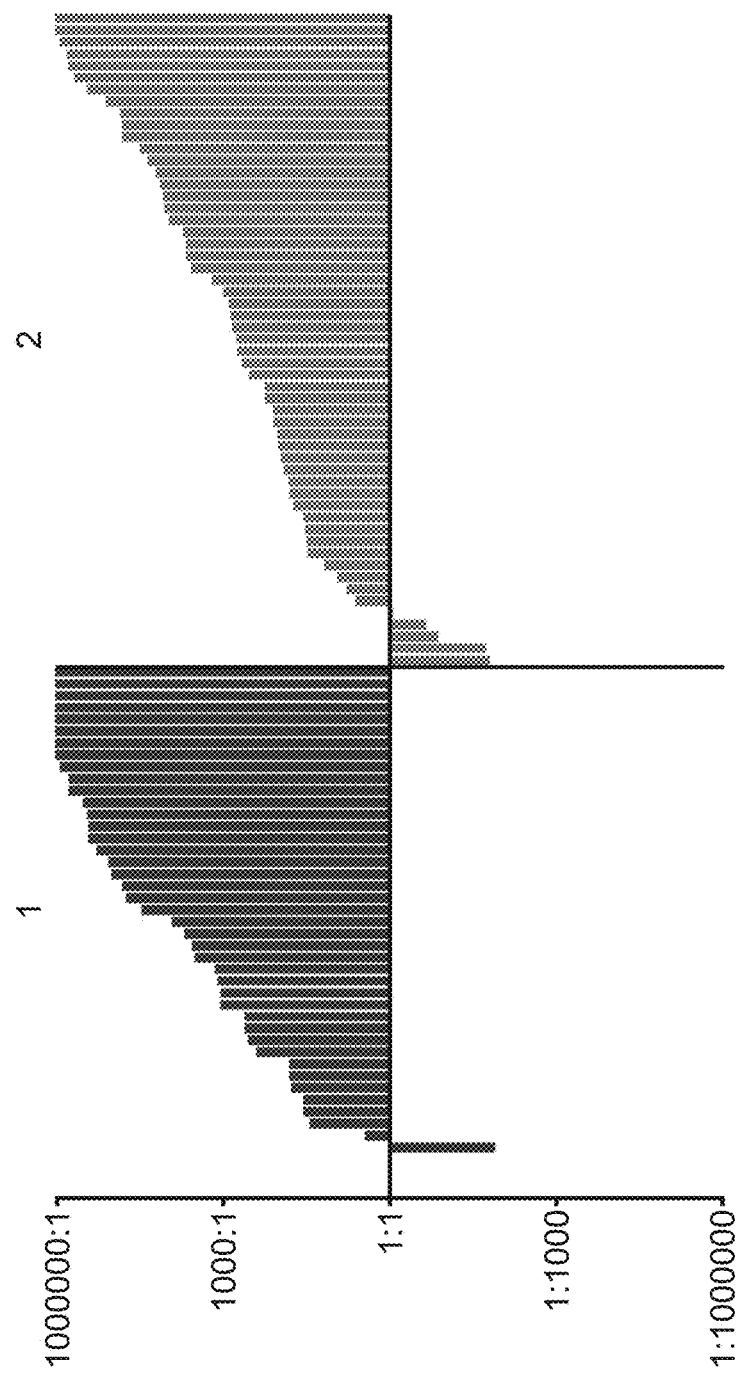

FIG. 25 shows NFkB cellular signaling pathway activity predictions of the trained exemplary Bayesian network model using the evidence curated list of target genes (see Table 3) for breast cancer samples from E-MTAB-1006. (Legend: 1—Inflammatory breast cancer; 2—Non-inflammatory breast cancer)

Figure 26:
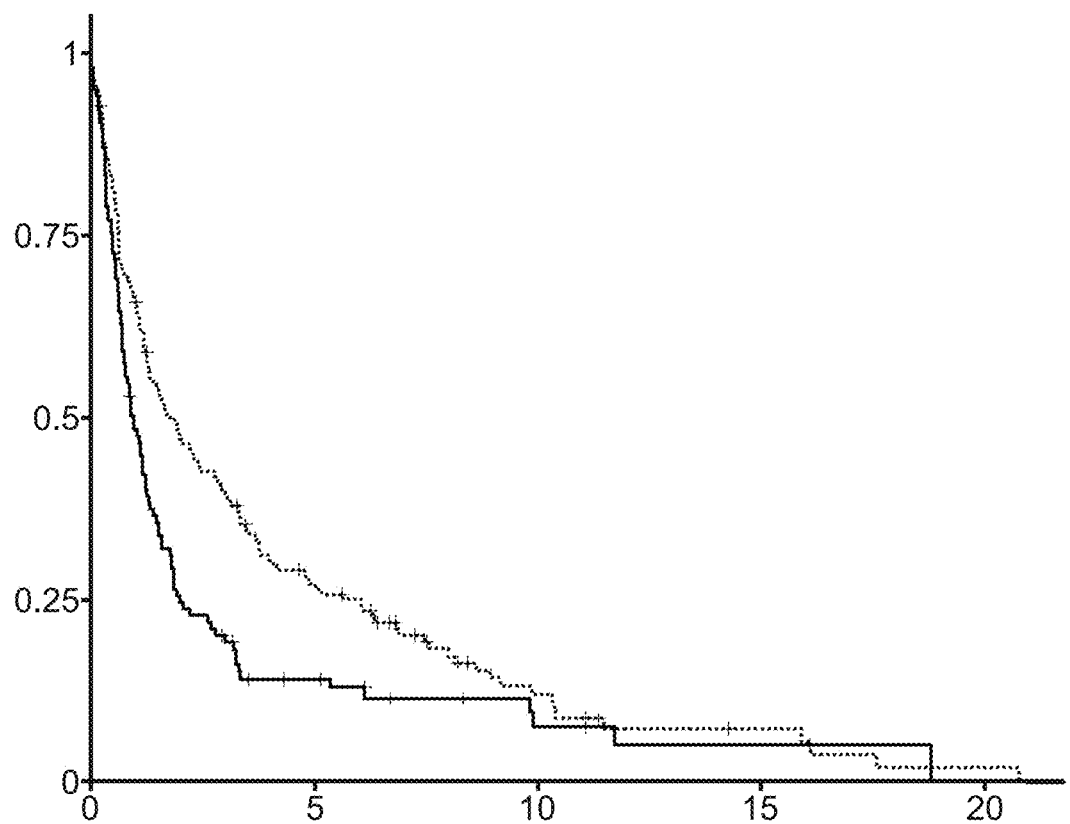

FIG. 26 illustrates a prognosis of glioma patients (GSE16011) depicted in a Kaplan-Meier plot, wherein the trained exemplary Bayesian network model using the evidence curated list of target genes (see Table 3) is employed.

Figure 27:
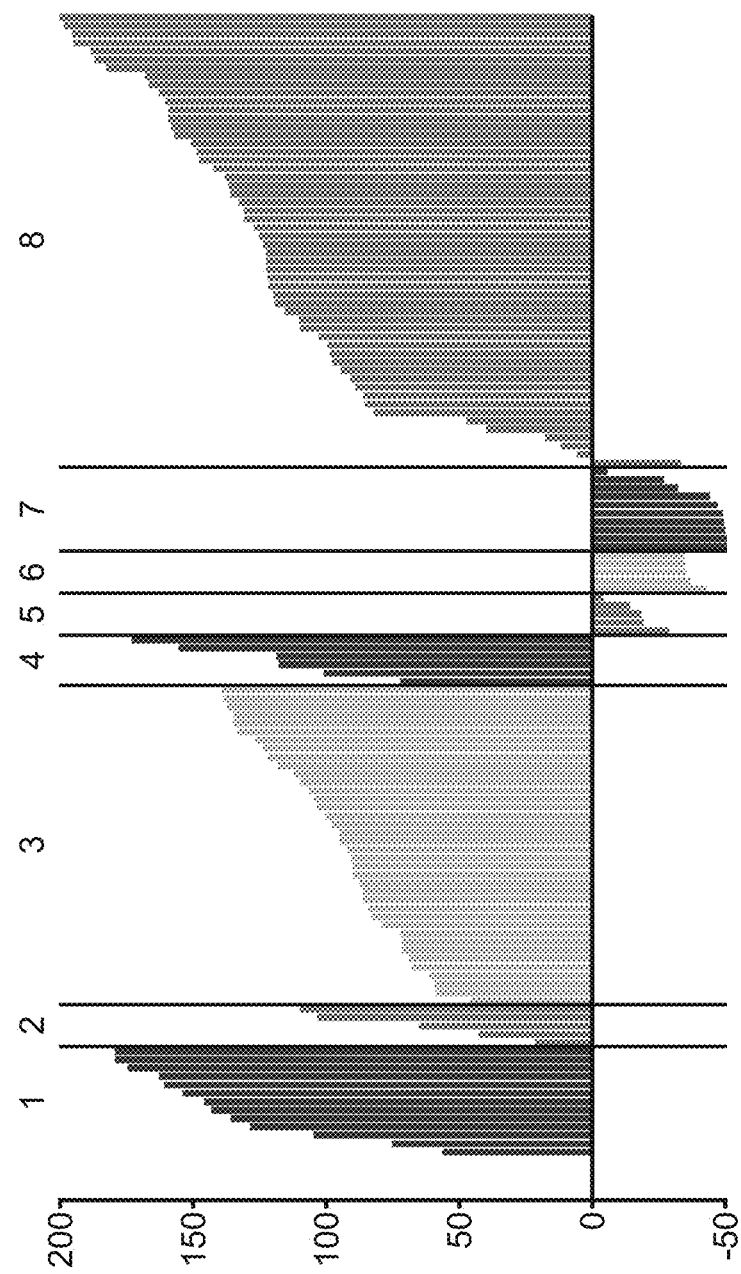

FIG. 27 shows training results of the exemplary linear model based on the evidence curated list of target genes (see Table 3). (Legend: 1—ABC DLBCL; 2—Lymphoblastoid cell line; 3—Follicular lymphoma; 4—GCB DLBCL; 5—Memory B-cells; 6—Naïve B-cells; 7—Normal; 8—DLBCL unknown subtype)

Figure 28:
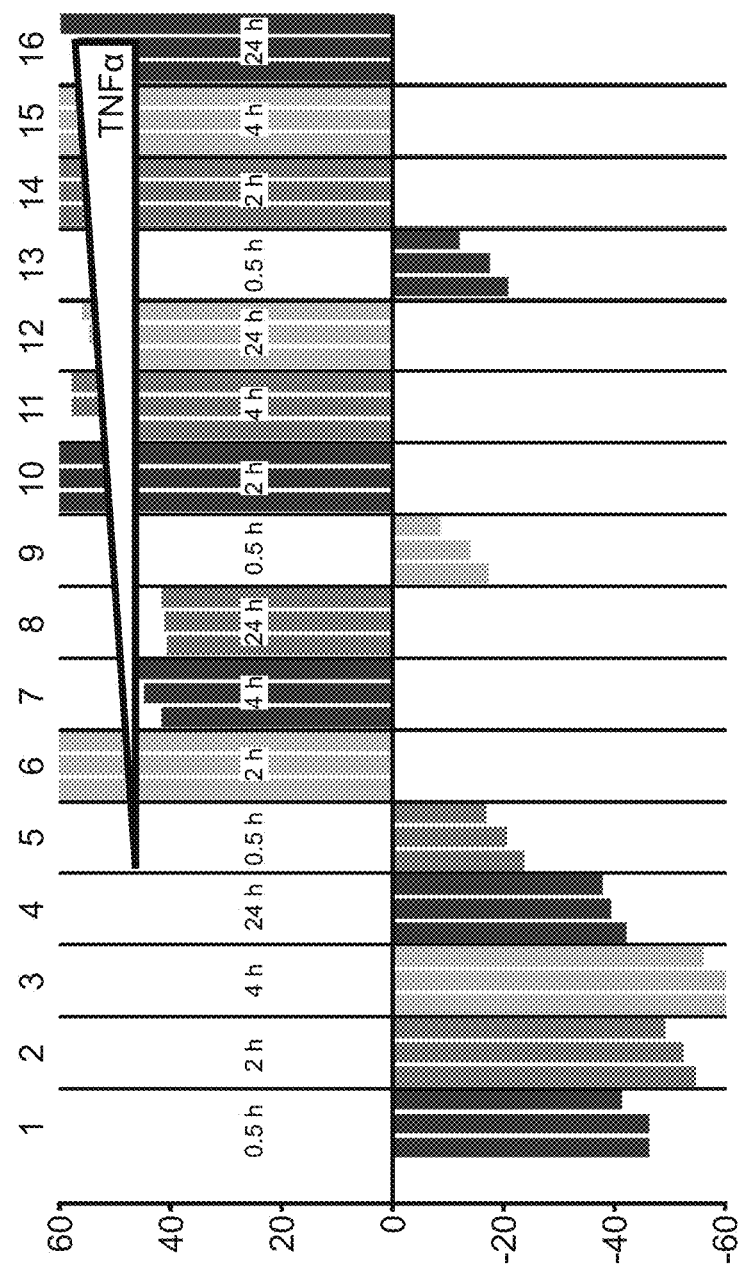

FIG. 28 shows NFkB cellular signaling pathway activity predictions of the trained exemplary linear model using the evidence curated list of target genes (see Table 3) for normal human bronchial epithelial (NHBE) cell line samples from E-MTAB-1312, which were stimulated with different TNFα concentrations for different stimulation times. (Legend: 1—No TNFα (0.5 h); 2—No TNFα (2 h); 3—No TNFα (4 h); 4—No TNFα (24 h); 5—Low TNFα (0.5 h); 6—Low TNFα (2 h); 7—Low TNFα (4 h); 8—Low TNFα (24 h); 9—Medium TNFα (0.5 h); 10—Medium TNFα (2 h); 11—Medium TNFα (4 h); 12—Medium TNFα (24 h); 13—High TNFα (0.5 h); 14—High TNFα (2 h); 15—High TNFα (4 h); 16—High TNFα (24 h))

Figure 29:
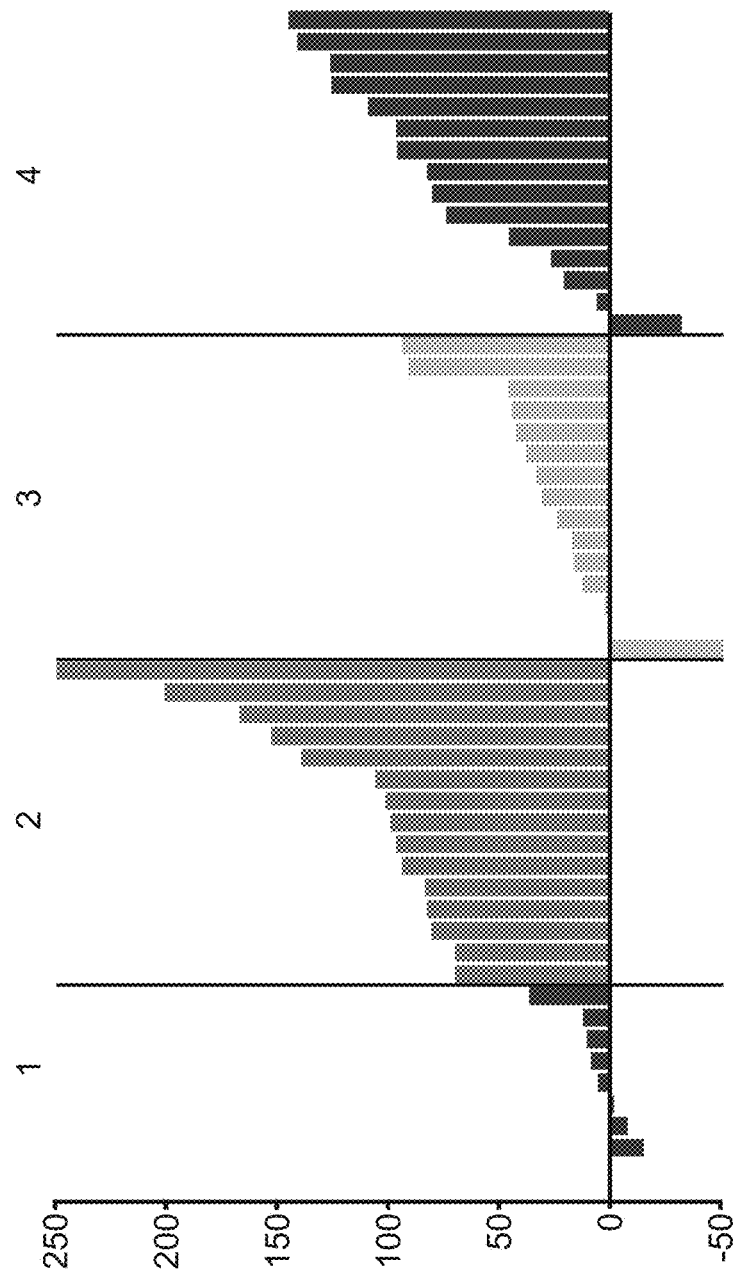

FIG. 29 shows NFkB cellular signaling pathway activity predictions of the trained exemplary linear model using the evidence curated list of target genes (see Table 3) for colon samples from GSE4183. (Legend: 1—Normal colon; 2—IBD; 3—Adenoma; 4—CRC)

Figure 30:
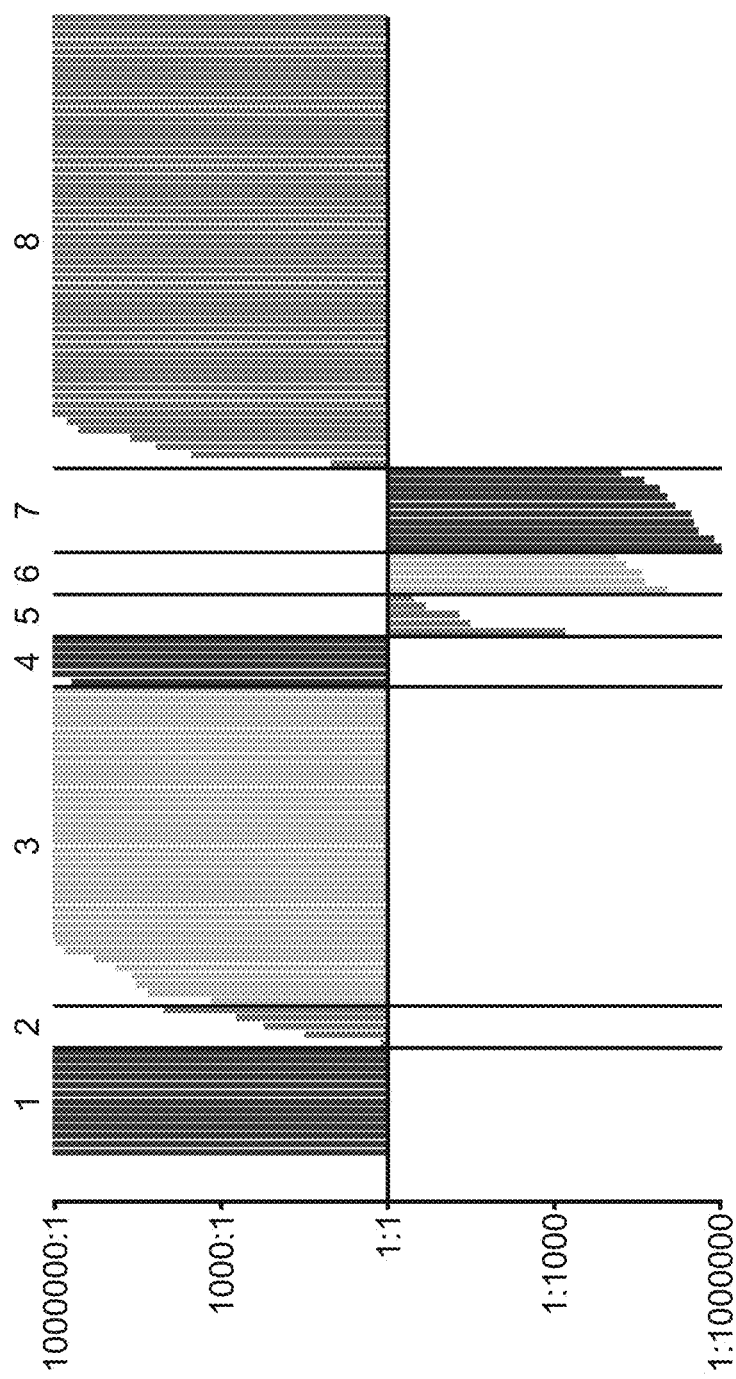

FIG. 30 shows training results of the exemplary Bayesian network model based on the broad literature list of putative target genes of the NFkB cellular signaling pathway (see Table 7). (Legend: 1—ABC DLBCL; 2—Lymphoblastoid cell line; 3—Follicular lymphoma; 4—GCB DLBCL; 5—Memory B-cells; 6—Naïve B-cells; 7—Normal; 8—DLBCL unknown subtype)

Figure 31:
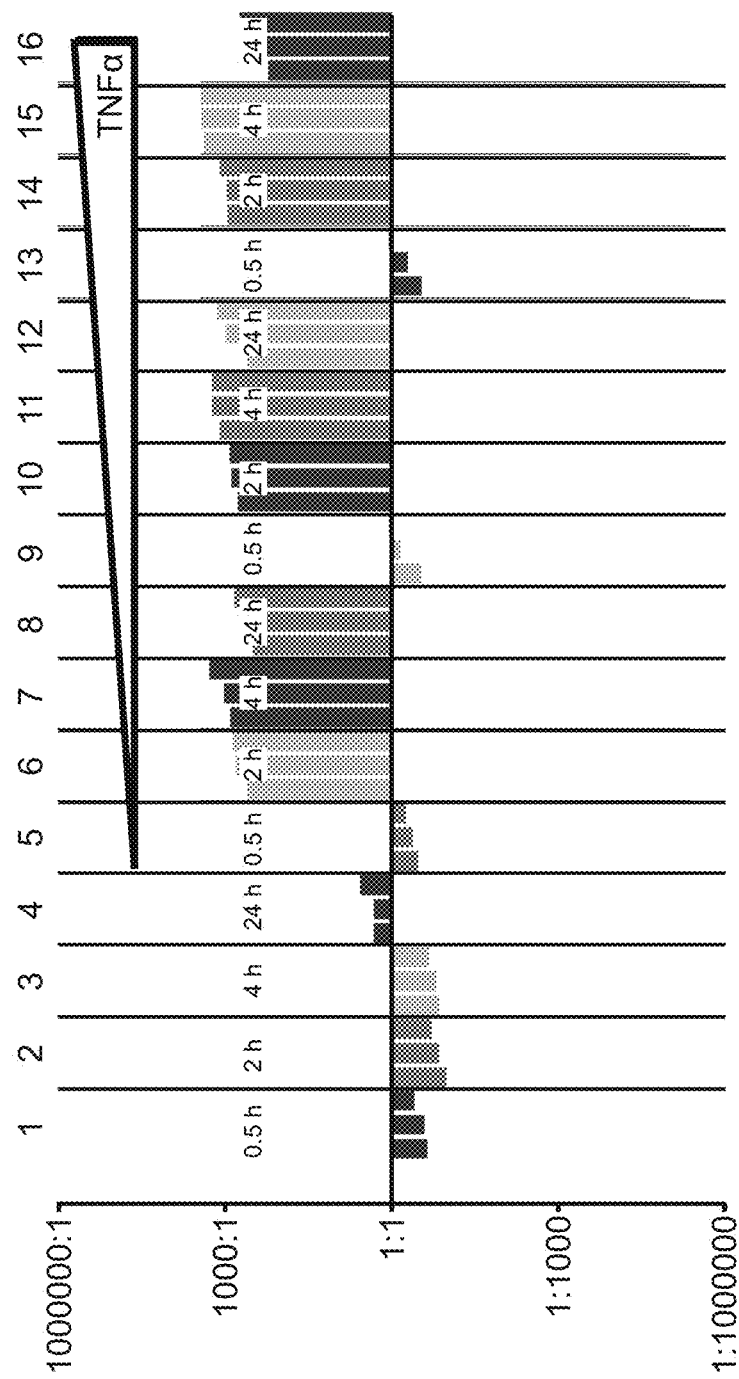

FIG. 31 shows NFkB cellular signaling pathway activity predictions of the trained exemplary Bayesian network model using the broad literature list of putative target genes of the NFkB cellular signaling pathway (see Table 7) for normal human bronchial epithelial (NHBE) cell line samples from E-MTAB-1312, which were stimulated with different TNFα concentrations for different stimulation times. (Legend: 1—No TNFα (0.5 h); 2—No TNFα (2 h); 3—No TNFα (4 h); 4—No TNFα (24 h); 5—Low TNFα (0.5 h); 6—Low TNFα (2 h); 7—Low TNFα (4 h); 8—Low TNFα (24 h); 9—Medium TNFα (0.5 h); 10—Medium TNFα (2 h); 11—Medium TNFα (4 h); 12—Medium TNFα (24 h);

13—High TNFα (0.5 h); 14—High TNFα (2 h); 15—High TNFα (4 h); 16—High TNFα (24 h))

Figure 32:
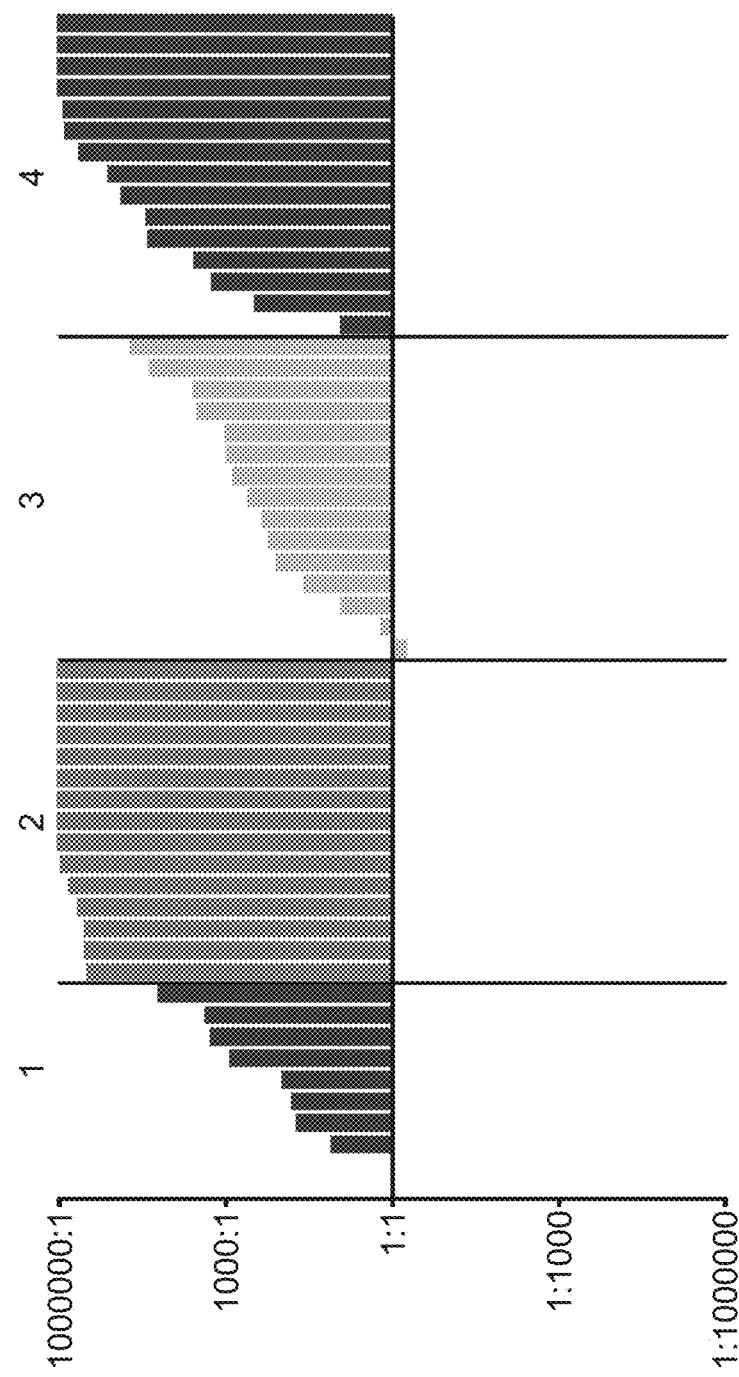

FIG. 32 shows NFkB cellular signaling pathway activity predictions of the trained exemplary Bayesian network model using the broad literature list of putative target genes of the NFkB cellular signaling pathway (see Table 7) for colon samples from GSE4183. (Legend: 1—Normal colin; 2—IBD; 3—Adenoma; 4—CRC)

DETAILED DESCRIPTION OF THE INVENTION

Provided herein are methods and apparatuses, and in particular computer implemented methods and apparatuses, for determining the activity levels of a NFkB cellular signaling pathway in a subject, wherein the NFkB cellular signaling is calculated by a) calculating an activity level of NFkB transcription factor element in a sample isolated from a subject, and wherein the activity levels of the NFkB transcription factor element in the sample is calculated by measuring the expression levels of a unique set of target genes, wherein the NFkB transcription factor element controls transcription of the target genes, calculating the levels of the NFkB transcription factor element in the sample using a calibrated pathway model, wherein the calibrated pathway model compares the expression levels of the target genes in the sample with expression levels of the target genes in the calibrated pathway model which define a level of a NFkB transcription factor element; and calculating the NFkB cellular signaling in the sample based on the calculated levels of NFkB transcription factor element in the sample.

In particular, the unique set of target genes whose expression level is analyzed in the model includes at least six target genes, at least seven target genes, at least eight target genes, at least nine target genes, at least ten or more target genes selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1. It has been discovered that analyzing a specific set of target genes as described herein in the disclosed pathway model provides for an advantageously accurate NFkB cellular signaling pathway activity determination. Accordingly, such status can be used to, for example but not limited to, identify the presence or absence of disease and/or particular disease state or advancement, diagnose a specific disease or disease state, or diagnose the presence or absence of a particular disease, derive a course of treatment based on the presence or absence of NFkB signaling activity, monitor disease progression in order to, for example, adjust therapeutic protocols based on a predicted drug efficacy in light of the determined activity of the NFkB signaling pathway in the sample, or develop NFkB targeted therapeutics.

Definitions

All terms used herein are intended to have their plain and ordinary meaning as normally ascribed in the art unless otherwise specifically indicated herein.

Herein, the "level" of a TF element denotes the level of activity of the TF element regarding transcription of its target genes.

The term "subject" or "host", as used herein, refers to any living being. In some embodiments, the subject is an animal, for example a mammal, including a human. In a particular embodiment, the subject is a human. In one embodiment, the human is suspected of having a disorder mediated or exacerbated by an active NFkB cellular signaling pathway, for example, a cancer. In one embodiment, the human has or is suspected of having a breast cancer.

The term "sample", as used herein, means any biological specimen isolated from a subject. Accordingly, "sample" as used herein is contemplated to encompasses the case where e.g. a tissue and/or cells and/or a body fluid of the subject have been isolated from the subject. Performing the claimed method may include where a portion of this sample is extracted, e.g., by means of Laser Capture Microdissection (LCM), or by scraping off the cells of interest from the slide, or by fluorescence-activated cell sorting techniques. In addition, the term "sample", as used herein, also encompasses the case where e.g. a tissue and/or cells and/or a body fluid of the subject has been taken from the subject and has been put on a microscope slide, and the claimed method is performed on the slide. In addition, the term "samples," as used herein, may also encompass circulating tumor cells or CTCs.

The term "NFkB transcriptional factor element" or "NFkB TF element" or "TF element" refers to a protein complex containing at least one or, preferably, a dimer of the NFkB members (NFKB1 or p50/p105, NFKB2 or p52/p100, RELA or p65, REL, and RELB), which is capable of binding to specific DNA sequences, thereby controlling transcription of target genes.

The term "target gene" as used herein, means a gene whose transcription is directly or indirectly controlled by a NFkB transcription factor element. The "target gene" may be a "direct target gene" and/or an "indirect target gene" (as described herein).

As contemplated herein, target genes include at least BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1.

As contemplated herein, the present invention includes:
A) A computer implemented method for determining the activity level of a NFkB cellular signaling pathway in a subject performed by a computerized device having a processor comprising:
  a. calculating an activity level of NFkB transcription factor element in a sample isolated from the subject, wherein the activity level of NFkB transcription factor element in the sample is calculated by:
    i. receiving data on the expression levels of at least six target genes derived from the sample, wherein the NFkB transcription factor element controls transcription of the at least six target genes, and wherein the at least six target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1;
    ii. calculating the activity level of the NFkB transcription factor element in the sample using a calibrated pathway model, wherein the calibrated pathway model compares the expression levels of the at least six target genes in the sample with expression levels of the at least six target genes in the model which define an activity level of NFkB transcription factor element; and, b. calculating the activity level of the NFkB cellular signaling pathway in the sample based on the calculated activity levels of NFkB transcription factor element in the sample.

In one embodiment, the method further comprises assigning a NFkB cellular signaling pathway activity status to the calculated activity level of the NFkB cellular signaling in the sample, wherein the activity status is indicative of either an active NFkB cellular signaling pathway or a passive NFkB cellular signaling pathway. In one embodiment, the method further comprises displaying the NFkB cellular signaling pathway activity status. In one embodiment, the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2. In one embodiment, the at least three target genes are selected from CCL5, CXCL2, ICAM1, IL6, IL8, NFKBIA, and TNFAIP2. In one embodiment, the calibrated pathway model is a probabilistic model incorporating conditional probabilistic relationships that compare the expression levels of the at least six target genes in the sample with expression levels of the at least six target genes in the model which define a level of NFkB transcription factor element to determine the activity level of the NFkB transcription factor element in the sample. In one embodiment, the probabilistic model is a Bayesian network model. In one embodiment, the calibrated pathway model is a linear model incorporating relationships that compare the expression levels of the at least six target genes in the sample with expression levels of the at least six target genes in the model which define a level of NFkB transcription factor element to determine the activity level of the NFkB transcription factor element in the sample.

B) A computer program product for determining the activity level of a NFkB cellular signaling pathway in a subject comprising
  a. a non-transitory computer readable storage medium having computer readable program code embodied therewith, the computer readable program code executable by at least one processor to:
    i. calculate a level of NFkB transcription factor element in a sample isolated from a subject, wherein the level of the NFkB transcription factor element in the sample is calculated by:
      1. receiving data on the expression levels of at least six target genes derived from the sample, wherein the at least six target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1;
      2. calculating the level of the NFkB transcription factor element in the sample using a calibrated pathway model, wherein the calibrated pathway model compares the expression levels of the at least six target genes in the sample with expression levels of the at least six target genes in the model which define an activity level of NFkB transcription factor element; and,
    ii. calculate the activity level of the NFkB cellular signaling pathway in the sample based on the calculated NFkB transcription factor element level in the sample.

In one embodiment, the computer readable program code is executable by at least one processor to assign a NFkB cellular signaling pathway activity status to the calculated activity level of the NFkB cellular signaling in the sample, wherein the activity status is indicative of either an active NFkB cellular signaling pathway or a passive NFkB cellular signaling pathway. In one embodiment, the computer readable program code is executable by at least one processor to display the NFkB signaling pathway activity status. In one embodiment, the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2. In one embodiment, the at least three target genes are selected from CCL5, CXCL2, ICAM1, IL6, IL8, NFKBIA, and TNFAIP2. In one embodiment, the calibrated pathway model is a probabilistic model incorporating conditional probabilistic relationships that compare the expression levels of the at least six target genes in the sample with expression levels of the at least six target genes in the model which define a level of NFkB transcription factor element to determine the activity level of NFkB transcription factor element in the sample. In one embodiment, the probabilistic model is a Bayesian network model. In one embodiment, the calibrated pathway model is a linear model incorporating relationships that compare the expression levels of the at least six target genes in the sample with expression levels of the at least six target genes in the model which define a level of NFkB transcription factor element to determine the activity level of a NFkB transcription factor element in the sample.

C) A method of treating a subject suffering from a disease associated with an activated NFkB cellular signaling pathway comprising:
  a. receiving information regarding the activity level of a NFkB cellular signaling pathway derived from a sample isolated from the subject, wherein the activity level of the NFkB cellular signaling pathway is determined by:
    i. calculating an activity level of NFkB transcription factor element in a sample isolated from the subject, wherein the level of the NFkB transcription factor element in the sample is calculated by:
      1. receiving data on the expression levels of at least six target genes derived from the sample, wherein the NFkB transcription factor element controls transcription of the at least six target genes, and wherein the at least six target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1;
      2. calculating the level of the NFkB transcription factor element in the sample using a calibrated pathway model, wherein the calibrated pathway model compares the expression levels of the at least six target genes in the sample with expression levels of the at least six target genes in the model which define an activity level of the NFkB transcription factor element; and, ii. calculating the activity level of the NFkB cellular signaling pathway in the sample based on the calculated NFkB transcription factor element level in the sample; and, b. administering to the subject a NFkB inhibitor if the information regarding the activity level of the NFkB cellular signaling pathway is indicative of a pathogenically active NFkB cellular signaling pathway.

In one embodiment, the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2. In one embodiment, the at least three target genes are selected from CCL5, CXCL2, ICAM1, IL6, IL8, NFKBIA, and TNFAIP2. In one embodiment, the calibrated pathway model is a probabilistic model incorporating conditional probabilistic relationships that compare the expression levels of the at least six target genes in the sample with expression levels of the at least six target genes in the model which define a level of NFkB transcription factor element to determine the activity level of the NFkB transcription factor element in the sample. In one embodiment, the probabilistic model is a Bayesian network model. In one embodiment, the calibrated pathway model is a linear model incorporating relationships that compare the expression levels of the at least six target genes in the sample with expression levels of the at least six target genes in the model which define a level of NFkB transcription factor element to determine the activity level of the NFkB transcription factor element in the human cancer sample. In an illustrative embodiment, the NFkB inhibitor is DHMEQ, bindarit, Bortesomib or BU-32 (proteazome inhibitors), BMS-345541, or glucocorticoids.

In one embodiment, the disease is a cancer. In one embodiment (not limited to), the cancer is a benign tumor (adenoma, hyperplasia) or a solid cancer: colon, breast, a male cancer (prostate, testicular, urethra, penis), pancreatic, liver, gastrointestinal tract cancer, head and neck cancer, lung, brain (medulloblastoma, glioblastoma, glioma), bladder cancer, an endocrine tumor (thyroid, parathyroid, adrenal, neuroendocrine, MEA), a female cancer (ovarian, cervical, endometrial, vagina), kidney cancer, skin cancer (BCC, squamous skin cancer, melanoma), a soft tissue cancer (sarcoma), childhood cancer (retinoblastoma, Wilms tumor), mesothelioma, or a hematological cancer (leukemia, lymphoma), or a glioma.

D) A kit for measuring expression levels of NFkB cellular signaling pathway target genes comprising:

a. a set of polymerase chain reaction primers directed to at least six NFkB cellular signaling pathway target genes from a sample isolated from a subject; and b. a set of probes directed to the at least six NFkB cellular signaling pathway target genes;

wherein the at least six NFkB cellular signaling pathway target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1.

In one embodiment, the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2. In one embodiment, the at least three target genes are selected from CCL5, CXCL2, ICAM1, IL6, IL8, NFKBIA, and TNFAIP2. In one embodiment, the probes are labeled. In one embodiment, the set of probes includes at least one of SEQ. ID. NOS. 46, 49, 52, 55, and 58. In one embodiment, the set of primers include at least one of SEQ. ID. NOS. 44 and 45, 47 and 48, 50 and 51, 53 and 54, and 56 and 57. In one embodiment, a computer program product for determining the activity level of a NFkB cellular signaling pathway in the subject comprising a non-transitory computer readable storage medium having computer readable program code embodied therewith, the computer readable program code executable by at least one processor to: (i) calculate a level of NFkB transcription factor element in the sample, wherein the level of the NFkB transcription factor element in the sample is associated with NFkB cellular signaling, and wherein the level of the NFkB transcription factor element in the sample is calculated by: (1) receiving data on the expression levels of the at least six target genes derived from the sample; (2) calculating the level of the NFkB transcription factor element in the sample using a calibrated pathway model, wherein the calibrated pathway model compares the expression levels of the at least six target genes in the sample with expression levels of the at least six target genes in the model which define an activity level of NFkB transcription factor element; and, (ii) calculate the activity level of the NFkB cellular signaling pathway in the sample based on the calculated NFkB transcription factor element level in the sample.

E) A kit for determining the activity level of a NFkB cellular signaling pathway in a subject comprising:

a. one or more components capable of identifying expression levels of at least six NFkB cellular signaling pathway target genes from a sample of the subject, wherein the at least six NFkB cellular signaling pathway target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1; and, b. optionally, a non-transitory computer readable storage medium having computer readable program code embodied therewith, the computer readable program code executable by at least one processor to:

i. calculate a level of NFkB transcription factor element in the sample, wherein the level of NFkB transcription factor element in the sample is associated with NFkB cellular signaling, and wherein the level of the NFkB transcription factor element in the sample is calculated by:

1. receiving data on the expression levels of the at least six target genes derived from the sample;

2. calculating the level of the NFkB transcription factor element in the sample using a calibrated pathway model, wherein the calibrated pathway model compares the expression levels of the at least six target genes in the sample with expression levels of the at least six target genes in the model which define an activity level of the NFkB transcription factor element; and, ii. calculate the activity level of the NFkB cellular signaling pathway in the sample based on the calculated NFkB transcription factor element level in the sample.

Determining the Activity Level of the NFkB Cellular Signaling Pathway

The present invention provides new and improved methods and apparatuses, and in particular computer implemented methods and apparatuses, as disclosed herein, to assess the functional state or activity of the NFkB cellular signaling pathway.

In one aspect of the invention, provided herein is a method of determining NFkB cellular signaling in a subject comprising the steps of:

a. calculating a level of NFkB transcription factor element in a sample isolated from a subject, wherein the level of NFkB transcription factor element in the sample is associated with an activity level of the NFkB cellular signaling pathway, and wherein the activity level of the NFkB transcription factor element in the sample is calculated by:
  i. receiving data on the expression levels of at least six target genes derived from the sample, wherein the NFkB transcription factor element controls transcription of the at least six target genes,
  ii. calculating the level of NFkB transcription factor element in the sample using a calibrated pathway model, wherein the calibrated pathway model compares the expression levels of the at least six genes in the sample with expression levels of the at least six target genes in the calibrated pathway model which define an activity level of the NFkB transcription factor element; and,
b. calculating the activity level of the NFkB cellular signaling pathway in the sample based on the calculated levels of NFkB transcription factor element in the sample. As contemplated herein, the method of calculating the activity level of the NFkB cellular signaling pathway is performed by a computer processor.

As a non-limiting generalized example, FIG. 2 provides an exemplary flow diagram used to determine the activity level of the NFkB cellular signaling pathway based on a computer implemented mathematical model constructed of three nodes: (a) a transcription factor (TF) element (for example, but not limited to being, discretized into the states "absent" and "present" or as a continuous observable) in a first layer 1; (b) target genes $TG_1$, $TG_2$, $TG_n$ (for example, but not limited to being, discretized into the states "down" and "up" or as a continuous observable) in a second layer 2, and; (c) measurement nodes linked to the expression levels of the target genes in a third layer 3. The expression levels of the target genes can be determined by, for example, but not limited to, microarray probesets $PS_{1,1}$, $PS_{1,2}$, $PS_{1,3}$, $PS_{2,1}$, $PS_{n,1}$, $PS_{n,m}$ (for example, but limited to being, discretized into the states "low" and "high" or as a continuous observable), but could also be any other gene expression measurements such as, for example, RNAseq or RT-qPCR. The expression of the target genes depends on the activation of the respective transcription factor element, and the measured intensities of the selected probesets depend in turn on the expression of the respective target genes. The model is used to calculate NFkB pathway activity by first determining probeset intensities, i.e., the expression level of the target genes, and calculating backwards in the model what the probability is that the transcription factor element must be present.

The present invention makes it possible to determine the activity of the NFkB cellular signaling pathway by (i) determining a level of an NFkB TF element in the sample, wherein the determining is based at least in part on evaluating a mathematical model relating expression levels of one or more target genes of the NFkB cellular signaling pathway, the transcription of which is controlled by the NFkB TF element, to the level of the NFkB TF element, and by (ii) inferring the activity of the NFkB cellular signaling pathway based on the determined level of the NFkB TF element in the sample. This preferably allows improving the possibilities of characterizing patients that have a cancer, e.g., a diffuse large B-cell lymphoma (DLBCL), a multiple myeloma, a cancer of another haematological origin, or a solid tumor, such as a breast, melanoma, or prostate tumor, which is at least partially driven by a deregulated NFkB cellular signaling pathway, and that are therefore likely to respond to inhibitors of the NFkB cellular signaling pathway. An important advantage of the present invention is that it makes it possible to determine the activity of the NFkB cellular signaling pathway using a single sample, rather than requiring a plurality of samples extracted at different points in time.

Generalized Workflow for Determining the Activity Level of NFkB Cellular Signaling An example flow chart illustrating an exemplary calculation of the activity level of NFkB cellular signaling from a sample isolated from a subject is provided in FIG. 3. First, the mRNA from a sample is isolated (11). Second, the mRNA expression levels of a unique set of at least three or more NFkB target genes, as described herein, are measured (12) using methods for measuring gene expression that are known in the art. Next, the calculation of transcription factor element (13) is calculated using a calibrated pathway model (14), wherein the calibrated pathway model compares the expression levels of the at least three or more target genes in the sample with expression levels of the at least three target genes in the calibrated pathway model which have been correlated with a level of a NFkB transcription factor element. Finally, the activity level of the NFkB cellular signaling pathway is calculated in the sample based on the calculated levels of NFkB transcription factor element in the sample (15). For example, the NFkB signaling pathway is determined to be active if the activity is above a certain threshold, and can be categorized as passive if the activity falls below a certain threshold.

Target Genes

The present invention utilizes the analyses of the expression levels of unique sets of target genes. Particularly suitable target genes are described in the following text passages as well as the examples below (see, e.g., Tables 3 to 6 below).

Thus, according to an embodiment the target genes are selected from the group consisting of the target genes listed in Table 3, Table 4, Table 5, or Table 6 below.

In particular, the unique set of target genes whose expression is analyzed in the model includes at least six target genes, for example, seven, eight, nine, ten, eleven or more, selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1.

In one embodiment, the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1.

In one embodiment, the at least six target genes comprise at least three target genes, for example, four, five, six or more, selected from CCL2, CCL5, CCL20, CXCL1, CXCL2, CXCL3, ICAM1, IL6, IL8, MMP9, NFKB2, NFKBIA, and TNFAIP2. In one embodiment, the at least three target genes are selected from CCL5, CXCL2, ICAM1, IL6, IL8, NFKBIA, and TNFAIP2.

It has been found by the present inventors that the genes in the successively shorter lists become more and more probative for determining the activity of the NFkB cellular signaling pathway.

Measuring Levels of Gene Expression

Data derived from the unique set of target genes described herein is further utilized to determine the activity level of the NFkB cellular signaling pathway using the methods described herein.

Methods for analyzing gene expression levels in isolated samples are generally known. For example, methods such as Northern blotting, the use of PCR, nested PCR, quantitative real-time PCR (qPCR), RNA-seq, or microarrays can all be used to derive gene expression level data. All methods known in the art for analyzing gene expression of the target genes are contemplated herein.

Methods of determining the expression product of a gene using PCR based methods may be of particular use. In order to quantify the level of gene expression using PCR, the amount of each PCR product of interest is typically estimated using conventional quantitative real-time PCR (qPCR) to measure the accumulation of PCR products in real time after each cycle of amplification. This typically utilizes a detectable reporter such as an intercalating dye, minor groove binding dye, or fluorogenic probe whereby the application of light excites the reporter to fluoresce and the resulting fluorescence is typically detected using a CCD camera or photomultiplier detection system, such as that disclosed in U.S. Pat. No. 6,713,297 which is hereby incorporated by reference.

In some embodiments, the probes used in the detection of PCR products in the quantitative real-time PCR (qPCR) assay can include a fluorescent marker. Numerous fluorescent markers are commercially available. For example, Molecular Probes, Inc. (Eugene, Oreg.) sells a wide variety of fluorescent dyes. Non-limiting examples include Cy5, Cy3, TAMRA, R6G, R110, ROX, JOE, FAM, Texas Red™, and Oregon Green™. Additional fluorescent markers can include IDT ZEN Double-Quenched Probes with traditional 5' hydrolysis probes in qPCR assays. These probes can contain, for example, a 5' FAM dye with either a 3' TAMRA Quencher, a 3' Black Hole Quencher (BHQ, Biosearch Technologies), or an internal ZEN Quencher and 3' Iowa Black Fluorescent Quencher (IBFQ).

Fluorescent dyes useful according to the invention can be attached to oligonucleotide primers using methods well known in the art. For example, one common way to add a fluorescent label to an oligonucleotide is to react an N-Hydroxysuccinimide (NHS) ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. Other means of fluorescently labeling nucleotides, oligonucleotides and polynucleotides are well known to those of skill in the art.

Other fluorogenic approaches include the use of generic detection systems such as SYBR-green dye, which fluoresces when intercalated with the amplified DNA from any gene expression product as disclosed in U.S. Pat. Nos. 5,436,134 and 5,658,751 which are hereby incorporated by reference.

Another useful method for determining target gene expression levels includes RNA-seq, a powerful analytical tool used for transcriptome analyses, including gene expression level difference between different physiological conditions, or changes that occur during development or over the course of disease progression.

Another approach to determine gene expression levels includes the use of microarrays for example RNA and DNA microarray, which are well known in the art. Microarrays can be used to quantify the expression of a large number of genes simultaneously.

Calibrated Pathway Model

As contemplated herein, the expression levels of the unique set of target genes described herein are used to calculate the level NFkB transcription factor element using a calibrated pathway model as further described below. The calibrated pathway model compares the expression levels of the at least three target genes in the sample with expression levels of the at least three target genes in the calibrated pathway model which define a level of NFkB transcription factor element.

As contemplated herein, the calibrated pathway model is based on the application of a mathematical model. For example, the calibrated model can be based on a probabilistic model, for example a Bayesian network, or a linear or pseudo-linear model.

In one embodiment, the calibrated pathway model is a probabilistic model incorporating conditional probabilistic relationships that compare the expression levels of the at least three target genes in the sample with expression levels of the at least three target genes in the calibrated pathway model which define a level NFkB transcription factor element to determine the level of the NFkB transcription factor element in the sample. In one embodiment, the probabilistic model is a Bayesian network model.

In an alternative embodiment, the calibrated pathway model can be a linear or pseudo-linear model. In an embodiment, the linear or pseudo-linear model is a linear or pseudo-linear combination model.

A non-limiting exemplary flow chart for a calibrated pathway model is shown in FIG. 4. As an initial step, the training data for the mRNA expression levels is collected and normalized. The data can be collected using, for example microarray probeset intensities (101), real-time PCR Cq values (102), raw RNAseq reads (103), or alternative measurement modalities (104) known in the art. The raw expression level data can then be normalized for each method, respectively, by normalization using a normalization algorithm, for example, frozen robust military analysis (fRMA) or MAS5.0 (111), normalization to average Cq of reference genes (112), normalization of reads into reads/fragments per kilobase of transcript per million mapped reads (RPKM/FPKM) (113), or normalization to w.r.t. reference genes/proteins (114). This normalization procedure leads to a normalized probeset intensity (121), normalized Cq values (122), normalized RPKM/FPKM (123), or normalized measurement (124) for each method, respectively, which indicate target gene expression levels within the training samples.

Once the training data has been normalized, a training sample ID or IDs (131) is obtained and the training data of these specific samples is obtained from one of the methods for determining gene expression (132). The final gene expression results from the training sample are output as training data (133). All of the data from various training samples are incorporated to calibrate the model (including for example, thresholds, CPTs, for example in the case of the probabilistic or Bayesian network, weights, for example, in the case of the linear or pseudo-linear model, etc) (144). In addition, the pathway's target genes and measurement nodes (141) are used to generate the model structure for example, as described in FIG. 2 (142). The resulting model structure (143) of the pathway is then incorporated with the training data (133) to calibrate the model (144), wherein the gene expression levels of the target genes is indicative of the transcription factor element activity. As a result of the transcription factor element calculations in the training samples, a calibrated pathway model (145) is calculated which assigns the NFkB cellular signaling pathway activity level for a subsequently examined sample of interest, for example from a subject with a cancer, based on the target gene expression levels in the training samples.

Transcription Factor Element Calculation

A non-limiting exemplary flow chart for calculating the Transcription Factor Element activity level is provided in FIG. 5. The expression level data (test data) (163) from a sample isolated from a subject is input into the calibrated pathway model (145). The mathematical model may be a probabilistic model, for example a Bayesian network model, a linear model, or pseudo-linear model.

The mathematical model may be a probabilistic model, for example a Bayesian network model, based at least in part on conditional probabilities relating the NFkB TF element and expression levels of the at least six target genes of the NFkB cellular signaling pathway measured in the sample of the subject, or the mathematical model may be based at least in part on one or more linear combination(s) of expression levels of the at least six target genes of the NFkB cellular signaling pathway measured in the sample of the subject. In particular, the determining of the activity of the NFkB cellular signaling pathway may be performed as disclosed in the published international patent application WO 2013/011479 A2 ("Assessment of cellular signaling pathway activity using probabilistic modeling of target gene expression"), and incorporated herein by reference. Briefly, the data is entered into a Bayesian network (BN) inference engine call (for example, a BNT toolbox) (154). This leads to a set of values for the calculated marginal BN probabilities of all the nodes in the BN (155). From these probabilities, the transcription factor (TF) node's probability (156) is determined and establishes the TF's element activity level (157).

Alternatively, the mathematical model may be a linear model. For example, a linear model can be used as described in the published international patent application WO 2014/102668 A2 ("Assessment of cellular signaling pathway activity using linear combination(s) of target gene expressions"), the contents of which are herewith incorporated in their entirety. Further details regarding the calculating/determining of cellular signaling pathway activity using mathematical modeling of target gene expression can also be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945. Briefly, the data is entered into a calculated weighted linear combination score (w/c) (151). This leads to a set of values for the calculated weighted linear combination score (152). From these weighted linear combination scores, the transcription factor (TF) node's weighted linear combination score (153) is determined and establishes the TF's element activity level (157).

Procedure for Discretized Observables

A non-limiting exemplary flow chart for calculating the activity level of a NFkB cellular signaling pathway as a discretized observable is shown in FIG. 6. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA or MAS5.0 (111), normalization to average Cq of reference genes (112), normalization of reads into RPKM/FPKM (113), and normalization to w.r.t. reference genes/proteins (114). This normalization procedure leads to a normalized probeset intensity (121), normalized Cq values (122), normalized RPKM/FPKM (123), or normalized measurement (124) for each method, respectively.

Once the test data has been normalized, the resulting test data (163) is analyzed in a thresholding step (164) based on the calibrated pathway model (145), resulting in the thresholded test data (165). In using discrete observables, in one non-limiting example, every expression above a certain threshold is, for example, given a value of 1 and values below the threshold are given a value of 0, or in an alternative embodiment, the probability mass above the threshold as described herein is used as a thresholded value. Based on the calibrated pathway model, this value represents the TF's element activity level (157), which is then used to calculate the pathway's activity level (171). The final output gives the pathway's activity level (172) in the test sample being examined from the subject.

Procedure for Continuous Observables

A non-limiting exemplary flow chart for calculating the activity level of a NFkB cellular signaling pathway as a continuous observable is shown in FIG. 7. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA (111), normalization to average Cq of reference genes (112), normalization of reads into RPKM/FPKM (113), and normalization to w.r.t. reference genes/proteins (114). This normalization procedure leads to a normalized probeset intensity (121), normalized Cq values (122), normalized RPKM/FPKM (123), or normalized measurement (124) for each method, respectively.

Once the test data has been normalized, the resulting test data (163) is analyzed in the calibrated pathway model (145). In using continuous observables, as one non-limiting example, the expression levels are converted to values between 0 and 1 using a sigmoid function as described in further detail below. The transcription factor element calculation as described herein is used to interpret the test data in combination with the calibrated pathway model, the resulting value represents the TF's element activity level (157), which is then used to calculate the pathway's activity level (171). The final output then gives the pathway's activity level (172) in the test sample.

Kits for Calculating NFkB Signaling Pathway Activity

In some embodiments, the present invention utilizes kits comprising primer and probe sets for the analyses of the expression levels of unique sets of target genes (see Target Gene discussion above). Particularly suitable oligo sequences for use as primers and probes for inclusion in a kit are described in the following text passages (see, e.g., Tables 1 and 2).

Also contemplated herein is a kit for measuring the expression levels of at least six or more NFkB cellular signaling pathway target genes, for example, seven, eight, nine, ten, eleven, twelve, or more target genes as described herein. In one embodiment, the kit includes one or more components, for example probes, for example labeled probes, and/or PCR primers, for measuring the expression levels of at least six target genes, at least seven target genes, at least eight target genes, or at least nine or more target genes selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1. In one embodiment, the kit includes one or more components for measuring the expression levels of at least six target genes, at least seven target genes, at least eight target genes, or at least nine or more target genes selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the one or more components comprise one or more components for measuring the expression levels of at least three target genes, at least four target genes, at least five target genes, or at least six or more target genes selected from CCL2, CCL5, CCL20, CXCL1, CXCL2, CXCL3, ICAM1, IL6, IL8, MMP9, NFKB2, NFKBIA, and TNFAIP2. In one embodiment, the one or more components comprise one or more components for measuring the expression levels of at least three target genes, at least four target genes, at least five target genes, or at least six or more target genes selected from CCL5, CXCL2, ICAM1, IL6, IL8, NFKBIA, and TNFAIP2.

In one embodiment, the kit includes one or more components for measuring the expression levels of at least six or more NFkB cellular signaling pathway target genes, wherein the at least six or more target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1, and the one or more components is selected from the PCR primers and probes listed in Table 1. In one embodiment, the at least six or more target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1, and the one or more components is selected from the PCR primers and probes listed in Table 1. In one embodiment, the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2, and the one or more components is selected from the PCR primers and probes listed in Table 1. In one embodiment, the at least three target genes are selected from CCL5, CXCL2, ICAM1, IL6, IL8, NFKBIA, and TNFAIP2, and the one or more components is selected from the PCR primers and probes listed in Table 1. The PCR primers for each gene are designated Forward (For) and Reverse (Rev) and the probes for detection of the PCR products for each gene are labeled Probe. In one non-limiting embodiment, the probes listed in Table 2 are labeled with a 5' FAM dye with an internal ZEN Quencher and 3' Iowa Black Fluorescent Quencher (IBFQ).

TABLE 1

Non-limiting example of primers and probes for a kit for measuring gene expression of NFkB target genes.

| Oligo Name | Sequence 5'-3' | SEQ ID No. | Target Gene |
|---|---|---|---|
| CXCL8_For1 | GGCAGCCTTCCTGATTTCTG | 44 | IL8 (a.k.a. CXCL8) |
| CXCL8_Rev1 | GGTGGAAAGGTTTGGAGTATG | 45 | IL8 (a.k.a. CXCL8) |
| CXCL8_Probe1 | CAGCTCTGTGTGAAGGTGCAGTTT | 46 | IL8 (a.k.a. CXCL8) |
| BIRC3_For | GGAGTTCATCCGTCAAGTTCAA | 47 | BIRC3 |
| BIRC3_Rev | TTTCATCTCCTGGGCTGTC | 48 | BIRC3 |
| BIRC3_Probe | ACCCTCATCTACTTGAACAGCTGCT | 49 | BIRC3 |
| ICAM1_For | TGCAGTAATACTGGGGAACC | 50 | ICAM1 |
| ICAM1_Rev | GCTTCGTCAGAATCACGTTGG | 51 | ICAM1 |
| ICAM1_Probe | TGACCATCTACAGCTTTCCGGCG | 52 | ICAM1 |
| NFKBIA_For | CCTCCACTCCATCCTGAAG | 53 | NFKBIA |
| NFKBIA_Rev | GCCATGGATAGAGGCTAAGT | 54 | NFKBIA |
| NFKBIA_Probe | ACCAACTACAATGGCCACACGTG | 55 | NFKBIA |
| PTGS2_For | TTTCAAGACAGATCATAAGCGAG | 56 | PTGS2 |
| PTGS2_Rev | AGCCAGAGTTTCACCGTAAATA | 57 | PTGS2 |
| PTGS2_Probe | TGGGCCATGGGGTGGACTTAAAT | 58 | PTGS2 |

In one non-limiting embodiment, the kit includes one or more components for measuring the expression levels of control genes, wherein the one or more components includes a PCR primer set and probe for at least one of the control genes listed in Table 2. The PCR primers for each gene are designated Forward (F) and Reverse (R) and the probes for detection of the PCR products for each gene are labeled Probe (P or FAM). In one non-limiting embodiment, the probes listed in Table 2 are labeled with a 5' FAM dye with an internal ZEN Quencher and 3' Iowa Black Fluorescent Quencher (IBFQ).

TABLE 2

Oligo Sequences for Controls

| Oligo Name | Sequence 5'-3' | SEQ ID No. | Reference gene |
|---|---|---|---|
| Hum_BACT_F1 | CCAACCGCGAGAAGATGA | 59 | ACTB |
| Hum_BACT_R1 | CCAGAGGCGTACAGGGATAG | 60 | ACTB |
| Hum_BACT_P1 | CCATGTACGTTGCTATCCAGGCT | 61 | ACTB |

TABLE 2-continued

Oligo Sequences for Controls

| Oligo Name | Sequence 5'-3' | SEQ ID No. | Reference gene |
|---|---|---|---|
| Hum_POLR2A_F1 | AGTCCTGAGTCCGGATGAA | 62 | POLR2A |
| Hum_POLR2A_R1 | CCTCCCTCAGTCGTCTCT | 63 | POLR2A |
| Hum_POLR2A_P1 | TGACGGAGGGTGGCATCAAATACC | 64 | POLR2A |
| Hum_PUM1_F2 | GCCAGCTTGTCTTCAATGAAAT | 65 | PUM1 |
| Hum_PUM1_R2 | CAAAGCCAGCTTCTGTTCAAG | 66 | PUM1 |
| Hum_PUM1_P1 | ATCCACCATGAGTTGGTAGGCAGC | 67 | PUM1 |
| Hum_TBP_F1 | GCCAAGAAGAAAGTGAACATCAT | 68 | TBP |
| Hum_TBP1_R1 | ATAGGGATTCCGGGAGTCAT | 69 | TBP |
| Hum_TBP_P1 | TCAGAACAACAGCCTGCCACCTTA | 70 | TBP |
| K-ALPHA-1_F1 | TGACTCCTTCAACACCTTCTTC | 71 | TUBA1B |
| K-ALPHA-1_R1 | TGCCAGTGCGAACTTCAT | 72 | TUBA1B |
| K-ALPHA-1_FAM1 | CCGGGCTGTGTTTGTAGACTTGGA | 73 | TUBA1B |
| ALAS1_F1 | AGCCACATCATCCCTGT | 74 | ALAS1 |
| ALAS1_R1 | CGTAGATGTTATGTCTGCTCAT | 75 | ALAS1 |
| ALAS1_FAM1 | TTTAGCAGCATCTGCAACCCGC | 76 | ALAS1 |
| Hum_HPRT1_F1 | GAGGATTTGGAAAGGGTGTTTATT | 77 | HPRT1 |
| Hum_HPRT1_R1 | ACAGAGGGCTACAATGTGATG | 78 | HPRT1 |
| Hum_HPRT1_P1 | ACGTCTTGCTCGAGATGTGATGAAGG | 79 | HPRT1 |
| Hum_RPLP0_F2 | TAAACCCTGCGTGGCAAT | 80 | RPLP0 |
| Hum_RPLP0_R2 | ACATTTCGGATAATCATCCAATAGTTG | 81 | RPLP0 |
| Hum_RPLP0_P1 | AAGTAGTTGGACTTCCAGGTCGCC | 82 | RPLP0 |
| Hum_B2M_F1 | CCGTGGCCTTAGCTGTG | 83 | B2M |
| Hum_B2M_R1 | CTGCTGGATGACGTGAGTAAA | 84 | B2M |
| Hum_B2M_P1 | TCTCTCTTTCTGGCCTGGAGGCTA | 85 | B2M |
| TPT1_F_PACE | AAATGTTAACAAATGTGGCAATTAT | 86 | TPT1 |
| TPT1_R_PACE | AACAATGCCTCCACTCCAAA | 87 | TPT1 |
| TPT1_P_PACE | TCCACACAACACCAGGACTT | 88 | TPT1 |
| EEF1A1_F_PACE | TGAAAACTACCCCTAAAAGCCA | 89 | EEF1A1 |
| EEF1A1_R_PACE | TATCCAAGACCCAGGCATACT | 90 | EEF1A1 |
| EEF1A1_P_PACE | TAGATTCGGGCAAGTCCACCA | 91 | EEF1A1 |
| RPL41_F_PACE | AAGATGAGGCAGAGGTCCAA | 92 | RPL41 |
| RPL41_R_PACE | TCCAGAATGTCACAGGTCCA | 93 | RPL41 |
| RPL41_P_PACE | TGCTGGTACAAGTTGTGGGA | 94 | RPL41 |

As contemplated herein, the one or more components for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to the cDNA sequence of the targeted genes as described herein contained in a standardized 96-well plate. In one embodiment, the kit further includes a non-transitory storage medium containing instructions that are executable by a digital processing device to perform a method according to the present invention as described herein.

In accordance with another disclosed aspect, a kit for measuring expression levels of at least six target genes of the NFkB cellular signaling pathway in a sample of a subject comprises:

one or more components for determining the expression levels of the at least six target genes of the NFkB cellular signaling pathway, wherein the one or more components are, for example, selected from the group consisting of: an DNA array chip, an oligonucleotide array chip, a protein array chip, an antibody, a plurality of probes, RNA sequencing and a set of primers, and wherein the at least six target genes of the NFkB cellular signaling pathway are selected from the group consisting of: BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1. In one embodiment, the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2. In one embodiment, the at least three target genes are selected from CCL5, CXCL2, ICAM1, IL6, IL8, NFKBIA, and TNFAIP2.

In one embodiment, the PCR cycling is performed in a microtiter or multi-well plate format. This format, which uses plates comprising multiple reaction wells, not only increases the throughput of the assay process, but is also well adapted for automated sampling steps due to the modular nature of the plates and the uniform grid layout of the wells on the plates. Common microtiter plate designs useful according to the invention have, for example 12, 24, 48, 96, 384, or more wells, although any number of wells that physically fit on the plate and accommodate the desired reaction volume (usually 10-100 µl) can be used according to the invention. Generally, the 96 or 384 well plate format can be utilized. In one embodiment, the method is performed in a 96 well plate format. In one embodiment, the method is performed in a 384 well plate format.

In one embodiment, the kit comprises an apparatus comprising a digital processor. In another embodiment, the kit comprises a non-transitory storage medium storing instructions that are executable by a digital processing device. In yet another embodiment, the kit comprises a computer program comprising program code means for causing a digital processing device to perform the methods described herein.

In an additional embodiment, the kit contains one or more components that are for example selected from the group consisting of: a DNA array chip, an oligonucleotide array chip, a protein array chip, an antibody, a plurality of probes, RNA sequencing and a set of primers. In one embodiment, the kit contains a plurality of probes. In one embodiment, the kit contains a set of primers. In one embodiment, the kit contains a 6, 12, 24, 48, 96, or 384-well PCR plate. In one embodiment, the kit includes a 96 well PCR plate. In one embodiment, the kit includes a 384 well PCR plate.

In one embodiment, a kit for measuring the expression levels of NFkB cellular signaling target genes comprises a 96-well plate and a set of labeled probes for detecting expression of a set of NFkB cellular signaling pathway genes comprising BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1. In one embodiment, a kit for measuring the expression levels of NFkB cellular signaling target genes comprises a 96-well plate and a set of labeled probes for detecting expression of a set of NFkB cellular signaling pathway genes comprising BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1. In one embodiment, a kit for measuring the expression levels of NFkB cellular signaling target genes comprises a 96-well plate and a set of labeled probes for detecting expression of a set of NFkB cellular signaling pathway genes comprising CCL2, CCL5, CCL20, CXCL1, CXCL2, CXCL3, ICAM1, IL6, IL8, MMP9, NFKB2, NFKBIA, and TNFAIP2. In one embodiment, a kit for measuring the expression levels of NFkB cellular signaling target genes comprises a 96-well plate and a set of labeled probes for detecting expression of a set of NFkB cellular signaling pathway genes comprising CCL5, CXCL2, ICAM1, IL6, IL8, NFKBIA, and TNFAIP2.

In one embodiment, the kit further comprises an instruction manual measuring the expression levels of NFkB cellular signaling target genes. In another embodiment, the kit further comprises an access code to access a computer program code for calculating the NFkB cellular signaling pathway activity in the sample. In a further embodiment, the kit further comprises an access code to access a website for calculating the NFkB cellular signaling pathway activity in the sample according to the methods described above.

Target Gene Expression Level Determination Procedure

A non-limiting exemplary flow chart for deriving target gene expression levels from a sample isolated from a subject is shown in FIG. 8. In one exemplary embodiment, samples are received and registered in a laboratory. Samples can include, for example, Formalin-Fixed, Paraffin-Embedded (FFPE) samples (181) or fresh frozen (FF) samples (180). FF samples can be directly lysed (183). For FFPE samples, the paraffin can be removed with a heated incubation step upon addition of Proteinase K (182). Cells are then lysed (183), which destroys the cell and nuclear membranes which makes the nucleic acid (NA) available for further processing. The nucleic acid is bound to a solid phase (184) which could for example, be beads or a filter. The nucleic acid is then washed with washing buffers to remove all the cell debris which is present after lysis (185). The clean nucleic acid is then detached from the solid phase with an elution buffer (186). The DNA is removed by DNAse treatment to ensure that only RNA is present in the sample (187). The nucleic acid sample can then be directly used in the RT-qPCR sample mix (188). The RT-qPCR sample mixes contains the RNA sample, the RT enzyme to prepare cDNA from the RNA sample and a PCR enzyme to amplify the cDNA, a buffer solution to ensure functioning of the enzymes and can potentially contain molecular grade water to set a fixed volume of concentration. The sample mix can then be added to a multiwell plate (i.e., 96 well or 384 well plate) which contains dried RT-qPCR assays (189). The RT-qPCR can then be run in a PCR machine according to a specified protocol (190). An example PCR protocol includes i) 30 minutes at 50° C.; ii) 5 minutes at 95° C.; iii) 15 seconds at 95° C.; iv) 45 seconds at 60° C.; v) 50 cycles repeating steps iii and iv. The Cq values are then determined with the raw data by using the second derivative method (191). The Cq values are exported for analysis (192).

Computer Programs and Computer Implemented Methods

As contemplated herein, the calculation of NFkB signaling in the sample is performed on a computerized device having a processor capable of executing a readable program code for calculating the NFkB cellular signaling pathway activity in the sample according to the methods described above. Accordingly, the computerized device can include means for receiving expression level data, wherein the data is expression levels of at least three target genes derived from the sample, a means for calculating the level of NFkB transcription factor element in the sample using a calibrated pathway model, wherein the calibrated pathway model compares the expression levels of the at least three target genes in the sample with expression levels of the at least three target genes in the model which have been correlated with a level NFkB transcription factor element; a means for calculating the NFkB cellular signaling in the sample based on the calculated levels of NFkB transcription factor element in the sample; and a means for assigning a NFkB cellular signaling pathway activity probability or status to the calculated NFkB cellular signaling in the sample, and a means for displaying the NFkB signaling pathway activity probability or status.

In accordance with another disclosed aspect, a non-transitory storage medium stores instructions that are executable by a digital processing device to perform a method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, an apparatus comprises a digital processor configured to perform a method according to the present invention as described herein.

In accordance with another disclosed aspect, a computer program comprises program code means for causing a digital processing device to perform a method according to the present invention as described herein. The digital processing device may be a handheld device (e.g., a personal data assistant or smartphone), a notebook computer, a desktop computer, a tablet computer or device, a remote network server, or so forth.

In one embodiment, a computer program or system is provided for predicting the activity status of a NFkB transcription factor element in a human cancer sample that includes a means for receiving data corresponding to the expression level of one or more NFkB target genes in a sample from a host. In some embodiments, a means for receiving data can include, for example, a processor, a central processing unit, a circuit, a computer, or the data can be received through a website.

In one embodiment, a computer program or system is provided for predicting the activity status of a NFkB transcription factor element in a human cancer sample that includes a means for displaying the NFkB pathway signaling status in a sample from a host. In some embodiments, a means for displaying can include a computer monitor, a visual display, a paper print out, a liquid crystal display (LCD), a cathode ray tube (CRT), a graphical keyboard, a character recognizer, a plasma display, an organic light-emitting diode (OLED) display, or a light emitting diode (LED) display, or a physical print out.

In accordance with another disclosed aspect, a signal represents a determined activity of a NFkB cellular signaling pathway in a subject, wherein the determined activity results from performing a method according to the present invention as described herein. The signal can be a digital signal or it can be an analog signal.

In one aspect of the present invention, a computer implemented method is provided for predicting the activity status of a NFkB signaling pathway in a human cancer sample performed by a computerized device having a processor comprising: a) calculating an activity level of a NFkB transcription factor element in a human cancer sample, wherein the level of the NFkB transcription factor element in the human cancer sample is associated with the activity of a NFkB cellular signaling pathway, and wherein the level of the NFkB transcription factor element in the human cancer sample is calculated by i) receiving data on the expression levels of at least six target genes derived from the human cancer sample, wherein the NFkB transcription factor controls transcription of the at least six target genes, and wherein the at least six target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1; ii) calculating the activity level of the NFkB transcription factor element in the human cancer sample using a calibrated pathway model, wherein the calibrated pathway model compares the expression levels of the at least six target genes in the human cancer sample with expression levels of the at least six target genes in the model which have been correlated with an activity level of a NFkB transcription factor element; b) calculating the NFkB cellular signaling pathway activity in the human cancer sample based on the calculated NFkB transcription factor element activity level in the human cancer sample; c) assigning a NFkB cellular signaling pathway activity status to the NFkB cellular signaling pathway in the human cancer sample, wherein the activity status is indicative of either an active NFkB cellular signaling pathway or a passive NFkB cellular signaling pathway; and d) displaying the NFkB signaling pathway activity status.

In one aspect of the invention, a system is provided for determining the activity level of a NFkB cellular signaling pathway in a subject comprising a) a processor capable of calculating an activity level of NFkB transcription factor element in a sample derived from the subject; b) a means for receiving data, wherein the data is an expression level of at least six target genes derived from the sample; c) a means for calculating the level of the NFkB transcription factor element in the sample using a calibrated pathway model, wherein the calibrated pathway model compares the expression levels of the at least six target genes in the sample with expression levels of the at least six target genes in the model which define an activity level of NFkB transcription factor element; d) a means for calculating the activity level of the NFkB cellular signaling pathway in the sample based on the calculated activity level of NFkB transcription factor element in the sample; a means for assigning a NFkB cellular signaling pathway activity status to the calculated activity level of the NFkB cellular signaling pathway in the sample, wherein the activity status is indicative of either an active NFkB cellular signaling pathway or a passive NFkB cellular signaling pathway; and f) a means for displaying the NFkB signaling pathway activity status.

NFkB Mediated Diseases and Disorders and Methods of Treatment

As contemplated herein, the methods and apparatuses of the present invention can be utilized to assess NFkB cellular signaling pathway activity in a subject, for example a subject suspected of having, or having, a disease or disorder wherein the status of the NFkB signaling pathway is probative, either wholly or partially, of disease presence or progression. In one embodiment, provided herein is a method of treating a subject comprising receiving information regarding the activity status of a NFkB cellular signaling pathway derived from a sample isolated from the subject using the methods described herein and administering to the subject a NFkB inhibitor if the information regarding the level of NFkB cellular signaling pathway is indicative of an active NFkB signaling pathway. In a particular embodiment, the NFkB cellular signaling pathway activity indication is set at a cutoff value of odds of the NFkB cellular signaling pathway being active of 10:1, 5:1, 4:1, 2:1, 1:1, 1:2, 1:4, 1:5, 1:10. NFkB inhibitors are known and include, but are not limited to, DHMEQ, bindarit, Bortesomib or BU-32 (proteazome inhibitors), BMS-345541, or glucocorticoids.

In a particular embodiment, the subject is suffering from, or suspected to have a benign or malignant tumor: a cancer or sarcoma or hematological malignancy, or brain tumor, for example, but not limited to, a primary tumor or a metastatic tumor, a solid tumor, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas and leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

In one embodiment, the methods described herein are useful for treating a host suffering from a lymphoma or lymphocytic or myelocytic proliferation disorder or abnormality. For example, the subject suffering from a Hodgkin Lymphoma of a Non-Hodgkin Lymphoma. For example, the subject can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In one embodiment, the subject may be suffering from a specific T-cell, a B-cell, or a NK-cell based lymphoma, proliferative disorder, or abnormality. For example, the subject can be suffering from a specific T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma. and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

Alternatively, the subject may be suffering from a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mantle cell lymphoma (MCL); Burkitt lymphoma; Mediastinal large B cell lymphoma; Waldenström macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis; Chronic lymphocytic leukemia/small lymphocytic lymphoma; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma.

In one embodiment, the subject is suffering from a leukemia. For example, the subject may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); T-cell prolymphocytic leukemia (TPLL); large granular lymphocytic leukemia; or Adult T-cell chronic leukemia; large granular lymphocytic leukemia (LGL). In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In a particular embodiment, the subject is suffering, or suspected to be suffering from, a breast cancer, lung cancer, a colon cancer, pancreatic cancer, or brain cancer. In a particular embodiment, the subject is suffering from, or suspected to be suffering from, a breast cancer.

The sample(s) to be used in accordance with the present invention can be an extracted sample, that is, a sample that has been extracted from the subject. Examples of the sample include, but are not limited to, a tissue, cells, blood and/or a body fluid of a subject. It can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, for example, via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, a body fluid of which a sample is extracted may be urine, gastrointestinal contents, or anextravasate.

In one aspect of the present invention, the methods and apparatuses described herein are used to identify an active NFkB cellular signaling pathway in a subject suffering from a cancer, and administering to the subject an anti-cancer agent, for example a NFkB inhibitor, selected from, but not limited to, DHMEQ, bindarit, Bortesomib or BU-32 (proteazome inhibitors), BMS-345541, or glucocorticoids. Another aspect of the present invention relates to a method (as described herein), further comprising:
  determining whether the NFkB cellular signaling pathway is operating abnormally in the subject based on the calculated activity of the NFkB cellular signaling pathway in the subject.

Here, the term "abnormally" denotes disease-promoting activity of the NFkB cellular signaling pathway, for example, a tumor-promoting activity.

The present invention also relates to a method (as described herein) further comprising:
  recommending prescribing a drug, for example a NFkB inhibitor, for the subject that corrects for abnormal operation of the NFkB cellular signaling pathway,
  wherein the recommending is performed if the NFkB cellular signaling pathway is determined to be operating abnormally in the subject based on the calculated/determined activity of the NFkB cellular signaling pathway.

The present invention also relates to a method (as described herein), wherein the calculating/determining comprises:
  calculating the activity of the NFkB cellular signaling pathway in the subject based at least on expression levels of two, three or more target genes of a set of target genes of the NFkB cellular signaling pathway measured in the sample of the subject.

The present invention as described herein can, e.g., also advantageously be used in connection with:
  diagnosis based on the determined activity of the NFkB cellular signaling pathway in the subject;
  prognosis based on the determined activity of the NFkB cellular signaling pathway in the subject;
  drug prescription based on the determined activity of the NFkB cellular signaling pathway in the subject;
  prediction of drug efficacy based on the determined activity of the NFkB cellular signaling pathway in the subject;
  prediction of adverse effects based on the determined activity of the NFkB cellular signaling pathway in the subject;
  monitoring of drug efficacy;
  drug development;
  assay development;
  pathway research;
  cancer staging;
  enrollment of the subject in a clinical trial based on the determined activity of the NFkB cellular signaling pathway in the subject;
  selection of subsequent test to be performed; and
  selection of companion diagnostics tests.

Further advantages will be apparent to those of ordinary skill in the art upon reading and understanding the attached figures, the following description and, in particular, upon reading the detailed examples provided herein below.

It shall be understood that an embodiment of the present invention can also be any combination of the dependent claims or above embodiments with the respective independent claim.

These and other aspects of the invention will be apparent from and elucidated with reference to the embodiments described hereinafter.

EXAMPLES

The following examples merely illustrate exemplary methods and selected aspects in connection therewith. The teaching provided therein may be used for constructing several tests and/or kits, e.g., to detect, predict and/or diagnose the abnormal activity of the NFKB cellular signaling pathways. Furthermore, upon using methods as described herein drug prescription can advantageously be guided, drug response prediction and monitoring of drug efficacy (and/or adverse effects) can be made, drug resistance can be predicted and monitored, e.g., to select subsequent test(s) to be performed (like a companion diagnostic test). The following examples are not to be construed as limiting the scope of the present invention.

Example 1

Mathematical Model Construction

As described in detail in the published international patent application WO 2013/011479 A2 ("Assessment of cellular signaling pathway activity using probabilistic modeling of target gene expression"), by constructing a probabilistic model, e.g., a Bayesian network model, and incorporating conditional probabilistic relationships between expression levels of at least six target genes of a cellular signaling pathway, herein, the NFkB cellular signaling pathway, and the level of a transcription factor (TF) element, herein, the NFkB TF element, the TF element controlling transcription of the at least six target genes of the cellular signaling pathway, such a model may be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

In another easy to comprehend and interpret approach described in detail in the published international patent application WO 2014/102668 A2 ("Assessment of cellular signaling pathway activity using linear combination(s) of target gene expressions"), the activity of a cellular signaling pathway, herein, the NFkB cellular signaling pathway, may be determined by constructing and evaluating a linear or (pseudo-)linear model incorporating relationships between expression levels of at least six target genes of the cellular signaling pathway and the level of a transcription factor (TF) element, herein, the NFkB TF element, the TF element controlling transcription of the at least six target genes of the cellular signaling pathway, the model being based at least in part on one or more linear combination(s) of expression levels of the at least six target genes.

In both approaches, the expression levels of the at least six target genes may, for example, be measurements of the level of mRNA, which can be the result of, e.g., (RT)-PCR and microarray techniques using probes associated with the target genes mRNA sequences, and of RNA-sequencing. In another embodiment, the expression levels of the at least six target genes can be measured by protein levels, e.g., the concentrations and/or activity of the protein(s) encoded by the target genes.

The aforementioned expression levels may optionally be converted in many ways that might or might not suit the application better. For example, four different transformations of the expression levels, e.g., microarray-based mRNA levels, may be:
- "continuous data", i.e., expression levels as obtained after preprocessing of microarrays using well known algorithms such as MAS5.0 and fRMA,
- "z-score", i.e., continuous expression levels scaled such that the average across all samples is 0 and the standard deviation is 1,
- "discrete", i.e., every expression above a certain threshold is set to 1 and below it to 0 (e.g., the threshold for a probeset may be chosen as the (weighted) median of its value in a set of a number of positive and the same number of negative clinical samples),
- "fuzzy", i.e., the continuous expression levels are converted to values between 0 and 1 using a sigmoid function of the following format: $1/(1+\exp((thr-expr)/se))$, with expr being the continuous expression levels, thr being the threshold as mentioned before and se being a softening parameter influencing the difference between 0 and 1.

One of the simplest linear models that can be constructed is a model having a node representing the transcription factor (TF) element, herein, the NFkB TF element, in a first layer and weighted nodes representing direct measurements of the target genes expression levels, e.g., by one probeset that is particularly highly correlated with the particular target gene, e.g., in microarray or (q) PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probeset with the lowest p-value is by definition the probeset with the least likely probability that the expression levels of the (known) active and passive samples overlap. Another selection method is based on odds-ratios. In such a model, one or more expression level(s) are provided for each of the at least six target genes and the one or more linear combination(s) comprise a linear combination including for each of the at least six target genes a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the at least six target genes and the one or more linear combination(s) comprise a linear combination of all expression levels of the one or more expression level(s) provided for the at least six target genes. In other words, for each of the at least six target genes, each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels of the one or more probeset of the one or more target genes.

After the level of the TF element, herein, the NFkB TF element, has been determined by evaluating the respective model, the determined TF element level can be thresholded in order to infer the activity of the cellular signaling pathway, herein, the NFkB cellular signaling pathway. An exemplary method to calculate such an appropriate threshold is by comparing the determined TF element levels w/c of training samples known to have a passive cellular signaling pathway and training samples with an active cellular signaling pathway. A method that does so and also takes into account the variance in these groups is given by using a threshold $$thr = \frac{\sigma_{wlc_{pas}}\mu_{wlc_{act}} + \sigma_{wlc_{act}}\mu_{wlc_{pas}}}{\sigma_{wlc_{pas}} + \sigma_{wlc_{act}}} \quad (1)$$

where $\sigma$ and $\mu$ are the standard deviation and the mean of the determined TF element levels w/c for the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

$$\tilde{v}_{wlc_{act}} = \frac{x\tilde{v} + (n_{act} - 1)v_{wlc_{act}}}{x + n_{act} - 1}$$

$$\tilde{v}_{wlc_{pas}} = \frac{x\tilde{v} + (n_{pas} - 1)v_{wlc_{pas}}}{x + n_{pas} - 1}$$

where v is the variance of the determined TF element levels w/c of the groups, x is a positive pseudocount, e.g., 1 or 10, and nact and npas are the number of active and passive samples, respectively. The standard deviation σ can next be obtained by taking the square root of the variance v.

The threshold can be subtracted from the determined TF element levels w/c for ease of interpretation, resulting in a cellular signaling pathway's activity score in which negative values correspond to a passive cellular signaling pathway and positive values correspond to an active cellular signaling pathway.

As an alternative to the above-described "single-layer" models, a "two-layer" may also be used in an example. In such a model, a summary value is calculated for every target gene using a linear combination based on the measured intensities of its associated probesets ("first (bottom) layer"). The calculated summary value is subsequently combined with the summary values of the other target genes of the cellular signaling pathway using a further linear combination ("second (upper) layer"). Again, the weights can be either learned from a training data set or based on expert knowledge or a combination thereof. Phrased differently, in the "two-layer" model, one or more expression level(s) are provided for each of the at least six target genes and the one or more linear combination(s) comprise for each of the at least six target genes a first linear combination of all expression levels of the one or more expression level(s) provided for the respective target gene ("first (bottom) layer"). The model is further based at least in part on a further linear combination including for each of the at least six target genes a weighted term, each weighted term being based on the first linear combination for the respective target gene ("second (upper) layer").

The calculation of the summary values can, in an exemplary version of the "two-layer" model, include defining a threshold for each target gene using the training data and subtracting the threshold from the calculated linear combination, yielding the target gene summary. Here the threshold may be chosen such that a negative target gene summary value corresponds to a down-regulated target gene and that a positive target gene summary value corresponds to an up-regulated target gene. Also, it is possible that the target gene summary values are transformed using, e.g., one of the above-described transformations (fuzzy, discrete, etc.), before they are combined in the "second (upper) layer".

After the level of the TF element has been determined by evaluating the "two-layer" model, the determined TF element level can be thresholded in order to infer the activity of the cellular signaling pathway, as described above.

In the following, the models described above are collectively denoted as "(pseudo-) linear" models. A more detailed description of the training and use of probabilistic models, e.g., a Bayesian network model, is provided in Example 3 below.

Example 2

Selection of Target Genes

A transcription factor (TF) is a protein complex (i.e., a combination of proteins bound together in a specific structure) or a protein that is able to regulate transcription from target genes by binding to specific DNA sequences, thereby controlling the transcription of genetic information from DNA to mRNA. The mRNA directly produced due to this action of the TF complex is herein referred to as a "direct target gene" (of the transcription factor). Cellular signaling pathway activation may also result in more secondary gene transcription, referred to as "indirect target genes". In the following, (pseudo-)linear models or Bayesian network models (as exemplary mathematical models) comprising or consisting of direct target genes as direct links between cellular signaling pathway activity and mRNA level, are exemplified, however the distinction between direct and indirect target genes is not always evident. Herein, a method to select direct target genes using a scoring function based on available scientific literature data is presented. Nonetheless, an accidental selection of indirect target genes cannot be ruled out due to limited information as well as biological variations and uncertainties. In order to select the target genes, the MEDLINE database of the National Institute of Health accessible at "www.ncbi.nlm.nih.gov/pubmed" and herein further referred to as "Pubmed" was employed to generate a lists of target genes. Furthermore, three additional lists of target genes were selected based on the probative nature of their expression.

Publications containing putative NFkB target genes were searched for by using queries such as ("NFkB" AND "target gene") in the period of the second and third quarter of 2013. The resulting publications were further analyzed manually following the methodology described in more detail below.

Specific cellular signaling pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a direct target gene, like for example an mRNA increasing as detected by means of an increasing intensity of a probeset on a microarray of a cell line in which it is known that the NFkB cellular signaling pathway is active, other evidence can be very strong, like the combination of an identified NFkB cellular signaling pathway TF binding site and retrieval of this site in a chromatin immunoprecipitation (ChIP) assay after stimulation of the specific cellular signaling pathway in the cell and increase in mRNA after specific stimulation of the cellular signaling pathway in a cell line.

Several types of experiments to find specific cellular signaling pathway target genes can be identified in the scientific literature:

1. ChIP experiments in which direct binding of a TF of the cellular signaling pathway of interest to its binding site on the genome is shown. Example: By using chromatin immunoprecipitation (ChIP) technology subsequently putative functional NFkB TF binding sites in the DNA of cell lines with and without active induction of the NFkB cellular signaling pathway, e.g., by stimulation with tumor necrosis factor α (TNFα) or lipopolysaccharide (LPS), were identified, as a subset of the binding sites recognized purely based on nucleotide sequence. Putative functionality was identified as ChIP-derived evidence that the TF was found to bind to the DNA binding site.

2. Electrophoretic Mobility Shift (EMSA) assays which show in vitro binding of a TF to a fragment of DNA containing the binding sequence. Compared to ChIP-based evidence EMSA-based evidence is less strong, since it cannot be translated to the in vivo situation.
3. Stimulation of the cellular signaling pathway and measuring mRNA expression using a microarray, RNA sequencing, quantitative PCR or other techniques, using NFkB cellular signaling pathway-inducible cell lines and measuring mRNA profiles measured at least one, but preferably several time points after induction—in the presence of cycloheximide, which inhibits translation to protein, thus the induced mRNAs are assumed to be direct target genes.
4. Similar to 3, but alternatively measure the mRNAs expression further downstream with protein abundance measurements, such as western blot.
5. Identification of TF binding sites in the genome using a bioinformatics approach. Example for the NFkB TF element: Using the NFkB binding motif 5'-GG-GRNWYYCC-3' (R: A or G, N: any nucleotide, W: A or T, Y: C or T), a software program was run on the human genome sequence, and potential binding sites were identified, both in gene promoter regions and in other genomic regions.
6. Similar as 3, only in the absence of cycloheximide.
7. Similar to 4, only in the absence of cycloheximide.

In the simplest form one can give every potential gene 1 point for each of these experimental approaches in which the gene was identified as being a target gene of the NFkB family of transcription factors. Using this relative ranking strategy, one can make a list of most reliable target genes.

Alternatively, ranking in another way can be used to identify the target genes that are most likely to be direct target genes, by giving a higher number of points to the technology that provides most evidence for an in vivo direct target gene. In the list above, this would mean 8 points for experimental approach 1), 7 for 2), and going down to 1 point for experimental approach 8). Such a list may be called a "general list of target genes".

Despite the biological variations and uncertainties, the inventors assumed that the direct target genes are the most likely to be induced in a tissue-independent manner. A list of these target genes may be called an "evidence curated list of target genes". Such an evidence curated list of target genes has been used to construct computational models of the NFkB cellular signaling pathway that can be applied to samples coming from different tissue sources.

The following will illustrate exemplary how the selection of an evidence curated target gene list specifically was constructed for the NFkB cellular signaling pathway.

A scoring function was introduced that gave a point for each type of experimental evidence, such as ChIP, EMSA, differential expression, knock down/out, luciferase gene reporter assay, sequence analysis, that was reported in a publication. The same experimental evidence is sometimes mentioned in multiple publications resulting in a corresponding number of points, e.g., two publications mentioning a ChIP finding results in twice the score that is given for a single ChIP finding. Further analysis was performed to allow only for genes that had diverse types of experimental evidence and not only one type of experimental evidence, e.g., differential expression. Finally, an evidence score was calculated for all putative NFkB target genes and all putative NFkB target genes with an evidence score of 5 or more were selected (shown in Table 3). The cut-off level of 5 was chosen heuristically as providing strong enough evidence.

A further selection of the evidence curated list of target genes (listed in Table 3) was made by the inventors. The target genes of the evidence curated list that were proven to be more probative in determining the activity of the NFkB cellular signaling pathway from the training samples were selected. The selection was performed using a combination of the literature evidence score and training results using two different datasets. Three rankings were made based on the evidence score, highest score ranked first and every point less result in a lower rank, and the "soft" odds ratios of all included probesets (see Table 3) calculated as described herein using the GSE12195 and E-MTAB-1312 datasets. The absolute values of the log 2 transformed "soft" odds ratios were used to rank the probesets; the highest odds ratio were ranked first, et cetera. As described herein, samples from ABC DLBCL samples from GSE12195 were chosen as active NFkB training samples whereas the normal samples from this dataset were chosen as the passive NFkB training samples. In addition, a second set of "soft" odds ratios were calculated using samples from E-MTAB-1312, an alternative NFkB training dataset, the control samples were used as passive NFkB samples and samples stimulated with different concentrations of TNFα for 2 hours were selected as active NFkB training samples. Based on the average rank a preferred set of target genes having at least one associated probeset with an average ranking of less than or equal to 20 was selected for the "19 target genes shortlist". A more preferred set of target genes having an average ranking of less than or equal to 15 was selected for the "13 target genes shortlist". A most preferred set of target genes having an average ranking of less than or equal to 12 were selected for the "7 target genes shortlist". The 19 target genes shortlist, the 13 target genes shortlist, and the 7 target genes shortlist are shown in Tables 4 to 6, respectively.

TABLE 3

"Evidence curated list of target genes" of the NFkB cellular signaling pathway used in the NFkB cellular signaling pathway models and associated probesets used to measure the mRNA expression level of the target genes.

| Target gene | Score | Probeset | Target gene | Score | Probeset |
|---|---|---|---|---|---|
| BCL2L1 | 5 | 206665_s_at | IL6 | 10 | 205207_at |
|  |  | 212312_at | IL8 | 12 | 202859_x_at |
|  |  | 215037_s_at |  |  | 211506_s_at |
|  |  | 231228_at | IRF1 | 5 | 202531_at |
| BIRC3 | 11 | 210538_s_at |  |  | 238725_at |
|  |  | 230499_at | MMP9 | 6 | 203936_s_at |

TABLE 3-continued

"Evidence curated list of target genes" of the NFkB cellular signaling pathway used in the NFkB cellular signaling pathway models and associated probesets used to measure the mRNA expression level of the target genes.

| Target gene | Score | Probeset | Target gene | Score | Probeset |
|---|---|---|---|---|---|
| CCL2 | 8 | 216598_s_at | NFKB2 | 14 | 207535_s_at |
| CCL3 | 8 | 205114_s_at | | | 209636_at |
| CCL4 | 5 | 204103_at | | | 211524_at |
| CCL5 | 11 | 1405_i_at | NFKBIA | 10 | 201502_s_at |
| | | 1555759_a_at | NFKBIE | 7 | 203927_at |
| | | 204655_at | PTGS2 | 13 | 1554997_a_at |
| CCL20 | 5 | 205476_at | | | 204748_at |
| CCL22 | 5 | 207861_at | SELE | 5 | 206211_at |
| CX3CL1 | 6 | 203687_at | STAT5A | 7 | 203010_at |
| | | 823_at | TNF | 9 | 207113_s_at |
| CXCL1 | 12 | 204470_at | TNFAIP2 | 5 | 202509_s_at |
| CXCL2 | 15 | 1569203_at | | | 202510_s_at |
| | | 209774_x_at | TNIP1 | 12 | 207196_s_at |
| | | 230101_at | | | 243423_at |
| CXCL3 | 9 | 207850_at | TRAF1 | 9 | 205599_at |
| ICAM1 | 10 | 202637_s_at | | | 235116_at |
| | | 202638_s_at | VCAM1 | 6 | 203868_s_at |
| | | 215485_s_at | | | |
| IL1B | 5 | 205067_at | | | |
| | | 39402_at | | | |

TABLE 4

"19 target genes shortlist" of target genes of the NFkB cellular signaling pathway based on the literature evidence score and "soft" odds ratios on GSE12195 and E-MAT-1312.

CXCL2
ICAM1
IL6
CCL5
NFKBIA
IL8
TNFAIP2
CXCL3
MMP9
NFKB2
CCL20
CCL2
CXCL1
TNF
IRF1
TRAF1
NFKBIE
VCAM1
BIRC3

TABLE 5

"13 target genes shortlist" of target genes of the NFkB cellular signaling pathway based on the literature evidence score and "soft" odds ratios on GSE12195 and E-MAT-1312.

CXCL2
ICAM1
IL6
CCL5
NFKBIA
IL8
TNFAIP2
CXCL3
MMP9
NFKB2
CCL20
CCL2
CXCL1

TABLE 6

"7 target genes shortlist" of target genes of the NFkB cellular signaling pathway based on the literature evidence score and "soft" odds ratios on GSE12195 and E-MAT-1312.

CXCL2
ICAM1
IL6
CCL5
NFKBIA
IL8
TNFAIP2

Example 3

Training and Using the Mathematical Model

Before the mathematical model can be used to infer the activity of the cellular signaling pathway, herein, the NFkB cellular signaling pathway, the model must be appropriately trained.

If the mathematical model is a probabilistic model, e.g., a Bayesian network model, based at least in part on conditional probabilities relating the NFkB TF element and expression levels of the at least six target genes of the NFkB cellular signaling pathway measured in a sample, the training may preferably be performed as described in detail in the published international patent application WO 2013/011479 A2 ("Assessment of cellular signaling pathway activity using probabilistic modeling of target gene expression").

If the mathematical model is based at least in part on one or more linear combination(s) of expression levels of the at least six target genes of the NFkB cellular signaling pathway measured in the sample, the training may preferably be performed as described in detail in the published international patent application WO 2014/102668 A2 ("Assessment of cellular signaling pathway activity using linear combination(s) of target gene expressions").

Herein, an exemplary Bayesian network model as shown in FIG. 2 was first used to model the transcriptional program of the NFkB cellular signaling pathway in a simple manner. The model consists of three types of nodes: (a) a transcription factor (TF) element (with states "absent" and "present") in a first layer 1; (b) target genes $TG_1$, $TG_2$, $TG_n$ (with states "down" and "up") in a second layer 2, and; (c) measurement nodes linked to the expression levels of the target genes in a third layer 3. These can be microarray probesets $PS_{1,1}$, $PS_{1,2}$, $PS_{1,3}$, $PS_{2,1}$, $PS_{n,1}$, $PS_{n,m}$ (with states "low" and "high"), as preferably used herein, but could also be other gene expression measurements such as RNAseq or RT-qPCR.

A suitable implementation of the mathematical model, herein, the exemplary Bayesian network model, is based on microarray data. The model describes (i) how the expression levels of the target genes depend on the activation of the TF element, and (ii) how probeset intensities, in turn, depend on the expression levels of the respective target genes. For the latter, probeset intensities may be taken from fRMA pre-processed Affymetrix HG-U133Plus2.0 microarrays, which are widely available from the Gene Expression Omnibus (GEO, www.ncbi.nlm.nih.gov/geo) and ArrayExpress (www.ebi.ac.uk/arrayexpress).

As the exemplary Bayesian network model is a simplification of the biology of a cellular signaling pathway, herein, the NFkB cellular signaling pathway, and as biological measurements are typically noisy, a probabilistic approach was opted for, i.e., the relationships between (i) the TF element and the target genes, and (ii) the target genes and their respective probesets, are described in probabilistic terms. Furthermore, it was assumed that the activity of the oncogenic cellular signaling pathway which drives tumor growth is not transiently and dynamically altered, but long term or even irreversibly altered. Therefore the exemplary Bayesian network model was developed for interpretation of a static cellular condition. For this reason complex dynamic cellular signaling pathway features were not incorporated into the model.

Once the exemplary Bayesian network model is built and calibrated (see below), the model can be used on microarray data of a new sample by entering the probeset measurements as observations in the third layer 3, and inferring backwards in the model what the probability must have been for the TF element to be "present". Here, "present" is considered to be the phenomenon that the TF element is bound to the DNA and is controlling transcription of the cellular signaling pathway's target genes, and "absent" the case that the TF element is not controlling transcription. This probability is hence the primary read-out that may be used to indicate activity of the cellular signaling pathway, herein, the NFkB cellular signaling pathway, which can next be translated into the odds of the cellular signaling pathway being active by taking the ratio of the probability of it being active vs. it being inactive (i.e., the odds are given by p/(1−p), where p is the predicted probability of the cellular signaling pathway being active).

In the exemplary Bayesian network model, the probabilistic relations have been made quantitative to allow for a quantitative probabilistic reasoning. In order to improve the generalization behavior across tissue types, the parameters describing the probabilistic relationships between (i) the TF element and the target genes have been carefully hand-picked. If the TF element is "absent", it is most likely that the target gene is "down", hence a probability of 0.95 is chosen for this, and a probability of 0.05 is chosen for the target gene being "up". The latter (non-zero) probability is to account for the (rare) possibility that the target gene is regulated by other factors or that it is accidentally observed as being "up" (e.g. because of measurement noise). If the TF element is "present", then with a probability of 0.70 the target gene is considered "up", and with a probability of 0.30 the target gene is considered "down". The latter values are chosen this way, because there can be several causes why a target gene is not highly expressed even though the TF element is present, e.g., because the gene's promoter region is methylated. In the case that a target gene is not up-regulated by the TF element, but down-regulated, the probabilities are chosen in a similar way, but reflecting the down-regulation upon presence of the TF element. The parameters describing the relationships between (ii) the target genes and their respective probesets have been calibrated on experimental data. For the latter, in this example, microarray data was used from patients samples which are known to have an active NFkB cellular signaling pathway whereas normal, healthy samples from the same dataset were used as inactive NFkB cellular signaling pathway samples, but this could also be performed using cell line experiments or other patient samples with known cellular signaling pathway activity status. The resulting conditional probability tables are given by:

A. for upregulated target genes

|  | $PS_{i,j}$ = low | $PS_{i,j}$ = high |
|---|---|---|
| $TG_i$ = down | $\dfrac{AL_{i,j}+1}{AL_{i,j}+AH_{i,j}+2}$ | $\dfrac{AH_{i,j}+1}{AL_{i,j}+AH_{i,j}+2}$ |
| $TG_i$ = up | $\dfrac{PL_{i,j}+1}{PL_{i,j}+PH_{i,j}+2}$ | $\dfrac{PH_{i,j}+1}{PL_{i,j}+PH_{i,j}+2}$ |

B. for downregulated target genes

|  | $PS_{i,j}$ = low | $PS_{i,j}$ = high |
|---|---|---|
| $TG_i$ = down | $\dfrac{PL_{i,j}+1}{PL_{i,j}+PH_{i,j}+2}$ | $\dfrac{PH_{i,j}+1}{PL_{i,j}+PH_{i,j}+2}$ |
| $TG_i$ = up | $\dfrac{AL_{i,j}+1}{AL_{i,j}+AH_{i,j}+2}$ | $\dfrac{AH_{i,j}+1}{AL_{i,j}+AH_{i,j}+2}$ |

In these tables, the variables $AL_{i,j}$, $AH_{i,j}$, $PL_{i,j}$, and $PH_{i,j}$ indicate the number of calibration samples with an "absent" (A) or "present" (P) transcription complex that have a "low" (L) or "high" (H) probeset intensity, respectively. Dummy counts have been added to avoid extreme probabilities of 0 and 1.

To discretize the observed probeset intensities, for each probeset $PS_{i,j}$ a threshold $t_{i,j}$ was used, below which the observation is called "low", and above which it is called "high". This threshold has been chosen to be the (weighted) median intensity of the probeset in the used calibration dataset. Due to the noisiness of microarray data, a fuzzy method was used when comparing an observed probeset intensity to its threshold, by assuming a normal distribution with a standard deviation of 0.25 (on a log 2 scale) around the reported intensity, and determining the probability mass below and above the threshold. Herein, an odds ratio calculated in combination with a pseudo-count and using probability masses instead of deterministic measurement values is called a "soft" odds ratio.

Further details regarding the inferring of cellular signaling pathway activity using mathematical modeling of target gene expression can be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945.

If instead of the exemplary Bayesian network described above, a (pseudo-) linear model as described in Example 1 above is employed, the weights indicating the sign and magnitude of the correlation between the nodes and a threshold to call whether a node is either "absent" or "present" would need to be determined before the model could be used to infer cellular signaling pathway activity in a test sample. One could use expert knowledge to fill in the weights and the threshold a priori, but typically the model would be trained using a representative set of training samples, of which preferably the ground truth is known, e.g. expression data of probesets in samples with a known "present" transcription factor complex (=active cellular signaling pathway) or "absent" transcription factor complex (=passive cellular signaling pathway).

Known in the field are a multitude of training algorithms (e.g., regression) that take into account the model topology and changes the model parameters, here, the weights and the threshold, such that the model output, here, a weighted linear score, is optimized. Alternatively, it is also possible to calculate the weights directly from the expression observed levels without the need of an optimization algorithm.

A first method, named "black and white"-method herein, boils down to a ternary system, in which each weight is an element of the set $\{-1, 0, 1\}$. If this is put in a biological context, the $-1$ and $1$ correspond to target genes or probesets that are down- and up-regulated in case of cellular signaling pathway activity, respectively. In case a probeset or target gene cannot be statistically proven to be either up- or down-regulated, it receives a weight of 0. In one example, a left-sided and right-sided, two sample t-test of the expression levels of the active cellular signaling pathway samples versus the expression levels of the samples with a passive cellular signaling pathway can be used to determine whether a probe or gene is up- or down-regulated given the used training data. In cases where the average of the active samples is statistically larger than the passive samples, i.e., the p-value is below a certain threshold, e.g., 0.3, the target gene or probeset is determined to be up-regulated. Conversely, in cases where the average of the active samples is statistically lower than the passive samples, the target gene or probeset is determined to be down-regulated upon activation of the cellular signaling pathway. In case the lowest p-value (left- or right-sided) exceeds the aforementioned threshold, the weight of the target gene or probeset can be defined to be 0.

A second method, named "log odds"-weights herein, is based on the logarithm (e.g., base e) of the odds ratio. The odds ratio for each target gene or probeset is calculated based on the number of positive and negative training samples for which the probeset/target gene level is above and below a corresponding threshold, e.g., the (weighted) median of all training samples. A pseudo-count can be added to circumvent divisions by zero. A further refinement is to count the samples above/below the threshold in a somewhat more probabilistic manner, by assuming that the probeset/target gene levels are e.g. normally distributed around its observed value with a certain specified standard deviation (e.g., 0.25 on a 2-log scale), and counting the probability mass above and below the threshold.

Herein, publically available data on the expression of patient samples from activated B-cell like (ABC), diffuse large B-cell lymphoma (DLBCL), which is known to have an active NFkB cellular signaling pathway, and normal cells that are known to have a passive NFkB cellular signaling pathway (GSE12195 available from the Gene Expression Omnibus (GEO, www.ncbi.nlm.nih.gov/geo, last accessed Oct. 9, 2013) was used as an example. Alternatively, one can use patient samples or cell lines stimulated with and deprived of NFkB activating agents such as TNFα and LPS or other inflammatory tissue versus normal tissue, e.g., E-MTAB-1312 or GSE16650.

FIGS. 9 to 12 show training results of the exemplary Bayesian network model based on the evidence curated list of target genes, the 19 target genes shortlist, the 13 target genes shortlist, and the 7 target genes shortlist of the NFkB cellular signaling pathway (see Tables 3 to 6), respectively. In the diagrams, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. The activated B-cell (ABC) group (group 1), which is known to have an active NFkB cellular signaling pathway, was assigned an active NFkB label, whereas the group encompassing the normal samples (group 7) known to have a passive NFkB cellular signaling pathway were labeled NFkB inactive. A perfect score for the training samples was achieved for all four models with all ABC being active and all normal samples having a passive NFkB cellular signaling pathway. Unsurprisingly, the probabilities of the training samples become less extreme as fewer target genes are included in the model. Within the same dataset, the healthy, unstimulated memory B-cells and naïve B-cells (groups 5 and 6, respectively) were correctly predicted to have a passive NFkB cellular signaling pathway with a few exceptions in the 19 and 7 target genes models. The vast majority of the other lymphoma samples in the germinal center B-cell (GCB) (group 4), follicular lymphoma (group 3), lymphoblastoid cell line (group 2) and all but one in further diffuse large B-cell lymphoma (DLBCL) samples with unknown subtype (group 8) were predicted to have an active NFkB cellular signaling pathway in all four models. For GCB, it is known that a high fraction of tumors (>50%) have a mutation in at least one NFkB regulatory genes, which is likely to correlate with aberrant NFkB activity (see, e.g., Campagno M. et al., "Mutations of multiple genes cause deregulation of NF-kappaB in diffuse large B-cell lymphoma", Nature, Vol. 459, No. 7247, 2009, pages 717 to 721). Also other studies pointed out that constitutive NFkB activation is a common feature for most haematological malignacies (see, e.g., Keutgens A. et al., "Deregulated NF-kB activity in haematological malignacies", Biochemical Pharmacology, Vol. 72, No. 9, 2006, pages 1069 to 1080), which might partially explain the high fraction of NFkB activity in these groups covering different hematological malignacies. (Legend: 1—ABC DLBCL;

2—Lymphoblastoid cell line; 3—Follicular lymphoma; 4—GCB DLBCL; 5—Memory B-cells; 6—Naïve B-cells; 7—Normal; 8—DLBCL unknown subtype)

In the following, validation results of the trained exemplary Bayesian network model using the evidence curated list of target genes, the 19 target genes shortlist, the 13 target genes shortlist, and the 7 target genes shortlist, respectively, are shown in FIGS. 13 to 25.

FIG. 13 shows NFkB cellular signaling pathway activity predictions of the trained exemplary Bayesian network model using the evidence curated list of target genes (see Table 3) for diffuse large B-cell lymphoma (DLBCL) samples from GSE34171. In the diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. All samples were predicted to have an active NFkB cellular signaling pathway. DLBCL lymphomas are known to have an aberrant NFkB activity (see, e.g., Keutgens A. et al., "Deregulated NF-kB activity in haematological malignancies", Biochemical Pharmacology, Vol. 72, No. 9, 2006, pages 1069 to 1080).

FIGS. 14 to 17 show NFkB cellular signaling pathway activity predictions of the trained exemplary Bayesian network model using the evidence curated list of target genes, the 19 target genes shortlist, the 13 target genes shortlist, and the 7 target genes shortlist (see Tables 3 to 6), respectively, for normal human bronchial epithelial (NHBE) cell line samples from E-MTAB-1312, which were stimulated with different TNFα concentrations for different stimulation times. In the diagrams, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. A stimulation of only 0.5 h is apparently too short for the NFkB cellular signaling pathway to become active (groups 5, 9, and 13), whereas a stimulation for longer than 4 hours, here, 24 hours (groups 8, 12, and 16), appears to lower the NFkB cellular signaling pathway activity, which is expected to be due to asynchronous NFkB oscillations that for longer stimulation times result in a dampened net NFkB cellular signaling pathway activity (see, e.g., D. E. Nelson et al., "Oscillations in NF-κB Signaling Control the Dynamics of Gene Expression", Science, Vol. 306, No. 5696, 2004, pages 704 to 708). The model using the evidence curated list of target genes shows an almost completely dampened NFkB cellular signaling pathway activity in the 24 hour samples, whereas the models using the 19 target genes shortlist, the 13 target genes shortlist, and the 7 target genes shortlist show a less strong decrease of NFkB cellular signaling pathway activity in the 24 hours samples. All control samples without TNFα stimulation (groups 1 to 4) were correctly predicted to have a passive NFkB cellular signaling pathway in all four models. There seemed to be not so much difference in cellular signaling pathway activity as a result of increased TNFα concentration as is apparent in the 2 and 4 hour stimulation; apparently all concentrations tested in this experiment were enough to have a full-blown NFkB cellular signaling pathway activity, even the lowest concentration. (Legend: 1—No TNFα (0.5 h), 2—No TNFα (2 h); 3—No TNFα (4 h), 4—No TNFα (24 h), 5—Low TNFα (0.5 h); 6—Low TNFα (2 h); 7—Low TNFα (4 h); 8—Low TNFα (24 h); 9—Medium TNFα (0.5 h); 10—Medium TNFα (2 h); 11—Medium TNFα (4 h); 12—Medium TNFα (24 h); 13—High TNFα (0.5 h); 14—High TNFα (2 h); 15—High TNFα (4 h); 16—High TNFα (24 h))

FIG. 18 shows NFkB cellular signaling pathway activity predictions of the trained exemplary Bayesian network model using the evidence curated list of target genes (see Table 3) for THP-1 monocytic cells. In the diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. The THP-1 cell line is known to express NFkB cellular signaling pathway activity upon stimulation with an immune response inducing agents such as lipopolysaccharide (LPS). The NFkB cellular signaling pathway activity in these monocytic cells is predicted to be low without LPS stimulation (group 1). Upon stimulation of these cells with LPS, the NFkB cellular signaling pathway activity is amplified (group 2). Coenzyme Q10 (CoQ10) has been reported to have anti-inflammatory effects, however, the effect on NFkB cellular signaling pathway activity was reported to be limited (see, e.g., C. Schmelzer and F. Döring, "Identification of LPS-inducible genes downregulated by ubiquinone in human THP-1 monocytes", Biofactors, Vol. 36, No. 3, 2010, pages 222 to 228). This is also reflected in the high predicted NFkB cellular signaling pathway activities in THP-1 cells treated with CoQ10 and stimulated with LPS (group 3). (Legend: 1—No LPS; 2—LPS stimulation; 3—LPS stimulation+coenzyme Q10)

FIGS. 19 to 22 show NFkB cellular signaling pathway activity predictions of the trained exemplary Bayesian network model using the evidence curated list of target genes, the 19 target genes shortlist, the 13 target genes shortlist, and the 7 target genes shortlist (see Tables 3 to 6), respectively, for colon samples from GSE4183. In the diagrams, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. Most normal samples (group 1) were rightfully predicted with a low probability of NFkB cellular signaling pathway activity by the model using the evidence curated list of target genes, nevertheless the cellular signaling pathway activity for normal samples seems to be higher than expected from other datasets in the 19 target genes shortlist, the 13 target genes shortlist, and the 7 target genes shortlist. On the other hand, all inflammatory bowel disease (IBD) (group 2) samples were predicted by all four models to have an active NFkB cellular signaling pathway significantly higher than the normal samples, which is as expected owing to the inflamed status of the colon in these patients and the NFkB cellular signaling pathway being activated as a result of inflammation. In addition, it is clear from all four models that the NFkB cellular signaling pathway is more active in the more progressed colorectal carcinomas (CRC) (group 4) compared to the benign adenomas (group 2), which might be a result of progression of the tumor into a more malignant tumor resulting in more mutations, inflammation as a result of the progressed tumor, or infiltration of white blood cells as a result of the immune response to the later stage cancers. Potentially, the NFkB cellular signaling pathway activity score might be used to predict the likelihood an adenoma will progress to become malignant. (Legend: 1—Normal colon; 2—IBD; 3—Adenoma; 4—CRC)

FIG. 23 shows NFkB cellular signaling pathway activity predictions of the trained exemplary Bayesian network model using the evidence curated list of target genes (see Table 3) for breast cancer cell lines from GSE10890. In the diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. Some of the breast cancer cell lines with still an unknown pathway driving cell survival and proliferation (groups 1 and 2) were identified as having an aberrantly active NFkB cellular signaling pathway, which may be causative for cell survival and proliferation. In the 3rd group that was previously identified as having an active Wnt cellular signaling pathway (see the published international patent application WO 2013/011479 A2 "Assessment of cellular signaling pathway activity using probabilistic modeling of target gene expression") no NFkB cellular signaling pathway active samples were found. (Legend: 1 and 2—Unknown cellular signaling pathway driven cell lines; 3: Wnt cellular signaling pathway driven cell lines)

FIG. 24 shows NFkB cellular signaling pathway activity predictions of the trained exemplary Bayesian network model using the evidence curated list of target genes (see Table 3) for ovarian samples from GSE20565. In the diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. The fraction of predicted NFkB cellular signaling pathway active samples is significantly higher in primary cancers (groups 1 and 2) compared to breast metastasis in the ovary (groups 3 and 4), p=6.0e-5 (Fisher's exact test). Chronic inflammation has been associated with tumor initiation and progression. Recurring inflammatory processes in the ovaries due to ovulation, endometriosis and pelvic infections have been shown to be correlated with NFkB cellular signaling pathway active tumors (see, e.g., Alvero A. B., "Recent insights into the role of NF-kappaB in ovarian carcinogenesis", Genome Medicine, Vol. 2, No. 8, 2010, page 56, and Guo R. X. et al., "Increased staining for phosphorylated AKT and nuclear factor-kappaB p65 and their relationship with prognosis in epithelial ovarian cancer", Pathology International, Vol. 58, No. 12, 2008, pages 746 to 756). In the ovary, carcinogenesis has been linked to inflammatory processes, such as repeated ovulation, endometriosis and pelvic infections, possibly resulting in a higher fraction of NFkB cellular signaling pathway active tumors originating in the ovary compared to the breast. (Legend: 1—Primary ovarian carcinoma; 2—Plausible primary ovarian carcinoma; 3—Breast metastasis in ovary; 4—Plausible breast metastasis in ovary)

FIG. 25 shows NFkB cellular signaling pathway activity predictions of the trained exemplary Bayesian network model using the evidence curated list of target genes (see Table 3) for breast cancer samples from E-MTAB-1006. In the diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. The average of the log it NFkB odds ratio is significantly higher in the inflammatory breast cancer samples (IBC) (group 1) compared to the non-inflamed breast cancers (nIBC) (group 2), p<0.01 (two-sample t-test). This is likely a reflection of the high inflammatory state in IBC compared to the nIBC. However, the predicted NFkB cellular signaling pathway activities in both groups largely overlap making a clear classification of IBC and nIBC based on NFkB cellular signaling pathway activity in the model's current state cumbersome. (Legend: 1—Inflammatory breast cancer; 2—Non-inflammatory breast cancer)

FIG. 26 illustrates overall survival of 272 glioma patients (GSE16011) depicted in a Kaplan-Meier plot, wherein the trained exemplary Bayesian network model using the evidence curated list of target genes (see Table 3) is employed. In the diagram, the vertical axis indicates the overall survival as a fraction of the patient group and the horizontal axis indicates time in years. The plot indicates that an active NFkB TF element (indicated by the steeper slope of the curve) is a prognostic marker for worse overall survival. (The patient group with a predicted active NFkB TF element consisted of 113 patients (solid line), whereas the patient group with a predicted passive NFkB TF element consisted of 159 patients (dotted line)). The prognostic value of the activity level of the NFkB TF element is also demonstrated in the hazard ratio of the predicted probability of NFkB activity: 1.83 (95% CI: 1.34-2.49, p=7.2e-5).

Further to the exemplary Bayesian network model described above, an exemplary linear model was used to model the transcriptional program of the NFkB cellular signaling pathway in a simple manner. The structure of the model corresponded to the one shown in FIG. 3 of the published international patent application WO 2014/102668 A2 ("Assessment of cellular signaling pathway activity using linear combination(s) of target gene expressions"). More specifically, the exemplary linear model consisted of a TF node, a layer of target gene expression and a layer of mRNA expression levels and made use of continuous expression data, all target genes from the evidence curated list of target genes (see Table 3) with all probesets included and without the use of a pseudocount. The training of the model was performed with the same active and passive training samples from GSE12195 and encompassed calculating the weights of the connections between the target genes expression levels, here represented by means of probeset intensities, and the target genes nodes using the "soft log odds"-method as described herein and subsequently the activity score of the transcription factor complex was calculated by summation of the calculated target genes expression score multiplied by either 1 or −1 for up-regulated or down-regulated target genes, respectively.

FIG. 27 shows training results of the exemplary linear model based on the evidence curated list of target genes (see Table 3). In the diagram, the vertical axis indicates the activity score, wherein positive values correspond to an active NFkB cellular signaling pathway and negative values correspond to a passive NFkB cellular signaling pathway. The activated B-cell (ABC) DLBCL (group 1) and normal (group 7) were used as active and passive training samples, respectively. All training samples were correctly classified; all ABC samples were predicted to have an active NFkB cellular signaling pathway, whereas the normal samples were predicted to have a passive NFkB cellular signaling pathway. Within the same dataset all other lymphoma samples and cell lines and DLBCL (groups 2 to 4, 8) except one were predicted NFkB active, similar to the Bayesian network model using the evidence curated list of target genes (FIG. 3), which is plausible given the literature evidence discussed herein. The healthy, unstimulated memory B-cells and naïve B-cells (groups 5 and 6) are correctly predicted to lack NFkB activity. (Legend: 1—ABC DLBCL; 2—Lymphoblastoid cell line; 3—Follicular lymphoma; 4—GCB DLBCL; 5—Memory B-cells; 6—Naïve B-cells; 7—Normal; 8—DLBCL unknown subtype)

FIG. 28 shows NFkB cellular signaling pathway activity predictions of the trained exemplary linear model using the evidence curated list of target genes (see Table 3) for normal human bronchial epithelial (NHBE) cell line samples from E-MTAB-1312, which were stimulated with different TNFα concentrations for different stimulation times. In the diagram, the vertical axis indicates the activity score, wherein positive values correspond to an active NFkB cellular signaling pathway and negative values correspond to a passive NFkB cellular signaling pathway. NHBE cell lines were unstimulated or stimulated with different TNFα concentrations for different timings. All unstimulated healthy cells (groups 1 to 4) are correctly predicted to have a passive NFkB cellular signaling pathway. A stimulation with all TNFα concentrations for only 0.5 h is predicted to be too short for the NFkB cellular signaling pathway to become active (groups 5, 9, and 13), similar to the Bayesian network model using the evidence curated list of target genes (FIG. 8), whereas stimulation times of 2 to 24 hours resulted in an active NFkB cellular signaling pathway. The lowering of the NFkB cellular signaling pathway activity after 4 hours observed with the Bayesian network model especially using the evidence curated list of target genes (see FIG. 8) could not be reproduced with the trained exemplary linear model. (Legend: 1—No TNFα (0.5 h); 2—No TNFα (2 h); 3—No TNFα (4 h); 4—No TNFα (24 h); 5—Low TNFα (0.5 h); 6—Low TNFα (2 h); 7—Low TNFα (4 h); 8—Low TNFα (24 h); 9—Medium TNFα (0.5 h); 10—Medium TNFα (2 h); 11—Medium TNFα (4 h); 12—Medium TNFα (24 h); 13—High TNFα (0.5 h); 14—High TNFα (2 h); 15—High TNFα (4 h); 16—High TNFα (24 h))

FIG. 29 shows NFkB cellular signaling pathway activity predictions of the trained exemplary linear model using the evidence curated list of target genes (see Table 3) for colon samples from GSE4183. In the diagram, the vertical axis indicates the activity score, wherein positive values correspond to an active NFkB cellular signaling pathway and negative values correspond to a passive NFkB cellular signaling pathway. Most normal samples (group 1) were predicted to have a low NFkB cellular signaling pathway activity, albeit at higher activity scores than expected from other datasets. Compared to normal samples all inflammatory bowel disease samples (group 2) were predicted to have a higher NFkB activity score compared to the normal samples which is very reasonable considering the inflamed status of the colon in these patients which activates the NFkB cellular signaling pathway as one of the inflammatory response. In addition, it is clear that the samples in the adenoma samples (group 3) is on average lower than the more progressed colorectal carcinomas (CRC, group 4), which might be partially explained by the progression of the tumor into a more malignant tumor resulting in more mutations, inflammation as a result of the progressed tumor, or infiltration of white blood cells as a result of the immune response to the later stage cancers. (Legend: 1—Normal colon; 2—IBD; 3—Adenoma; 4—CRC)

Instead of applying the mathematical model, e.g., the exemplary Bayesian network model, on mRNA input data coming from microarrays or RNA sequencing, it may be beneficial in clinical applications to develop dedicated assays to perform the sample measurements, for instance on an integrated platform using qPCR to determine mRNA levels of target genes. The RNA/DNA sequences of the disclosed target genes can then be used to determine which primers and probes to select on such a platform.

Validation of such a dedicated assay can be done by using the microarray-based mathematical model as a reference model, and verifying whether the developed assay gives similar results on a set of validation samples. Next to a dedicated assay, this can also be done to build and calibrate similar mathematical models using mRNA-sequencing data as input measurements.

The set of target genes which are found to best indicate specific cellular signaling pathway activity, based on microarray/RNA sequencing based investigation using the mathematical model, e.g., the exemplary Bayesian network model, can be translated into a multiplex quantitative PCR assay to be performed on a sample and/or a computer to interpret the expression measurements and/or to infer the activity of the NFkB cellular signaling pathway. To develop such a test (e.g., FDA-approved or a CLIA waived test in a central service lab) for cellular signaling pathway activity, development of a standardized test kit is required, which needs to be clinically validated in clinical trials to obtain regulatory approval.

The present invention relates to a method comprising inferring activity of an NFkB cellular signaling pathway based at least on expression levels of one or more target genes of the NFkB cellular signaling pathway measured in a sample. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

The method may be used, for instance, in diagnosing an (abnormal) activity of the NFkB cellular signaling pathway, in prognosis based on the inferred activity of the NFkB cellular signaling pathway, in the enrollment in a clinical trial based on the inferred activity of the NFkB cellular signaling pathway, in the selection of subsequent test(s) to be performed, in the selection of companion diagnostics tests, in clinical decision support systems, or the like. In this regard, reference is made to the published international patent application WO 2013/011479 A2 ("Assessment of cellular signaling pathway activity using probabilistic modeling of target gene expression"), to the published international patent application WO 2014/102668 A2 ("Assessment of cellular signaling pathway activity using linear combination(s) of target gene expressions"), and to Verhaegh W. et al., "Selection of personalized patient therapy through the use of knowledge-based computational models that identify tumor-driving signal transduction pathways", Cancer Research, Vol. 74, No. 11, 2014, pages 2936-2945, which describe these applications in more detail.

Example 4

Comparison of the Evidence Curated List with a Broad Literature List

The list of target genes of the NFkB cellular signaling pathway constructed based on literature evidence following the procedure as described herein ("evidence curated list of target genes", see Table 3) is compared here with a "broad literature list" of putative target genes of the NFkB cellular signaling pathway constructed not following above mentioned procedure. The alternative list is a compilation of genes attributed to responding to activity of the NFkB cellular signaling pathway provided within Thomson-Reuters's Metacore (last accessed Sep. 6, 2013). This database was queried for genes that are transcriptionally regulated directly downstream of the family of NFkB proteins, i.e., NFKB1 or p50/p105, NFKB2 or p52/p100, RELA or p65, REL, and RELB. This query resulted in 343 unique genes. A further selection was made based on the number of publication references supporting the attributed transcriptional regulation of the respective gene by the NFkB family. Genes that had ten or more references were selected for the broad literature list. In other words, no manual curation of the references and no calculation of an evidence score based on the experimental evidence was performed. This procedure resulted in 32 genes, see Table 7. The expression of the genes was measured by 56 probesets on the Affymetrix HG-U133Plus2.0 microarray platform which were selected using the Bioconductor plugin of R and one manually added probeset for DEFB4A, see Table 7.

depicted in FIG. 24. In the diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. The activated B-cell (ABC) DLBCL (group 1) were used as active training samples and the normal samples (group 7) were used as passive training samples. The training results depicted in FIG. 24 show a clear separation between passive (group 7) and active (group 1) training samples as expected. Within the same dataset all other lymphoma samples and cell lines and DLBCL (groups 2 to 4, 8) were predicted NFkB active which is plausible given the literature evidence discussed herein. The healthy, unstimulated memory B-cells and naïve B-cells (groups 5 and 6) are correctly predicted a lack of NFkB cellular signaling pathway activity. (Legend: 1—ABC DLBCL; 2—Lymphoblastoid cell line; 3—Follicular lymphoma; 4—GCB DLBCL; 5—Memory B-cells; 6—Naïve B-cells; 7—Normal; 8—DLBCL unknown subtype).

Next the trained exemplary network Bayesian model based on the broad literature list was tested on a number of datasets.

FIG. 31 shows NFkB cellular signaling pathway activity predictions of the trained exemplary Bayesian network model using the broad literature list of putative target genes of the NFkB cellular signaling pathway (see Table 7) for normal human bronchial epithelial (NHBE) cell line samples from E-MTAB-1312, which were stimulated with different TNFα concentrations for different stimulation times. In the

TABLE 7

"Broad literature list" of putative target genes of the NFkB cellular signaling pathway used in the NFkB cellular signaling pathway models and associated probesets used to measure the mRNA expression level of the genes.

| Gene | Probeset | Gene | Probeset | Gene | Probeset |
|---|---|---|---|---|---|
| PTGS2 | 1554997_a_at | VCAM1 | 203868_s_at | FASLG | 210865_at |
|  | 204748_at | SELE | 206211_at |  | 211333_s_at |
| IL8 | 202859_x_at | IFNB1 | 208173_at | CXCL1 | 204470_at |
|  | 211506_s_at | IL12B | 207901_at | IL1B | 205067_at |
| NOS2 | 210037_s_at | BCL2L1 | 206665_s_at |  | 39402_at |
| IL6 | 205207_at |  | 212312_at | CXCL10 | 204533_at |
| MMP9 | 203936_s_at |  | 215037_s_at | BIRC3 | 210538_s_at |
| TNF | 207113_s_at |  | 231228_at |  | 230499_at |
| ICAM1 | 202637_s_at | NFKBIA | 201502_s_at | MYC | 202431_s_at |
|  | 202638_s_at |  | 231699_at | CXCL3 | 207850_at |
|  | 215485_s_at | SOD2 | 1566342_at | IER3 | 201631_s_at |
| CCL2 | 216598_s_at | IL2 | 207849_at | IL23A | 216857_at |
| CCL5 | 1405_i_at | CCL20 | 205476_at |  | 217328_at |
|  | 1555759_a_at | GCLC | 1555330_at |  | 220054_at |
|  | 204655_at |  | 202922_at |  | 234377_at |
| BCL2 | 203684_s_at |  | 202923_s_at |  | 234865_at |
|  | 203685_at | CSF2 | 210228_at | TRAF1 | 205599_at |
|  | 207004_at |  | 210229_s_at |  | 235116_at |
|  | 207005_s_at |  |  | DEFB4A | 207356_at |

Subsequently an exemplary Bayesian network model was constructed using the procedure as explained herein. Similarly to the description of the NFkB cellular signaling pathway model based on the evidence curated list, the conditional probability tables of the edges between probesets and their respective putative target genes of this model including the broad literature list were trained using fRMA processed data from GSE12195. The training results are diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. All unstimulated healthy cells up to 24 hours (groups 1 to 3) are correctly predicted to have a passive NFkB cellular signaling pathway. Lack of stimulation for 24 hours resulted in an unexpected activation of the NFkB cellular signaling pathway prediction. A stimulation with all TNFα concentrations for only 0.5 h is predicted by the broad literature Bayesian model also to be too short for the NFkB cellular signaling pathway to become active (groups 5, 9, and 13), whereas stimulation times of 2-24 hours resulted in an active NFkB cellular signaling pathway (groups 5 to 8, 9 to 12 and 13 to 15). The lowering of the NFkB cellular signaling pathway activity after 4 hours observed with the Bayesian network model using the evidence curated list of target genes (see FIG. 8) was not reproduced with the trained broad literature Bayesian network model. (Legend: 1—No TNFα (0.5 h); 2—No TNFα (2 h); 3—No TNFα (4 h); 4—No TNFα (24 h); 5—Low TNFα (0.5 h); 6—Low TNFα (2 h); 7—Low TNFα (4 h); 8—Low TNFα (24 h); 9—Medium TNFα (0.5 h); 10—Medium TNFα (2 h); 11—Medium TNFα (4 h); 12—Medium TNFα (24 h); 13—High TNFα (0.5 h); 14—High TNFα (2 h); 15—High TNFα (4 h); 16—High TNFα (24 h))

FIG. 32 shows NFkB cellular signaling pathway activity predictions of the trained exemplary Bayesian network model using the broad literature list of putative target genes of the NFkB cellular signaling pathway (see Table 7) for colon samples from GSE4183. In the diagram, the vertical axis indicates the odds that the TF element is "present" resp. "absent", which corresponds to the NFkB cellular signaling pathway being active resp. inactive, wherein values above the horizontal axis correspond to the TF element being more likely "present"/active and values below the horizontal axis indicate that the odds that the TF element is "absent"/inactive are larger than the odds that it is "present"/active. All but one adenoma sample are predicted by the broad literature Bayesian network model to have an active NFkB cellular signaling pathway, which is especially not expected to be the case in normal, healthy colon samples (group 1). (Legend: 1—Normal colin; 2—IBD; 3—Adenoma; 4—CRC)

As evidenced by the above example, the selection of unique NFkB target gene sets in combination with the mathematical models described herein for determining the activity level of NFkB cellular signaling pathway in a sample produces a more robust, precise, and accurate activity status determination than the use of a broader literature list, despite the fact that the number of target genes is larger. By focusing on the specific target genes identified herein, a useful determination of NFkB cellular signaling pathway activity is provided that can be further used in treatment or prognostic modalities as described herein.

This specification has been described with reference to embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the disclosure.

| Sequence Listing: | |
|---|---|
| Seq. No. | Gene: |
| Seq. 1 | BCL2 |
| Seq. 2 | BCL2L1 |
| Seq. 3 | BIRC3 |
| Seq. 4 | CCL2 |
| Seq. 5 | CCL3 |
| Seq. 6 | CCL4 |
| Seq. 7 | CCL5 |
| Seq. 8 | CCL20 |
| Seq. 9 | CCL22 |
| Seq. 10 | CSF2 |
| Seq. 11 | CX3CL1 |
| Seq. 12 | CXCL1 |
| Seq. 13 | CXCL2 |
| Seq. 14 | CXCL3 |
| Seq. 15 | CXCL10 |
| Seq. 16 | DEFB4A |
| Seq. 17 | FASLG |
| Seq. 18 | GCLC |
| Seq. 19 | ICAM1 |
| Seq. 20 | IER3 |
| Seq. 21 | IFNB1 |
| Seq. 22 | IL12B |
| Seq. 23 | IL1B |
| Seq. 24 | IL2 |
| Seq. 25 | IL23A |
| Seq. 26 | IL6 |
| Seq. 27 | IL8 |
| Seq. 28 | IRF1 |
| Seq. 29 | MMP9 |
| Seq. 30 | MYC |
| Seq. 31 | NFKB2 |
| Seq. 32 | NFKBIA |
| Seq. 33 | NFKBIE |
| Seq. 34 | NOS2 |
| Seq. 35 | PTGS2 |
| Seq. 36 | SELE |
| Seq. 37 | SOD2 |
| Seq. 38 | STAT5A |
| Seq. 39 | TNF |
| Seq. 40 | TNFAIP2 |
| Seq. 41 | TNIP1 |
| Seq. 42 | TRAF1 |
| Seq. 43 | VCAM1 |

The invention claimed is:

1. A method of treating a subject suffering from a disease associated with an activated NFkB cellular signaling pathway comprising:

obtaining information regarding the activity level of a NFkB cellular signaling pathway derived from a sample isolated from the subject, wherein the activity level of the NFkB cellular signaling pathway is determined by:

determining an activity level of NFkB transcription factor element in a sample isolated from the subject, wherein the level of the NFkB transcription factor element in the sample is determined by:

obtaining data on the expression levels of at least six target genes derived from the sample, wherein the NFkB transcription factor element controls transcription of the at least six target genes, and wherein the at least six target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1;

determining the level of the NFkB transcription factor element in the sample using a calibrated pathway model, wherein the calibrated pathway model compares the expression levels of the at least six target genes in the sample with expression levels of the at least six target genes in the model which define an activity level of NFkB transcription factor element; and, determining the activity level of the NFkB cellular signaling pathway in the sample based on the determined NFkB transcription factor element level in the sample; and, administering to the subject a NFkB inhibitor if the information regarding the activity level of the NFkB cellular signaling pathway is indicative of an active NFkB cellular signaling pathway.

2. The method of claim 1, wherein the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1.

3. The method of claim 1, wherein the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2.

4. The method of claim 3, wherein the at least three target genes are selected from CCL5, CXCL2, ICAM1, IL6, IL8, NFKBIA, and TNFAIP2.

5. The method of claim 1, wherein the calibrated pathway model is a probabilistic model incorporating conditional probabilistic relationships that compare the expression levels of the at least six target genes in the sample with expression levels of the at least six target genes in the model which define a level of NFkB transcription factor element to determine the activity level of the NFkB transcription factor element in the sample.

6. The method of claim 1, wherein the calibrated pathway model is a linear model incorporating relationships that compare the expression levels of the at least six target genes in the sample with expression levels of the at least six target genes in the model which define a level of NFkB transcription factor element to determine the activity level of the NFkB transcription factor element in the human cancer sample.

7. The method of claim 1, wherein the NFkB inhibitor is DHMEQ, bindarit, Bortesomib or BU-32 (proteazome inhibitors), BMS-345541, or glucocorticoids.

8. The method of claim 1, wherein the disease is a cancer.

9. The method of claim 8, wherein the cancer is colon, breast, prostate, pancreatic, lung, brain, leukemia, lymphoma, or glioma.

10. The method of claim 9, wherein the cancer is breast cancer.

11. A method of treating a subject suffering from a disease associated with an activated NFkB cellular signaling pathway, comprising:
receiving information regarding the activity level of a NFkB cellular signaling pathway derived from a sample isolated from the subject, wherein the activity level of the NFkB cellular signaling pathway is determined by:
determining an activity level of NFkB transcription factor element in a sample isolated from the subject, wherein the level of the NFkB transcription factor element in the sample is determined by:
obtaining data on the expression levels of at least six target genes derived from the sample, wherein the NFkB transcription factor element controls transcription of the at least six target genes, and wherein the at least six target genes are selected from BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1;
determining the level of the NFkB transcription factor element in the sample using a calibrated pathway model, wherein the calibrated pathway model compares the expression levels of the at least six target genes in the sample with expression levels of the at least six target genes in the model which define an activity level of NFkB transcription factor element; and,
determining the activity level of the NFkB cellular signaling pathway in the sample based on the determined NFkB transcription factor element level in the sample; and,
administering to the subject a NFkB inhibitor if the received information regarding the activity level of the NFkB cellular signaling pathway is indicative of an active NFkB cellular signaling pathway.

12. The method of claim 11, further comprising assigning a NFkB cellular signaling pathway activity status to the determined activity level of the NFkB cellular signaling in the sample, wherein the activity status is indicative of either an active NFkB cellular signaling pathway or a passive NFkB cellular signaling pathway.

13. The method of claim 12, further comprising displaying the NFkB cellular signaling pathway activity status.

14. The method of claim 11, wherein the at least six target genes are selected from BIRC3, CCL2, CCL5, CCL20, CXCL1, CXCL2, CXCL3, ICAM1, IL6, IL8, IRF1, MMP9, NFKB2, NFKBIA, NFKBIE, TNF, TNFAIP2, TRAF1, and VCAM1.

15. The method of claim 11, wherein the at least six target genes comprise at least three target genes selected from CCL2, CCL5, CCL20, CXCL1, CXCL2, CXCL3, ICAM1, IL6, IL8, MMP9, NFKB2, NFKBIA, and TNFAIP2.

16. The method of claim 15, wherein the at least three target genes are selected from CCL5, CXCL2, ICAM1, IL6, IL8, NFKBIA, and TNFAIP2.

17. The method of claim 11, wherein the calibrated pathway model is a probabilistic model incorporating conditional probabilistic relationships that compare the expression levels of the at least six target genes in the sample with expression levels of the at least six target genes in the model which define a level of NFkB transcription factor element to determine the activity level of NFkB transcription factor element in the sample.

18. The method of claim 11, wherein the calibrated pathway model is a linear model incorporating relationships that compare the expression levels of the at least six target genes in the sample with expression levels of the at least six target genes in the model which define a level of NFkB transcription factor element to determine the activity level of NFkB transcription factor element in the sample.

19. The method of claim 11, wherein the NFkB inhibitor is DHMEQ, bindarit, Bortesomib or BU-32 (proteazome inhibitors), BMS-345541, or glucocorticoids.

20. The method of claim 11, wherein the disease is a cancer.

21. The method of claim 20, wherein the cancer is colon, breast, prostate, pancreatic, lung, brain, leukemia, lymphoma, or glioma.

* * * * *